(12) United States Patent
Xie et al.

(10) Patent No.: US 12,122,774 B2
(45) Date of Patent: Oct. 22, 2024

(54) COMPOUNDS AS MYT1 INHIBITORS

(71) Applicant: WIGEN BIOMEDICINE TECHNOLOGY (SHANGHAI) CO., LTD., Shanghai (CN)

(72) Inventors: Yuli Xie, Shanghai (CN); Yingming Wu, Shanghai (CN); Lihui Qian, Shanghai (CN)

(73) Assignee: WIGEN BIOMEDICINE TECHNOLOGY (SHANGHAI) CO., LTD., Shanghai (CN)

( * ) Notice: Subject to any disclaimer, the term of this patent is extended or adjusted under 35 U.S.C. 154(b) by 0 days.

(21) Appl. No.: 18/633,460

(22) Filed: Apr. 11, 2024

(65) Prior Publication Data

US 2024/0287067 A1 Aug. 29, 2024

Related U.S. Application Data

(63) Continuation of application No. PCT/CN2023/106585, filed on Oct. 7, 2023.

(30) Foreign Application Priority Data

| Jul. 12, 2022 | (CN) | 202210822834.5 |
| Jan. 31, 2023 | (CN) | 202310048632.4 |

(51) Int. Cl.
C07D 471/04 (2006.01)
A61K 31/437 (2006.01)

(52) U.S. Cl.
CPC .......... *C07D 471/04* (2013.01); *A61K 31/437* (2013.01)

(58) Field of Classification Search
None
See application file for complete search history.

(56) References Cited

U.S. PATENT DOCUMENTS

2023/0122909 A1* 4/2023 Szychowski ......... C07D 209/12
548/453
2023/0142913 A1 5/2023 Szychowski et al.

FOREIGN PATENT DOCUMENTS

| WO | 2021195781 A1 | 10/2021 | |
| WO | 2021195782 A1 | 10/2021 | |
| WO | 2022213204 A1 | 10/2022 | |
| WO | 2022226655 A1 | 11/2022 | |
| WO | WO-2023249563 A1 * | 12/2023 | ............. A61P 35/00 |

OTHER PUBLICATIONS

The role of fluorine in medicinal chemistry Shah et al. Journal of Enzyme Inhibition and Medicinal Chemistry, Oct. 2007; 22(5): 527-540 (Year: 2007).*

* cited by examiner

*Primary Examiner* — Jeffrey S Lundgren
*Assistant Examiner* — Eric Tran
(74) *Attorney, Agent, or Firm* — SZDC Law PC

(57) ABSTRACT

Disclosed in the present invention are compounds as MYT1 inhibitors. Particularly, the present invention relates to compounds represented by general formula (1) and a preparation method therefor, as well as the use of the compounds of general formula (1), and isomers, crystal forms, pharmaceutically acceptable salts, hydrates or solvates thereof as MYT1 inhibitors. The compounds of the present invention as well as the isomers, crystal forms, pharmaceutically acceptable salts, hydrates or solvates thereof can be used for preparing drugs for treating or preventing diseases related to MYT1 protein.

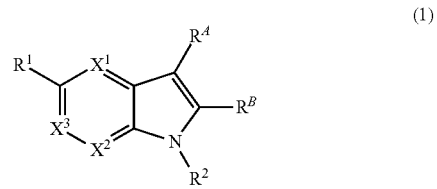

(1)

16 Claims, No Drawings

COMPOUNDS AS MYT1 INHIBITORS

The present application is a Continuation Application of PCT/CN2023/106585, filed on Jul. 10, 2023, which claims priority to Chinese Patent Application Nos. 202210822834.5, filed on Jul. 12, 2022 and 202310048632.4, filed on Jan. 31, 2023, which are incorporated herein by reference in their entirety.

TECHNICAL FIELD

The present invention belongs to the field of pharmaceutical chemistry, and particularly relates to a class of compounds with an inhibitory effect on MYT1 protein, a preparation method therefor, and use of the compounds in the preparation of a medicament for treating or preventing a related disease mediated by MYT1.

BACKGROUND

The cell cycle incudes two checkpoints, G1 and G2, which enable cells to perform efficient DNA damage repair, thereby maintaining genomic stability. Both Wee1 and MYT1 of the Wee kinase family are involved in the regulation of this cell cycle. MYT1 is mainly present in the nucleus of the cell and specifically phosphorylates threonine at position 14 of its substrate, cyclin-dependent kinase 1 (CDK1). This MYT1-mediated phosphorylation inhibits the activity of the CDK1/cyclin B complex, thereby preventing cells from entering mitosis. Since many tumor cells carry the p53 mutation, leading to repair defects at the G1 checkpoint, these tumor cells are highly dependent on the G2 checkpoint to repair the DNA damage. Therefore, inhibiting MYT1 activity to interfere with the G2 checkpoint, thereby selectively damaging tumor cells that are highly dependent on the G2 checkpoint and reducing damage to normal cells at the same time, is a promising targeting strategy. In view of the above, there is an urgent need to study and discover compounds with good activity targeting MYT1.

SUMMARY

The present invention provides a compound of general formula (1) or an isomer, a crystalline form, a pharmaceutically acceptable salt, a hydrate or a solvate thereof:

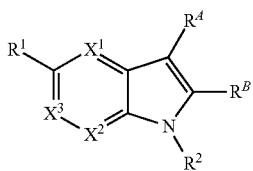

(1)

wherein in general formula (1):
$R^A$ is —C(O)NH($R^4$), —C(O)($R^{3a}$), or —SO$_2R^{3a}$;
$R^B$ is —H or —N($R^3$)$_2$;
$X^1$ is $CR^{a1}$ or N;
$X^2$ is $CR^{a2}$ or N;
$X^3$ is $CR^{a3}$ or N;
$R^{a1}$, $R^{a2}$, $R^{a3}$, and $R^1$ are each independently —H, halogen, —CN, (C1-C6) alkyl, (C1-C6) haloalkyl, (C2-C6) alkenyl, (C2-C6) alkynyl, (C3-C8) cycloalkyl, (3-9 membered) heterocycloalkyl, (C6-C10) aryl, (5-10 membered) heteroaryl, —N($R^3$)$_2$, —OR$^3$, —C(O)N($R^4$)$_2$, —SO$_2$N($R^4$)$_2$, —SO$_2R^{3a}$, or -Q-$R^{3b}$, wherein the (C1-C6) alkyl, (C1-C6) haloalkyl, (C2-C6) alkenyl, (C2-C6) alkynyl, (C3-C8) cycloalkyl, (C6-C10) aryl, (5-10 membered) heteroaryl, or (3-9 membered) heterocycloalkyl may be each independently and optionally substituted with 1, 2, 3, or 4 of the following groups: —H, halogen, —OH, —OR$^5$, —N($R^5$)$_2$, —CN, (C1-C6) alkyl, (C1-C6) haloalkyl, (C2-C6) alkenyl, (C2-C6) alkynyl, (C3-C8) cycloalkyl, (3-9 membered) heterocycloalkyl, (C6-C10) aryl, and (5-10 membered) heteroaryl; or $R^{a3}$ and $R^1$, together with the carbon atom to which they are each attached, form (C4-C9) cycloalkyl, (C4-C9) cycloalkenyl, (4-9 membered) heterocycloalkyl, phenyl, or (5-10 membered) heteroaryl, wherein the (C4-C9) cycloalkyl, (C4-C9) cycloalkenyl, (4-9 membered) heterocycloalkyl, phenyl, or (5-10 membered) heteroaryl may be each independently and optionally substituted with 1, 2, 3, or 4 of the following groups: —H, halogen, —OH, —OR$^5$, —N($R^5$)$_2$, —CN, (C1-C6) alkyl, (C1-C6) haloalkyl, (C2-C6) alkenyl, (C2-C6) alkynyl, and (C3-C8) cycloalkyl; when none of $R^{a1}$, $R^{a2}$, $R^{a3}$, and $R^1$ is —CN, $R^2$ is

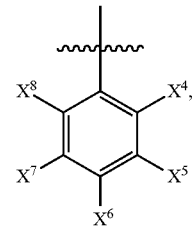

wherein $X^4$, $X^5$, $X^6$, $X^7$, and $X^8$ are each independently —H, —OH, —OR$^3$, halogen, —CN, (C1-C6) alkyl, (C1-C6) haloalkyl, (C2-C6) alkenyl, (C2-C6) alkynyl, (C3-C6) cycloalkyl, or (3-6 membered) heterocycloalkyl, and 4 of $X^4$, $X^3$, $X^6$, $X^7$, and $X^8$ are not simultaneously —H; or each of the pairs of $X^4/X^5$, $X^5/X^6$, $X^6/X^7$, and $X^1/X^8$, with the carbon atom to which they are each attached, may independently form (C4-C10) cycloalkyl, (4-10 membered) heterocycloalkyl, phenyl, or (5-10 membered) heteroaryl, wherein the (C4-C10) cycloalkyl, (4-10 membered) heterocycloalkyl, phenyl, or (5-10 membered) heteroaryl may be each independently and optionally substituted with 1, 2, 3, or 4 of the following groups: —H, halogen, —OH, —OR$^5$, —N($R^5$)$_2$, —CN, (C1-C6) alkyl, (C1-C6) haloalkyl, (C2-C6) alkenyl, (C2-C6) alkynyl, and (C3-C8) cycloalkyl: or $R^2$ is (6-10 membered) heterocycloalkyl or (6-10 membered) heteroaryl, wherein the (6-10 membered) heterocycloalkyl or (6-10 membered) heteroaryl may be each independently and optionally substituted with 1, 2, 3, or 4 of the following groups: —H, —OH, —OR$^3$, halogen, —CN, (C1-C6) alkyl, (C1-C6) haloalkyl, (C2-C6) alkenyl, (C2-C6) alkynyl, (C3-C6) cycloalkyl, and (3-6 membered) heterocycloalkyl;
when at least one of $R^{a1}$, $R^{a2}$, $R^{a3}$, and $R^1$ is —CN; or when $R^{a3}$ and $R^1$, together with the carbon atom to which they are each attached, form (C4-C9) cycloalkenyl, (4-9 membered) heterocycloalkyl, or (5-10 membered) heteroaryl, wherein the (4-9 membered) heterocycloalkyl or (5-10 membered) heteroaryl may be each independently and optionally substituted with 1, 2, 3, or 4 of the following groups: —H, halogen, —OH, —OR⁵, —N(R⁵)₂, —CN, (C1-C6) alkyl, (C1-C6) haloalkyl, (C2-C6) alkenyl, (C2-C6) alkynyl, and (C3-C8) cycloalkyl, R² is

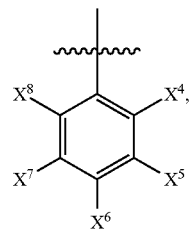

wherein X⁴, X³, X⁶, X⁷, and X⁸ are each independently —H, —OH, —OR³, halogen, —CN, (C1-C6) alkyl, (C1-C6) haloalkyl, (C2-C6) alkenyl, (C2-C6) alkynyl, (C3-C6) cycloalkyl, or (3-6 membered) heterocycloalkyl, and at least 2 of X⁴, X³, X⁶, X⁷, and X⁸ are not simultaneously —H: or each of the pairs of X⁴/X⁵, X⁵/X⁶, X⁶/X⁷, and X⁷/X⁸, with the carbon atom to which they are each attached, may independently form (C4-C10) cycloalkyl, (4-10 membered) heterocycloalkyl, phenyl, or (5-10 membered) heteroaryl, wherein the (C4-C10) cycloalkyl, (4-10 membered) heterocycloalkyl, phenyl, or (5-10 membered) heteroaryl may be each independently and optionally substituted with 1, 2, 3, or 4 of the following groups: —H, halogen, —OH, —OR³, —N(R³)₂, —CN, (C1-C6) alkyl, (C1-C6) haloalkyl, (C2-C6) alkenyl, (C2-C6) alkynyl, and (C3-C8) cycloalkyl: or R² is (6-10 membered) heterocycloalkyl or (6-10 membered) heteroaryl, wherein the (6-10 membered) heterocycloalkyl or (6-10 membered) heteroaryl may be each independently and optionally substituted with 1, 2, 3, or 4 of the following groups: —H, —OH, —OR³, halogen, —CN, (C1-C6) alkyl, (C1-C6) haloalkyl, (C2-C6) alkenyl, (C2-C6) alkynyl, (C3-C6) cycloalkyl, and (3-6 membered) heterocycloalkyl;

each R³ is independently —H, (C1-C6) alkyl, (C1-C6) haloalkyl, (C2-C6) alkenyl, (C2-C6) alkynyl. (C3-C8) cycloalkyl, (3-9 membered) heterocycloalkyl, (C6-C10) aryl, (5-10 membered) heteroaryl, or —SO₂R³ᵃ, wherein the (C1-C6) alkyl, (C1-C6) haloalkyl, (C2-C6) alkenyl, (C2-C6) alkynyl, (C3-C8) cycloalkyl, (C6-C10) aryl, (5-10 membered) heteroaryl, or (3-9 membered) heterocycloalkyl may be each independently and optionally substituted with 1, 2, 3, or 4 of the following groups: —H, —OH, (C1-C6) alkyl, (C1-C6) alkoxy; or halogen: or two R³ on the same nitrogen atom, together with the nitrogen atom to which they are attached, may form (3-9 membered) heterocycloalkyl, wherein the (3-9 membered) heterocycloalkyl may be each independently and optionally substituted with 1, 2, 3, or 4 of the following groups: —H, halogen, —OH, —OR⁵, —N(R⁵)₂, —CN, (C1-C6) alkyl, (C1-C6) haloalkyl, (C2-C6) alkenyl, (C2-C6) alkynyl, and (C3-C8) cycloalkyl: each R³ᵃ is independently (C1-C6) alkyl, (C1-C6) haloalkyl, (C3-C8) cycloalkyl, (3-9 membered) heterocycloalkyl, (C6-C10) aryl, or (5-10 membered) heteroaryl, wherein the (C1-C6) alkyl, (C1-C6) haloalkyl, (C3-C8) cycloalkyl, (3-9 membered) heterocycloalkyl, (C6-C10) aryl, or (5-10 membered) heteroaryl may be each independently and optionally substituted with 1, 2, 3, or 4 of the following groups: —H, —OH, (C1-C6) alkyl, (C1-C6) alkoxy, or halogen:

each R³ᵇ is independently (C1-C6) alkyl, (C1-C6) haloalkyl, (C2-C6) alkenyl, (C2-C6) alkynyl, (C3-C8) cycloalkyl, (3-9 membered) heterocycloalkyl, (C6-C10) aryl. (5-10 membered) heteroaryl, —N(R³)₂, —OR³, —C(O)N(R⁴)₂, —SON(R⁴)₂, or —SOR³ᵃ, wherein the (C1-C6) alkyl, (C1-C6) haloalkyl, (C2-C6) alkenyl, (C2-C6) alkynyl, (C3-C8) cycloalkyl, (C6-C10) aryl, (5-10 membered) heteroaryl, or (3-9 membered) heterocycloalkyl may be each independently and optionally substituted with 1, 2, 3, or 4 of the following groups: —H, halogen, —OH, —OR⁵, —N(R⁵)₂, —CN, (C1-C6) alkyl, (C1-C6) haloalkyl, (C2-C6) alkenyl, (C2-C6) alkynyl, (C3-C8) cycloalkyl, (3-9 membered) heterocycloalkyl, (C6-C10) aryl, and (5-10 membered) heteroaryl;

Q is (C1-C6) alkylene, (C2-C6) alkenylene, (C2-C6) alkynylene, (C3-C8) cycloalkylene, (3-9 membered) heterocycloalkylene, (C6-C10) arylene, or (5-10 membered) heteroarylene, wherein the (C1-C6) alkylene, (C2-C6) alkenylene. (C2-C6) alkynylene, (C3-C8) cycloalkylene. (C6-C10) arylene, (5-10 membered) heteroarylene, or (3-9 membered) heterocycloalkylene may be each independently and optionally substituted with 1, 2, 3, or 4 of the following groups: —H, halogen, —OH, —OR⁵, —N(R⁵)₂, —CN, (C1-C6) alkyl, (C1-C6) haloalkyl, (C2-C6) alkenyl. (C2-C6) alkynyl. (C3-C8) cycloalkyl, (3-9 membered) heterocycloalkyl, (C6-C10) aryl, and (5-10 membered) heteroaryl;

each R⁴ is independently —H, (C1-C6) alkyl, (C1-C6) haloalkyl, (C1-C6) alkoxy; (C3-C8) cycloalkyl, (3-9 membered) heterocycloalkyl, (C6-C10) aryl, or (5-10 membered) heteroaryl, wherein the (C1-C6) alkyl, (C1-C6) haloalkyl, (C1-C6) alkoxy, (C3-C8) cycloalkyl, (3-9 membered) heterocycloalkyl, (C6-C10) aryl, or (5-10 membered) heteroaryl may be each independently and optionally substituted with 1, 2, 3, or 4 of the following groups: —H, —OH, (C1-C6) alkyl, (C1-C6) alkoxy; or halogen; or two R⁴ on the same nitrogen atom, together with the nitrogen atom to which they are attached, may form (3-9 membered) heterocycloalkyl, wherein the (3-9 membered) heterocycloalkyl may be each independently and optionally substituted with 1, 2, 3, or 4 of the following groups: —H, halogen, —OH, —OR⁵, —N(R⁵)₂, —CN, (C1-C6) alkyl, (C1-C6) haloalkyl, (C2-C6) alkenyl, (C2-C6) alkynyl, and (C3-C8) cycloalkyl;

each R⁵ is independently —H, (C1-C6) alkyl, (C1-C6) haloalkyl, (C2-C6) alkenyl, (C2-C6) alkynyl, (C3-C8) cycloalkyl, (3-9 membered) heterocycloalkyl, (C6-C10) aryl, (5-10 membered) heteroaryl, or —SOR³ᵃ, wherein the (C1-C6) alkyl, (C1-C6) haloalkyl, (C2-C6) alkenyl, (C2-C6) alkynyl, (C3-C8) cycloalkyl, (C6-C10) aryl, (5-10 membered) heteroaryl, or (3-9 membered) heterocycloalkyl may be each independently and optionally substituted with 1, 2, 3, or 4 of the following groups: —H, —OH, (C1-C6) alkyl, (C1-C6) alkoxy, or halogen; or two R⁵ on the same nitrogen atom, together with the nitrogen atom to which they are attached, may form (3-9 membered) heterocycloalkyl, wherein the (3-9 membered) heterocycloalkyl may be each independently and optionally substituted with 1, 2, 3, or 4 of the following groups: —H, halogen, —OH, —CN, (C1-C6) alkyl, (C1-C6) alkoxy, (C1-C6) haloalkyl, (C2-C6) alkenyl, (C2-C6) alkynyl, and (C3-C8) cycloalkyl.

In another preferred embodiment, in general formula (1), R^{a1}, R^{a2}, R^{a3}, and R¹ are each independently —H, halogen, —CN, (C1-C6) alkyl, (C1-C6) haloalkyl, (C2-C6) alkenyl, (C2-C6) alkynyl, (C3-C8) cycloalkyl, (3-9 membered) heterocycloalkyl, (C6-C10) aryl, (5-10 membered) heteroaryl, —N(R³)₂, —OR³, —C(O)N(R⁴)₂, —SON(R⁴)₂, —SOR³ᵃ, or -Q-R³ᵇ, wherein the (C1-C6) alkyl, (C1-C6) haloalkyl, (C2-C6) alkenyl, (C2-C6) alkynyl, (C3-C8) cycloalkyl, (C6-C10) aryl, (5-10 membered) heteroaryl, or (3-9 membered) heterocycloalkyl may be each independently and optionally substituted with 1, 2, 3, or 4 of the following groups: —H, —F, —Cl, —Br, —I, —OH, —OCH₃, —NH₂, —NH(CH₃), —N(CH₃)₂, —CN, (C1-C3) alkyl, (C1-C3) haloalkyl, (C2-C4) alkenyl, (C2-C4) alkynyl, (C3-C6) cycloalkyl, (3-6 membered) heterocycloalkyl, aryl, and (5-6 membered) heteroaryl: or R^{a3} and R¹, together with the carbon atom to which they are each attached, form (C3-C8 membered) cycloalkyl, (4-8 membered) heterocycloalkyl, phenyl, or (5-6 membered) heteroaryl, wherein the (C3-C8 membered) cycloalkyl, (4-8 membered) heterocycloalkyl, phenyl, or (5-6 membered) heteroaryl may be each independently and optionally substituted with 1, 2, 3, or 4 of the following groups: —F, —Cl, —Br, —I, —OH, —OCH₃, —NH₂, —N(CH₃)₂, —CN, (C1-C3) alkyl, (C1-C3) haloalkyl, (C2-C4) alkenyl, (C2-C4) alkynyl, and (C3-C6) cycloalkyl.

In another preferred embodiment, in general formula (1), $R^{a1}$, $R^{12}$, $R^{13}$, and $R^1$ are each independently —H, —OH, —OCH₃, —NH₂, —NH(CH₃), —N(CH₃)₂, —CN, —C(O)N(CH₃)₂, —C(O)NH(CH₃), —C(O)NH₂, —SO₂N(CH₃)₂, —SO₂NH(CH₃), —SO₂NH₂, —SO₂CH₃, —SO₂CH₂CH₃, —SO₂CH(CH₃)₂,

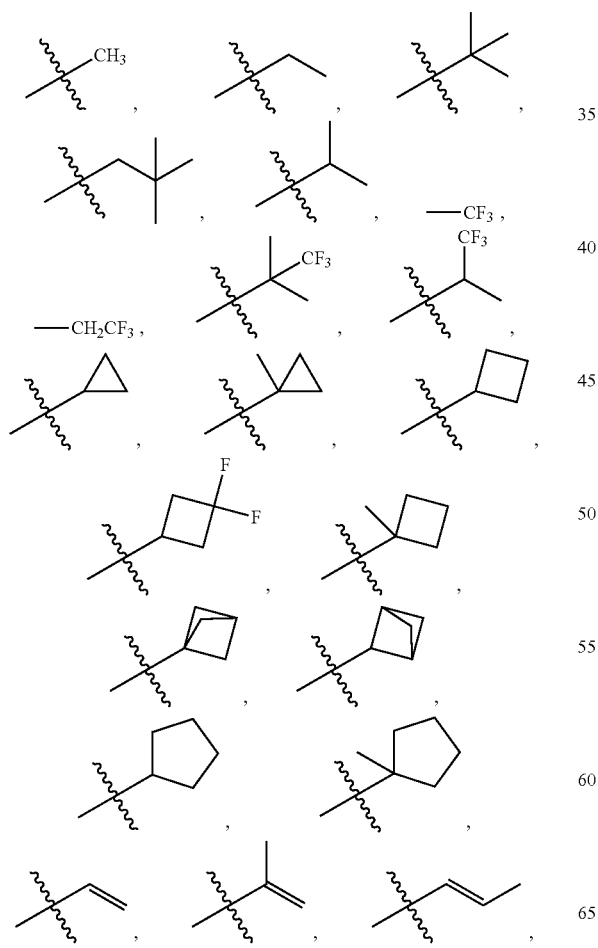

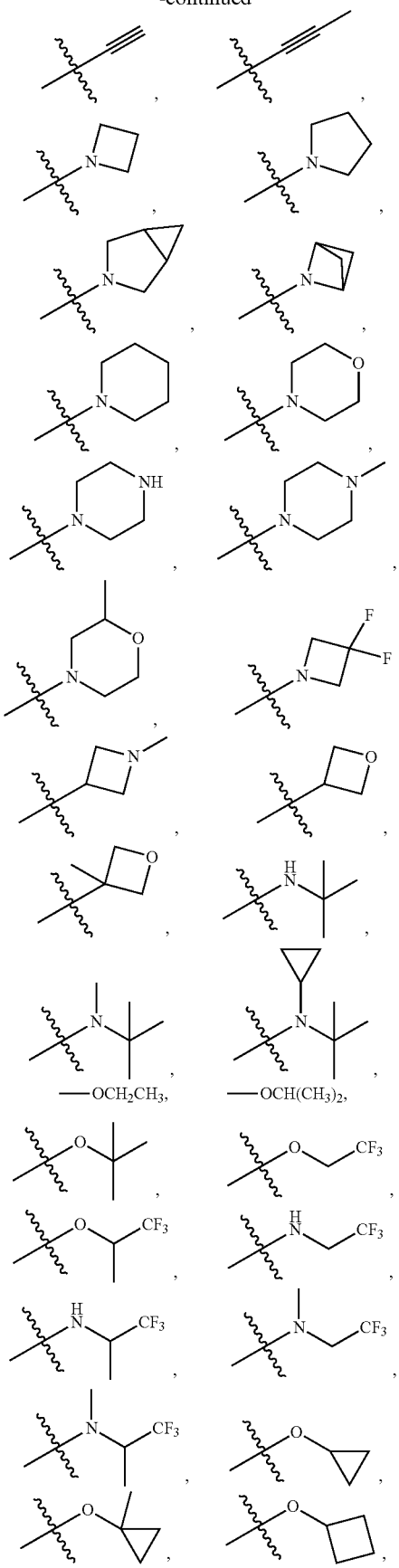

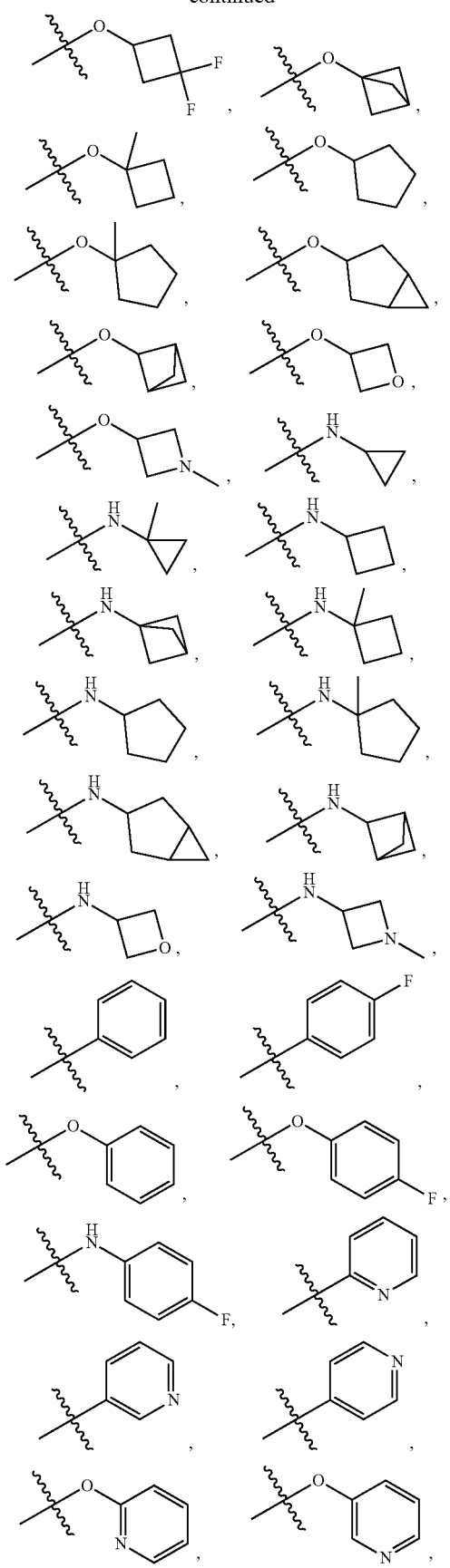
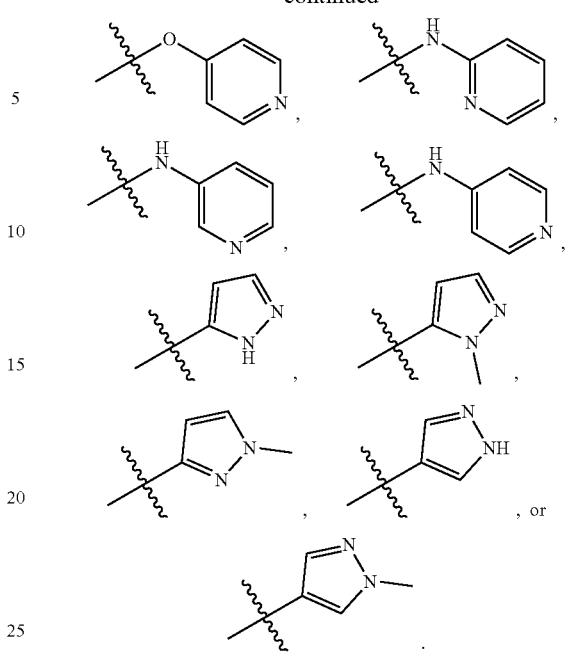
In another preferred embodiment, in general formula (1), $R^{a3}$ and $R^1$, together with the carbon atom to which they are each attached, form the following structural unit:
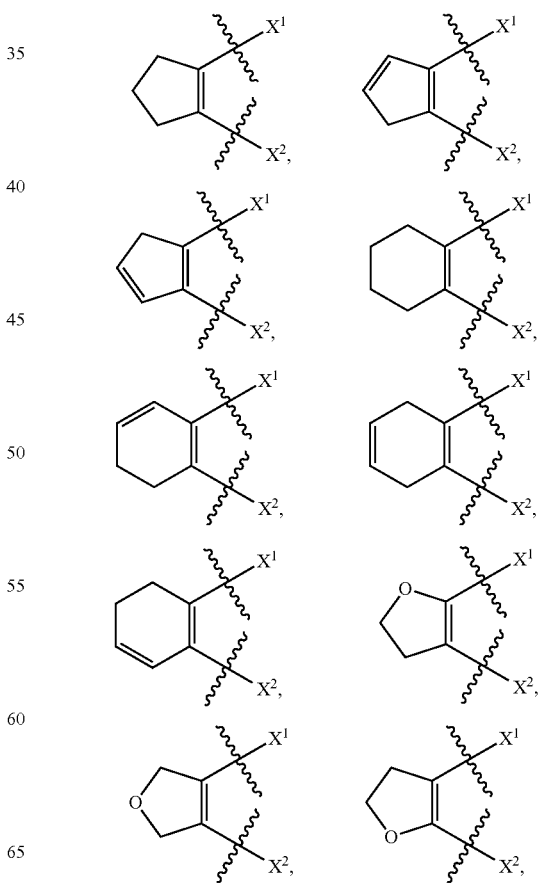

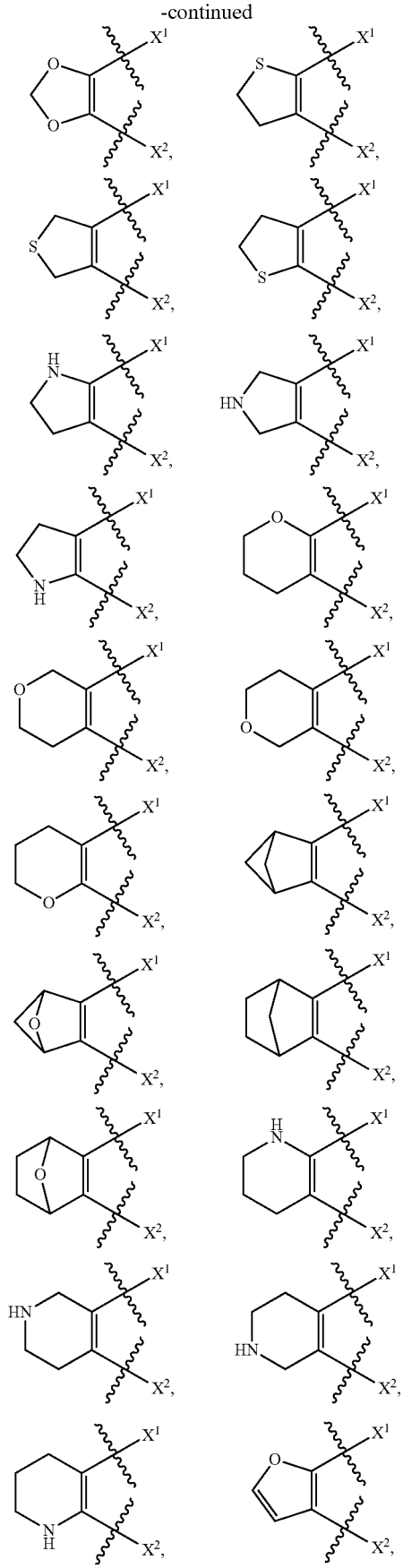
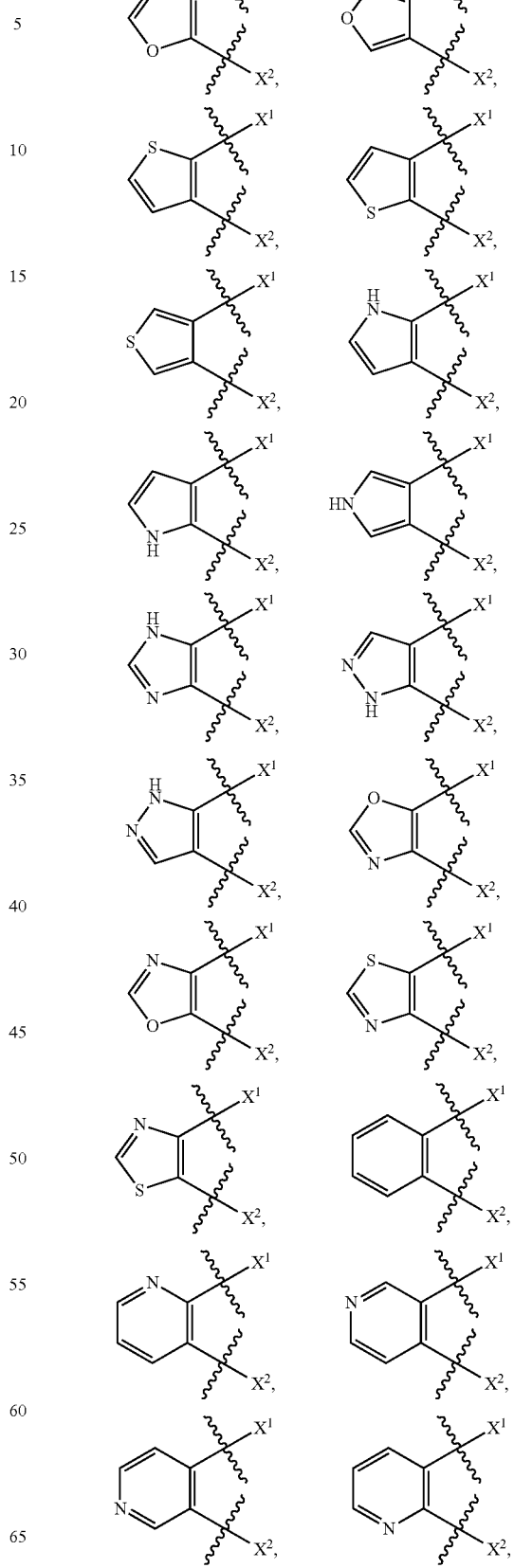

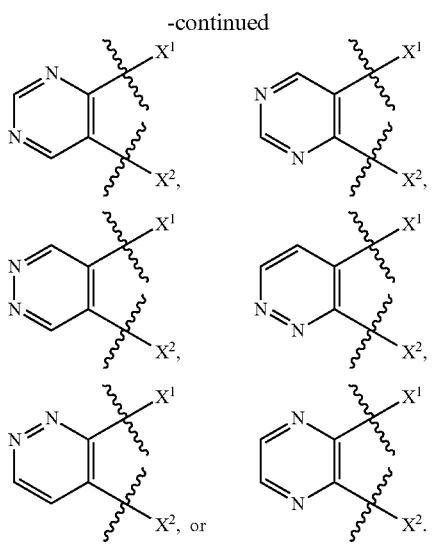

In another preferred embodiment, in general formula (1), when none of $R^{a1}$, $R^{a2}$, $R^{a3}$, and $R^1$ is —CN, $R^2$ is

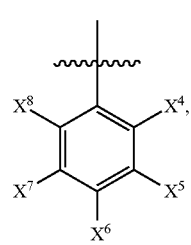

wherein $X^4$, $X^3$, $X^6$, $X^7$, and $X^8$ are each independently —H, —OH, —OR$^3$, halogen, —CN, (C1-C3) alkyl, (C1-C3) haloalkyl, (C2-C4) alkenyl, (C2-C4) alkynyl, (C3-C6) cycloalkyl, or (3-6 membered) heterocycloalkyl, and 4 of $X^4$, $X^3$, $X^6$, $X^7$, and $X^8$ are not simultaneously —H; or each of the pairs of $X^4/X^3$, $X^3/X^6$, $X^6/X^7$, and $X^7/X^8$, with the carbon atom to which they are each attached, may independently form (C4-C6) cycloalkyl, (4-6 membered) heterocycloalkyl, phenyl, or (5-6 membered) heteroaryl, wherein the (C4-C6) cycloalkyl, (4-6 membered) heterocycloalkyl, phenyl, or (5-6 membered) heteroaryl may be each independently and optionally substituted with 1, 2, 3, or 4 of the following groups: —H, —F, —Cl, —Br, —I, —OH, —OCH$_3$, —NH$_2$, —N(CH$_3$)$_2$, —CN, (C1-C3) alkyl, (C1-C3) haloalkyl, (C2-C4) alkenyl, (C2-C4) alkynyl, and (C3-C6) cycloalkyl; or $R^2$ is (6-10 membered) heterocycloalkyl or (6-10 membered) heteroaryl, wherein the (6-10 membered) heterocycloalkyl or (6-10 membered) heteroaryl may be each independently and optionally substituted with 1, 2, 3, or 4 of the following groups: —H, —F, —Cl, —Br, —I, —OH, —OCH$_3$, —CN, (C1-C3) alkyl, (C1-C3) haloalkyl, (C2-C4) alkenyl, (C2-C4) alkynyl, (C3-C6) cycloalkyl, and (3-6 membered) heterocycloalkyl.

In another preferred embodiment, in general formula (1), when none of $R^{a1}$, $R^{a2}$, $R^{a3}$, and $R^1$ is —CN, $R^2$ is

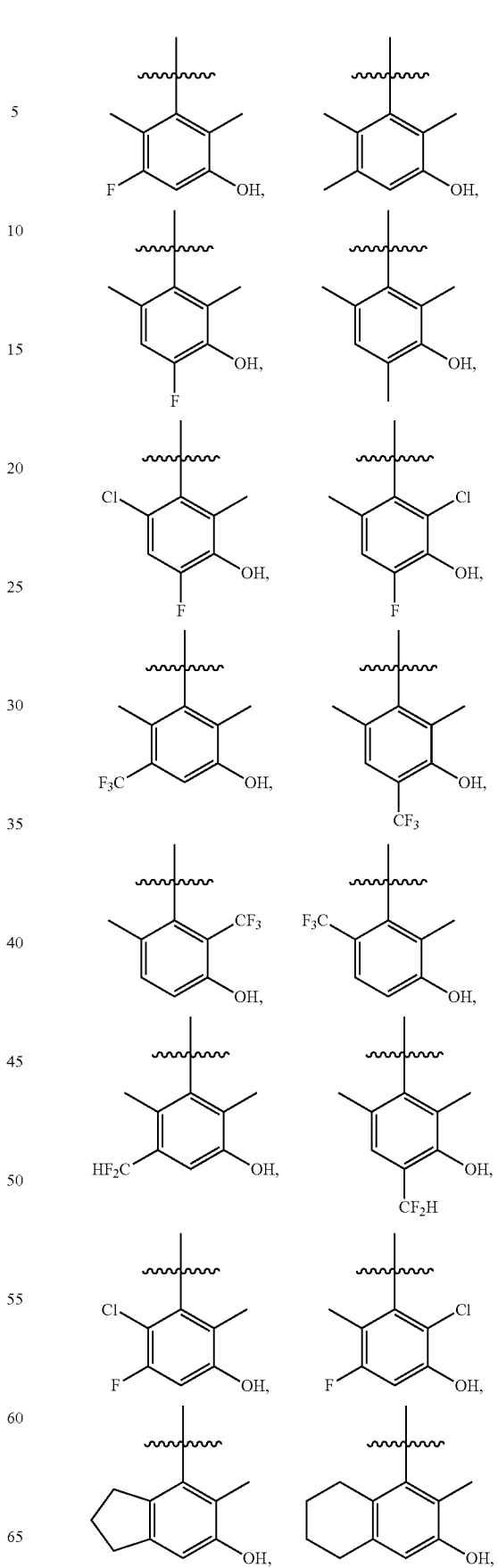

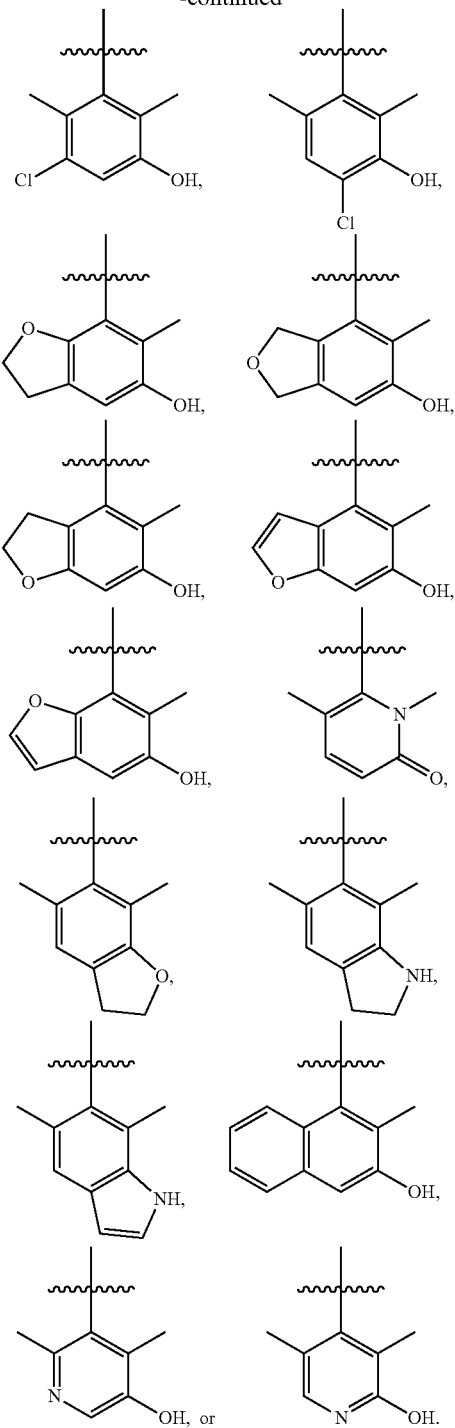

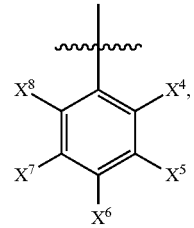

wherein $X^4$, $X^5$, $X^6$, $X^7$, and $X^8$ are each independently —H, —OH, —OR$^3$, halogen, —CN, (C1-C3) alkyl, (C1-C3) haloalkyl, (C2-C4) alkenyl, (C2-C4) alkynyl, (C3-C6) cycloalkyl, or (3-6 membered) heterocycloalkyl, and at least 4 of $X^4$, $X^3$, $X^6$, $X^7$, and $X^8$ are not simultaneously —H; or each of the pairs of $X^4/X^5$, $X^5/X^6$, $X^6/X^7$, and $X^7/X^8$, with the carbon atom to which they are each attached, may independently form (C4-C6) cycloalkylo, (4-6 membered) heterocycloalkylo, phenyl, or (5-6 membered) heteraryleno, wherein the (C4-C6) cycloalkylo, (4-6 membered) heterocycloalkylo, phenyl, or (5-6 membered) heteraryleno may be each independently and optionally substituted with 1, 2, 3, or 4 of the following groups: —H, —F, —Cl, —Br, —I, —OH, —OCH$_3$, —NH$_2$, —N(CH$_3$)$_2$, —CN, (C1-C3) alkyl, (C1-C3) haloalkyl, (C2-C4) alkenyl, (C2-C4) alkynyl, and (C3-C6) cycloalkyl: or $R^2$ is (6-10 membered) heterocycloalkyl or (6-10 membered) heteroaryl, wherein the (6-10 membered) heterocycloalkyl or (6-10 membered) heteroaryl may be each independently and optionally substituted with 1, 2, 3, or 4 of the following groups: —H, —F, —Cl, —Br, —I, —OH, —OCH$_3$, —CN, (C1-C3) alkyl, (C1-C3) haloalkyl, (C2-C4) alkenyl, (C2-C4) alkynyl, (C3-C6) cycloalkyl, and (3-6 membered) heterocycloalkyl.

In another preferred embodiment, in general formula (1), when at least one of $R^{a1}$, $R^{a2}$, $R^{a3}$, and $R^1$ is —CN: or when $R^{a3}$ and $R^1$, together with the carbon atom to which they are each attached, form (C4-C9) cycloalkenyl, (4-9 membered) heterocycloalkyl, or (5-10 membered) heteroaryl, wherein the (C4-C9) cycloalkenyl, (4-9 membered) heterocycloalkyl, or (5-10 membered) heteroaryl may be each independently and optionally substituted with 1, 2, 3, or 4 of the following groups: —H, halogen, —OH, —OR$^5$, —N(R$^5$)$_2$, —CN, (C1-C6) alkyl, (C1-C6) haloalkyl, (C2-C6) alkenyl, (C2-C6) alkynyl, and (C3-C8) cycloalkyl, $R^2$ is

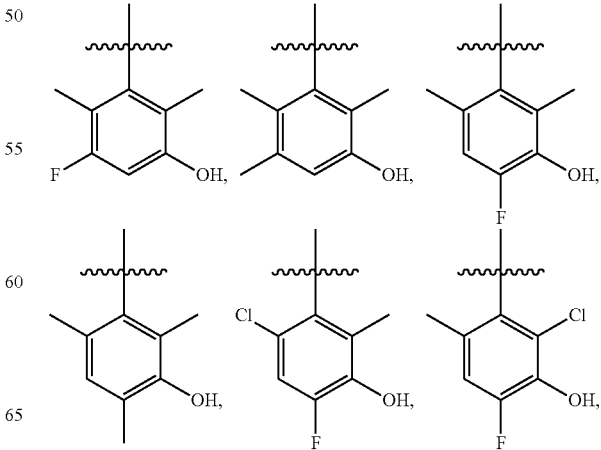

In another preferred embodiment, in general formula (1), when at least one of $R^{a1}$, $R^{a2}$, $R^{a3}$, and $R^1$ is —CN; or when $R^{a3}$ and $R^1$, together with the carbon atom to which they are each attached, form (C4-C9) cycloalkenyl, (4-9 membered) heterocycloalkyl, or (5-10 membered) heteroaryl, wherein the (C4-C9) cycloalkenyl, (4-9 membered) heterocycloalkyl, or (5-10 membered) heteroaryl may be each independently and optionally substituted with 1, 2, 3, or 4 of the following groups: —H, halogen, —OH, —OR$^5$, —N(R$^5$)$_2$, —CN, (C1-C6) alkyl, (C1-C6) haloalkyl, (C2-C6) alkenyl, (C2-C6) alkynyl, and (C3-C8) cycloalkyl, $R^2$ is

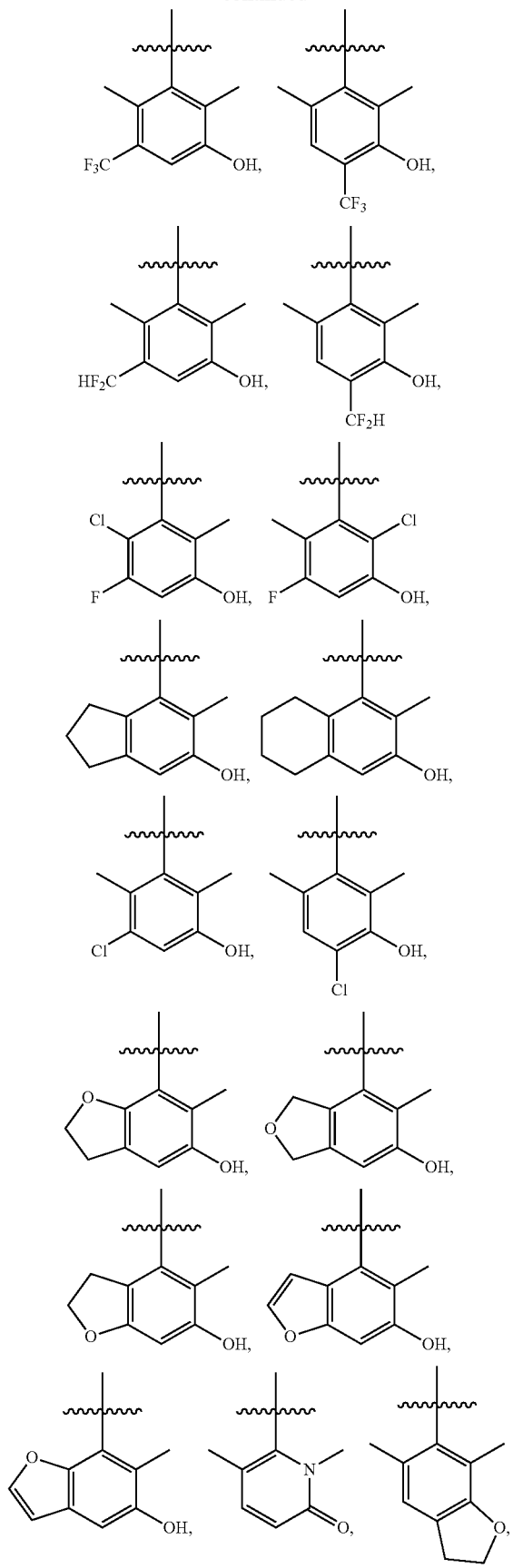

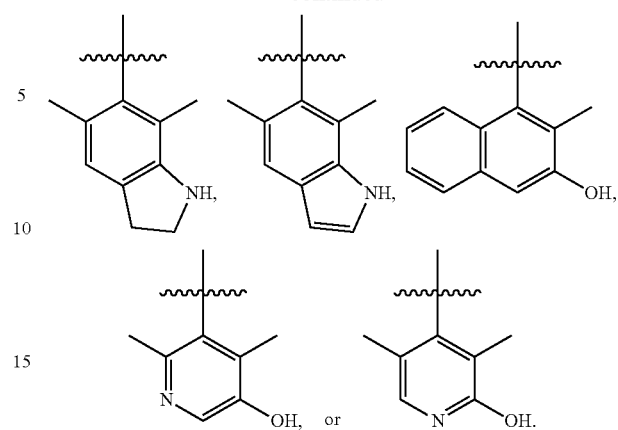

In another preferred embodiment, in general formula (1), each $R^3$ is independently —H, (C1-C5) alkyl, (C1-C5) haloalkyl, (C2-C4) alkenyl, (C2-C4) alkynyl, (C3-C6) cycloalkyl, (3-6 membered) heterocycloalkyl, phenyl, (5-6 membered) heteroaryl, or —SO$_2$R$^{3a}$, wherein the (C1-C5) alkyl, (C1-C5) haloalkyl, (C2-C4) alkenyl, (C2-C4) alkynyl, (C3-C6) cycloalkyl, (3-6 membered) heterocycloalkyl, phenyl, or (5-6 membered) heteroaryl may be each independently and optionally substituted with 1, 2, 3, or 4 of the following groups: —H, —OH, (C1-C3) alkyl, (C1-C3) alkoxy, —F, —Cl, —Br, or —I; or two $R^3$ on the same nitrogen atom, together with the nitrogen atom to which they are attached, may form (3-6 membered) heterocycloalkyl, wherein the (3-6 membered) heterocycloalkyl may be each independently and optionally substituted with 1, 2, 3, or 4 of the following groups: —H, —F, —Cl, —Br, —I, —OH, —OCH$_3$, —NH$_2$, —NH(CH$_3$), —N(CH$_3$)$_2$, —CN, (C1-C3) alkyl, (C1-C3) haloalkyl, (C2-C4) alkenyl, (C2-C4) alkynyl, and (C3-C6) cycloalkyl.

In another preferred embodiment, in general formula (1), each $R^3$ is independently —H,

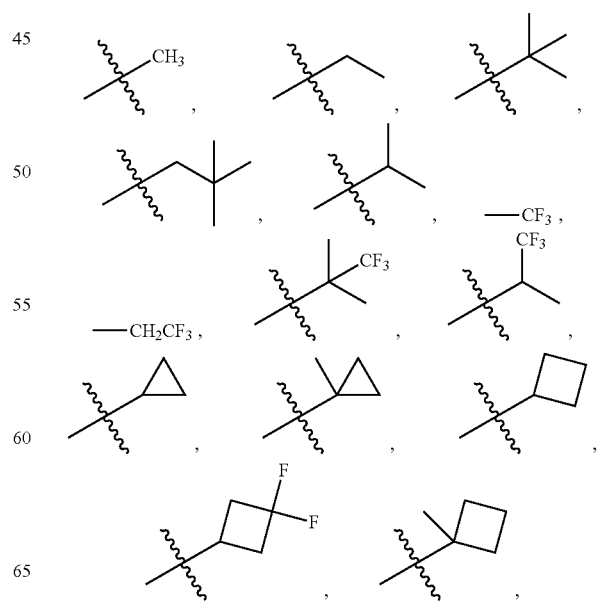

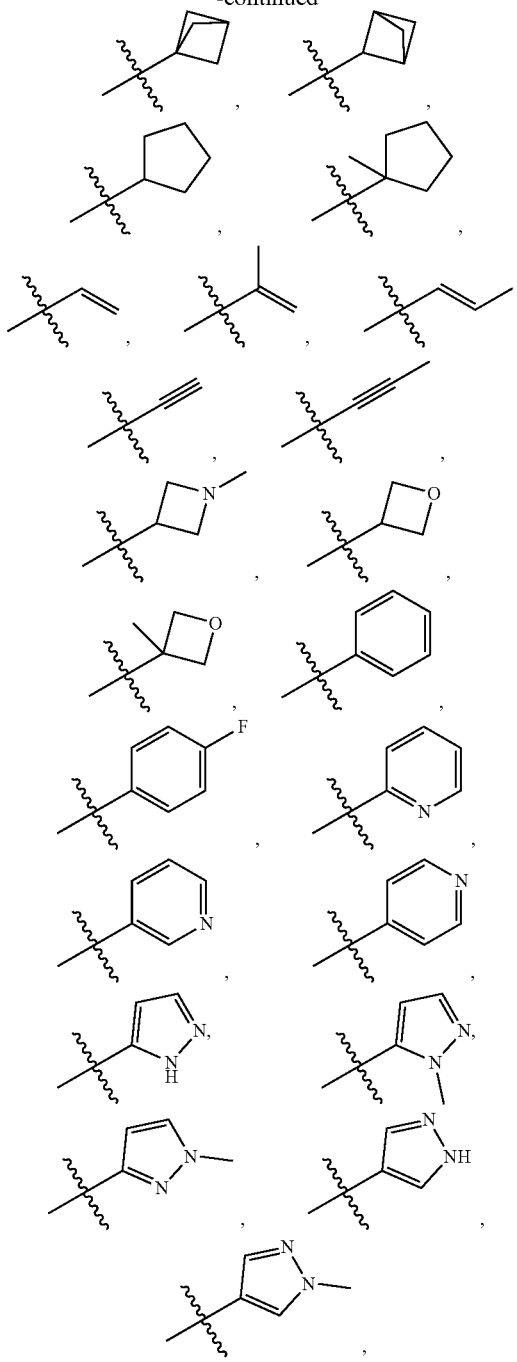

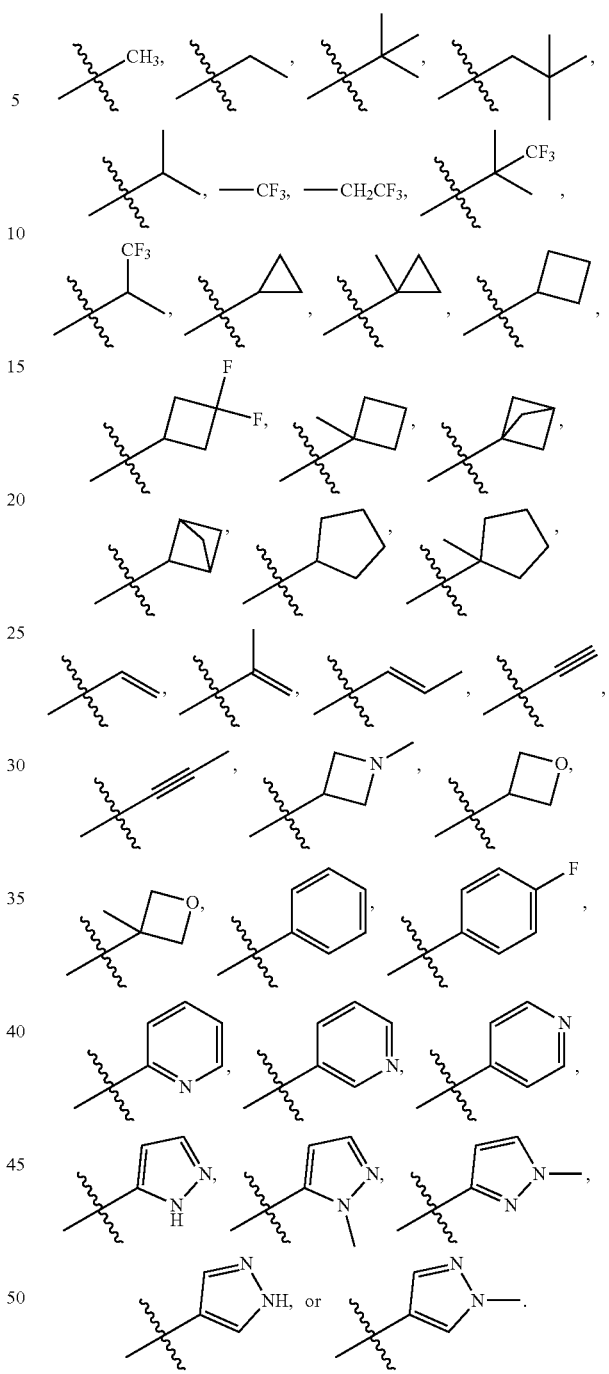

—SO$_2$CH$_3$, —SO$_2$CH$_2$CH$_3$, or —SO$_2$CH(CH$_3$)$_2$.

In another preferred embodiment, in general formula (1), each R$^{3a}$ is independently (C1-C5) alkyl, (C1-C5) haloalkyl, (C3-C6) cycloalkyl, (3-6 membered) heterocycloalkyl, phenyl, or (5-6 membered) heteroaryl, wherein the (C1-C5) alkyl, (C1-C5) haloalkyl, (C3-C6) cycloalkyl, (3-6 membered) heterocycloalkyl, phenyl, or (5-6 membered) heteroaryl may be each independently and optionally substituted with 1, 2, 3, or 4 of the following groups: —H, —OH, (C1-C3) alkyl, (C1-C3) alkoxy, —F, —Cl, —Br, or —I.

In another preferred embodiment, in general formula (1), each R$^{3a}$ is independently In another preferred embodiment, in general formula (1), each R$^{3b}$ is independently (C1-C5) alkyl, (C1-C5) haloalkyl, (C2-C4) alkenyl, (C2-C4) alkynyl, (C3-C6) cycloalkyl, (3-6 membered) heterocycloalkyl, phenyl, (5-6 membered) heteroaryl, —N(R$^3$)$_2$, —OR$^3$, —C(O)N(R$^4$)$_2$, —SO$_2$N(R$^4$)$_2$, or —SO$_2$R$^{3a}$, wherein the (C1-C5) alkyl, (C1-C5) haloalkyl, (C2-C4) alkenyl, (C2-C4) alkynyl, (C3-C6) cycloalkyl, phenyl, (5-6 membered) heteroaryl, or (3-6 membered) heterocycloalkyl may be each independently and optionally substituted with 1, 2, 3, or 4 of the following groups: —H, —F, —Cl, —Br, —I, —OH, —OCH$_3$, —NH$_2$, —NH(CH$_3$), —N(CH$_3$)$_2$, —CN, (C1-C3) alkyl, (C1-C3) haloalkyl, (C2-

C4) alkenyl, (C2-C4) alkynyl, (C3-C6) cycloalkyl, (3-6 membered) heterocycloalkyl, phenyl, and (5-6 membered) heteroaryl.
In another preferred embodiment, in general formula (1), each $R^{3b}$ is independently —H, —OH, —OCH$_3$, —NH$_2$, —NH(CH$_3$), —N(CH$_3$)$_2$, —C(O)N(CH$_3$)$_2$, —C(O)NH(CH$_3$), —C(O)NH$_2$, —SO$_2$N(CH$_3$)$_2$, —SO$_2$NH(CH$_3$), —SO$_2$NH$_2$, —SO$_2$CH$_3$, —SO$_2$CH$_2$CH$_3$, —SO$_2$CH(CH$_3$)$_2$,
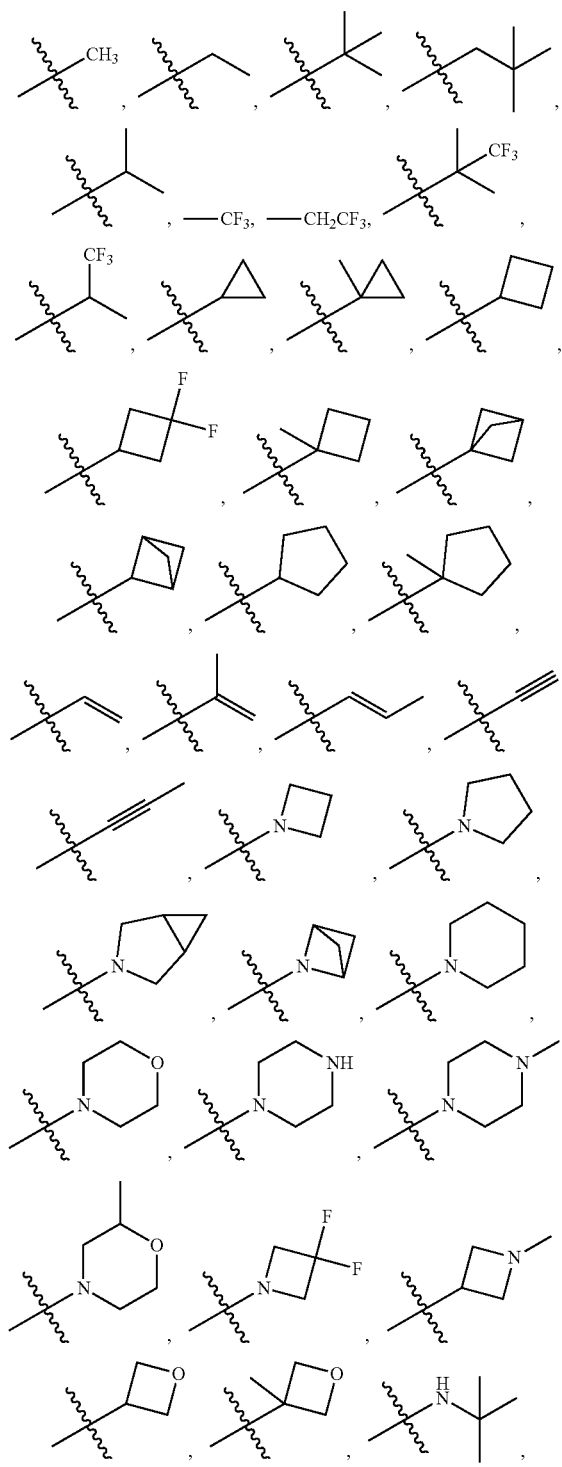
-continued
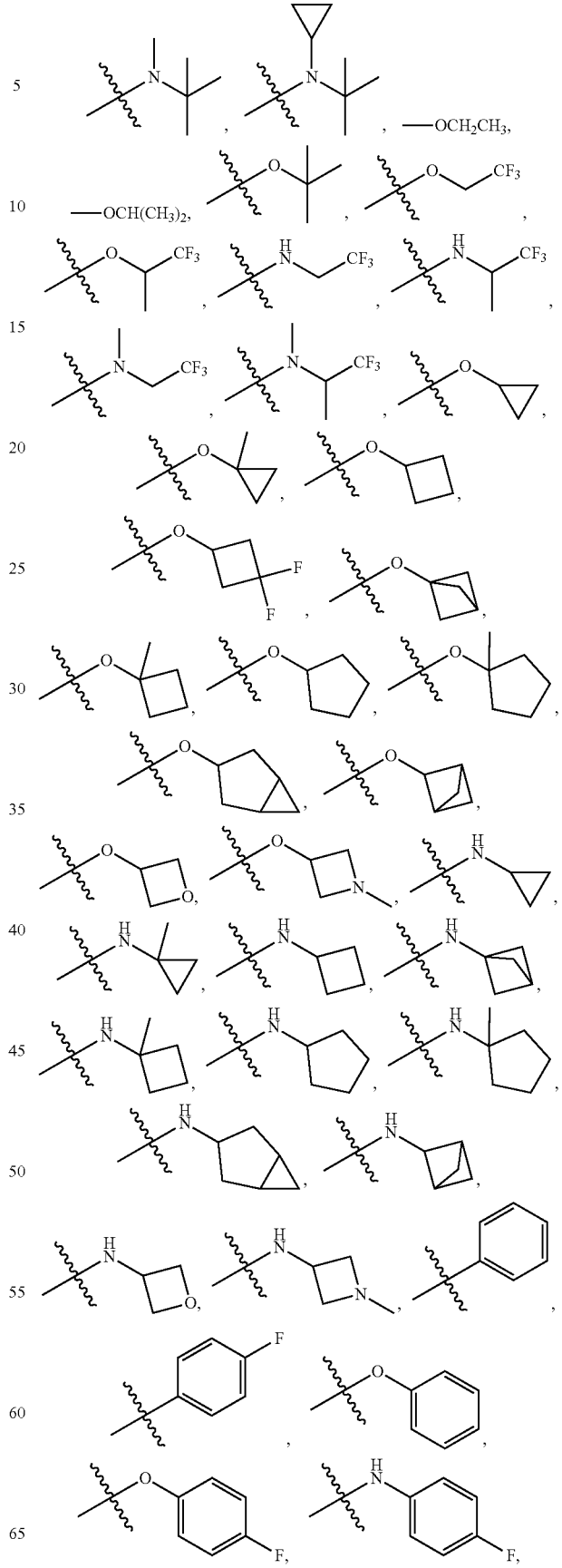

-continued

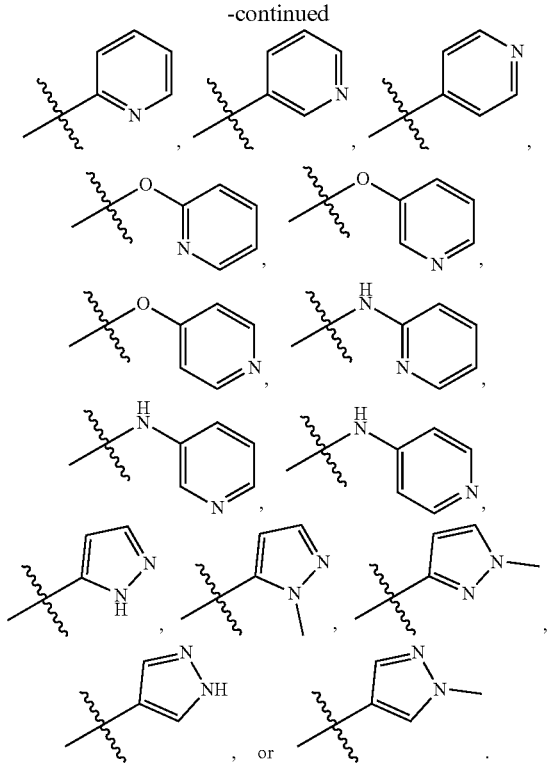

In another preferred embodiment, in general formula (1), Q is (C1-C3) alkylene, (C2-C4) alkenylene, (C2-C4) alkynylene, (C3-C6) cycloalkylene, (3-6 membered) heterocycloalkylene, phenylene, or (5-6 membered) heteroarylene, wherein the (C1-C3) alkylene, (C2-C4) alkenylene, (C2-C4) alkynylene, (C3-C6) cycloalkylene, phenylene, (5-6 membered) heteroarylene, or (3-6 membered) heterocycloalkylene may be each independently and optionally substituted with 1, 2, 3, or 4 of the following groups: —H, —F, —Cl, —Br, —I, —OH, —OCH$_3$, —NH$_2$, —NH(CH$_3$), —N(CH$_3$)$_2$, —CN, (C1-C3) alkyl, (C1-C3) haloalkyl, (C2-C4) alkenyl, (C2-C4) alkynyl, (C3-C6) cycloalkyl, (3-6 membered) heterocycloalkyl, phenyl, and (5-6 membered) heteroaryl.

In another preferred embodiment, in general formula (1), each Q is independently

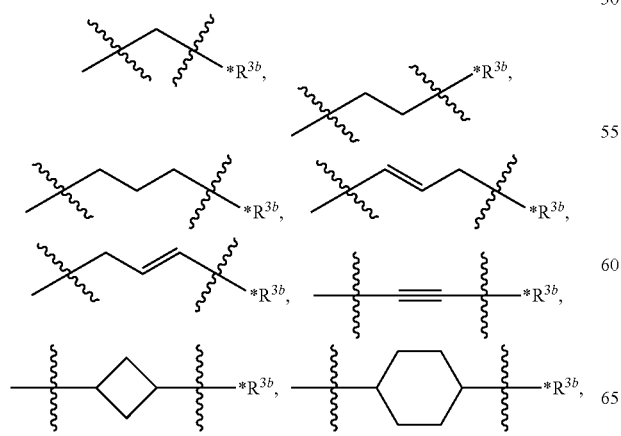

-continued

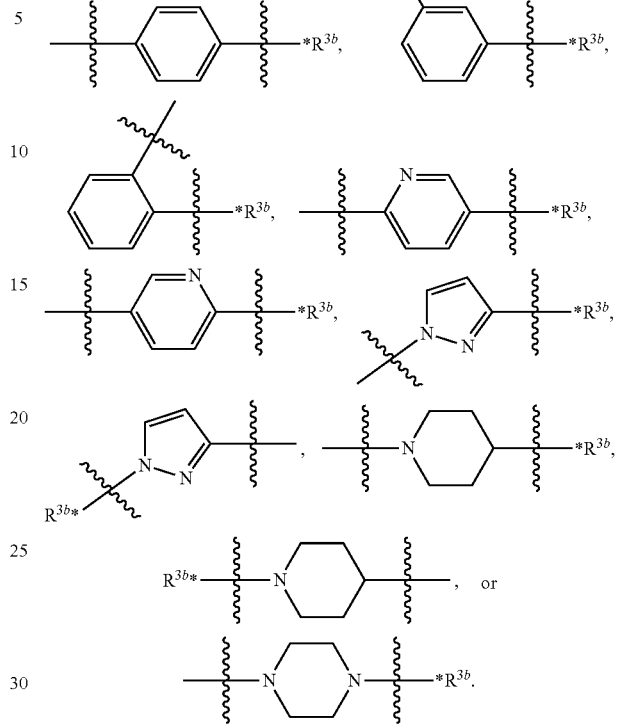

In another preferred embodiment, in general formula (1), each $R^4$ is independently —H, (C1-C5) alkyl, (C1-C5) haloalkyl, (C1-C5) alkoxy, (C3-C6) cycloalkyl, (3-6 membered) heterocycloalkyl, phenyl, or (5-6 membered) heteroaryl, wherein the (C1-C5) alkyl, (C1-C5) haloalkyl, (C1-C5) alkoxy, (C3-C6) cycloalkyl, (3-6 membered) heterocycloalkyl, phenyl, or (5-6 membered) heteroaryl may be each independently and optionally substituted with 1, 2, 3, or 4 of the following groups: —H, —OH, (C1-C3) alkyl, (C1-C3) alkoxy, —F, —Cl, —Br, or —I; or two $R^4$ on the same nitrogen atom, together with the nitrogen atom to which they are attached, may form (3-6 membered) heterocycloalkyl, wherein the (3-6 membered) heterocycloalkyl may be each independently and optionally substituted with 1, 2, 3, or 4 of the following groups: —H, —F, —Cl, —Br, —I, —OH, —OCH$_3$, —NH$_2$, —NH(CH$_3$), —N(CH$_3$)$_2$, —CN, (C1-C3) alkyl, (C1-C3) haloalkyl, (C2-C4) alkenyl, (C2-C4) alkynyl, and (C3-C6) cycloalkyl.

In another preferred embodiment, in general formula (1), each $R^4$ is independently —H, —OCH$_3$, —OCH$_2$CH$_3$, —OCH(CH$_3$)$_2$,

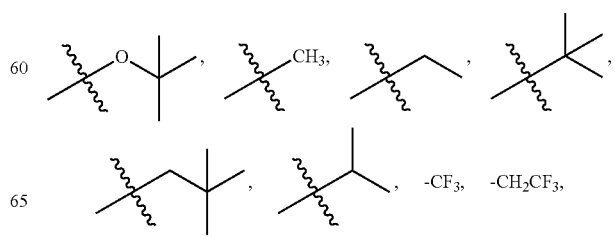

-continued

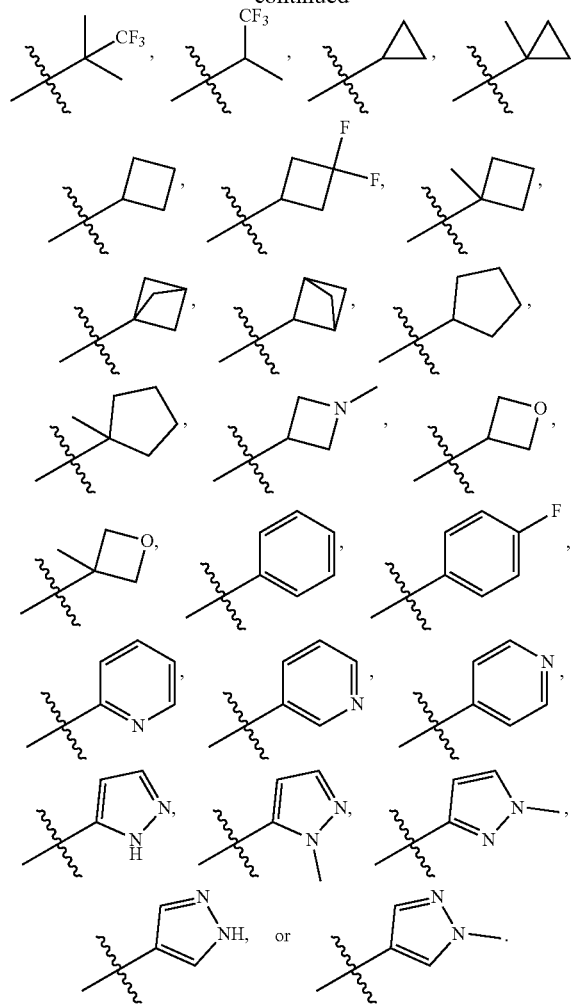

In another preferred embodiment, in general formula (1), each $R^5$ is independently —H, (C1-C5) alkyl, (C1-C5) haloalkyl, (C2-C4) alkenyl, (C2-C4) alkynyl, (C3-C6) cycloalkyl, (3-6 membered) heterocycloalkyl, phenyl, (5-6 membered) heteroaryl, or —SO$_2$R$^{3a}$, wherein the (C1-C5) alkyl, (C1-C5) haloalkyl, (C2-C4) alkenyl, (C2-C4) alkynyl, (C3-C6) cycloalkyl, phenyl, (5-6 membered) heteroaryl, or (3-6 membered) heterocycloalkyl may be each independently and optionally substituted with 1, 2, 3, or 4 of the following groups: —H, —OH, (C1-C3) alkyl, (C1-C3) alkoxy, —F, —Cl, —Br, or —I; or two $R^5$ on the same nitrogen atom, together with the nitrogen atom to which they are attached, may form (3-6 membered) heterocycloalkyl, wherein the (3-6 membered) heterocycloalkyl may be each independently and optionally substituted with 1, 2, 3, or 4 of the following groups: —H, —F, —Cl, —Br, —I, —OH, —CN, (C1-C3) alkyl, (C1-C3) alkoxy, (C1-C3) haloalkyl, (C2-C4) alkenyl, (C2-C4) alkynyl, and (C3-C6) cycloalkyl.

In another preferred embodiment, in general formula (1), each $R^5$ is independently —H,

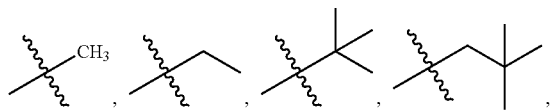

-continued

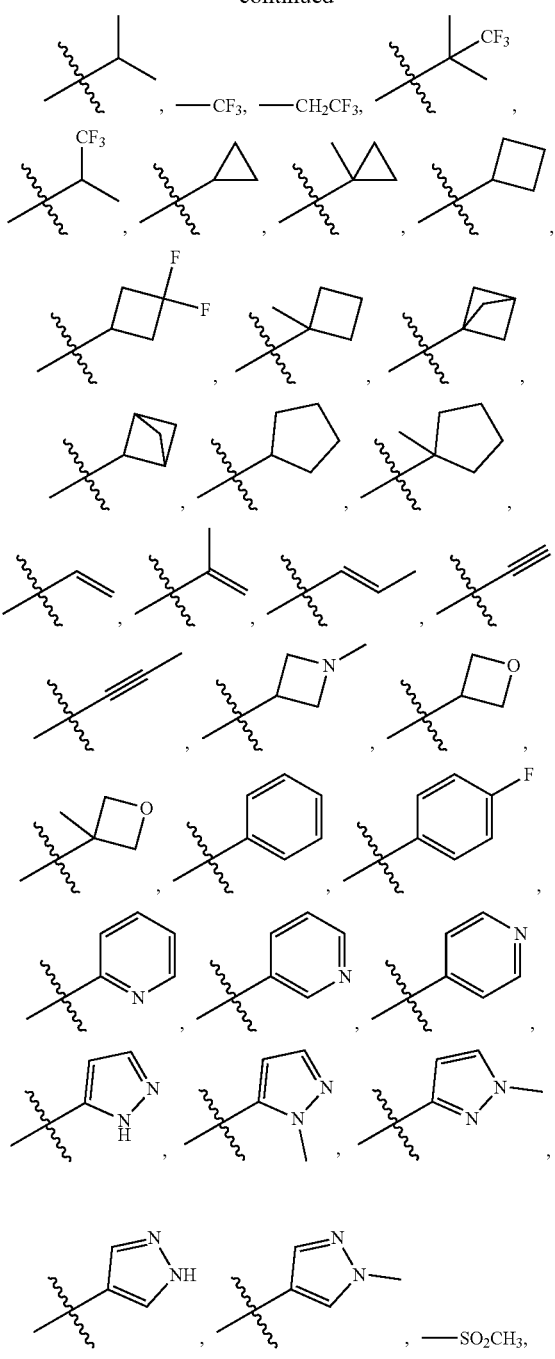

—SO$_2$CH$_2$CH$_3$, or —SO$_2$CH(CH$_3$)$_2$.

In another specific embodiment of the present invention, the compound of general formula (1) has one of the following structures:

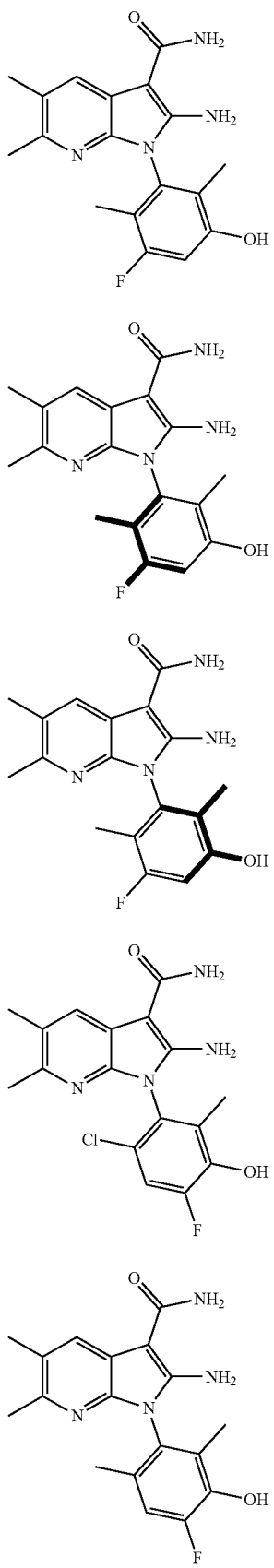
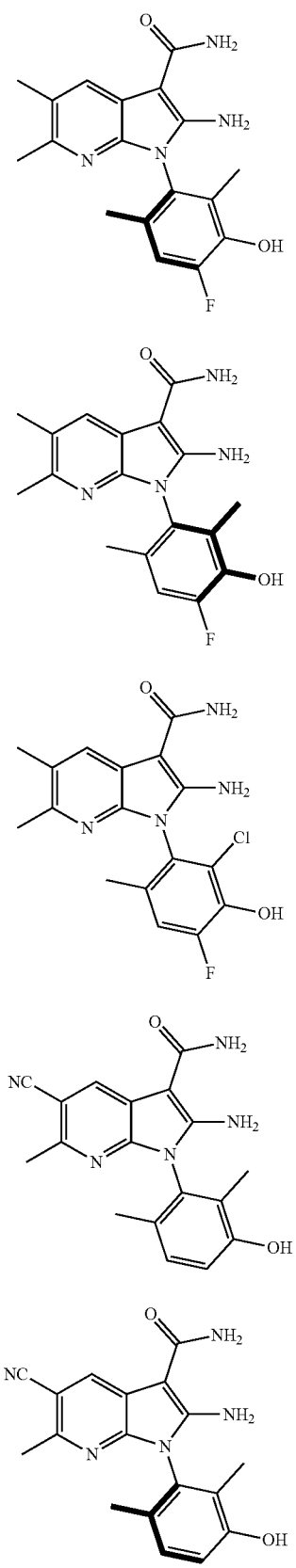

11
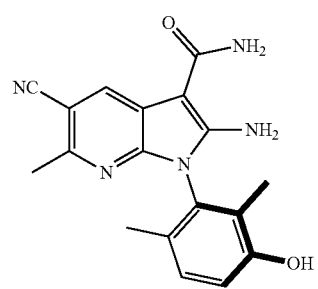
12
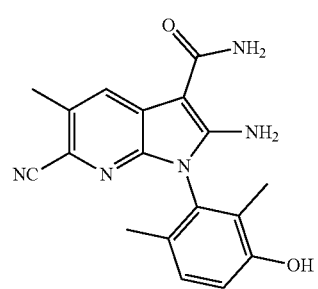
13
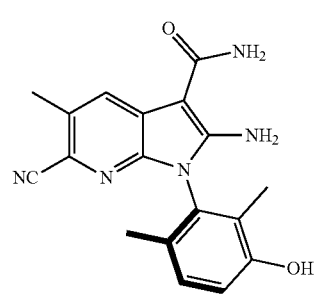
14
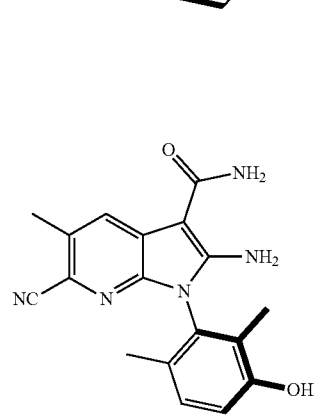
15
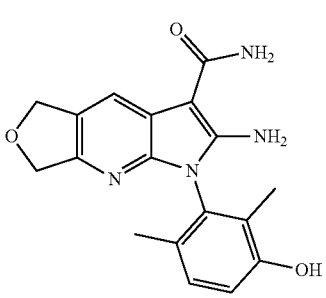
16
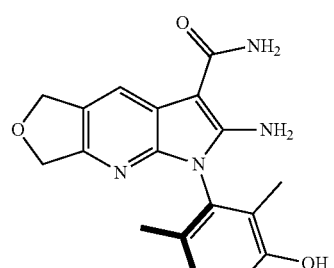
17
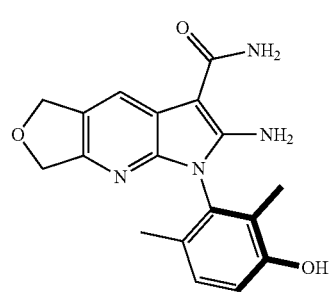
18
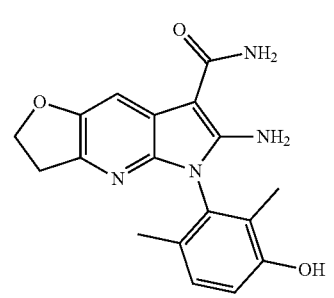
19
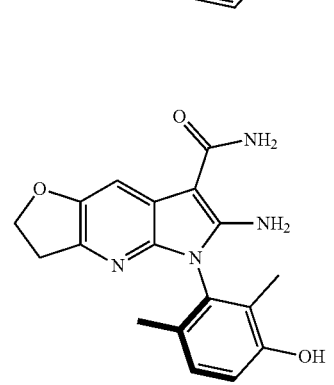
20
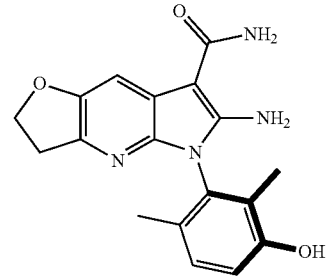

-continued
21
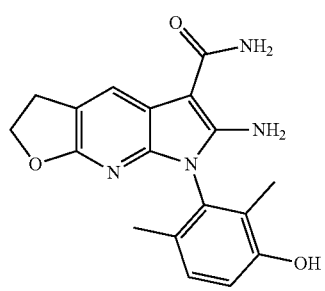
22
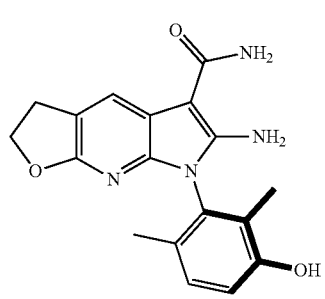
23
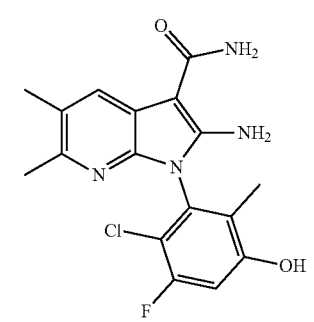
24
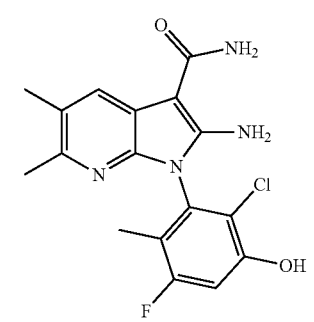
25
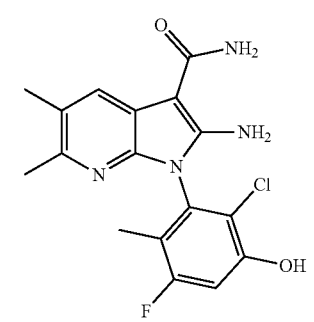
-continued
26
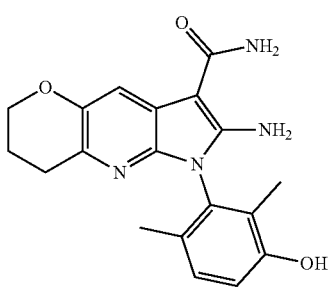
27
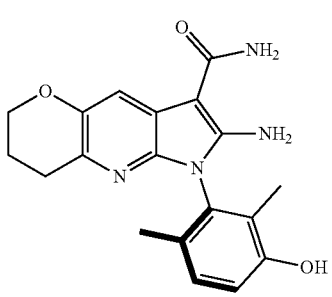
28
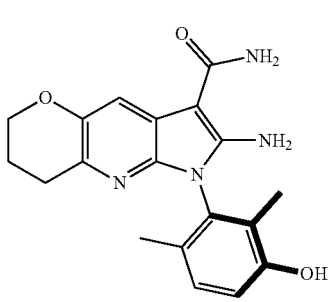
29
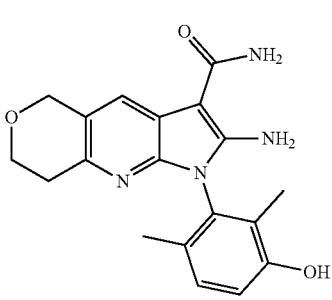
30
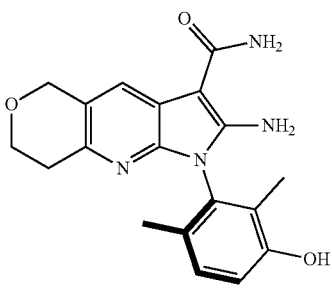

31 32
-continued -continued
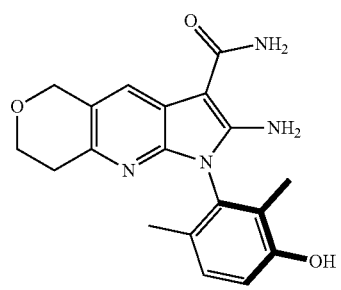
31
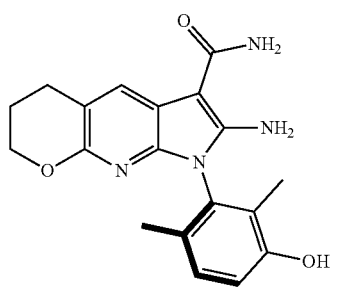
36
32 37
33 38
34 39
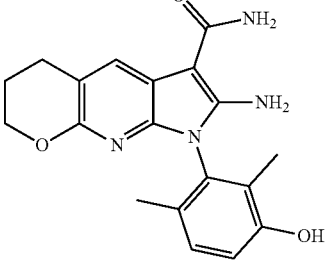
35
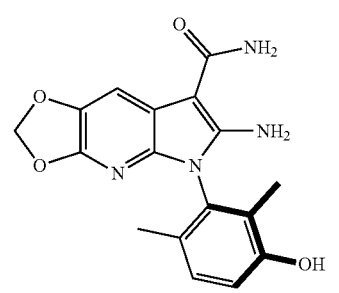
40

-continued
41
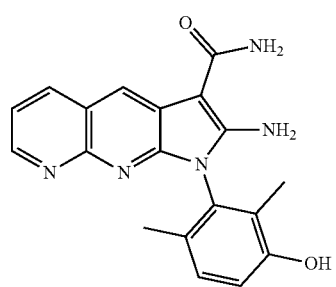
42
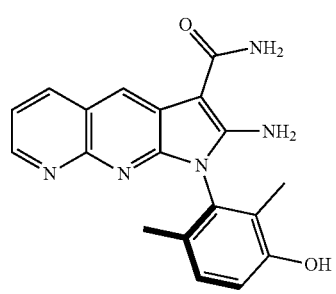
43
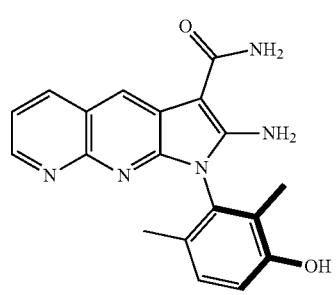
44
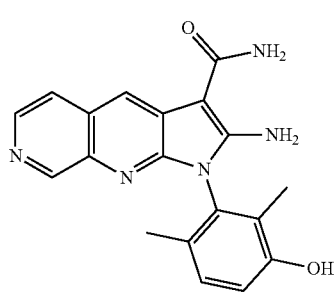
45
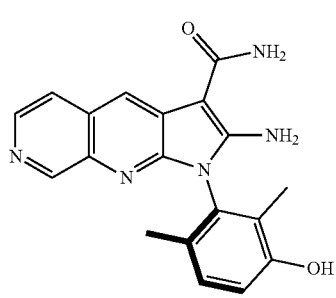
-continued
46
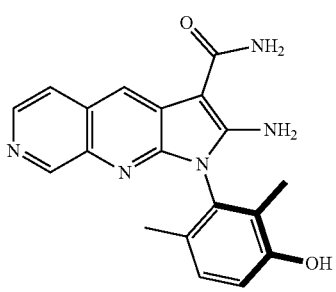
47
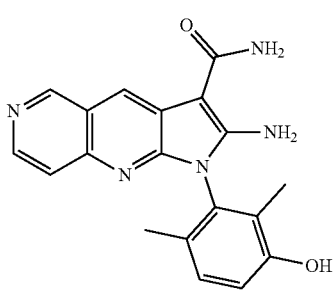
48
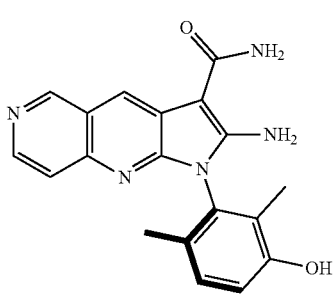
49
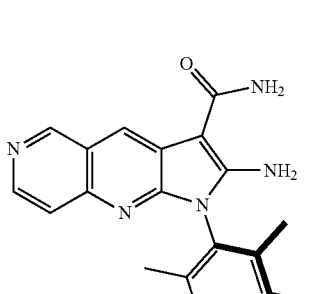
50
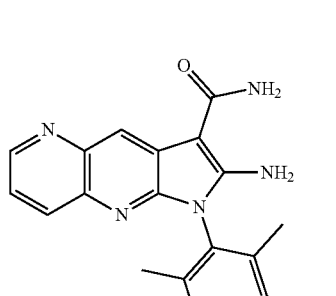

51
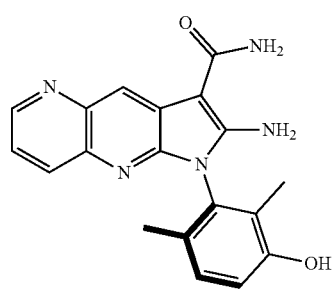
52
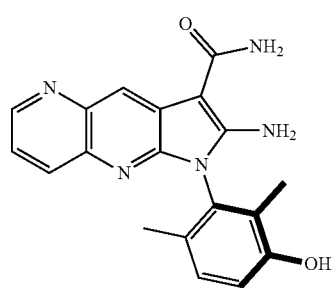
53
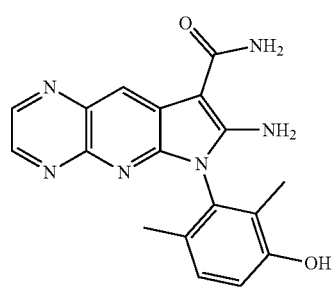
54
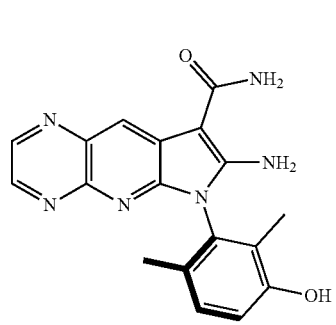
55
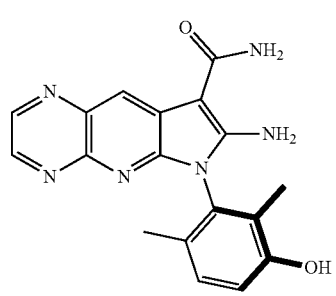
56
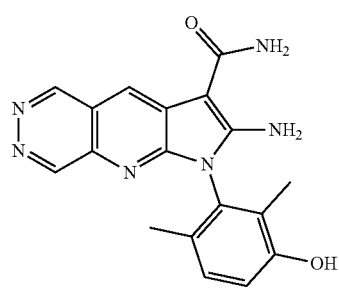
57
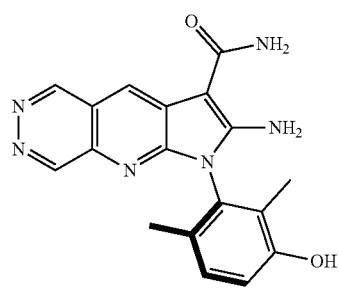
58
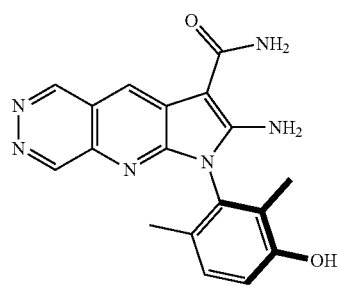
59
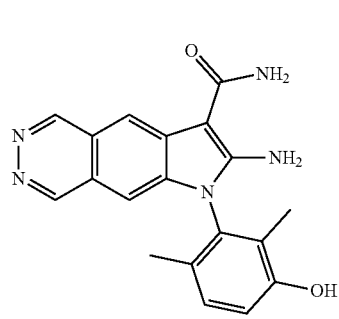
60
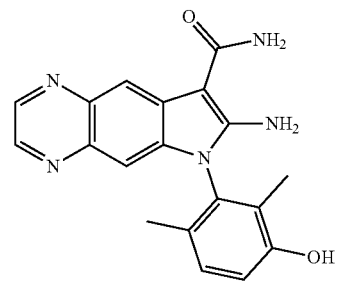

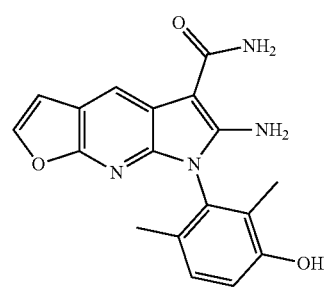
61
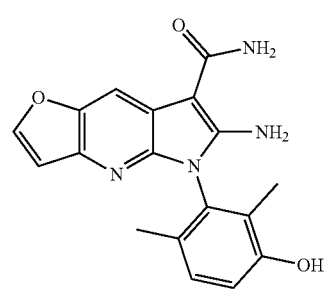
62
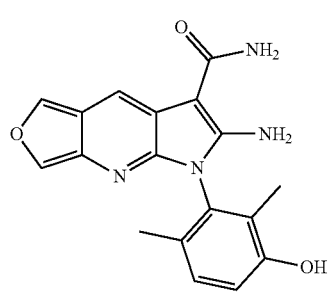
63
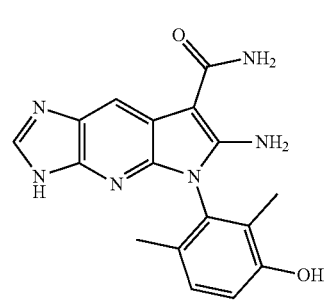
64
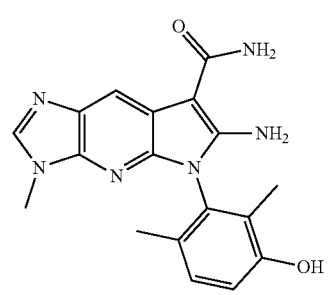
65
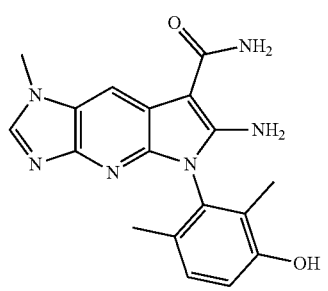
66
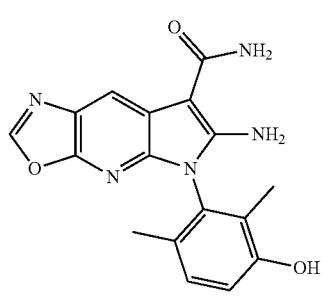
67
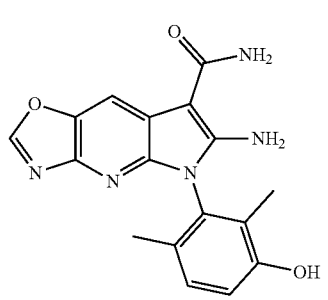
68
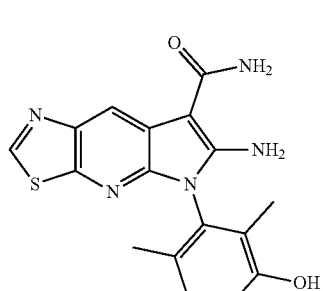
69
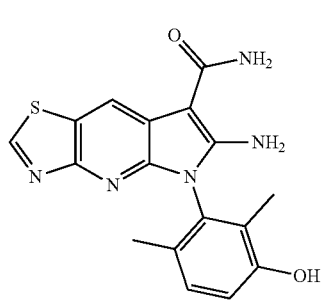
70

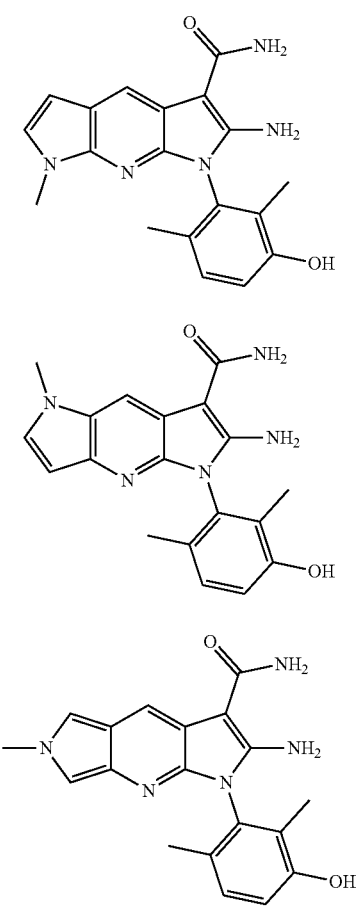
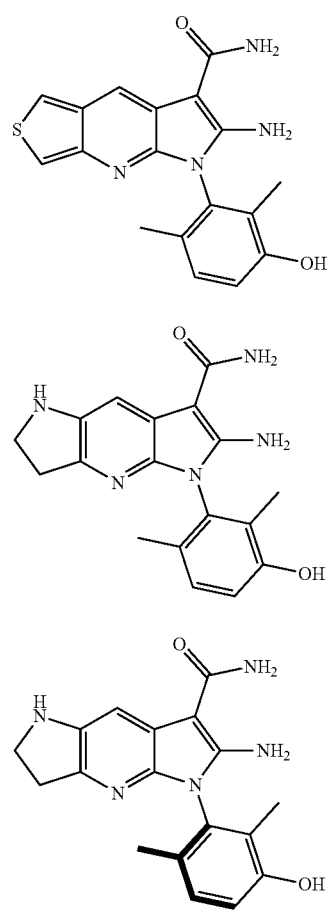

81
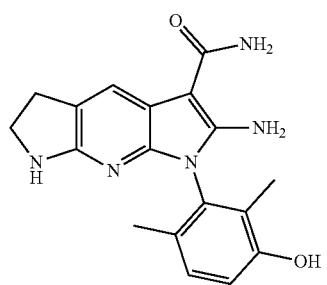
82
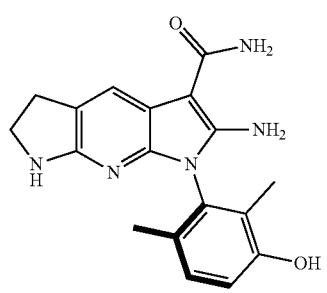
83
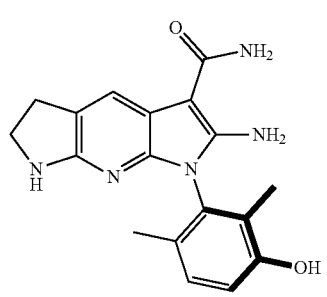
84
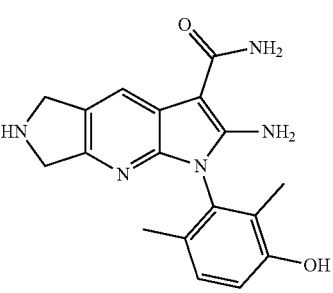
85
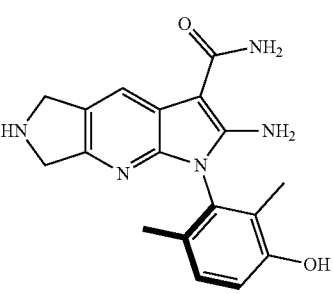
86
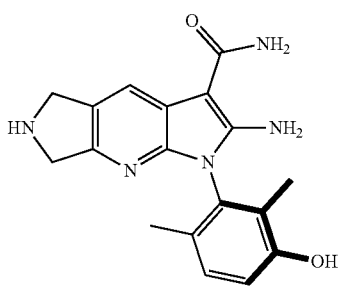
87
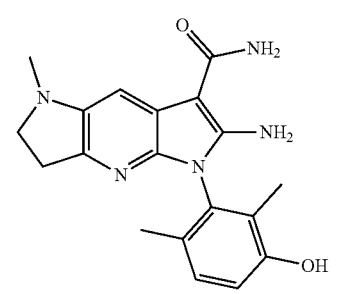
88
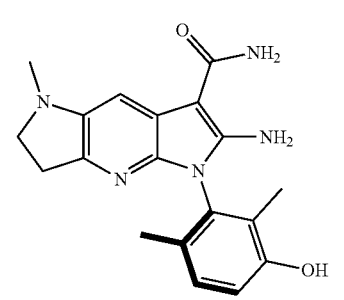
89
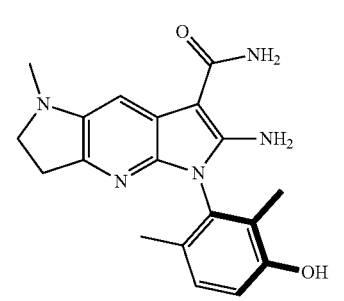
90
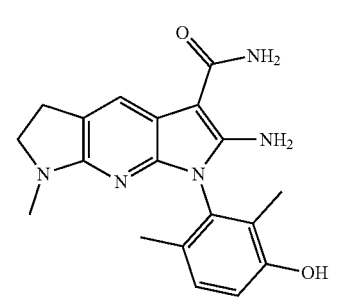

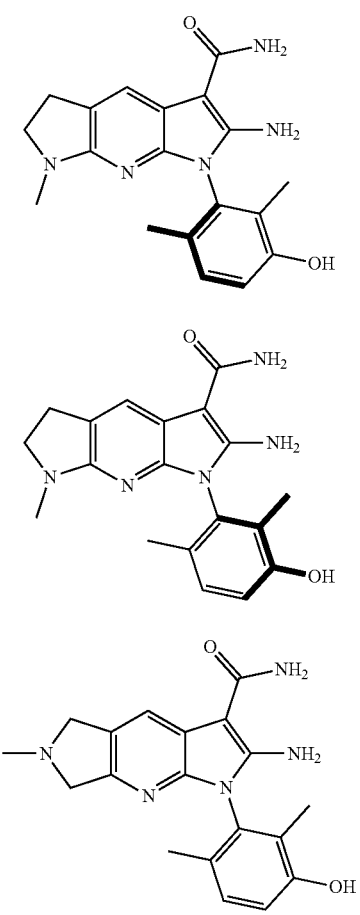
91
92
93
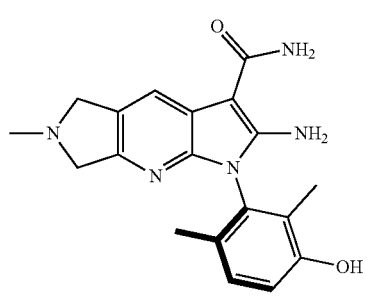
94
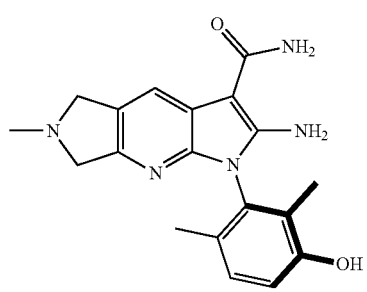
95
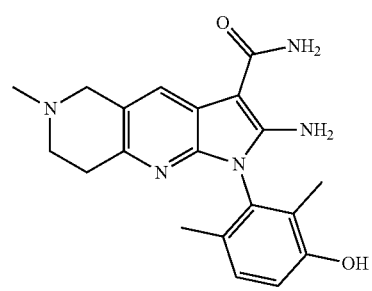
96
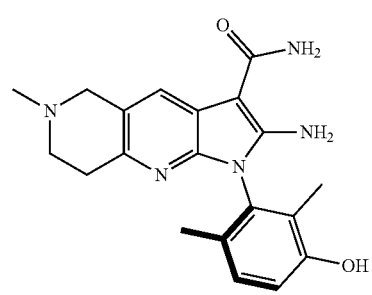
97
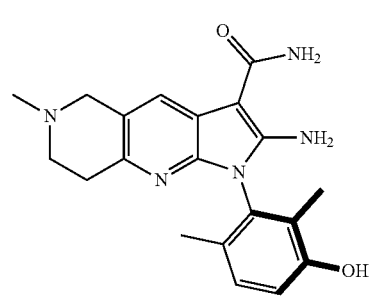
98
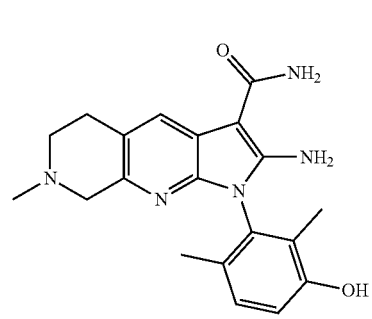
99
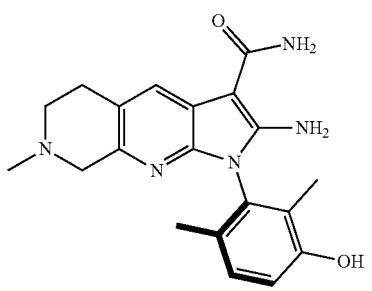
100

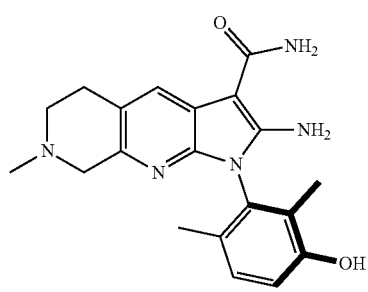
101
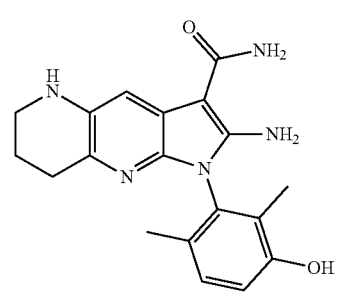
102
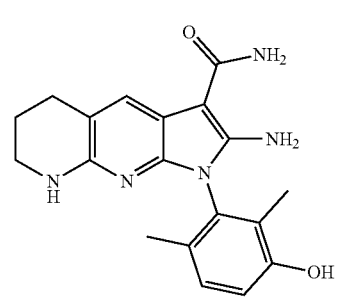
103
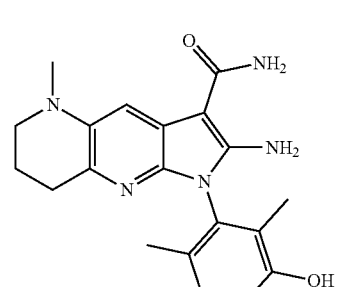
104
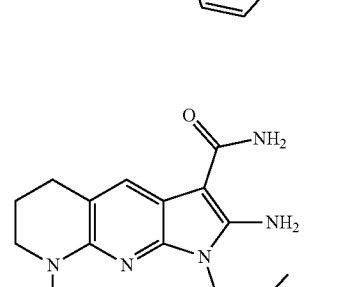
105
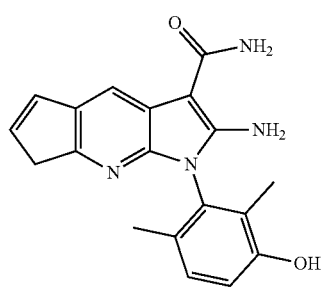
106
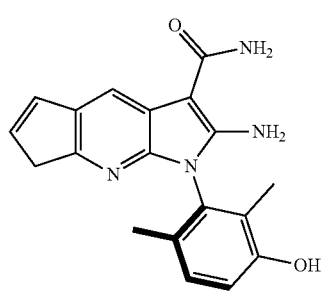
107
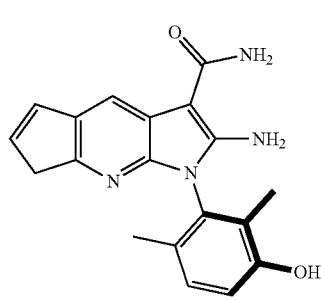
108
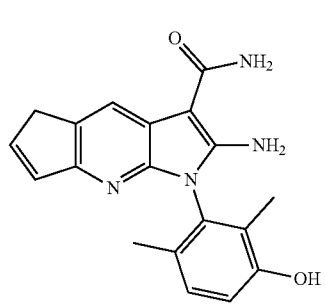
109
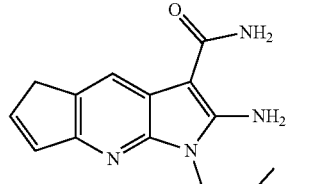
110

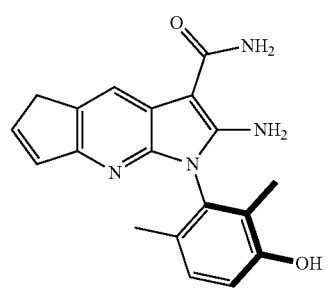
111
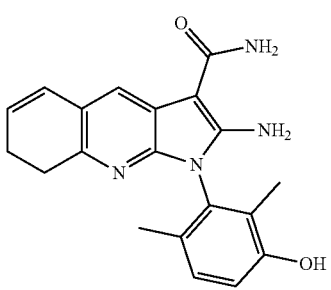
112
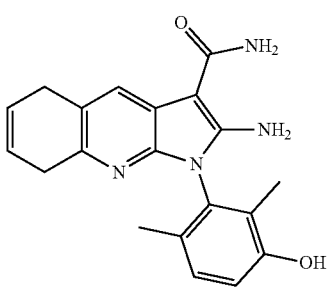
113
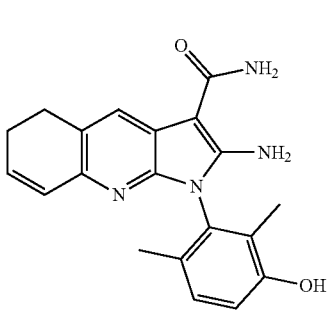
114
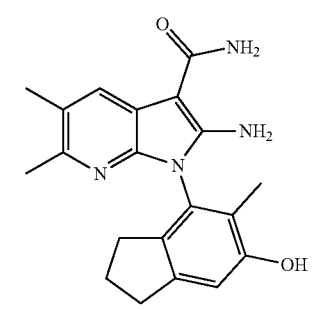
115
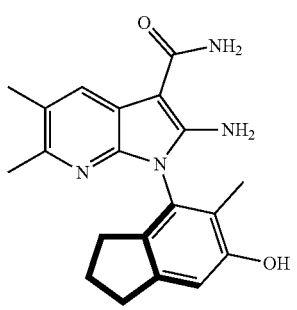
116
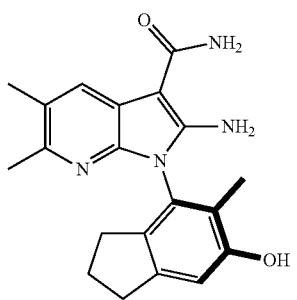
117
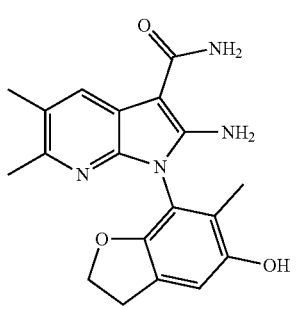
118
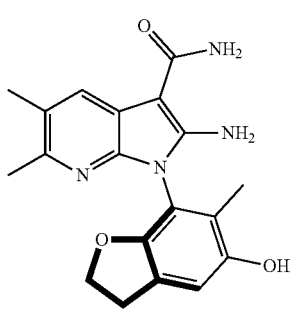
119
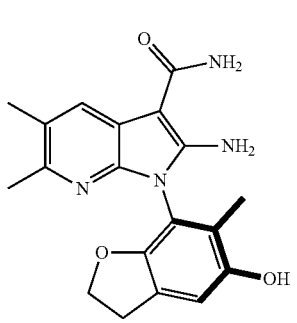
120

49
-continued
121
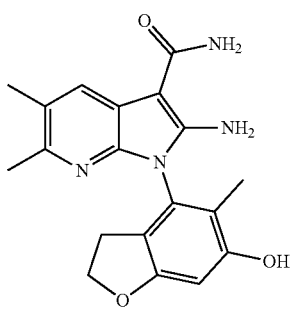
122
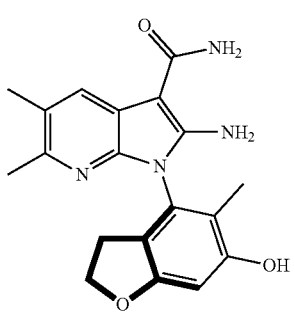
123
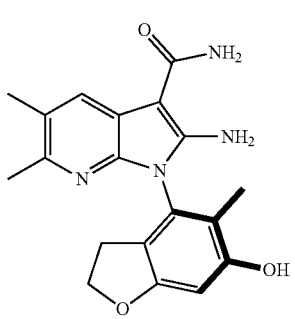
124
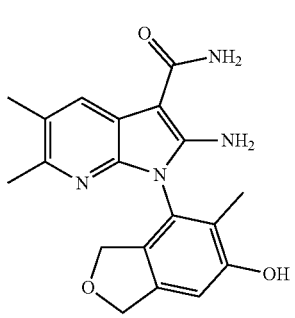
125
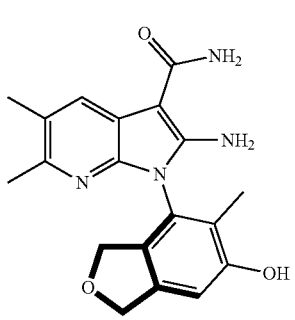
50
-continued
126
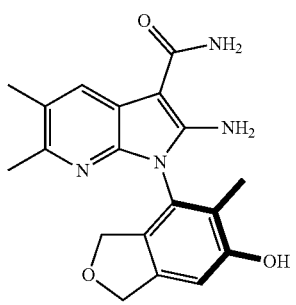
127
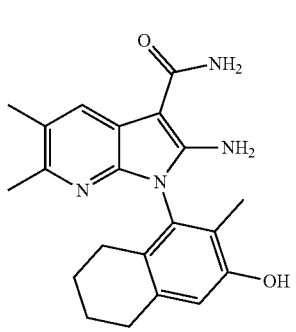
128
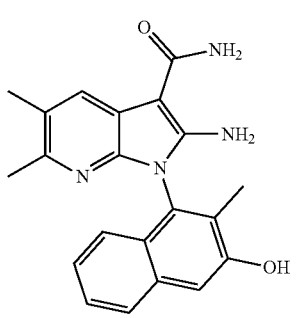
129
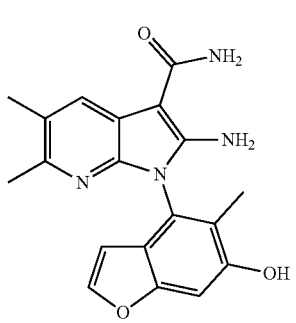
130
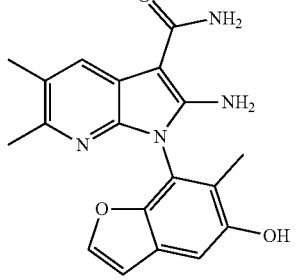

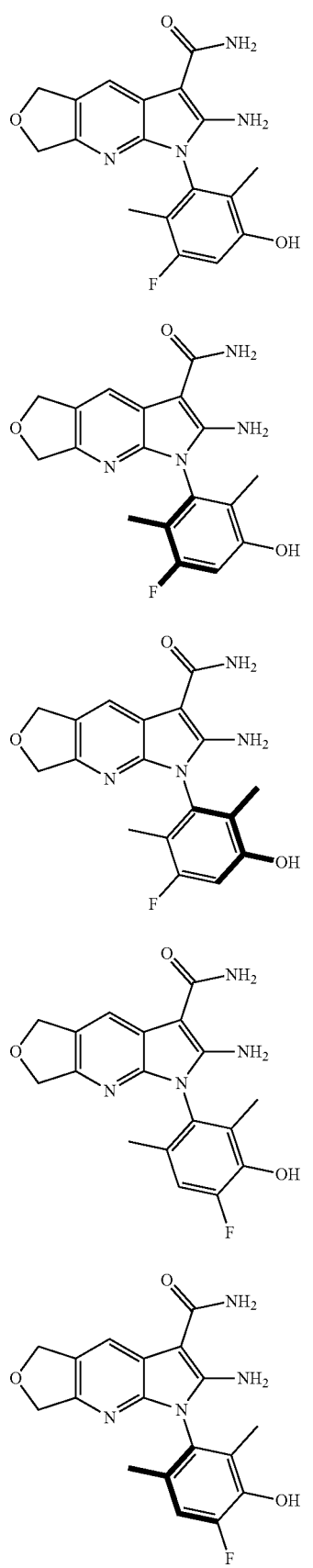
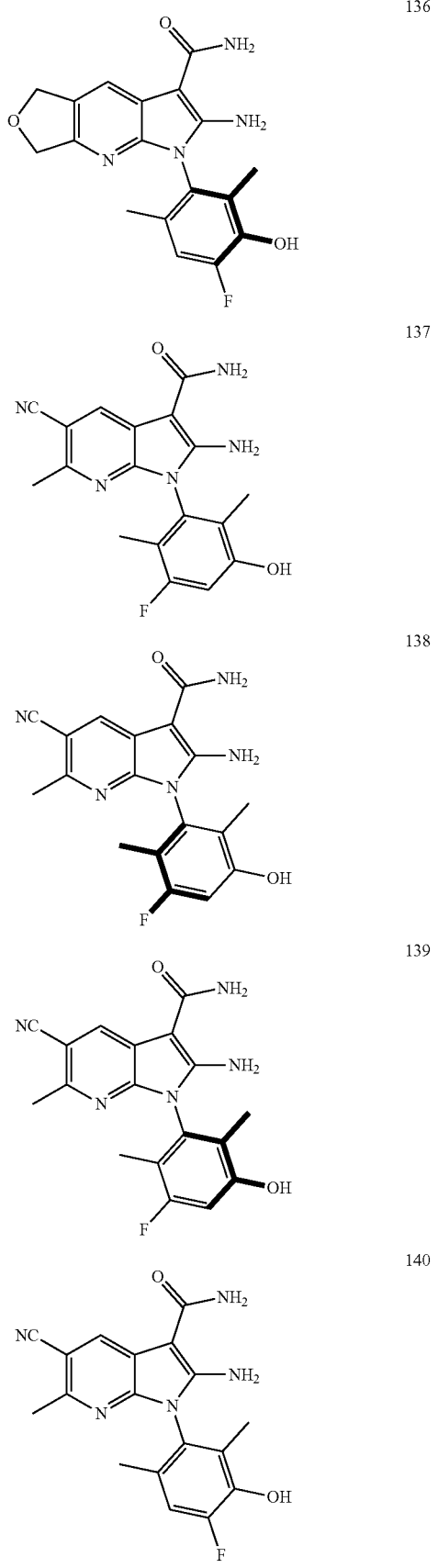

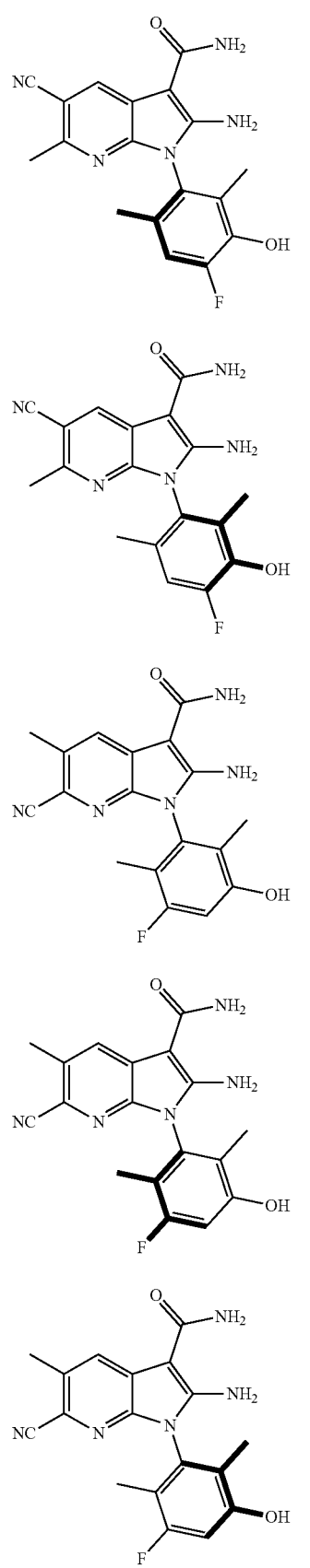
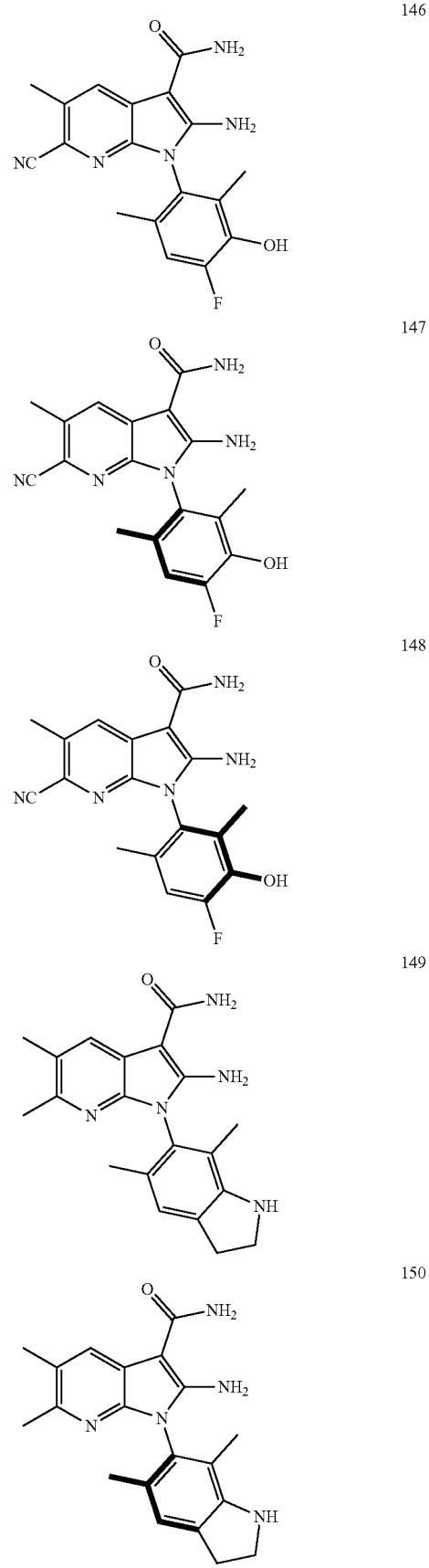

151 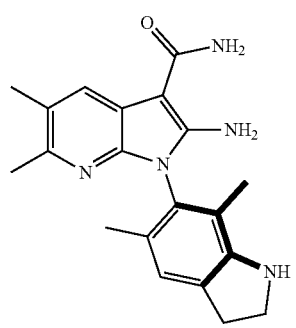
152 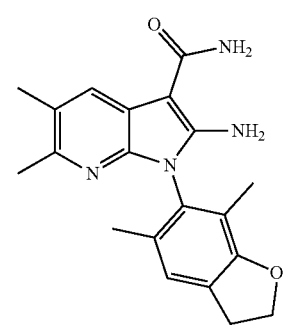
153 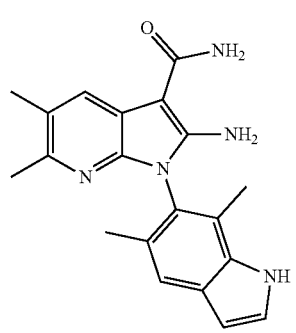
154 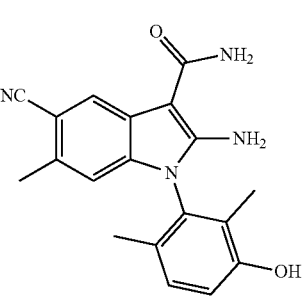
155 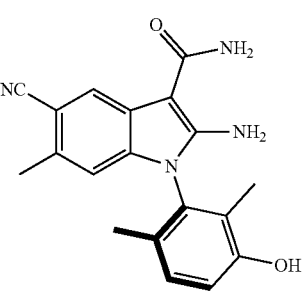
156 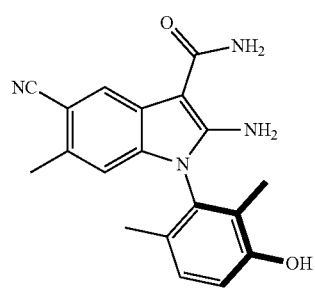
157 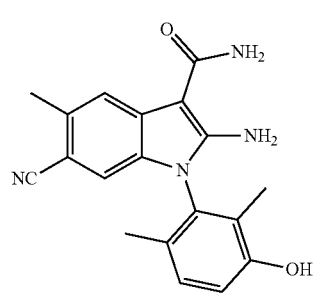
158 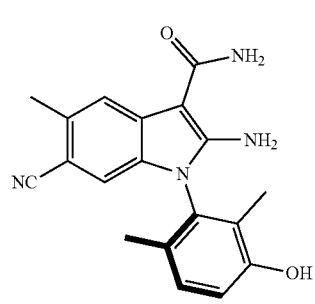
159 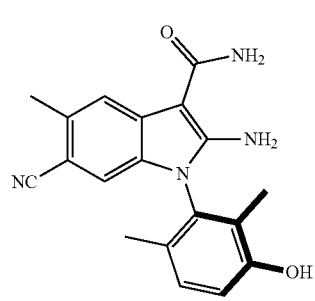
160 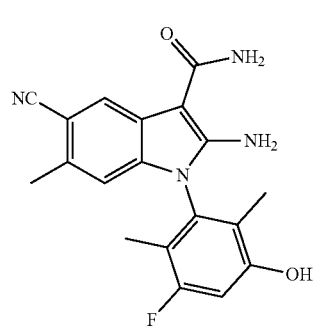

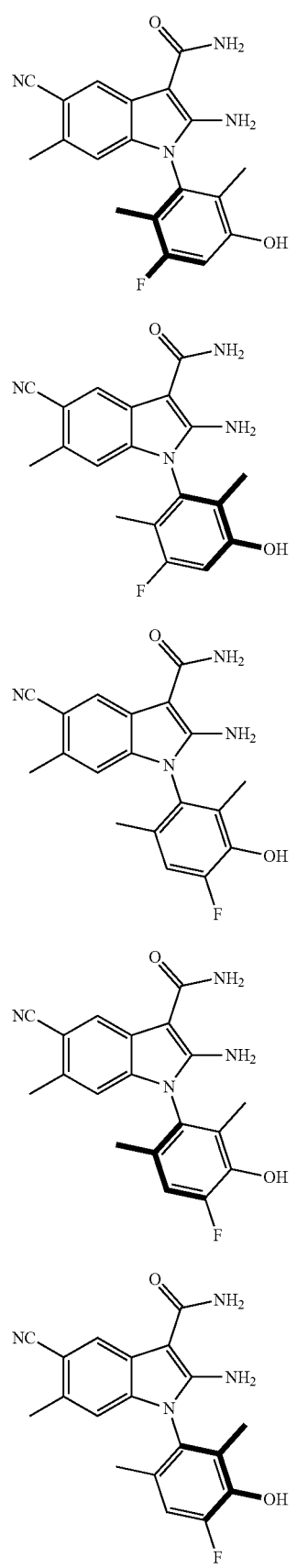
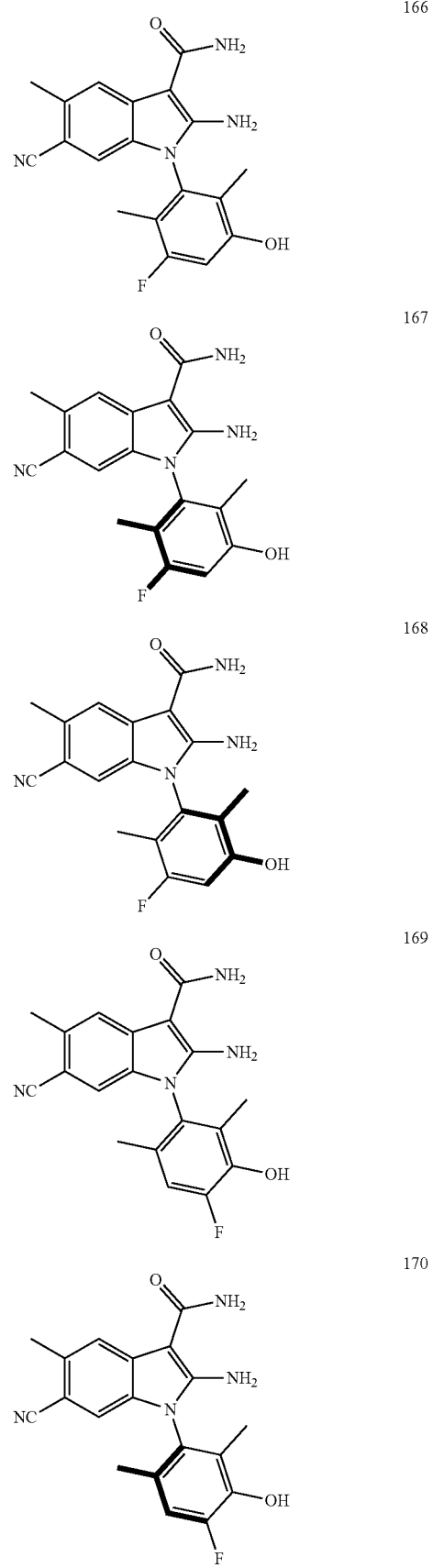

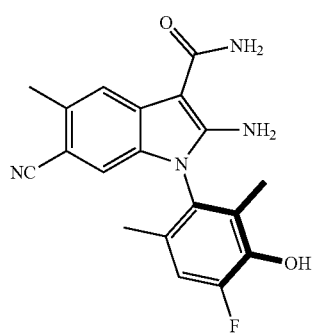
171
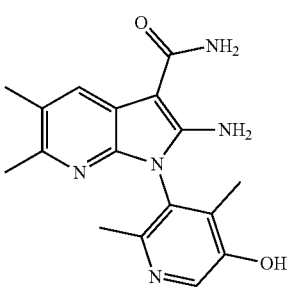
172
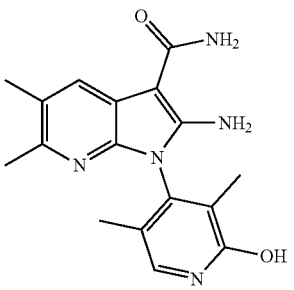
173
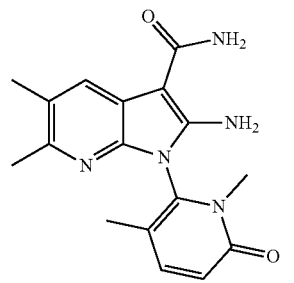
174
175
176
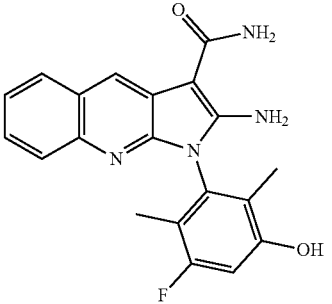
177
178
179
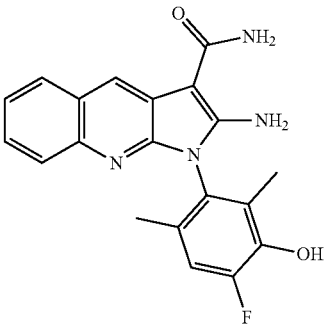
180

181 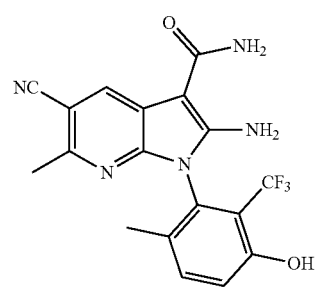
182 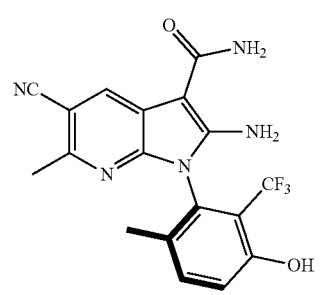
183 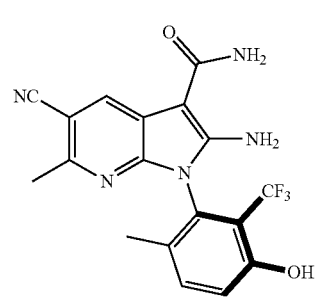
184 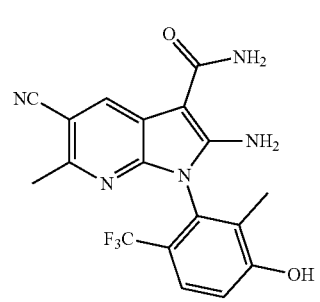
185 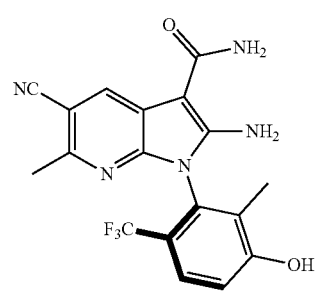
186 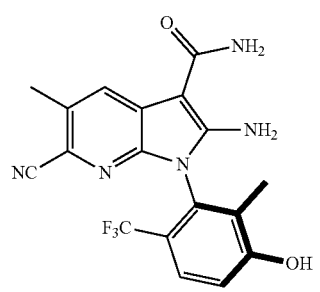
187 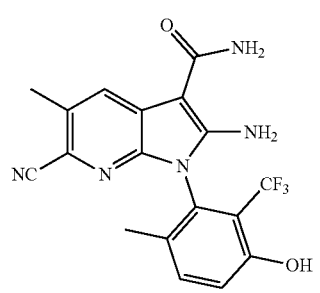
188 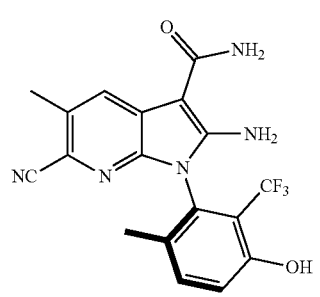
189 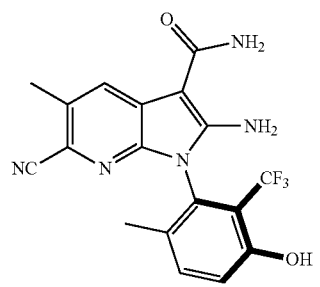
190 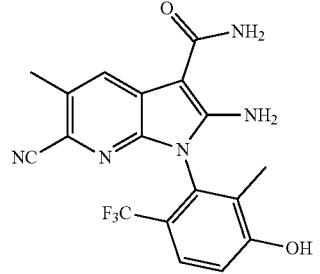

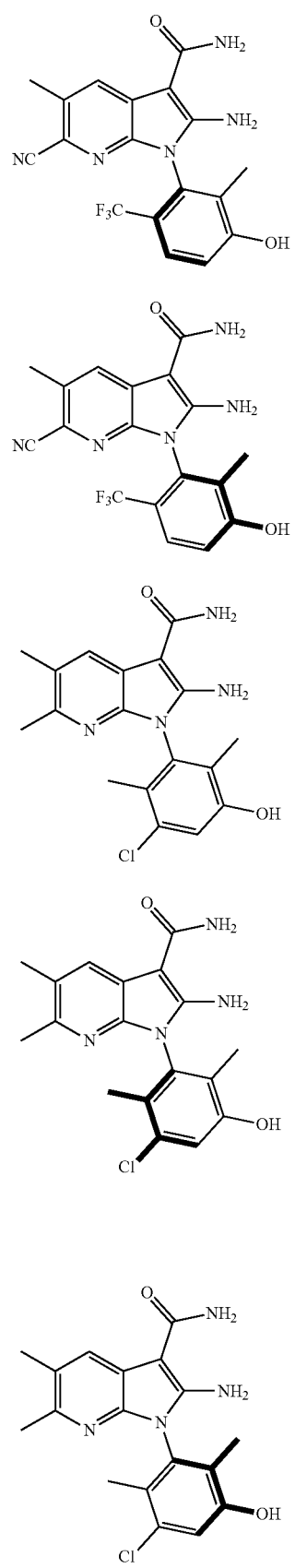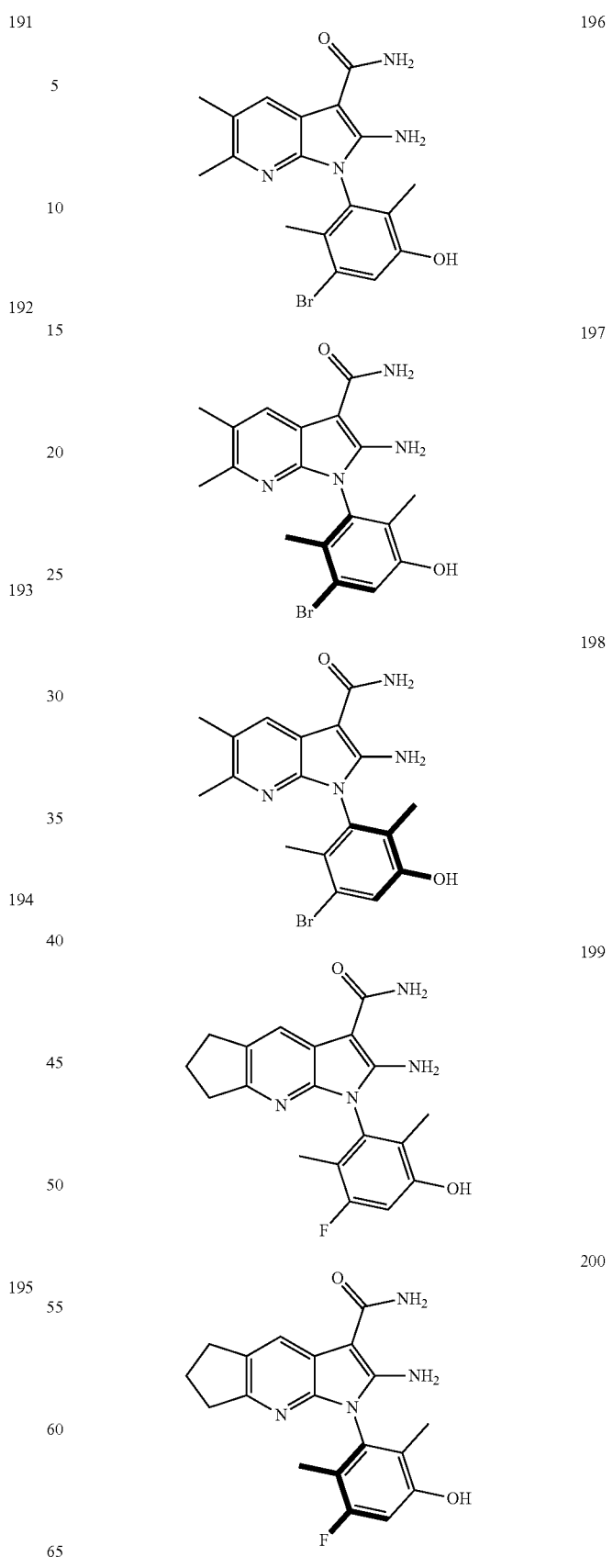

201 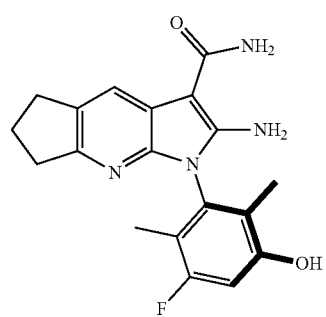
202 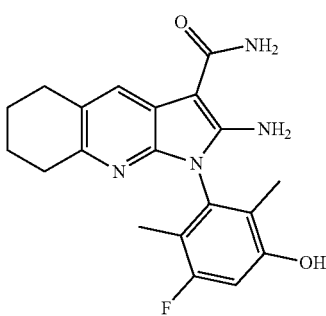
203 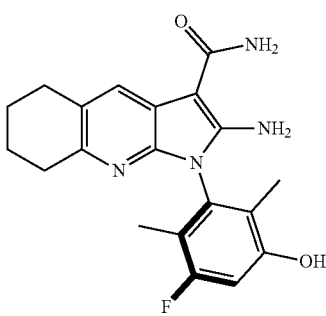
204 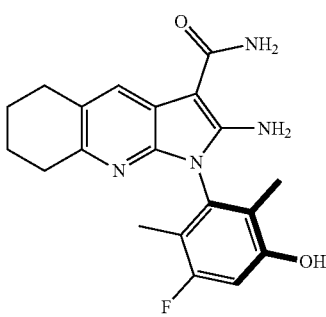
205 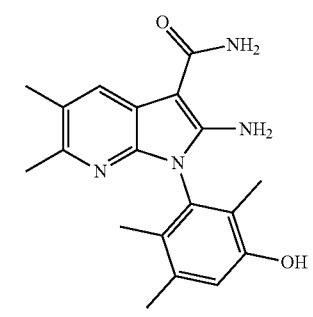
206 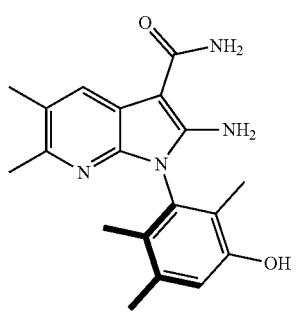
207 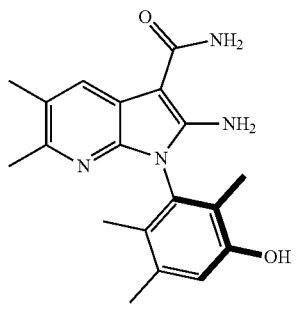
208 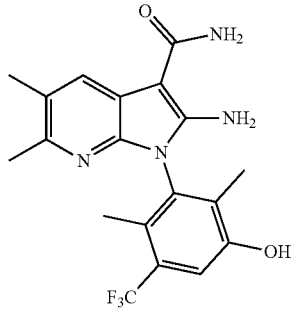
209 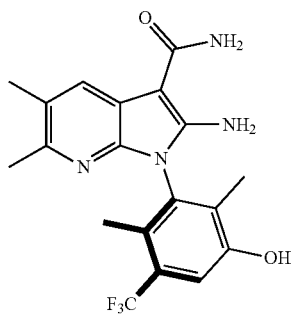
210 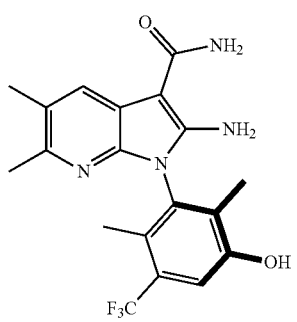

211 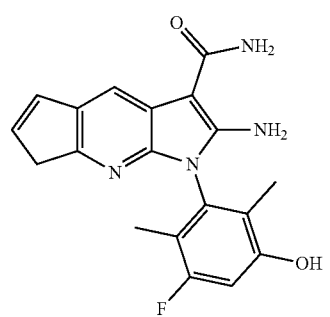
212 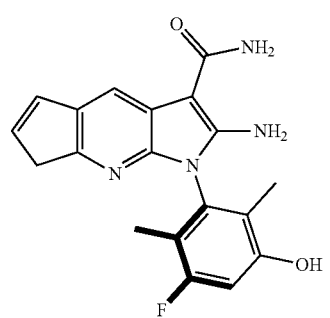
213 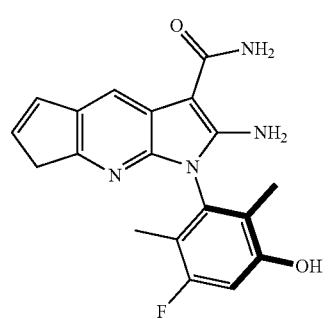
214 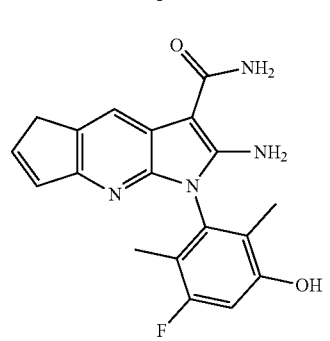
215 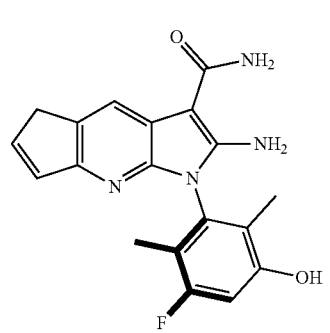
216 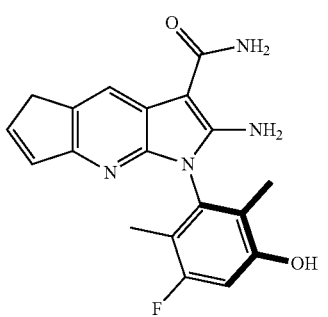
217 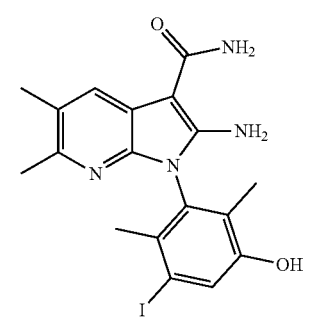
218 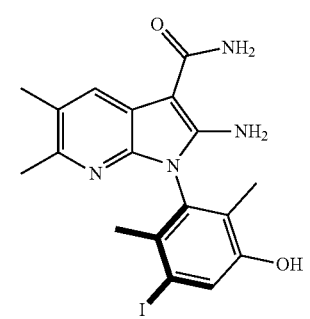
219 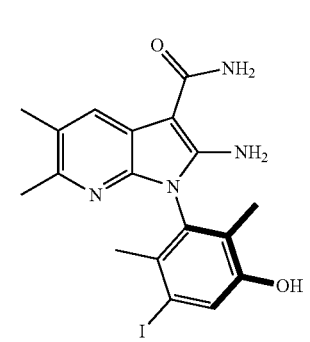
220 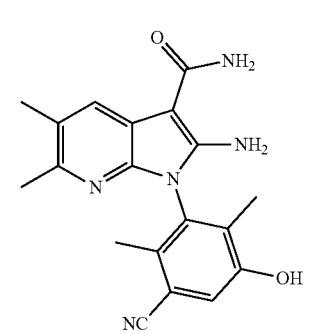

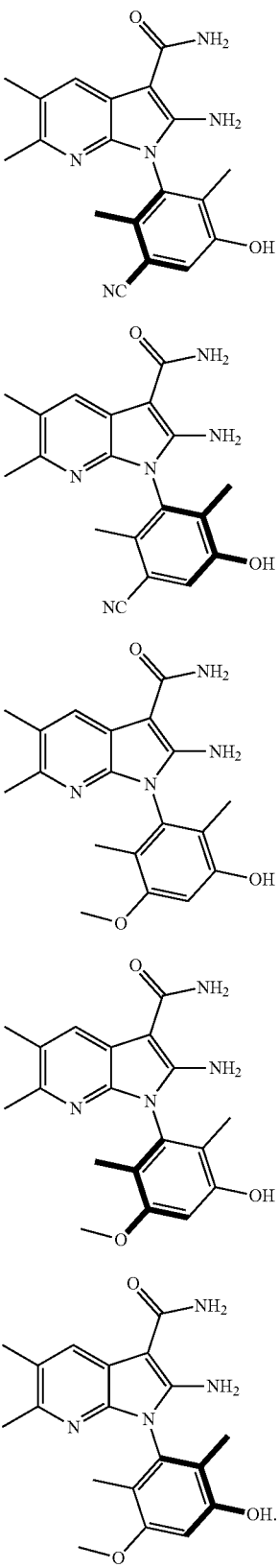

The present invention is further intended to provide a pharmaceutical composition comprising a pharmaceutically acceptable carrier, diluent and/or excipient, and the compound of general formula (1) or the isomer, the crystalline form, the pharmaceutically acceptable salt, the hydrate or the solvate thereof of the present invention as an active ingredient.

The present invention is still further intended to provide use of the compound of general formula (1) or the isomer, the crystalline form, the pharmaceutically acceptable salt, the hydrate or the solvate thereof of the present invention, or the pharmaceutical composition described above in the preparation of a medicament for treating, regulating, or preventing a disease related to MYT1 protein, wherein the disease is preferably a cancer, and the cancer is a hematologic cancer or a solid tumor.

The present invention is even further intended to provide a method for treating, regulating, or preventing a disease related to MYT1 protein, comprising: administering to a subject a therapeutically effective amount of the compound of general formula (1) or the isomer, the crystalline form, the pharmaceutically acceptable salt, the hydrate or the solvate thereof of the present invention, or the pharmaceutical composition described above.

Through synthesis and careful studies of various classes of novel compounds with inhibitory effects on MYT1, the inventors have discovered that the compound of general formula (1) has surprisingly strong inhibitory activity against MYT1.

It should be understood that both the above general description and the following detailed description of the present invention are exemplary and explanatory, and are intended to provide further explanation of the present invention claimed.

Synthesis of Compounds

Methods for preparing the compounds of general formula (1) of the present invention are specifically described below, but these specific methods do not limit the present invention in any way.

The compounds of general formula (1) described above can be synthesized using standard synthetic techniques or well-known techniques in combination with the methods described herein. In addition, the solvents, temperatures and other reaction conditions mentioned herein can vary. Starting materials for the synthesis of the compounds can be obtained synthetically or commercially. The compounds described herein and other related compounds with different substituents can be synthesized using well-known techniques and starting materials, including the methods found in March, ADVANCED ORGANIC CHEMISTRY, 4$^{th}$ Ed., (Wiley 1992); Carey and Sundberg, ADVANCED ORGANIC CHEMISTRY, 4$^{th}$ Ed., Vols. A and B (Plenum 2000, 2001); and Green and Wuts, PROTECTIVE GROUPS IN ORGANIC SYNTHESIS, 3$^{rd}$ Ed., (Wiley 1999). General methods for preparing the compounds can be changed by using appropriate reagents and conditions for introducing different groups into the molecular formulas provided herein.

In one aspect, the compounds described herein are prepared according to methods well known in the art. However, the conditions of the methods, such as reactants, solvents, bases, the amount of the compounds used, reaction temperature and time required for the reaction are not limited to the following explanation. The compounds of the present invention can also be conveniently prepared by optionally combining various synthetic methods described herein or known in the art, and such combinations can be easily determined by those skilled in the art to which the present invention pertains. In one aspect, the present invention further provides a method for preparing the compound of general formula (1), which is prepared using general reaction scheme 1 below:

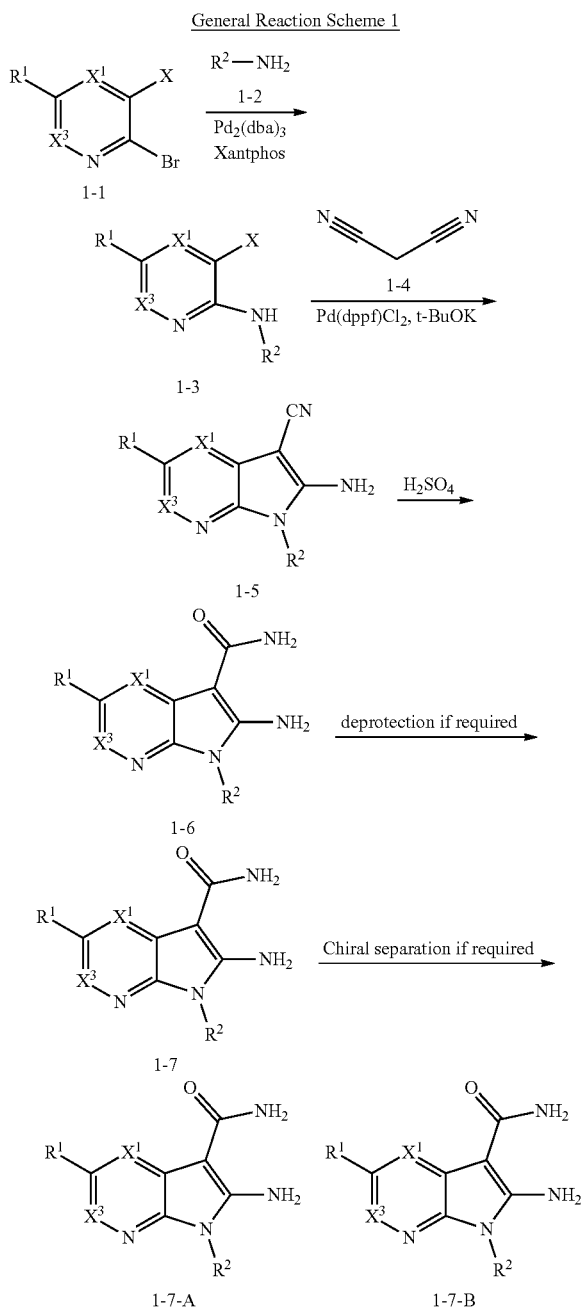

Embodiments of the compound of general formula (1) may be prepared according to general reaction scheme 1, wherein $R^1$, $R^2$, $X^1$, and $X^3$ are as defined above, X represents iodine or bromine, N represents nitrogen, O represents oxygen, and Br represents bromine. As shown in general reaction scheme 1, compound 1-1 is subjected to a coupling reaction with compound 1-2 in the presence of $Pd_2(dba)_3$ to produce compound 1-3; compound 1-3 is subjected to a coupling reaction with compound 1-4 in the presence of $Pd(dppf)Cl_2$ to produce compound 1-5; the cyano group in compound 1-5 is hydrolyzed under an acidic condition to produce amide compound 1-6; in some cases, compound 1-6 is subjected to deprotection to produce compound 1-7; and in some cases, compound 1-7 is chirally resolved to produce atropisomers 1-7-A and 1-7-B.

Further Forms of Compounds

"Pharmaceutically acceptable" herein refers to a substance, such as a carrier or diluent, which will not lead to loss of biological activity or properties of a compound and is relatively non-toxic. For example, when an individual is given a substance, the substance will not cause undesired biological effects or interact with any component contained therein in a deleterious manner.

The term "pharmaceutically acceptable salt" refers to a form of a compound that does not cause significant irritation to the organism receiving the administration or eliminate the biological activity and properties of the compound. In certain specific aspects, the pharmaceutically acceptable salt is obtained by subjecting the compound of the general formula to a reaction with acids or bases, wherein the acids or bases include, but are not limited to, those found in Stahl and Wermuth, Handbook of Pharmaceutical Salts: Properties. Selection, and Use, $1^{st}$ Ed., (Wiley, 2002).

It should be understood that references to pharmaceutically acceptable salts include solvent addition forms or crystalline forms, especially solvates or polymorphs. A solvate contains either stoichiometric or non-stoichiometric amount of solvent and is selectively formed during crystallization in a pharmaceutically acceptable solvent such as water and ethanol. Hydrates are formed when the solvent is water, or alcoholates are formed when the solvent is ethanol. The solvates of the compound of general formula (1) are conveniently prepared or formed according to the methods described herein. For example, hydrates of the compound of general formula (1) are conveniently prepared by recrystallization in a mixed solvent of water/organic solvent, wherein the organic solvent used includes, but is not limited to, tetrahydrofuran, acetone, ethanol or methanol. Furthermore, the compounds described herein may be present in either a non-solvated form or a solvated form. In general, the solvated forms are considered equivalent to the non-solvated forms for purposes of the compounds and methods provided herein.

In other specific examples, the compound of general formula (1) is prepared in different forms including, but not limited to, amorphous, pulverized and nanoparticle forms. In addition, the compound of general formula (1) includes crystalline forms, and may also be polymorphs. Polymorphs include different lattice arrangements of the same elements of a compound. The polymorphs generally have different X-ray diffraction spectra, infrared spectra, melting points, density, hardness, crystalline forms, optical and electrical properties, stability and solubility: Different factors such as a recrystallization solvent, crystallization rate, and storage temperature may lead to a single dominant crystalline form.

In another aspect, the compound of general formula (1) may have a chiral center and/or axial chirality, and thus may be present in the form of a racemate, a racemic mixture, a single enantiomer, a diastereomeric compound, a single diastereomer, an atropisomer and a cis-trans isomer. Each chiral center or axial chirality will independently produce two optical isomers or atropisomers, and all possible optical isomers, atropisomers, diastereomeric mixtures, and pure or partially pure compounds are included within the scope of the present invention. The present invention is meant to include all such isomeric forms of these compounds.

The compound of the present invention may contain unnatural proportions of atomic isotopes at one or more of the atoms that constitute the compound. For example, the compound may be labeled with radioactive isotopes, such as tritium (3H), iodine-125 (125I), and C-14 (14C). For another example, deuterium can be used to substitute a hydrogen atom to form a deuterated compound. The bond formed by deuterium and carbon is stronger than that formed by common hydrogen and carbon, and compared with an undeuterated medicament, the deuterated medicament generally has the advantages of reduced adverse effects, increased medicament stability, enhanced efficacy; prolonged in vivo half-life, and the like. All isotopic variations of the compound of the present invention, whether radioactive or not, are contained within the scope of the present invention.

Terminology

Unless otherwise stated, the terms used in the present application, including those in the specification and claims, are defined as follows. It must be noted that in the specification and the appended claims, the singular forms "a" and "an" include plural meanings unless clearly indicated otherwise. Unless otherwise stated, conventional methods for mass spectrometry; nuclear magnetic resonance spectroscopy; HPLC, protein chemistry, biochemistry, recombinant DNA technology and pharmacology are used. As used herein, "or" or "and" refers to "and/or" unless otherwise stated.

Unless otherwise specified, "alkyl" refers to a saturated aliphatic hydrocarbon group, including linear and branched groups containing 1 to 6 carbon atoms. Lower alkyl groups containing 1 to 4 carbon atoms, such as methyl, ethyl, propyl, 2-propyl, n-butyl, isobutyl, or tert-butyl, are preferred. As used herein, "alkyl" includes unsubstituted and substituted alkyl, particularly alkyl substituted with one or more halogens. Preferred alkyl is selected from $CH_3$, $CH_3CH_2$, $CF_3$, $CHF_2$, $CF_3CH_2$, $CF_3(CH_3)CH$, $^iPr$, $^nPr$, $^iBu$, $^nBu$ or $^tBu$. Unless otherwise specified, "alkylene" refers to a divalent alkyl as defined above. Examples of alkylene include, but are not limited to, methylene and ethylene.

Unless otherwise specified, "alkenyl" refers to an unsaturated aliphatic hydrocarbon group containing carbon-carbon double bonds, including linear or branched groups containing 1 to 14 carbon atoms. Lower alkenyl groups containing 1 to 4 carbon atoms, such as vinyl, 1-propenyl, 1-butenyl, or 2-methylpropenyl, are preferred.

Unless otherwise specified, "alkenylene" refers to a divalent alkenyl as defined above.

Unless otherwise specified, "alkynyl" refers to an unsaturated aliphatic hydrocarbon group containing carbon-carbon triple bonds, including linear and branched groups containing 1 to 14 carbon atoms. Lower alkynyl groups containing 1 to 4 carbon atoms, such as ethynyl, 1-propynyl, or 1-butynyl, are preferred. Unless otherwise specified, "alkynylene" refers to a divalent alkynyl as defined above. Unless otherwise specified, "cycloalkyl" refers to a non-aromatic hydrocarbon ring system (monocyclic, bicyclic or polycyclic), and partially unsaturated cycloalkyl may be referred to as "cycloalkenyl" if the carbocyclic ring contains at least one double bond, or "cycloalkynyl" if the carbocyclic ring contains at least one triple bond. Cycloalkyl may include monocyclic or polycyclic groups (e.g., having 2, 3 or 4 fused rings) and spiro rings. In some embodiments, cycloalkyl is monocyclic. In some embodiments, cycloalkyl is monocyclic or bicyclic. The ring carbon atoms of cycloalkyl may optionally be oxidized to form an oxo or thio group. Cycloalkyl further includes cycloalkylene. In some embodiments, cycloalkyl contains 0, 1 or 2 double bonds. In some embodiments, cycloalkyl contains 1 or 2 double bonds (partially unsaturated cycloalkyl). In some embodiments, cycloalkyl may be fused to aryl, heteroaryl, cycloalkyl and heterocycloalkyl. In some embodiments, cycloalkyl may be fused to aryl, cycloalkyl and heterocycloalkyl. In some embodiments, cycloalkyl may be fused to aryl and heterocycloalkyl. In some embodiments, cycloalkyl may be fused to aryl and cycloalkyl. Examples of cycloalkyl include cyclopropyl, cyclobutyl, cyclopentyl, cyclohexyl, cycloheptyl, cyclopentenyl, cyclohexenyl, cyclohexadienyl, cycloheptatrienyl, norcamphanyl, norpinanyl, norcarnyl, bicyclo[1.1.1]pentyl, bicyclo[2.1.1]hexyl and the like. Unless otherwise specified, "cycloalkylene" refers to a divalent cycloalkyl as defined above. Unless otherwise specified, "alkoxy" refers to an alkyl group that bonds to the rest of the molecule through an ether oxygen atom. Representative alkoxy groups are those having 1-6 carbon atoms, such as methoxy, ethoxy, propoxy, isopropoxy, butoxy; isobutoxy, sec-butoxy and tert-butoxy: As used herein, "alkoxy" includes unsubstituted and substituted alkoxy, particularly alkoxy substituted with one or more halogens. Preferred alkoxy is selected from $OCH_3$, $OCF_3$, $CHF_2O$, $CF_3CH_2O$, $^iPrO$, $^nPrO$, $^iBuO$, $^nBuO$ or $^tBuO$. Unless otherwise specified, "aryl" refers to an aromatic hydrocarbon group, which is monocyclic or polycyclic; for example, a monocyclic aryl ring may be fused to one or more carbocyclic aromatic groups. Examples of aryl include, but are not limited to, phenyl, naphthyl, and phenanthryl.

Unless otherwise specified, "aryloxy" refers to an aryl group that bonds to the rest of the molecule through an ether oxygen atom. Examples of aryloxy include, but are not limited to, phenoxy and naphthoxy. Unless otherwise specified, "arylene" refers to a divalent aryl as defined above. Examples of arylene include, but are not limited to, phenylene, naphthylene, and phenanthrylene.

Unless otherwise specified, "heteroaryl" refers to an aromatic group containing one or more heteroatoms (O, S, or N), preferably an aromatic group containing 1 to 4 heteroatoms selected from oxygen, sulfur, and nitrogen, and more preferably an aromatic group containing 1 to 2 heteroatoms selected from any of oxygen, sulfur, or nitrogen. Heteroaryl is monocyclic or polycyclic. For example, a monocyclic heteroaryl ring is fused to one or more carbocyclic aromatic groups or other monocyclic heterocycloalkyl groups. Examples of heteroaryl include, but are not limited to, pyridinyl, pyridazinyl, imidazolyl, pyrimidinyl, pyrazolyl, triazolyl, pyrazinyl, quinolinyl, isoquinolinyl, furanyl, thienyl, isoxazolyl, thiazolyl, oxazolyl, isothiazolyl, benzofuranyl, benzothiazolyl, benzothienyl, benzoxazolyl, pyrrolyl, indolyl, benzimidazolyl, benzopyridinyl, pyrrolopyrimidinyl, 1H-pyrrolo[3,2-b]pyridinyl, 1H-pyrrolo[2,3-c]pyridinyl, 1H-pyrrolo[3,2-c]pyridinyl, 1H-pyrrolo[2,3-b]pyridinyl,

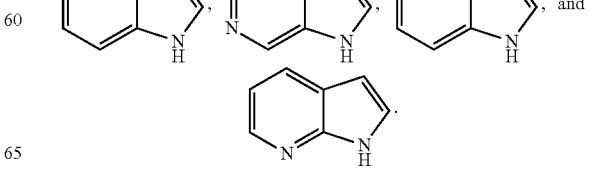

Unless otherwise specified, "heteroarylene" refers to a divalent heteroaryl defined as above.

Unless otherwise specified, "heterocycloalkyl" refers to a non-aromatic ring or ring system, which may optionally contain one or more alkenylene as part of the ring structure, having at least one heteroatom ring member independently selected from boron, phosphorus, nitrogen, sulfur, oxygen, and phosphorus; heterocycloalkyl is preferably a saturated or partially unsaturated ring containing 1 to 4 heteroatoms selected from oxygen, sulfur, or nitrogen, more preferably a saturated or partially unsaturated ring containing 1 to 2 heteroatoms selected from oxygen, sulfur, or nitrogen. Partially unsaturated heterocycloalkyl may be referred to as "heterocycloalkenyl" if heterocycloalkyl contains at least one double bond, or "heterocycloalkynyl" if the heterocycloalkyl contains at least one triple bond. Heterocycloalkyl may include monocyclic, bicyclic, spiro ring, or polycyclic systems (e.g., having two fused or bridged rings). In some embodiments, heterocycloalkyl is a monocyclic group having 1, 2, or 3 heteroatoms independently selected from nitrogen, sulfur, and oxygen. The ring carbon atoms and heteroatoms of heterocycloalkyl may optionally be oxidized to form oxo or thio groups or other oxidized bonds (e.g., C(O), S(O), C(S) or S(O)$_2$, N-oxides, etc.), or the nitrogen atoms may be quaternized. Heterocycloalkyl may be attached via a ring carbon atom or a ring heteroatom. In some embodiments, heterocycloalkyl contains 0 to 3 double bonds. In some embodiments, heterocycloalkyl contains 0 to 2 double bonds. The definition of heterocycloalkyl further includes moieties (also referred to as partially unsaturated heterocyclic rings) having one or more aromatic rings fused to (i.e., sharing a bond with) the heterocycloalkyl ring, for example, benzo-derivatives of piperidine, morpholine, azepin, thienyl, or the like. Heterocycloalkyl containing a fused aromatic ring may be attached via any ring atom, including ring atoms of the fused aromatic ring. Examples of heterocycloalkyl include, but are not limited to, azetidinyl, azepinyl, dihydrobenzofuranyl, dihydrofuranyl, dihydropyranyl, N-morpholinyl, 3-oxa-9-azaspiro[5.5]undecyl, 1-oxa-8-azaspiro[4.5]decyl, piperidinyl, piperazinyl, oxopiperazinyl, pyranyl, pyrrolidinyl, quininyl, tetrahydrofuranyl, tetrahydropyranyl, 1,2,3,4-tetrahydroquinolinyl, tropanyl, 4,5,6,7-tetrahydrothiazolo[5,4-c]pyridinyl, 4,5,6,7-tetrahydro-1H-imidazo[4,5-c]pyridine, N-methylpiperidinyl, tetrahydroimidazolyl, pyrazolidinyl, butyrolactam, valerolactam, imidazolidinonyl, hydantoinyl, dioxolanyl, phthalimidyl, pyrimidine-2,4(1H,3H)-dione, 1,4-dioxanyl, morpholinyl, thiomorpholinyl, thiomorpholinyl-S-oxide, thiomorpholinyl-S,S-oxide, piperazinyl, pyranyl, pyridonyl, 3-pyrrolinyl, thiopyranyl, pyronyl, tetrahydrothienyl, 2-azaspiro[3.3]heptanyl, indolinyl,

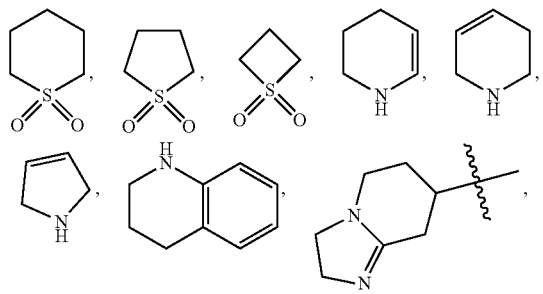

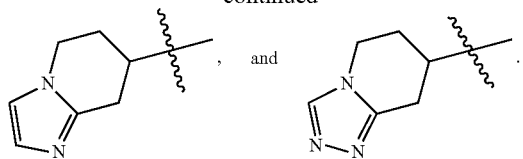

Unless otherwise specified, "heterocycloalkylene" refers to a divalent heterocycloalkyl as defined above.

Unless otherwise specified, "oxo" refers to =O: for example, a group formed by substitution of carbon with one oxo is "carbonyl

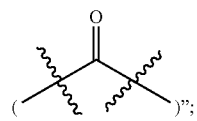 [SMILES: *C(*)=O]

";

a group formed by substitution of sulfur with one oxo is "sulfinyl

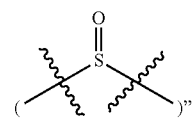

"

and a group formed by substitution of sulfur with two oxos is "sulfonyl

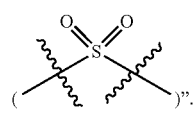

".

Unless otherwise specified, "halogen" (or halo) refers to fluorine, chlorine, bromine or iodine. The term "halo" (or "halogenated") before a group name indicates that the group is partially or fully halogenated, that is, substituted in any combination with F, Cl, Br or I, preferably with F or Cl.

Unless otherwise specified, the term "substituted" means that one or more hydrogen atoms on a designated atom or group are substituted with one or more substituents other than hydrogen without exceeding the normal valence of the designated atom. For example, one or more hydrogens of alkyl, alkylene, alkenyl, alkynyl, hydroxy, amino, or the like may be substituted with one or more substituents, wherein the substituents include, but are not limited to, alkyl, alkenyl, alkynyl, alkoxy, acyl, amino, amido, amidino, aryl, azido, carbamoyl, carboxy, carboxylate, cyano, guanidino, halogen, haloalkyl, heteroalkyl, heteroaryl, heterocyclyl, hydroxy, hydrazino, imino, oxo, nitro, alkylsulfinyl, sulfonic acid, alkylsulfonyl, thiocyanate, thiol, thione, or combinations thereof. The definition of "substituted" does not include analogous indeterminate structures obtained by defining substituents having further substituents attached to infinity (e.g., substituted aryl having substituted alkyl is itself substituted with substituted aryl, which is further substituted with substituted heteroalkyl, and the like). Unless otherwise specified, the maximum number of consecutive substitutions in the compound described herein is three. For example, the consecutive substitutions of substituted aryl with two other substituted aryls are limited to ((substituted aryl)substituted aryl)substituted aryl. Similarly, the definitions described above do not include impermissible substitution patterns (e.g., methyl substituted with 5 fluorines or heteroaryl having two adjacent oxygen ring atoms). Such impermissible substitution patterns are well known to those skilled in the art. When used to modify a chemical group, "substituted" may describe other chemical groups as defined herein. For example, the term "substituted aryl" includes, but is not limited to, "alkylaryl". Unless otherwise specified, if a group is described as optionally substituted, any substituent of the group is itself unsubstituted.

"Optional" or "optionally" means that the subsequently described event or circumstance may; but does not necessarily, occur, and the description includes instances where the event or circumstance occurs and instances where the event or circumstance does not occur.

Unless otherwise specified, it will be understood that the word "comprise" or variations thereof such as "comprises" or "comprising" refers to the inclusion of a stated element or integer or a group of elements or integers, but not the exclusion of any other element or integer or a group of elements or integers.

The substituent "—O—CH$_2$—O—" means that two oxygen atoms in the substituent are linked to two adjacent carbon atoms in the heterocycloalkyl, aryl or heteroaryl, for example:

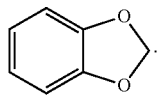

When the number of a linker group is 0, such as —(CH$_2$)$_0$—, it means that the linker group is a single bond. When one of the variables is selected from a chemical bond, it means that the two groups linked by this variable are linked directly. For example, when L in X-L-Y represents a chemical bond, it means that the structure is actually X-Y.

The term "membered ring" includes any cyclic structure. The term "membered" is intended to refer to the number of backbone atoms that form a ring. For example, cyclohexyl, pyridinyl, pyranyl and thiopyranyl are six-membered rings, and cyclopentyl, pyrrolyl, furanyl and thienyl are five-membered rings.

The term "moiety" refers to a specific portion or functional group of a molecule. A chemical moiety is generally considered to be a chemical entity contained in or attached to a molecule.

The term "atropisomer" refers to a conformational stereoisomer that results when rotation about a single bond within a molecule is hindered or greatly slowed due to the steric interaction with other parts of the molecule, and the substituents at both ends of the single bond are asymmetric, i.e., the atropisomer does not require a stereocenter. In the case of sufficiently high rotational hindrance around the single bond and sufficiently slow interconversion between conformations, the separation of individual isomers may be allowed (LaPlante et al., J. Med. Chem. 2011, 54, 20, 7005), preferably by a chiral resolution method.

Unless otherwise stated, the absolute configuration of a stereocenter is represented by a wedged solid bond (◢) and a wedged dashed bond (⋰), and a wedged solid bond (◢) or a wedged dashed bond (⋰) is represented by a wavy line (∿).

Unless otherwise stated, a single bond or a double bond is represented by ⹀.

Specific Pharmaceutical and Medical Terminology

The term "acceptable", as used herein, means that a formula component or an active ingredient does not unduly and adversely affect a general therapeutic target's health.

The terms "treatment", "treatment course", and "therapy", as used herein, include alleviating, inhibiting, or ameliorating a symptom or condition of a disease; inhibiting the development of complications; ameliorating or preventing underlying metabolic syndrome; inhibiting the development of a disease or symptom, e.g., controlling the progression of a disease or condition; alleviating a disease or symptom; leading to disease or symptom regression; and alleviating a complication caused by a disease or symptom, or preventing or treating a sign caused by a disease or symptom. As used herein, a compound or pharmaceutical composition, when administered, can ameliorate a disease, symptom, or condition, which particularly refers to ameliorating the severity; delaying the onset, slowing the progression, or reducing the duration of the disease. Fixed or temporary administration, or continuous or intermittent administration, may be attributed to or associated with the administration.

"Active ingredient" refers to the compound of general formula (1), and pharmaceutically acceptable inorganic or organic salts of the compound of general formula (1). The compound of the present invention may contain one or more asymmetric centers (chiral center or axial chirality) and thus occurs in the forms of a racemate, a racemic mixture, a single enantiomer, a diastereomeric compound, a single diastereomer, and an atropisomer. Asymmetric centers that may be present depend on the nature of the various substituents on the molecule. Each of such asymmetric centers will independently produce two optical isomers, and all possible optical isomers, atropisomers, diastereomeric mixtures, and pure or partially pure compounds are included within the scope of the present invention. The present invention is meant to include all such isomeric forms of these compounds.

The terms such as "compound", "composition", "agent", or "medicine or medicament" are used interchangeably herein and all refer to a compound or composition that, when administered to an individual (human or animal), is capable of inducing a desired pharmacological and/or physiological response by local and/or systemic action.

The term "administered, administering, or administration" refers herein to the direct administration of the compound or composition, or the administration of a prodrug, derivative, analog, or the like of the active compound.

Although the numerical ranges and parameters defining the broad scope of the present invention are approximations, the related numerical values set forth in the specific examples have been presented herein as precisely as possible. Any numerical value, however, inherently contains a standard deviation necessarily resulting from certain methods of testing. Herein, "about" generally means that the actual value is within a particular value or range ±10%, 5%, 1% or 0.5%. Alternatively, the term "about" indicates that the actual numerical value falls within the acceptable standard error of a mean, as considered by those skilled in the art. All ranges, quantities, numerical values, and percentages used herein (e.g., to describe an amount of a material, a length of time, a temperature, an operating condition, a quantitative ratio, and the like) are to be understood as being modified by the word "about", except in the experimental examples or where otherwise explicitly indicated. Accordingly, unless otherwise contrarily stated, the numerical parameters set forth in the specification and the appended claims are all approximations that may vary as desired. At least, these numerical parameters should be understood as the significant digits indicated or the numerical values obtained using conventional rounding rules.

Unless otherwise defined in the specification, the scientific and technical terms used herein have the same meaning as commonly understood by those skilled in the art. Furthermore, nouns in their singular forms used in the specification encompass their plural forms, unless contradicted by context: nouns in their plural forms used also encompass their singular forms.

Therapeutic Use

The compound of general formula (1) or the pharmaceutical composition of the present invention is generally useful for inhibiting MYT1 protein, and therefore, for treating one or more disorders related to the activity of MYT1 protein. Therefore, in certain embodiments, the present invention provides a method for treating MYT1 protein-mediated disorders, which comprises the step of administering to a patient in need thereof the compound of general formula (1) or the pharmaceutically acceptable composition thereof of the present invention.

In some embodiments, a method for treating cancer is provided, the method including administering to an individual in need thereof an effective amount of any aforementioned pharmaceutical composition including the compound of structural general formula (1). In some embodiments, the cancer includes, but is not limited to, hematologic malignancies (leukemias, lymphomas, and myelomas including multiple myeloma, myelodysplastic syndrome and myeloproliferative family syndrome), solid tumors (carcinomas such as prostate, breast, lung, colon, pancreatic, kidney; ovarian and soft tissue cancers, osteosarcoma, and interstitial tumors), and the like, preferably breast cancer, endometrial cancer, ovarian cancer, uterine carcinosarcoma, ovarian carcinosarcoma, pancreatic ductal adenocarcinoma, lung cancer, intestinal cancer, colorectal cancer, and esophageal cancer.

Route of Administration

The compound and the pharmaceutically acceptable salt thereof of the present invention can be made into various formulations including a safe and effective amount of the compound or the pharmaceutically acceptable salt thereof of the present invention, and a pharmaceutically acceptable excipient or carrier, wherein the "safe and effective amount" means that the amount of the compound is sufficient to significantly improve the condition without causing serious adverse effects. The safe and effective amount of the compound is determined according to the age, condition, course of treatment, and other specific conditions of a treated subject.

The "pharmaceutically acceptable excipient or carrier" refers to one or more compatible solid or liquid fillers or gel substances that are suitable for human use and must be of sufficient purity and sufficiently low toxicity. "Compatible" herein means that the components of the composition are capable of intermixing with the compound of the present invention and with each other, without significantly diminishing the pharmaceutical efficacy of the compound. Examples of pharmaceutically acceptable excipients or carriers include cellulose and derivatives thereof (e.g., sodium carboxymethylcellulose, sodium ethylcellulose, or cellulose acetate), gelatin, talc, solid lubricants (e.g., stearic acid or magnesium stearate), calcium sulfate, vegetable oil (e.g., soybean oil, sesame oil, peanut oil, or olive oil), polyols (e.g., propylene glycol, glycerol, mannitol, or sorbitol), emulsifiers (e.g., Tween R), wetting agents (e.g., sodium lauryl sulfate), colorants, flavoring agents, stabilizers, antioxidants, preservatives, pyrogen-free water, etc.

When the compound of the present invention is administered, it may be administered orally, rectally, parenterally (intravenously; intramuscularly, or subcutaneously), or topically.

Solid dosage forms for oral administration include capsules, tablets, pills, pulvises, and granules. In these solid dosage forms, the active compound is mixed with at least one conventional inert excipient (or carrier), such as sodium citrate or dicalcium phosphate, or with the following ingredients: (a) fillers or extenders, such as starch, lactose, sucrose, glucose, mannitol, and silicic acid; (b) binders, such as hydroxymethyl cellulose, alginate, gelatin, polyvinylpyrrolidone, sucrose, and acacia; (c) humectants, such as glycerol; (d) disintegrants, such as agar, calcium carbonate, potato or tapioca starch, alginic acid, certain complex silicates, and sodium carbonate; (e) solution retarders, such as paraffin; (f) absorption accelerators, such as quaternary ammonium compounds; (g) wetting agents, such as cetyl alcohol and glycerol monostearate; (h) adsorbents, such as kaolin; and (i) lubricants, such as talc, calcium stearate, magnesium stearate, solid polyethylene glycol and sodium lauryl sulfate, or mixtures thereof. In the case of capsules, tablets, and pills, the dosage forms may further include buffers.

Solid dosage forms such as tablets, dragees, capsules, pills, and granules can be prepared using coatings and shells such as enteric coatings and other materials well known in the art. They may include opacifying agents, and the active compound or compound in such a composition may be released in a certain part of the digestive tract in a delayed manner. Examples of embedding components that can be used are polymeric substances and wax-based substances. If necessary, the active compound can also be in microcapsule form with one or more of the excipients described above.

Liquid dosage forms for oral administration include pharmaceutically acceptable emulsions, solutions, suspensions, syrups, and elixirs. In addition to the active compound, the liquid dosage form may include inert diluents commonly used in the art, such as water or other solvents, solubilizers and emulsifiers, for example, ethanol, isopropanol, ethyl carbonate, ethyl acetate, propylene glycol, 1,3-butanediol, dimethylformamide, and oils, especially cottonseed oil, peanut oil, corn germ oil, olive oil, castor oil and sesame oil, or mixtures of these substances.

Besides such inert diluents, the composition may further include adjuvants, such as wetting agents, emulsifiers, suspending agents, sweeteners, flavoring agents, and perfuming agents.

In addition to the active compound, suspensions may include suspending agents, such as ethoxylated isostearyl alcohols, polyoxyethylene sorbitol and sorbitan esters, microcrystalline cellulose, aluminum methylate and agar, or mixtures of these substances.

Compositions for parenteral injection may include physiologically acceptable sterile aqueous or anhydrous solutions, dispersions, suspensions or emulsions, and sterile powders for redissolving into sterile injectable solutions or dispersions. Suitable aqueous and non-aqueous carriers, diluents, solvents, or excipients include water, ethanol, polyols, and suitable mixtures thereof.

Dosage forms for topical administration of the compound of the present invention include ointments, pulvises, patches, sprays, and inhalants. The active ingredient is mixed under sterile conditions with a physiologically acceptable carrier and any preservatives, buffers or propellants that may be required if necessary.

The compound of the present invention may be administered alone or in combination with other pharmaceutically acceptable compounds. When the pharmaceutical composition is used, a safe and effective amount of the compound of the present invention is administered to a mammal (such as a human) to be treated, wherein the dose of administration is a pharmaceutically effective dose. For a human of 60 kg, the daily dose of administration is usually 1-2000 mg, preferably 50-1000 mg. In determining a specific dose, such factors as the route of administration, the health condition of the patient and the like will also be considered, which are well-known to skilled physicians.

The above features mentioned in the present invention or those mentioned in the examples may be combined arbitrarily: All the features disclosed in this specification may be used with any composition form and the various features disclosed in this specification may be replaced with any alternative features that provide the same, equivalent, or similar purpose. Thus, unless otherwise specified, the features disclosed herein are merely general examples of equivalent or similar features.

DETAILED DESCRIPTION

Various specific aspects, features, and advantages of the compounds, methods, and pharmaceutical compositions described above will be set forth in detail in the following description, which will make the content of the present invention very clear. It should be understood that the detailed description and examples below describe specific examples for reference only: After reading the description of the present invention, those skilled in the art can make various changes or modifications to the present invention, and such equivalents also fall within the scope of the present application defined herein.

In all the examples, 1H-NMR spectra were recorded with a Varian Mercury 400 nuclear magnetic resonance spectrometer, and chemical shifts are expressed in δ (ppm); silica gel for separation was 200-300 mesh silica gel if not specified, and the ratio of the eluents was a volume ratio.

The following abbreviations are used in the present invention: (Boc)$_2$O for di-tert-butyl dicarbonate; CDCl$_3$ for deuterated chloroform; Cs$_2$CO$_3$ for cesium carbonate; CuI for cuprous iodide; EtOAc for ethyl acetate; Hexane for n-hexane; HPLC for high-performance liquid chromatography; MeCN for acetonitrile; DCM for dichloromethane; DDQ for 2,3-dichloro-5,6-dicyan-p-benzoquinone; DIPEA for diisopropylethylamine; Dioxane for 1,4-dioxane; DME for glycol dimethyl ether; DMEDA for N,N-dimethylethylenediamine; DMF for N,N-dimethylformamide; DMAP for 4-(dimethylamino)pyridine; DMSO for dimethyl sulfoxide; EtOH for ethanol; EtOAc for ethyl acetate; EA for ethyl acetate; h for hour; IPA for isopropanol; ISCO® for a Biotage Isolera Prime flash preparative liquid chromatography min for minute: K$_2$CO$_3$ for potassium carbonate; KOAc for potassium acetate; KOH for potassium hydroxide; K$_3$PO$_4$ for potassium phosphate; LiBH$_4$ for lithium borohydride; min for minute; m-CPBA for m-chloroperoxybenzoic acid; MeOH for methanol; MeONa for sodium methoxide; MS for mass spectrometry; NaBH(OAc)$_3$ for sodium triacetoxyborohydride; NaH for sodium hydrogen; NMR for nuclear magnetic resonance; NBS for bromosuccinimide; NIS for iodosuccinimide; Pd/C for palladium on carbon; Pd(PPh$_3$)$_4$ for tetrakis(triphenylphosphine)palladium: Pd(OAc)$_2$ for palladium acetate: Pd(dppf)Cl$_2$ for [1,1'-bis(diphenylphosphino)ferrocene]dichloropalladium (II); PE for petroleum ether; Petroleum ether for petroleum ether; PMBNH$_2$ for 4-methoxy benzylamine; PPh$_3$ for triphenylphosphine; TEA for triethylamine; TFA for trifluoroacetic acid; TFAA for trifluoroacetic anhydride; THF for tetrahydrofuran; TsOH for p-toluenesulfonic acid: TsCl for p-toluenesulfonyl chloride; TfOH for trifluoromethanesulfonic acid; TLC for thin-layer chromatography; SFC for supercritical fluid chromatography; XantPhos for 4,5-bis(diphenylphosphino)-9,9-dimethylxanthene; XPhos for 2-dicyclohexyl phosphonium-2',4',6'-triisopropylbiphenyl; XantPhos Pd G3 for [(4,5-bis(diphenylphosphino)-9,9-dimethylxanthene)-2-(2'-amino-1,1'-biphenyl)]palladium(II) methanesulfonate.

Example 1. Synthesis of Compound 1

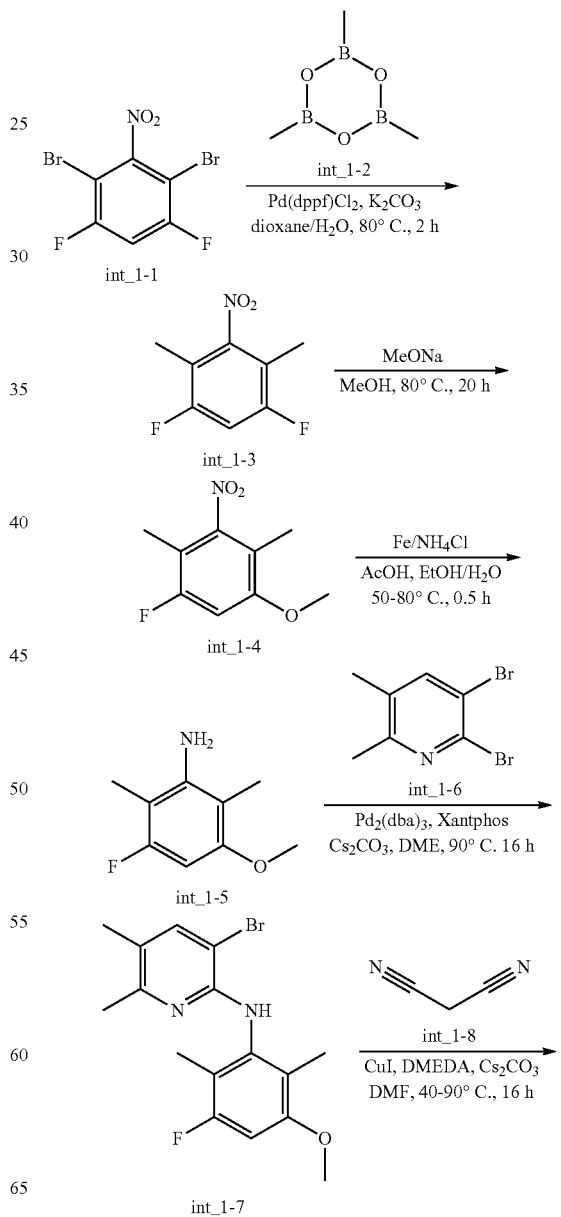

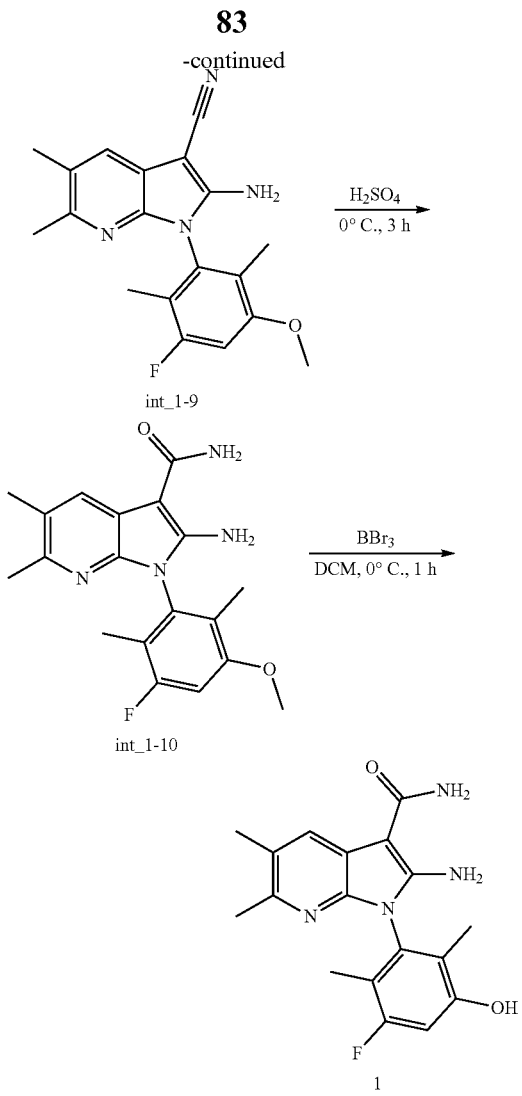

¹H NMR: (400 MHZ, CHLOROFORM-d) δ 6.94 (t, J=9.0 Hz, 1H), 2.24-2.13 (m, 6H).

Step 2: Synthesis of Compound Int_1-4

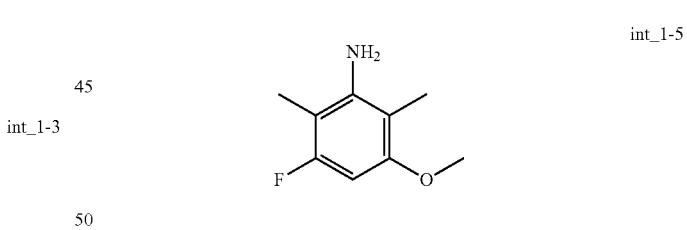

Int_1-3 (1.00 g, 5.34 mmol) was dissolved in methanol (10 mL), and MeONa (1.06 g, 5.88 mmol, 30% purity) was added at 0° C. The reaction solution was reacted at 80° C. for 2 h. Additional MeONa (3.85 g, 21.37 mmol, 30% purity) was added, and the reaction solution was reacted at 80° C. for 8 h. Additional MeONa (4.81 g, 26.7 mmol, 30% purity) was added, and the reaction solution was reacted at 80° C. for 10 h. TLC monitoring showed the reaction was completed. Water (100 mL) was added to the reaction solution. The aqueous phase was extracted with ethyl acetate (200 mL×3), and the organic phase was dried over anhydrous sodium sulfate. The organic phase was concentrated under reduced pressure to give a crude product (880 mg), which was directly used in the next step.

¹H NMR: (400 MHZ, CHLOROFORM-d) δ 6.69 (d, J=11.0 Hz, 1H), 3.86 (s, 3H), 2.13 (dd, J=1.3, 14.5 Hz, 6H).

Step 3: Synthesis of Compound Int_1-5

Step 1: Synthesis of Compound Int_1-3

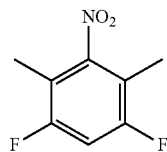

Int_1-1 (3.00 g, 9.47 mmol), int_1-2 (16.6 g, 66.3 mmol, 18.5 mL, 50% purity), Pd(dppf)Cl₂ (693 mg, 947 μmol), and K₂CO₃ (5.23 g, 37.9 mmol) were dissolved in a mixed solvent of 1,4-dioxane (60 mL) and water (12 mL). The mixed solution was purged with nitrogen three times, heated to 80° C., and stirred for 2 h. TLC monitoring showed the reaction was completed. Water (100 mL) was added to the reaction solution. The aqueous phase was extracted with ethyl acetate (200 mL×3), and the organic phase was dried over anhydrous sodium sulfate. The organic phase was concentrated under reduced pressure to give a crude product. The crude product was purified by preparative column chromatography (SiO₂, PE/DCM=19/1) to give a white solid (1.2 g, 67.7% yield).

Int_1-4 (880 mg, 4.42 mmol) was dissolved in ethanol (3 mL) and water (2 mL), and NH₄Cl (2.36 g, 44.2 mmol) and acetic acid (133 mg, 2.21 mmol, 126 μL) were added. The mixed solution was heated to 50° C., and iron powder ((1.23 g, 22.1 mmol) was slowly added. After the addition, the mixed solution was heated to 80° C. and stirred for 0.5 h. LC-MS monitoring showed the reaction was completed. The reaction solution was filtered while hot, and the filtrate was concentrated under reduced pressure to give a crude product. The crude product was purified by preparative column chromatography (SiO₂, PE/EtOAc=10/1 to 5/1) to give a solid (730 mg, 97.7% yield).

¹H NMR: (400 MHz, CHLOROFORM-d) δ 6.15 (d, J=11.7 Hz, 1H), 3.83 (br s, 2H), 3.78 (s, 3H), 2.06 (d, J=1.5 Hz, 3H), 2.04 (s, 3H).

ESI-MS m/z: 170 [M+H]⁺.

Step 4: Synthesis of Compound Int_1-7

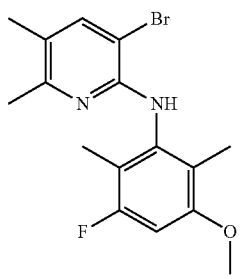

Int_1-5 (700 mg, 4.14 mmol) and int_1-6 (1.10 g, 4.14 mmol) were dissolved in DME (10 mL), and $Cs_2CO_3$ (3.24 g, 9.93 mmol), Xantphos (239 mg, 414 μmol), and $Pd_2(dba)_3$ (379 mg, 414 μmol) were added. The reaction solution was purged with nitrogen three times, heated to 90° C., and reacted for 16 h. LC-MS monitoring showed the reaction was completed. After the reaction solution was cooled to room temperature, water (50 mL) was added to the reaction solution. The aqueous phase was extracted with ethyl acetate (50 mL×3), and the organic phase was dried over anhydrous sodium sulfate. The organic phase was concentrated under reduced pressure to give a crude product. The crude product was purified by preparative column chromatography ($SiO_2$, PE/EtOAc=10/1) to give a solid (1.2 g, 82.1% yield).

$^1$H NMR: (400 MHZ, CHLOROFORM-d) δ 7.45 (s, 1H), 6.55 (d, J=11.4 Hz, 1H), 6.20 (br s, 1H), 3.82 (s, 3H), 2.24-2.11 (m, 6H), 2.05 (d, J=2.8 Hz, 6H).

ESI-MS m/z: 353 [M+H]$^+$.

Step 5: Synthesis of Compound Int_1-9

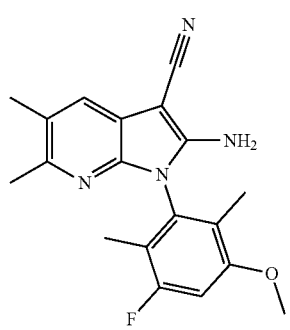

Int_1-8 (118 mg, 1.78 mmol, 112 μL) and $Cs_2CO_3$ (609 mg, 1.87 mmol) were dissolved in DMF (4 mL). The reaction solution was heated to 40° C. and reacted for 0.5 h. int_1-7 (300 mg, 849 μmol), CuI (80.9 mg, 425 μmol), and DMEDA (37.4 mg, 425 μmol) were added to the reaction solution. The reaction solution was purged with nitrogen three times, heated to 90° C., and reacted for 16 h. LC-MS monitoring showed the reaction was completed. After the reaction solution was cooled to room temperature, water (50 mL) was added to the reaction solution. The aqueous phase was extracted with ethyl acetate (50 mL×3), and the organic phase was dried over anhydrous sodium sulfate. The organic phase was concentrated under reduced pressure to give a crude product. The crude product was purified by preparative column chromatography ($SiO_2$, PE/EtOAc=1/0 to 4/1) to give a solid (270 mg, 94.0% yield).

$^1$H NMR: (400 MHZ, CHLOROFORM-d) δ 7.51 (s, 1H), 6.78 (d, J=11.1 Hz, 1H), 4.53 (s, 2H), 3.87 (s, 3H), 2.39 (s, 3H), 2.33 (s, 3H), 1.82 (d, J=2.0 Hz, 3H), 1.80 (s, 3H).

ESI-MS m/z: 339 [M+H]$^+$.

Step 6: Synthesis of Compound Int_1-10

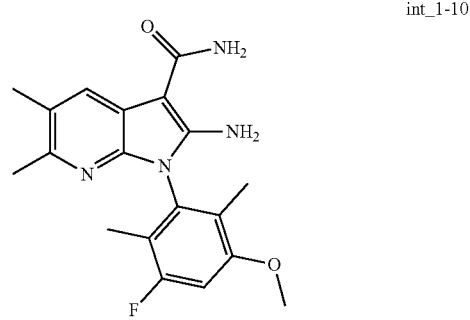

At 0° C., sulfuric acid (4 mL) was slowly added to int_1-9 (220 mg, 650 μmol). The reaction solution was reacted at 0° C. for 3 h. LC-MS monitoring showed the reaction was completed. Ice water (30 mL) was slowly added to the reaction solution. The aqueous phase was adjusted to pH 8 with saturated aqueous sodium bicarbonate solution and extracted with ethyl acetate (30 mL×3), and the organic phase was dried over anhydrous sodium sulfate. The organic phase was concentrated under reduced pressure to give a crude product. The crude product was purified by preparative column chromatography ($SiO_2$, PE/EtOAc=1/0 to 3/1) to give a solid (160 mg, 69.1% yield).

$^1$H NMR: (400 MHZ, CHLOROFORM-d) δ 7.38 (s, 1H), 6.77 (d, J=11.2 Hz, 1H), 5.89 (br s, 2H), 5.43 (br s, 2H), 3.87 (s, 3H), 2.38 (d, J=19.8 Hz, 6H), 1.88-1.78 (m, 6H).

MS (ESI): 357 [M+H]$^+$.

Step 7: Synthesis of Compound 1

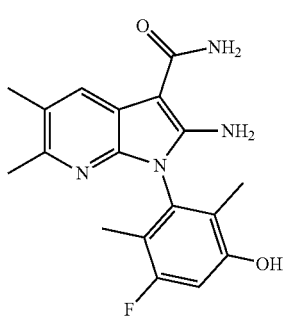

Int_1-10 (80.0 mg, 224 μmol) was dissolved in dichloromethane (2 mL) under nitrogen atmosphere, and $BBr_3$ (562 mg, 2.24 mmol, 216 μL) was added to the reaction solution at 0° C. The reaction solution was reacted at 0° C. for 1 h under nitrogen atmosphere. LC-MS monitoring showed the reaction was completed. Ice water (20 mL) was slowly added to the reaction solution, and NaH$_2$PO$_4$ (1.5 g) was added. The aqueous phase was adjusted to pH 8 with saturated aqueous sodium bicarbonate solution and extracted with ethyl acetate (30 mL×3), and the organic phase was dried over anhydrous sodium sulfate. The organic phase was concentrated under reduced pressure to give a crude product. The crude product was purified by preparative column chromatography to give compound 1 (70 mg, 91.3% yield).

$^1$H NMR (400 MHZ, DMSO-d6) δ 10.03 (br s, 1H), 7.83 (s, 1H), 6.84 (s, 2H), 6.79 (d, J=11.3 Hz, 1H), 6.65 (br s, 2H), 2.26 (s, 3H), 2.24 (s, 3H), 1.63 (s, 3H), 1.61 (s, 3H).

MS (ESI): 343 [M+H]$^+$.

Example 2. Synthesis of Compound 2 and Compound 3

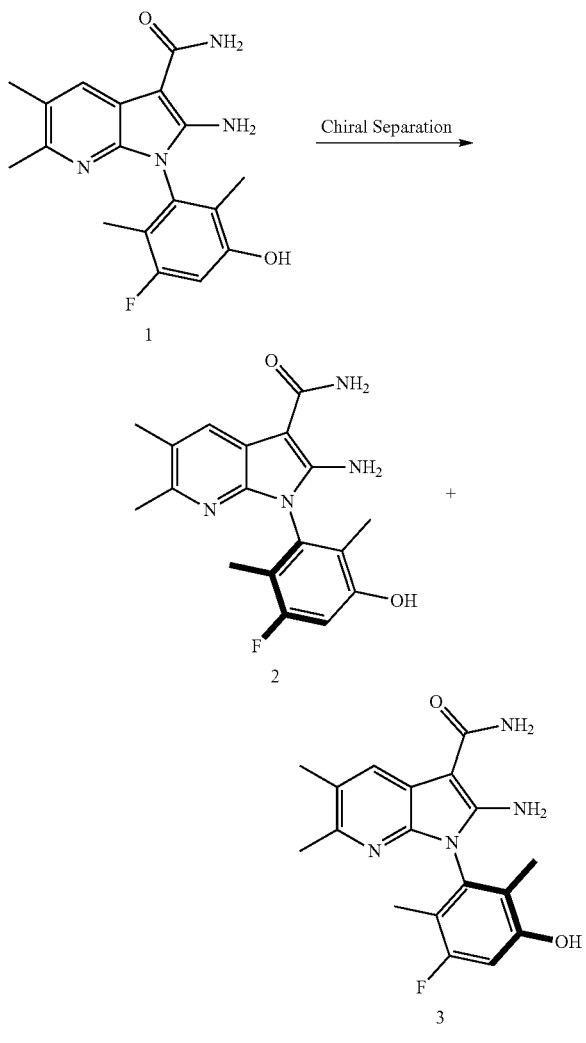

Compound 1 (120 mg, 0.35 mmol) was subjected to preparative SFC chiral resolution (column: Phenomenex-Cellulose-2 (250 mm×30 mm, 10 μm); mobile phase: A: CO$_2$, B; EtOH (0.1% NH$_3$H$_2$O); B %: 50%-50%, min) to give compound 3 (20 mg, 33.3% yield) and compound 2 (20 mg, 33.3% yield).

Compound 2: $^1$H NMR (400 MHz, DMSO-d6) δ 10.03 (br s, 1H), 7.83 (s, 1H), 6.84 (s, 2H), 6.79 (d, J=11.3 Hz, 1H), 6.65 (br s, 2H), 2.26 (s, 3H), 2.24 (s, 3H), 1.65 (s, 3H), 1.61 (s, 3H).

MS (ESI): 343 [M+H]$^+$.

Analytical SFC retention time: 2.129 min (Instrument: Waters UPCC with PDA Detector; Column: Cellulose-2, 100×4.6 mm, I.D., 3 μm; Mobile phase: A: CO$_2$, B: Ethanol (0.05% DEA); Isocratic: 40% B; Flow rate: 2.8 mL/min; Column temp: 35° C.; ABPR: 1500 psi).

Compound 3: $^1$H NMR (400 MHZ, DMSO-d6) δ 9.98 (br s, 1H), 7.84 (s, 1H), 6.85 (s, 2H), 6.79 (d, J=11.3 Hz, 1H), 6.66 (br s, 2H), 2.27 (s, 3H), 2.25 (s, 3H), 1.65 (s, 3H), 1.62 (s, 3H).

MS (ESI): 343 [M+H]$^+$.

Analytical SFC retention time: 2.708 min (Instrument: Waters UPCC with PDA Detector; Column: Cellulose-2, 100×4.6 mm, I.D., 3 μm; Mobile phase: A: CO$_2$, B: Ethanol (0.05% DEA); Isocratic: 40% B; Flow rate: 2.8 mL/min; Column temp.: 35° C.; ABPR: 1500 psi).

Example 3. Synthesis of Compound 5

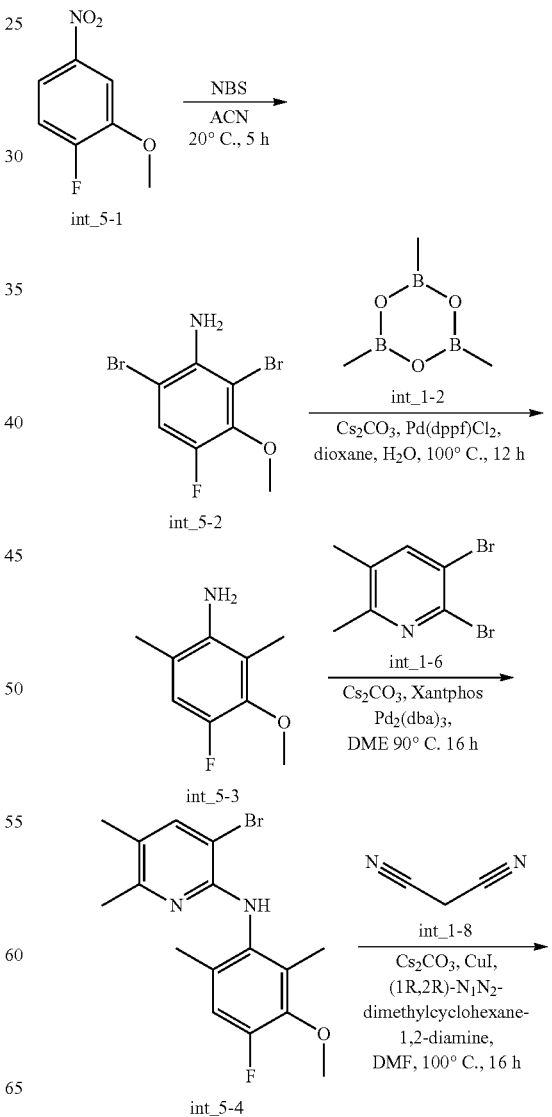

-continued

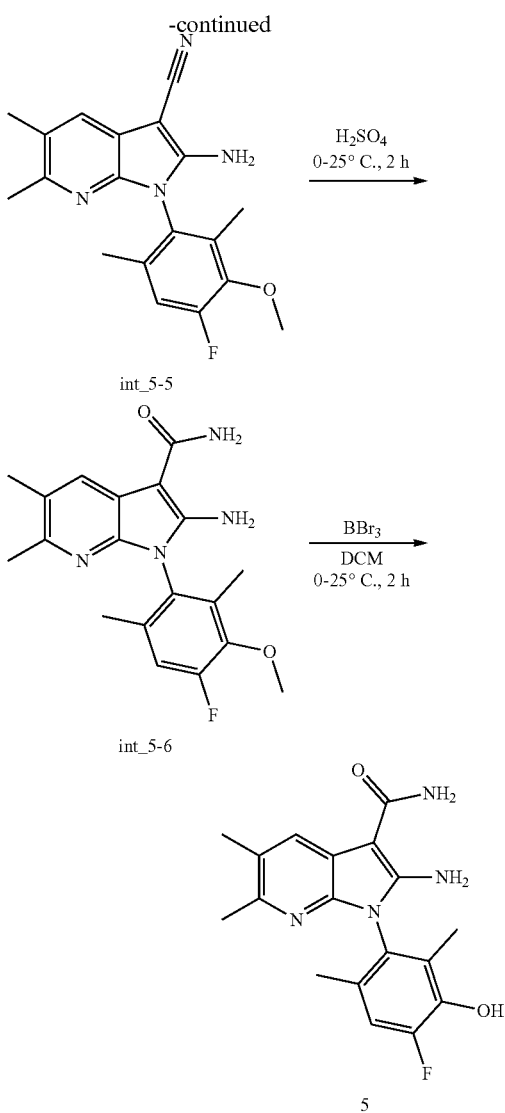

product was purified by preparative column chromatography (ISCO®; Silica Flash Column, Eluent of 0-10% THF/Petroleum ether gradient) to give an orange solid (7 g, 14.4% yield).

ESI-MS m/z: 299 [M+H]$^+$.

Step 2: Synthesis of Compound Int_5-3

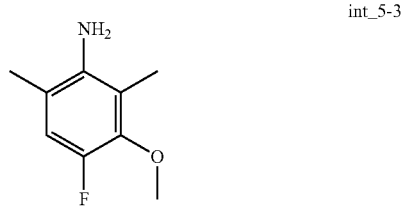

Int_5-2 (7.00 g, 23.4 mmol), int_1-2 (4.41 g, 35.1 mmol, 4.91 mL), Pd(dppf)Cl$_2$ (1.71 g, 2.34 mmol), and Cs$_2$CO$_3$ (22.9 g, 70.3 mmol) were dissolved in a mixed solvent of 1,4-dioxane (80 mL) and water (8 mL).

The mixed solution was purged with nitrogen three times, heated to 100° C., and stirred for 12 h. TLC monitoring showed the reaction was completed. Water (100 mL) was added to the reaction solution. The aqueous phase was extracted with ethyl acetate (200 mL×3), and the organic phase was dried over anhydrous sodium sulfate. The organic phase was concentrated under reduced pressure to give a crude product. The crude product was purified by preparative column chromatography (ISCO®; Silica Flash Column, Eluent of 0-50% THF/Petroleum ether gradient) to give a white solid (2.2 g, 55.5% yield).

ESI-MS m/z: 170 [M+H]$^+$.

Step 3: Synthesis of Compound Int_5-4

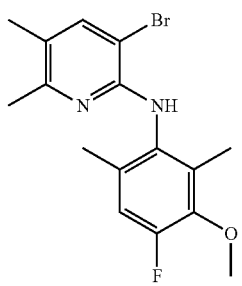

Step 1: Synthesis of Compound Int_5-2

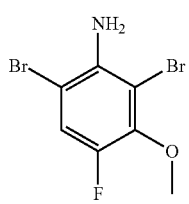

Int_5-1 (23.0 g, 163 mmol) was dissolved in acetonitrile (400 mL), and NBS (72.5 g, 407 mmol) was slowly added thereto. The reaction solution was stirred at room temperature for 5 h. TLC monitoring showed the reaction was completed. Water (500 mL) was added to the reaction solution. The aqueous phase was extracted with ethyl acetate (500 mL×3), and the organic phase was dried over anhydrous sodium sulfate. The organic phase was concentrated under reduced pressure to give a crude product. The crude Int_5-3 (2.00 g, 11.8 mmol) and int_1-6 (3.44 g, 13.0 mmol) were dissolved in DME (25 mL), and Cs$_2$CO$_3$ (9.24 g, 28.4 mmol), Xantphos (684 mg, 1.18 mmol), and Pd$_2$(dba)$_3$ (1.08 g, 1.18 mmol) were added. The reaction solution was purged with nitrogen three times, heated to 90° C., and reacted for 16 h. LC-MS monitoring showed the reaction was completed. After the reaction solution was cooled to room temperature, water (50 mL) was added to the reaction solution. The aqueous phase was extracted with ethyl acetate (50 mL×3), and the organic phase was dried over anhydrous sodium sulfate. The organic phase was concentrated under reduced pressure to give a crude product. The crude product was purified by preparative column chromatography (ISCOR; Silica Flash Column, Eluent of 0-50% THF/Petroleum ether gradient) to give a solid (3.8 g, 91.3% yield).

¹H NMR: (400 MHz, DMSO-d6) δ 7.59 (s, 1H), 7.32 (s, 1H), 7.00 (d, J=12.0 Hz, 1H), 3.78 (s, 3H), 2.08 (s, 3H), 2.06 (s, 6H), 2.02 (s, 3H).

ESI-MS m/z: 353 [M+H]⁺

Step 4: Synthesis of Compound Int_5-5

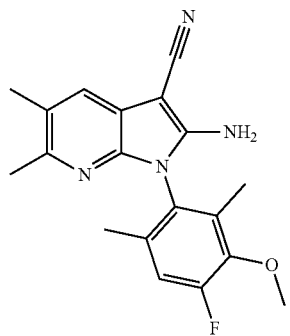

int_5-5

Int_1-8 (823 mg, 12.5 mmol, 784 μL) and Cs₂CO₃ (3.69 g, 11.3 mmol) were dissolved in DMF (20 mL). The reaction solution was heated to 40° C. and reacted for 0.5 h. int_5-4 (2.00 g, 5.66 mmol), CuI (324 mg, 1.70 mmol), and (1R, 2R)—N1,N2-dimethylcyclohexane-1,2-diamine (242 mg, 1.70 mmol) were added to the reaction solution. The reaction solution was purged with nitrogen three times, heated to 100° C., and reacted for 16 h. LC-MS monitoring showed the reaction was completed. After the reaction solution was cooled to room temperature, water (50 mL) was added to the reaction solution. The aqueous phase was extracted with ethyl acetate (50 mL×3), and the organic phase was dried over anhydrous sodium sulfate. The organic phase was concentrated under reduced pressure to give a crude product. The crude product was purified by preparative column chromatography (ISCOR; Silica Flash Column, Eluent of 0-50% THF/Petroleum ether gradient) to give a solid (400 mg, 20.9% yield).

ESI-MS m/z: 339 [M+H]⁺.

Step 5: Synthesis of Compound Int_5-6

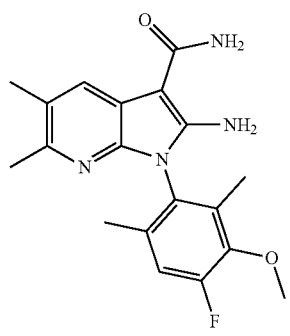

int_5-6

At 0° C., sulfuric acid (6 mL) was slowly added to int_5-5 (0.500 g, 1.48 mmol). The reaction solution was reacted at 25° C. for 2 h. LC-MS monitoring showed the reaction was completed. Ice water (30 mL) was slowly added to the reaction solution. The aqueous phase was adjusted to pH 8 with saturated aqueous sodium bicarbonate solution and extracted with ethyl acetate (50 mL×3), and the organic phase was dried over anhydrous sodium sulfate. The organic phase was concentrated under reduced pressure to give a crude product. The crude product was purified by preparative column chromatography (ISCOR; Silica Flash Column, Eluent of 0-80% EA/Petroleum ether gradient) to give a solid (300 mg, 57% yield).

MS (ESI): 357 [M+H]⁺.

Step 6: Synthesis of Compound 5

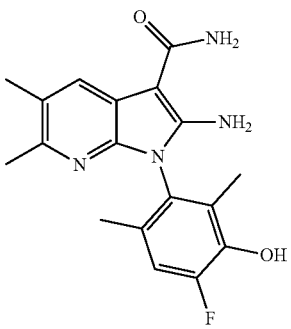

5

Int_1-10 (0.300 g, 842 μmol) was dissolved in dichloromethane (3 mL) under nitrogen atmosphere, and BBr₃ (2.11 g, 8.42 mmol, 811 μL) was added to the reaction solution at 0° C. The reaction solution was reacted at 0° C. for 2 h under nitrogen atmosphere. LC-MS monitoring showed the reaction was completed. The reaction solution was adjusted to pH 7 with saturated aqueous sodium carbonate solution and extracted with ethyl acetate (40 mL×3), and the organic phase was dried over anhydrous sodium sulfate. The organic phase was concentrated under reduced pressure to give a crude product. The crude product was purified by preparative column chromatography (ISCO®; Silica Flash Column, Eluent of 0-10% MeOH/DCM gradient) to give compound 5 (150 mg, 52.1% yield)

¹H NMR (400 MHZ, DMSO-d6) δ 7.83 (s, 1H), 7.10 (d, J=11.5 Hz, 1H), 6.86-6.77 (m, 2H), 6.65 (br s, 2H), 2.26 (s, 3H), 2.24 (s, 3H), 1.76 (s, 3H), 1.71 (s, 3H).

MS (ESI): 343 [M+H]⁺.

Example 4. Synthesis of Compound 6 and Compound 7

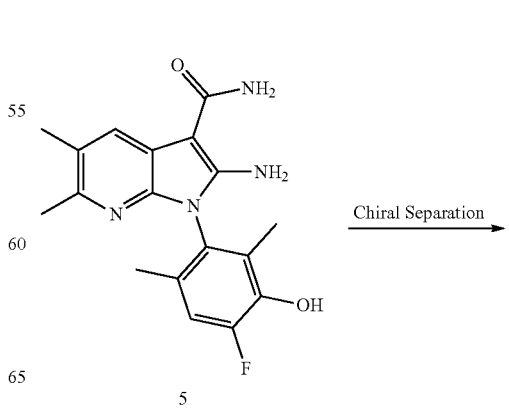

5

-continued

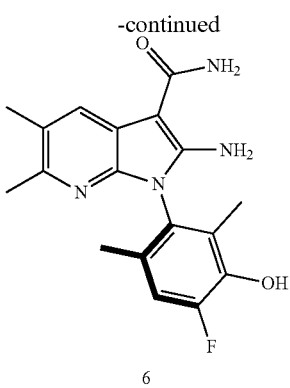

6

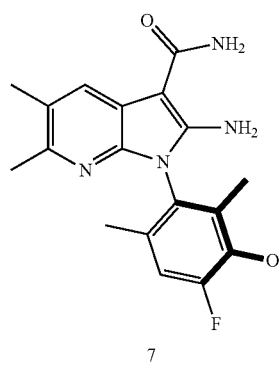

7

Compound 5 (150 mg, 438 µmol) was subjected to preparative SFC chiral resolution (column: DAICEL CHIRALPAK AD (250 mm×30 mm, 10 µm); mobile phase: A: $CO_2$, B: EtOH (0.1% $NH_3H_2O$); B %: 25%-25%, min) to give compound 6 (30 mg, 40% yield) and compound 7 (30 mg, 40% yield).

Compound 7: $^1$H NMR (400 MHZ, DMSO-d6) δ 9.56 (br s, 1H), 7.83 (s, 1H), 7.10 (d, J=11.5 Hz, 1H), 6.82 (br s, 2H), 6.65 (br s, 2H), 2.26 (s, 3H), 2.24 (s, 3H), 1.76 (s, 3H), 1.71 (s, 3H).

MS (ESI): 343 [M+H]$^+$.

Analytical SFC retention time: 3.545 min (Instrument: Waters UPCC with PDA Detector; Column: Chiralpak AD-3, 150×4.6 mm, I.D., 3 µm; Mobile phase: A: $CO_2$, B: Ethanol (0.05% DEA); Gradient: from 5% to 40% of B in 4 min and from 40% to 5% of B in 0.2 min, then hold 5% of B for 1.8 min; Flow rate: 2.5 mL/min; Column temp: 35° C.; ABPR: 1500 psi).

Compound 6: $^1$H NMR (400 MHZ, DMSO-d6) δ 9.55 (d, J=1.3 Hz, 1H), 7.83 (s, 1H), 7.10 (d, J=11.5 Hz, 1H), 6.85-6.77 (m, 2H), 6.65 (br s, 2H), 2.27 (s, 3H), 2.25 (s, 3H), 1.76 (s, 3H), 1.71 (s, 3H).

MS (ESI): 343 [M+H]$^+$.

Analytical SFC retention time: 3.727 min (Instrument: Waters UPCC with PDA Detector; Column: Chiralpak AD-3, 150×4.6 mm, I.D., 3 µm; Mobile phase: A: $CO_2$, B: Ethanol (0.05% DEA); Gradient: from 5% to 40% of B in 4 min and from 40% to 5% of B in 0.2 min, then hold 5% of B for 1.8 min; Flow rate: 2.5 mL/min; Column temp.: 35° C.; ABPR: 1500 psi).

Example 5. Synthesis of Compound 9

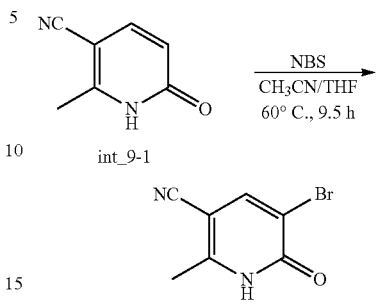

int_9-1

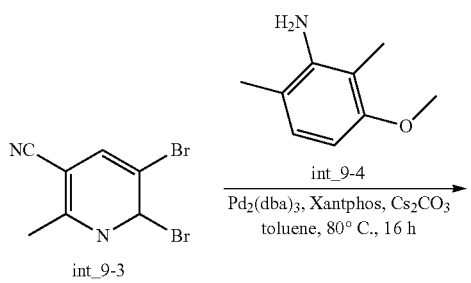

int_9-3

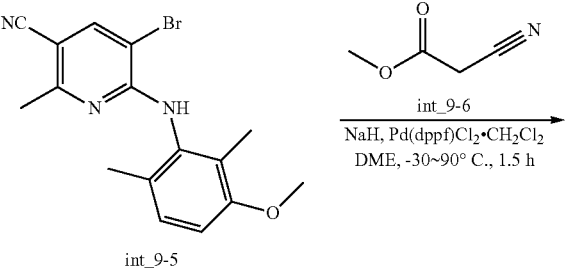

int_9-5

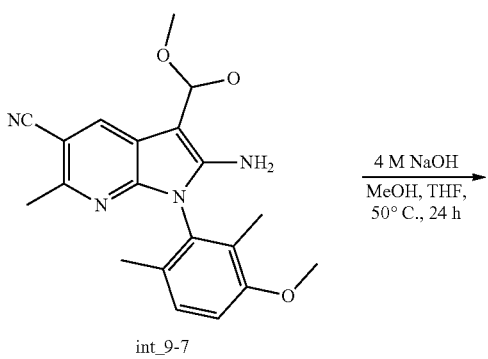

int_9-7

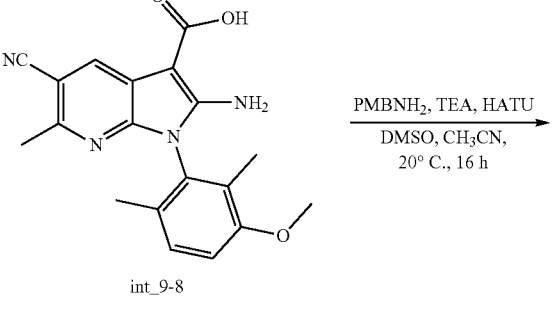

int_9-8

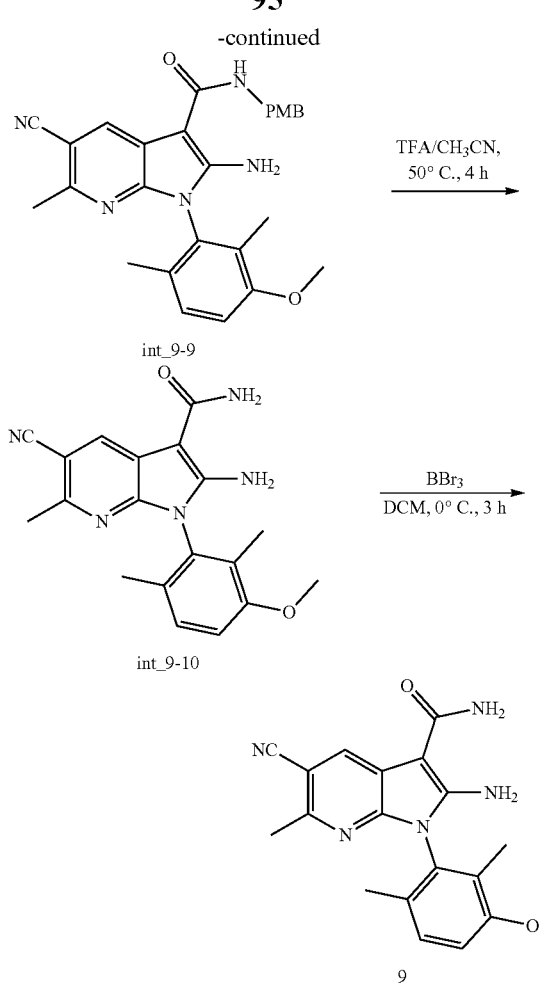

Step 2: Synthesis of Compound Int_9-3

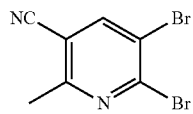

POBr₃ (81.4 g, 284 mmol, 28.9 mL) was heated to 60° C., and then int_9-2 (6.05 g, 28.4 mmol) was slowly added to POBr₃. The reaction solution was heated to 100° C. and reacted for 1 h. TLC monitoring showed the reaction was completed. The reaction solution was cooled to room temperature, and saturated aqueous sodium bicarbonate solution (800 mL) was added to the reaction solution to adjust the pH value to 8. The aqueous phase was extracted with ethyl acetate (500 mL×3), and the organic phase was dried over anhydrous sodium sulfate. The organic phase was concentrated under reduced pressure to give a crude product. The crude product was purified by preparative column chromatography (SiO₂, PE/EtOAc=10/1) to give a solid (6.1 g, 77.9% yield).

¹H NMR: (400 MHz, CHLOROFORM-d) δ 8.03 (s, 1H), 2.72 (s, 3H).

Step 3: Synthesis of Compound Int_9-5

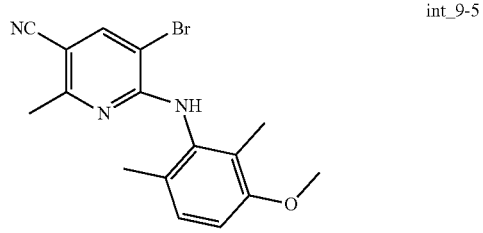

Step 1: Synthesis of Compound Int_9-2

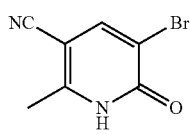

Int_9-1 (7.30 g, 41.0 mmol) was dissolved in THF (25 mL), and NBS (7.30 g, 41.0 mmol) was slowly added to the reaction solution. The reaction solution was heated to 60° C. and stirred for 9.5 h. TLC monitoring showed the reaction was completed. Water (30 mL) was added to the reaction solution, and a solid precipitated. The reaction solution was filtered. The filter cake was washed with water (10 mL), collected, and dried under vacuum to give a crude product (6.05 g, 69.3% yield). The crude product was directly used in the next step.

¹H NMR: (400 MHz, DMSO-d6) δ 12.91 (br s, 1H), 8.19 (s, 1H), 2.38 (s, 3H).

Int_9-3 (3.80 g, 13.8 mmol) and int_9-4 (2.50 g, 16.5 mmol) were dissolved in toluene (40 mL), and Cs₂CO₃ (4.71 g, 14.5 mmol), Xantphos (797 mg, 1.38 mmol), and Pd:(dba)₃ (1.26 g, 1.38 mmol) were added. The reaction solution was purged with nitrogen three times, heated to 80° C., and reacted for 16 h. LC-MS monitoring showed the reaction was completed. After the reaction solution was cooled to room temperature, water (100 mL) was added to the reaction solution. The aqueous phase was extracted with ethyl acetate (200 mL×3), and the organic phase was dried over anhydrous sodium sulfate. The organic phase was concentrated under reduced pressure to give a crude product. The crude product was purified by preparative column chromatography (SiO₂, PE/EtOAc=30/1) to give a solid (1.2 g, 25.1% yield).

¹H NMR: (400 MHZ, CHLOROFORM-d) δ 7.81 (s, 1H), 7.07 (d, J=8.4 Hz, 1H), 6.79 (d, J=8.5 Hz, 2H), 3.84 (s, 3H), 2.42 (s, 3H), 2.12 (s, 3H), 2.05 (s, 3H).

Step 4: Synthesis of Compound Int_9-7

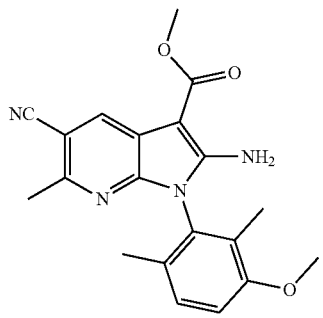

Int_9-6 (859 mg, 8.66 mmol, 767 μL) was dissolved in DME (12 mL). The reaction solution was cooled to −30° C., and NaH (693 mg, 17.3 mmol, 60% purity) was slowly added to the reaction solution under nitrogen atmosphere. The reaction solution was heated to 0° C. and reacted for 0.5 h. Int_9-5 (500 mg, 1.44 mmol) and Pd(dppf)Cl$_2$·CH$_2$Cl$_2$ (118 mg, 144 μmol) were then added to the reaction solution at 0° C. The reaction solution was heated to 90° C. and reacted for 1 h under nitrogen atmosphere. LC-MS monitoring showed the reaction was completed. After the reaction solution was cooled to room temperature, water (50 mL) was added to the reaction solution. The aqueous phase was extracted with ethyl acetate (50 mL×3), and the organic phase was dried over anhydrous sodium sulfate. The organic phase was concentrated under reduced pressure to give a crude product. The crude product was purified by preparative column chromatography (SiO$_2$, PE/EtOAc=3/1) to give a solid (423 mg, 80.7% yield).

$^1$H NMR: (400 MHZ, CHLOROFORM-d) δ 8.16 (br s, 1H), 7.22 (d, J=8.5 Hz, 1H), 6.97 (d, J=8.4 Hz, 1H), 5.72 (br s, 2H), 3.95 (s, 3H), 3.88 (s, 3H), 2.63 (s, 3H), 1.90 (s, 3H), 1.83 (s, 3H).

ESI-MS m/z: 365 [M+H]$^+$.

Step 5: Synthesis of Compound Int_9-8

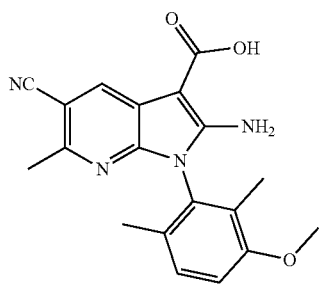

Int_9-7 (335 mg, 919 μmol) and NaOH (4 M, 6.89 mL) were dissolved in a mixed solvent of methanol (6 mL) and tetrahydrofuran (6 mL). The reaction solution was heated to 50° C. and reacted for 24 h. TLC monitoring showed the reaction was completed. The reaction solution was cooled to room temperature, and tetrahydrofuran (10 mL) was added to the reaction solution. The resulting mixture was concentrated under reduced pressure to give a solid, which was dissolved in DMSO (10 mL) and filtered. The filter cake was washed with water (10 mL), collected, and dried under vacuum to give a crude product (128 mg, 40% yield), which was directly used in the next step.

ESI-MS m/z: 351 [M+H]$^+$.

Step 6: Synthesis of Compound Int_9-9

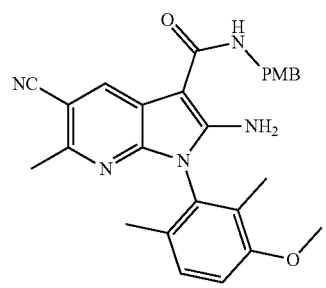

Int_9-8 (385 mg, 1.10 mmol), PMBNH$_2$ (756 mg, 5.51 mmol, 716 μL), and TEA (893 mg, 8.82 mmol, 1.23 mL) were dissolved in a mixed solvent of acetonitrile (15 mL) and DMSO (15 mL), and HATU (1.47 g, 3.86 mmol) was slowly added to the reaction solution at 0° C. The reaction solution was then heated to 20° C. and reacted for 16 h. LC-MS monitoring showed the reaction was completed. Water (100 mL) was added to the reaction solution. The aqueous phase was extracted with ethyl acetate (100 mL×3), and the organic phase was dried over anhydrous sodium sulfate. The organic phase was concentrated under reduced pressure to give a crude product. The crude product was purified by preparative column chromatography (SiO$_2$, PE/EtOAc=2/1) to give a solid (150 mg, 29% yield).

$^1$H NMR: (400 MHz, CHLOROFORM-d) δ 7.71 (s, 1H), 7.38 (d, J=8.6 Hz, 2H), 7.24 (d, J=8.4 Hz, 1H), 6.99 (d, J=8.4 Hz, 1H), 6.96 (br d, J=8.6 Hz, 2H), 6.10 (br s, 2H), 5.77 (s, 1H), 4.66 (d, J=5.5 Hz, 2H), 3.91 (s, 3H), 3.85 (s, 3H), 2.62 (s, 3H), 1.92 (s, 3H), 1.85 (s, 3H).

ESI-MS m/z: 470 [M+H]$^+$.

Step 7: Synthesis of Compound Int_9-10

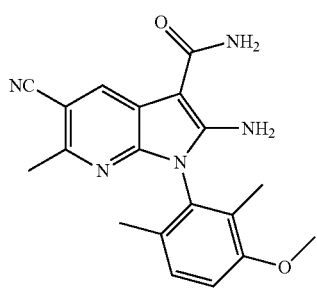

Int_9-9 (150 mg, 319 μmol) and TFA (3 mL) were dissolved in acetonitrile (1 mL). The reaction solution was then heated to 50° C. and reacted for 4 h. LC-MS monitoring showed the reaction was completed. Saturated aqueous sodium bicarbonate solution (20 mL) was added to the reaction solution. The aqueous phase was extracted with ethyl acetate (30 mL×3), and the organic phase was dried over anhydrous sodium sulfate. The organic phase was concentrated under reduced pressure to give a crude product. The crude product was purified by preparative plate chromatography (SiO₂, PE/EtOAc=2/3) to give a solid (53 mg, 47.7% yield).

ESI-MS m/z: 350 [M+H]⁺.

Step 8: Synthesis of Compound 9

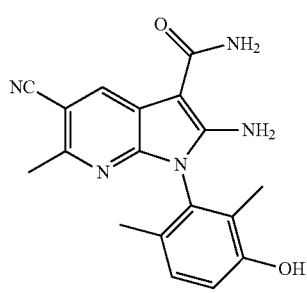

9

Int_9-10 (53.1 mg, 152 μmol) was dissolved in dichloromethane (3 mL) under nitrogen atmosphere, and BBr₃ (653 mg, 2.60 mmol, 251 μL) was added to the reaction solution at 0° C. The reaction solution was reacted at 0° C. for 3 h under nitrogen atmosphere. LC-MS monitoring showed the reaction was completed. Ice water (20 mL) was slowly added to the reaction solution. The aqueous phase was adjusted to pH 8 with saturated aqueous sodium bicarbonate solution and extracted with ethyl acetate (30 mL×3), and the organic phase was dried over anhydrous sodium sulfate. The organic phase was concentrated under reduced pressure to give a crude product. The crude product was purified by preparative column chromatography (SiO₂, PE/EtOAc=1/2) to give compound 9 (40 mg, 78.5% yield).

¹H NMR: (400 MHZ, DMSO-d6) δ 9.62 (br s, 1H), 8.41 (s, 1H), 7.15 (s, 2H), 7.08 (d, J=8.1 Hz, 1H), 6.93 (d, J=8.4 Hz, 1H), 6.91 (br s, 2H), 2.54 (s, 3H), 1.74 (s, 3H), 1.65 (s, 3H).

MS (ESI): 336 [M+H]⁺.

Example 6. Synthesis of Compound 10 and Compound 11

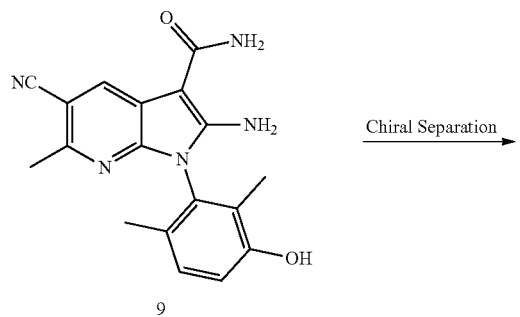

9

Chiral Separation →

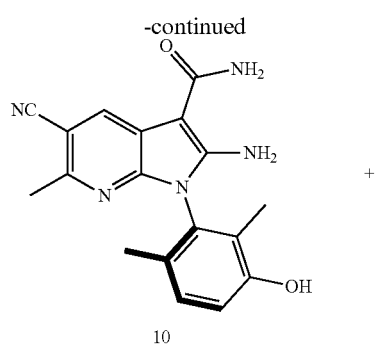

10

+

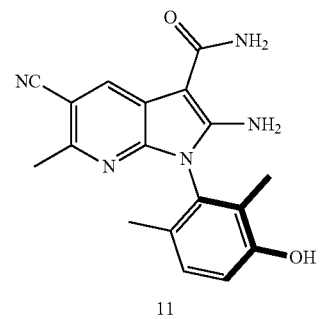

11

Compound 9 (40 mg, 119 μmol) was subjected to preparative SFC chiral resolution (column: DAICEL CHIRALCEL OJ (250 mm×30 mm, 10 μm); mobile phase: A: CO₂, B: EtOH (0.1% NH₃H₂O); B %: 30%-30%, min) to give compound 10 (9 mg, 45% yield) and compound 11 (10 mg, 50% yield).

Compound 10: ¹H NMR: (400 MHZ, DMSO-d6) δ 9.62 (br s, 1H), 8.41 (s, 1H), 7.15 (s, 2H), 7.08 (d, J=8.1 Hz, 1H), 6.93 (d, J=8.4 Hz, 1H), 6.91 (br s, 2H), 2.54 (s, 3H), 1.74 (s, 3H), 1.65 (s, 3H).

MS (ESI): 336 [M+H]⁺.

Analytical SFC retention time: 3.941 min (Instrument: Waters UPCC with PDA Detector; Column: Chiralcel OJ-3, 150×4.6 mm, I.D., 3 μm; Mobile phase: A: CO₂, B: Ethanol (0.05% DEA); Gradient: from 5% to 40% of B in 4 min and hold 40% for 2 min, then 5% of B for 2 min; Flow rate: 2.5 mL/min; Column temp: 35° C.; ABPR: 1500 psi).

Compound 11: ¹H NMR: (400 MHZ, DMSO-d6) δ 9.61 (s, 1H), 8.41 (s, 1H), 7.15 (s, 2H), 7.08 (d, J=8.4 Hz, 1H), 6.93 (d, J=8.1 Hz, 1H), 6.91 (br s, 2H), 2.58-2.52 (m, 3H), 1.74 (s, 3H), 1.65 (s, 3H).

MS (ESI): 336 [M+H]⁺.

Analytical SFC retention time: 4.240 min (Instrument: Waters UPCC with PDA Detector; Column: Chiralcel OJ-3, 150×4.6 mm, I.D., 3 μm; Mobile phase: A: CO₂, B: Ethanol (0.05% DEA); Gradient: from 5% to 40% of B in 4 min and hold 40% for 2 min, then 5% of B for 2 min; Flow rate: 2.5 mL/min; Column temp.: 35° C.; ABPR: 1500 psi).

Example 7. Synthesis of Compound 12

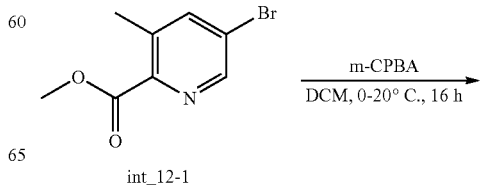

int_12-1

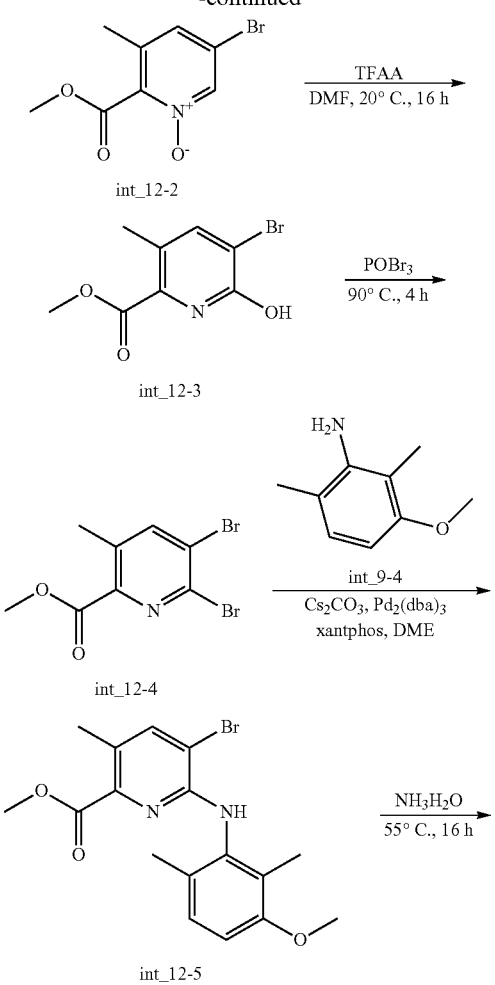
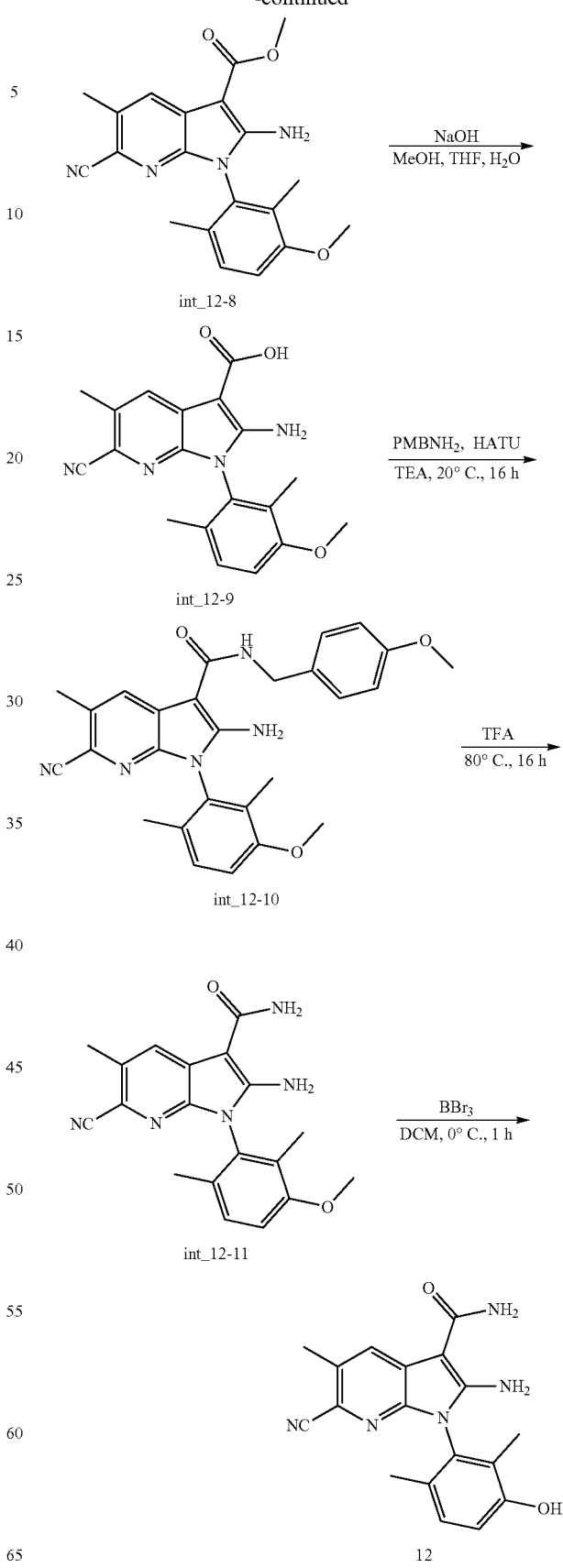

Step 1: Synthesis of Compound Int_12-2

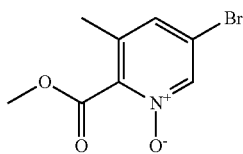

Int_12-1 (40.0 g, 174 mmol) was dissolved in DCM (1500 mL), and m-CPBA (106 g, 522 mmol, 85.0% purity) was slowly added to the reaction solution at 0° C. The reaction solution was heated to room temperature and stirred for 16 h. TLC monitoring showed the reaction was completed. The reaction solution was filtered to remove excess m-CPBA, and the filtrate was collected. The filtrate was added to a saturated $Na_2S_2O_3$ solution and stirred for 1 h. The aqueous phase was extracted with ethyl acetate (200 mL×3), and the organic phase was dried over anhydrous sodium sulfate. The organic phase was concentrated under reduced pressure to give a crude product. The crude product was purified by preparative column chromatography (ISCO®; Silica Flash Column, Eluent of 0-30% EA/Petroleum ether gradient) to give a solid (17 g, 39.7% yield).

$^1$H NMR (400 MHZ, CHLOROFORM-d) δ=8.18 (d, J=0.6 Hz, 1H), 7.23 (s, 1H), 7.20 (s, 1H), 3.94 (s, 3H), 2.22 (s, 3H).

Step 2: Synthesis of Compound Int_12-3

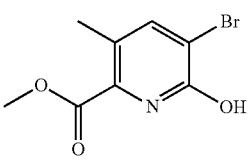

Int_12-2 (16.0 g, 65.0 mmol) was dissolved in DMF (200 mL), and TFAA (150 g, 715 mmol, 99.4 mL) was slowly added to the reaction solution at 20° C. The reaction solution was stirred at room temperature for 16 h. TLC monitoring showed the reaction was completed. The reaction solution was poured into ice water and neutralized by adding saturated sodium bicarbonate solution. The aqueous phase was extracted with ethyl acetate (200 mL×3), and the organic phase was dried over anhydrous sodium sulfate. The organic phase was concentrated under reduced pressure to give a crude product. The crude product was purified by preparative column chromatography (ISCOR; Silica Flash Column, Eluent of 0-10% EA/Petroleum ether gradient) to give a solid (12 g, 75% yield).

Step 3: Synthesis of Compound Int_12-4

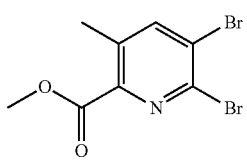

Int_12-3 (4.00 g, 16.3 mmol) was slowly added to $POBr_3$ (46.6 g, 163 mmol, 16.5 mL). The reaction solution was heated to 90° C. and reacted for 4 h. TLC monitoring showed the reaction was completed. The reaction solution was cooled to room temperature and poured into ice water. The aqueous phase was extracted with dichloromethane (100 mL×3), and the organic phase was dried over anhydrous sodium sulfate. The organic phase was concentrated under reduced pressure to give a crude product. The crude product was purified by preparative column chromatography (ISCOR; Silica Flash Column, Eluent of 0-10% EA/Petroleum ether gradient) to give a solid (3 g, 59.7% yield).

$^1$H NMR (400 MHZ, CHLOROFORM-d) δ=7.87 (s, 1H), 3.99 (s, 3H), 3.52 (s, 1H), 2.56 (s, 3H).

Step 4: Synthesis of Compound Int_12-5

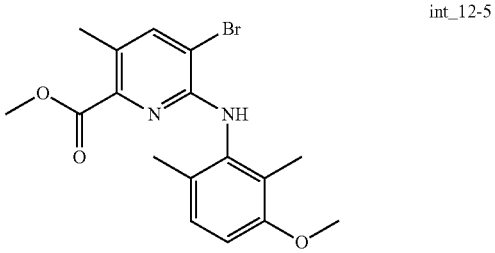

Int_12-4 (2.00 g, 6.47 mmol) and int_9-4 (979 mg, 6.47 mmol) were dissolved in DME (30.0 mL), and $Cs_2CO_3$ (4.22 g, 13.0 mmol), Xantphos (375 mg, 647 μmol), and $Pd_2(dba)_3$ (593 mg, 647 μmol) were added. The reaction solution was purged with nitrogen three times, heated to 95° C., and reacted for 16 h. LC-MS monitoring showed the reaction was completed. After the reaction solution was cooled to room temperature, water (50 mL) was added to the reaction solution. The aqueous phase was extracted with ethyl acetate (50 mL×3), and the organic phase was dried over anhydrous sodium sulfate. The organic phase was concentrated under reduced pressure to give a crude product. The crude product was purified by preparative column chromatography (IS-COR; Silica Flash Column, Eluent of 0-10% EA/Petroleum ether gradient) to give a solid (1 g, 40.7% yield).

ESI-MS m/z: 379 $[M+H]^+$.

Step 5: Synthesis of Compound Int_12-6

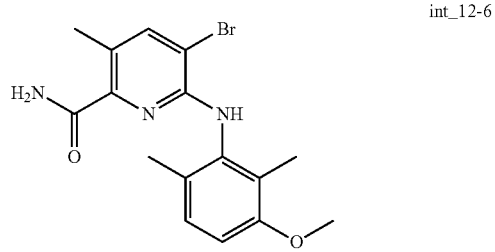 [SMILES: COc1ccc(C)c(Nc2nc(C(N)=O)c(C)cc2Br)c1C]

Int_12-5 (1.00 g, 2.64 mmol) was dissolved in ammonia water (20.0 mL). The reaction solution was heated to 55° C. and reacted for 16 h. LC-MS monitoring showed the reaction was completed. After the reaction solution was cooled to room temperature, the aqueous phase was extracted with ethyl acetate (30 mL×3), and the organic phase was dried over anhydrous sodium sulfate. The organic phase was concentrated under reduced pressure to give a crude product. The crude product was purified by preparative column chromatography (ISCOR; Silica Flash Column, Eluent of 0-20% EA/Petroleum ether gradient) to give a solid (0.6 g, 62.5% yield).

¹H NMR (400 MHZ, CHLOROFORM-d) δ=7.68 (s, 1H), 7.32-7.23 (m, 2H), 7.09 (d, J=8.4 Hz, 1H), 6.77 (d, J=8.4 Hz, 1H), 6.37 (s, 1H), 3.86 (s, 3H), 2.60 (s, 3H), 2.16 (s, 3H), 2.10 (s, 3H).

ESI-MS m/z: 364 [M+H]⁺.

Step 6: Synthesis of Compound Int_12-7

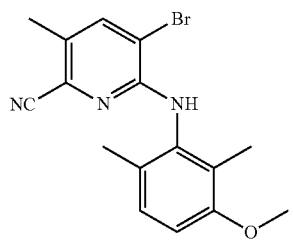

Int_12-6 (0.600 g, 1.65 mmol) was dissolved in tetrahydrofuran (10 mL), and TEA (1.08 g, 10.7 mmol, 1.49 mL) and TFAA (900 mg, 4.28 mmol, 595 μL) were slowly added to the reaction solution at 0° C. The reaction solution was heated to room temperature and stirred for 16 h. TLC monitoring showed the reaction was completed. The reaction solution was poured into ice water. The aqueous phase was extracted with ethyl acetate (50 mL×3), and the organic phase was dried over anhydrous sodium sulfate. The organic phase was concentrated under reduced pressure to give a crude product. The crude product was purified by preparative column chromatography (ISCOR; Silica Flash Column, Eluent of 0-20% EA/Petroleum ether gradient) to give a solid (550 mg, 96.4% yield).

¹H NMR (400 MHz, CHLOROFORM-d) δ=7.71 (s, 1H), 7.13-7.03 (m, 1H), 6.84-6.73 (m, 1H), 6.54-6.41 (m, 1H), 3.87 (s, 3H), 2.40 (s, 3H), 2.15 (s, 3H), 2.08 (s, 3H).

ESI-MS m/z: 346 [M+H]⁺.

Step 7: Synthesis of Compound Int_12-8

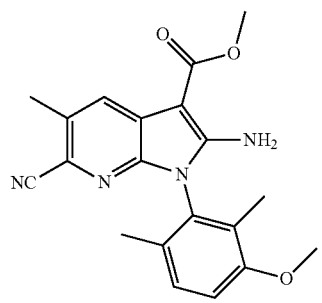

Int_9-6 (1.22 g, 8.66 mmol, 1.24 mL) was dissolved in DME (15 mL). The reaction solution was cooled to −30° C., and NaH (693 mg, 17.3 mmol, 60.0% purity) was slowly added to the reaction solution under nitrogen atmosphere. The reaction solution was heated to 0° C. and reacted for 0.5 h. Int_12-7 (500 mg, 1.44 mmol) and Pd(dppf)Cl₂·CH₂Cl₂ (118 mg, 144 μmol) were then added to the reaction solution at 0° C. The reaction solution was heated to 90° C. and reacted for 1 h under nitrogen atmosphere. LC-MS monitoring showed the reaction was completed. After the reaction solution was cooled to room temperature, water (50 mL) was added to the reaction solution. The aqueous phase was extracted with ethyl acetate (50 mL×3), and the organic phase was dried over anhydrous sodium sulfate. The organic phase was concentrated under reduced pressure to give a crude product. The crude product was purified by preparative column chromatography (ISCO®; Silica Flash Column, Eluent of 0-100% EA/Petroleum ether gradient) to give a solid (500 mg, 95.2% yield).

¹H NMR (400 MHZ, CHLOROFORM-d) δ=7.93-7.84 (m, 1H), 7.28 (s, 2H), 7.23 (d, J=8.3 Hz, 1H), 6.99 (d, J=8.4 Hz, 1H), 3.98 (s, 3H), 3.90 (s, 3H), 2.61 (s, 3H), 1.95-1.89 (m, 3H), 1.85 (s, 3H).

ESI-MS m/z: 365 [M+H]⁺.

Step 8: Synthesis of Compound Int_12-9

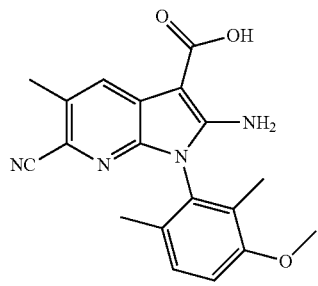

Int_12-8 (400 mg, 1.10 mmol) and NaOH (4.00 M, 8.23 mL) were dissolved in a mixed solvent of methanol (10 mL) and tetrahydrofuran (5 mL). The reaction solution was heated to 50° C. and reacted for 72 h. TLC monitoring showed the reaction was completed. The reaction solution was cooled to room temperature and concentrated under reduced pressure to give a solid, which was dissolved in water (30 mL). The aqueous phase was extracted with ethyl acetate (30 mL×3) and neutralized with 1 M aqueous hydrochloric acid solution to pH 5-6. The aqueous phase was then extracted with ethyl acetate (30 mL×3), and the organic phases at this time were combined and dried over anhydrous sodium sulfate. The organic phase was concentrated under reduced pressure to give a crude product (208 mg, 54% yield). The crude product was directly used in the next step.

ESI-MS m/z: 351 [M+H]⁺.

Step 9: Synthesis of Compound Int_12-10

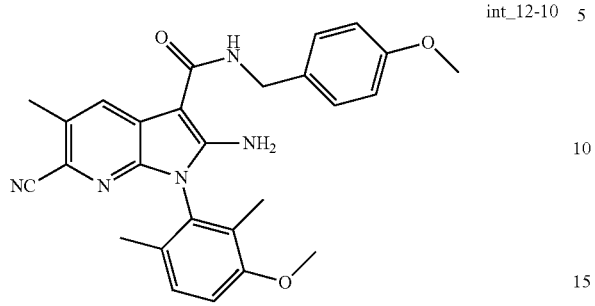

Int_12-9 (223 mg, 639 μmol), PMBNH₂ (263 mg, 1.92 mmol, 249 μL), and TEA (323 mg, 3.20 mmol, 445 μL) were dissolved in a mixed solvent of acetonitrile (5 mL) and DMSO (5 mL), and HATU (851 mg, 2.24 mmol) was slowly added to the reaction solution at 0° C. The reaction solution was then heated to 20° C. and reacted for 16 h. LC-MS monitoring showed the reaction was completed. Water (30 mL) was added to the reaction solution. The aqueous phase was extracted with ethyl acetate (30 mL×3), and the organic phase was dried over anhydrous sodium sulfate. The organic phase was concentrated under reduced pressure to give a crude product. The crude product was purified by preparative column chromatography (ISCO®; Silica Flash Column, Eluent of 0-10% EA/Petroleum ether gradient) to give a solid (160 mg, 53.3% yield).

¹H NMR (400 MHZ, CHLOROFORM-d) δ=7.43-7.36 (m, 3H), 7.26-7.20 (m, 1H), 6.96 (br d, J=8.6 Hz, 3H), 6.44-6.10 (m, 1H), 5.95-5.81 (m, 1H), 4.71-4.66 (m, 2H), 3.91 (s, 3H), 3.85 (s, 3H), 2.59 (s, 3H), 1.92 (s, 4H), 1.85 (s, 4H).

ESI-MS m/z: 470 [M+H]⁺.

Step 10: Synthesis of Compound Int_12-11

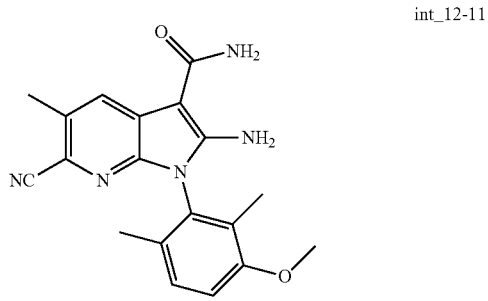

Int_12-10 (100 mg, 213 μmol) was dissolved in TFA (11.5 g, 101 mmol, 7.50 mL). The reaction solution was heated to 80° C. and reacted for 16 h under nitrogen atmosphere. LC-MS monitoring showed the reaction was completed. Saturated aqueous sodium bicarbonate solution (20 mL) was added to the reaction solution. The aqueous phase was extracted with ethyl acetate (30 mL×3), and the organic phase was dried over anhydrous sodium sulfate. The organic phase was concentrated under reduced pressure to give a crude product. The crude product was purified by preparative plate chromatography (SiO₂, PE/EtOAc=1/2) to give a solid (40 mg, 53.8% yield).

ESI-MS m/z: 350 [M+H]⁺.

Step 11: Synthesis of Compound 12

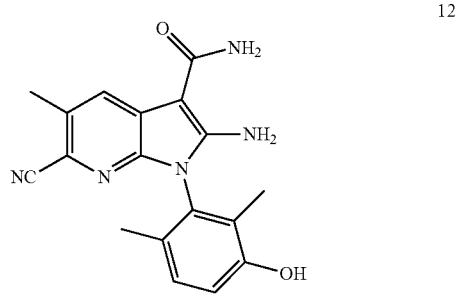 [SMILES: Cc1cc2c(C(N)=O)c(N)n(-c3c(C)ccc(O)c3C)c2nc1C#N]

Int_12-11 (35.0 mg, 100 μmol) was dissolved in dichloromethane (3 mL) under nitrogen atmosphere, and BBr₃ (376 mg, 1.50 mmol, 145 μL) was added to the reaction solution at 0° C. The reaction solution was reacted at 0° C. for 1 h under nitrogen atmosphere. LC-MS monitoring showed the reaction was completed. Ice water (20 mL) was slowly added to the reaction solution. The aqueous phase was adjusted to pH 8 with saturated aqueous sodium bicarbonate solution and extracted with ethyl acetate (30 mL×3), and the organic phase was dried over anhydrous sodium sulfate. The organic phase was concentrated under reduced pressure to give a crude product. The crude product was purified by preparative plate chromatography (SiO₂, PE/EtOAc=1/4) to give compound 12 (5.7 mg, 17% yield).

¹H NMR (400 MHZ, CHLOROFORM-d) δ=9.57 (s, 1H), 7.93 (s, 1H), 7.17 (br s, 2H), 7.13-7.04 (m, 3H), 6.94 (d, J=8.3 Hz, 1H), 6.84 (br s, 2H), 2.61 (s, 3H), 1.79 (s, 3H), 1.70 (s, 3H).

MS (ESI): 336 [M+H]⁺.

Example 8. Synthesis of Compound 15

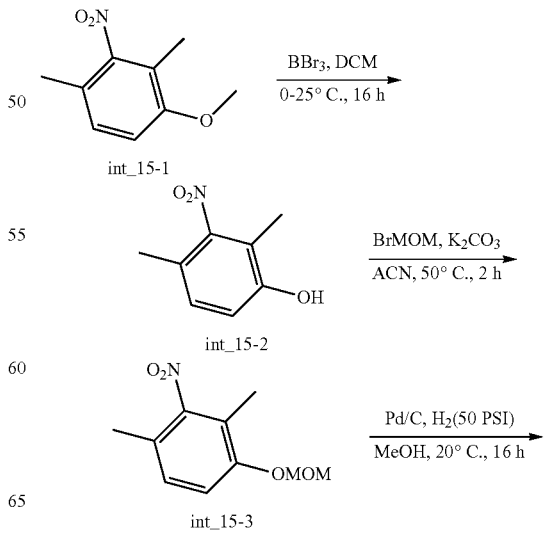

109
-continued

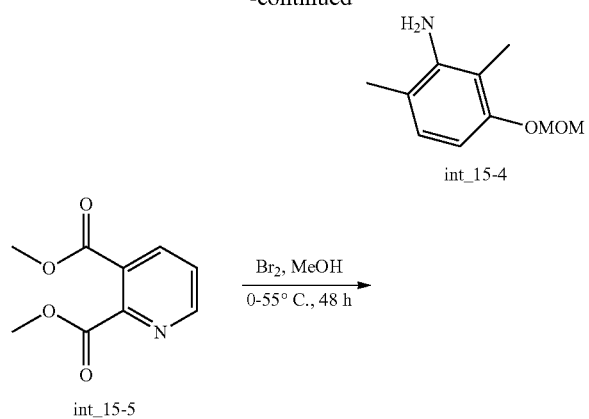

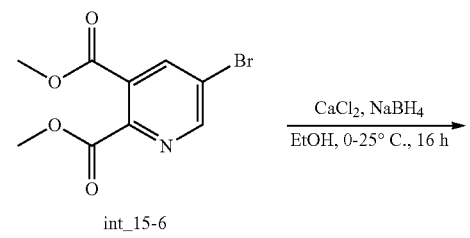

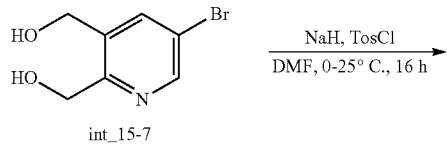

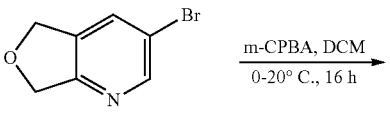

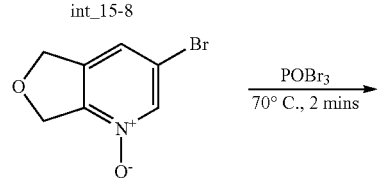

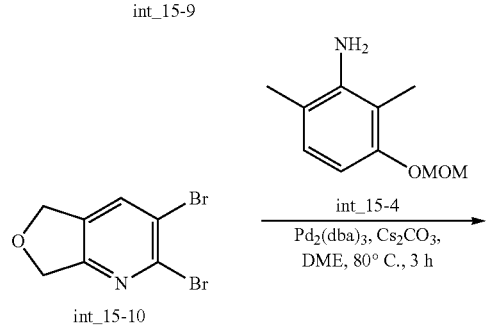

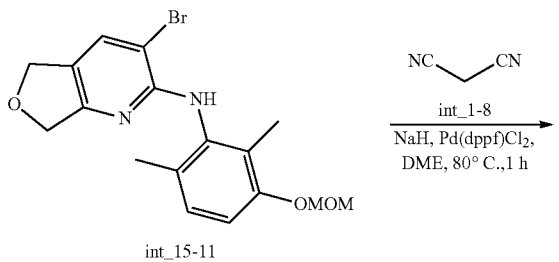

110
-continued

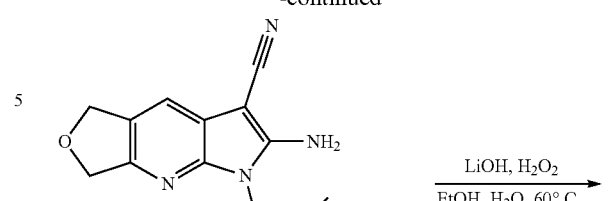

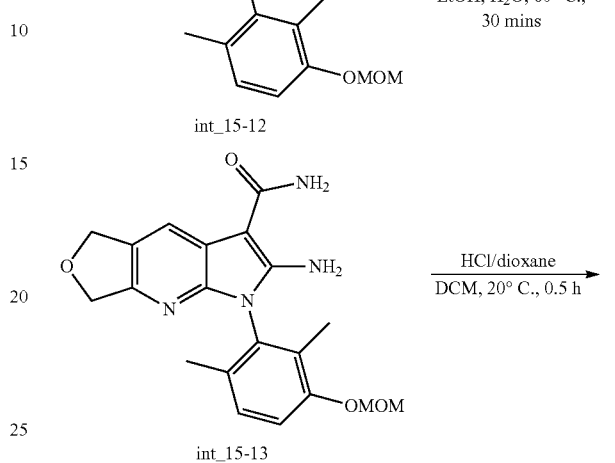

Step 1: Synthesis of Compound Int_15-2

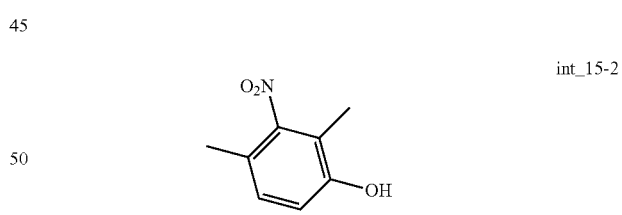

Int_15-1 (15.0 g, 82.8 mmol) was dissolved in DCM (150 mL), and BBr$_3$ (31.1 g, 124 mmol, 12.0 mL) was slowly added to the reaction solution at 0° C. under nitrogen atmosphere. The reaction solution was heated to room temperature and stirred for 16 h. TLC monitoring showed the reaction was completed. The reaction solution was cooled to 0° C., and methanol (100 mL) was added to the reaction solution. The reaction solution was stirred at room temperature for another 2 h and then concentrated under reduced pressure to give a crude product. The crude product was purified by preparative column chromatography (IS-COR: Silica Flash Column, Eluent of 0-80% EA/Petroleum ether gradient) to give a solid (12 g, 86.7% yield).

Step 2: Synthesis of Compound Int_15-3

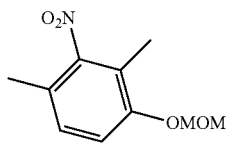

Int_15-2 (16.0 g, 65.0 mmol) and K$_2$CO$_3$ (18.2 g, 132 mmol) were dissolved in acetonitrile (100 mL), and bromomethyl methyl ether (9.87 g, 78.9 mmol, 6.45 mL) was slowly added to the reaction solution at 20° C. The reaction solution was heated to 50° C. and stirred for 2 h. TLC monitoring showed the reaction was completed. The reaction solution was concentrated under reduced pressure to give a crude product. The crude product was purified by preparative column chromatography (ISCOR: Silica Flash Column, Eluent of 0-30% EA/Petroleum ether gradient) to give a solid (10 g, 72.9% yield).

$^1$H NMR (400 MHZ, CHLOROFORM-d) δ=7.12-7.05 (m, 2H), 7.97 (s, 1H), 5.22 (s, 2H), 3.50 (s, 3H), 2.19-2.55 (d, 6H), 5.10 (s, 2H), 4.81 (s, 2H), 1.76 (s, 3H), 1.67 (s, 3H).

Step 3: Synthesis of Compound Int_15-4

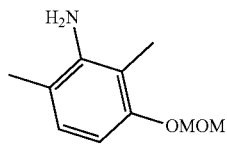

Int_15-3 (10.0 g, 47.4 mmol) and Pd/C (5 g, 10% purity) were dissolved in methanol (100 mL). The reaction solution was stirred at room temperature for 16 h under hydrogen atmosphere (50 psi). TLC monitoring showed the reaction was completed. The reaction solution was filtered to remove palladium on carbon, and the filtrate was concentrated under reduced pressure to give a crude product. The crude product was purified by preparative column chromatography (ISCO®: Silica Flash Column, Eluent of 0-30% EA/Petroleum ether gradient) to give a solid (8 g, 93.2% yield).

ESI-MS m/z: 182 [M+H]$^+$.

Step 4: Synthesis of Compound Int_15-6

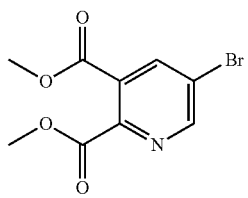

Int_15-5 (50.0 g, 256 mmol) was dissolved in methanol (500 mL), and Br$_2$ (81.9 g, 512 mmol, 26.4 mL) was slowly added to the reaction solution at 0° C. The reaction solution was heated to 55° C. and stirred for 48 h. LC-MS monitoring showed the reaction was completed. The reaction solution was concentrated under reduced pressure to give a crude product. The crude product was diluted with ammonia water to adjust the pH value to 8. The aqueous phase was extracted with ethyl acetate (300 mL×3), and the organic phase was dried over anhydrous sodium sulfate. The organic phase was concentrated under reduced pressure to give a crude product. The crude product was purified by preparative column chromatography (ISCOR: Silica Flash Column, Eluent of 0-50% EA/Petroleum ether gradient) to give a solid (56 g, 79.8% yield).

ESI-MS m/z: 274 [M+H]$^+$.

Step 5: Synthesis of Compound Int_15-7

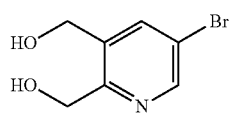

Under nitrogen atmosphere, int_15-6 (30.0 g, 109 mmol) was dissolved in ethanol (350 mL), NaBH$_4$ (24.9 g, 657 mmol) was slowly added to the reaction solution at 0° C., and then CaCl$_2$) (10.9 g, 98.5 mmol) was slowly added. The reaction solution was heated to room temperature and stirred for 16 h. LC-MS monitoring showed the reaction was completed. 2 N aqueous hydrochloric acid solution was added to the reaction solution to adjust the pH value to 2-3. The reaction solution was stirred at room temperature for another 2 h and then concentrated under reduced pressure to give a solid. The solid was neutralized with saturated aqueous sodium bicarbonate solution and adjusted to pH 7. The aqueous phase was extracted with ethyl acetate (500 mL×3), and the organic phase was dried over anhydrous sodium sulfate. The organic phase was concentrated under reduced pressure to give a crude product. The crude product was purified by preparative column chromatography (IS-COR: Silica Flash Column, Eluent of 0-80% EA/Petroleum ether gradient) to give a solid (15 g, 62.9% yield).

ESI-MS m/z: 217 [M+H]$^+$.

Step 6: Synthesis of Compound Int_15-8

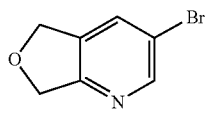

Int_15-7 (15.0 g, 68.8 mmol) was dissolved in DMF (200 mL) under nitrogen atmosphere, and NaH (16.5 g. 413 mmol, 60% purity) was slowly added to the reaction solution at 0° C. first. The reaction solution was stirred at 0° C. for 0.5 h, and TosCl (13.1 g, 68.8 mmol) was added to the reaction solution at 0° C. The reaction solution was heated to room temperature and reacted for 16 h. LC-MS monitoring showed the reaction was completed. Water (700 mL) was added to the reaction solution to quench the reaction. The aqueous phase was extracted with ethyl acetate (600 mL×3), and the organic phase was dried over anhydrous sodium sulfate. The organic phase was concentrated under reduced pressure to give a crude product. The crude product was purified by preparative column chromatography (ISCOR; Silica Flash Column, Eluent of 0-30% EA/Petroleum ether gradient) to give a solid (2.5 g, 18.2% yield). 1H NMR (400 MHZ, CHLOROFORM-d) d=7.70 (s, 1H), 5.02 (m, 2H), 4.92 (m, 2H).

Step 7: Synthesis of Compound Int_15-9

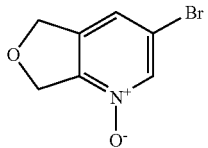

int_15-9

Int_15-8 (5.00 g, 25.0 mmol) was dissolved in DCM (100 mL), and m-CPBA (15.39 g, 25.0 mmol, 80% purity) was slowly added to the reaction solution at 0° C. The reaction solution was heated to room temperature and stirred for 16 h. LC-MS monitoring showed the reaction was completed. The reaction solution was concentrated under reduced pressure to give a crude product. The crude product was purified by preparative column chromatography (ISCOR: Silica Flash Column, Eluent of 0-100% EA/Petroleum ether gradient) to give a solid (5 g, 92.6% yield).

ESI-MS m/z: 216 [M+H]$^+$.

Step 8: Synthesis of Compound Int_15-10

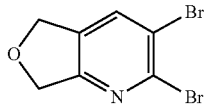

int_15-10

Int_15-9 (1.00 g, 4.63 mmol) was slowly added to POBr$_3$ (7.00 g, 24.4 mmol, 2.48 mL). The reaction solution was heated to 70° C. and reacted for 2 h. LC-MS monitoring showed the reaction was completed. The reaction solution was cooled to room temperature and concentrated under reduced pressure to give a crude product. The crude product was firstly purified by preparative column chromatography (ISCOR: Silica Flash Column, Eluent of 0-30% EA/Petroleum ether gradient) and then purified by preparative SFC (column: DAICEL CHIRALPAK AD (250 mm×30 mm, 10 μm); mobile phase: [Neu-EtOH]: B %: 30%-30%, min) to give a solid (0.3 g, 23.2% yield).

$^1$H NMR (400 MHZ, CHLOROFORM-d) δ=7.73 (s, 1H), 5.15-5.02 (m, 2H), 4.92-4.91 (m, 2H).

Step 9: Synthesis of Compound Int_15-11

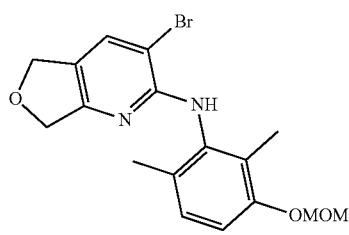

int_15-11

Int_15-10 (0.300 g, 1.08 mmol) and int_15-4 (292 mg, 1.61 mmol) were dissolved in DME (10.0 mL), and Cs$_2$CO$_3$ (701 mg, 2.15 mmol), Xantphos (62.2 mg, 108 μmol), and Pd$_2$(dba)$_3$ (98.5 mg, 108 μmol) were added. The reaction solution was purged with nitrogen three times, heated to 90° C., and reacted for 3 h. LC-MS monitoring showed the reaction was completed. After the reaction solution was cooled to room temperature, water (50 mL) was added to the reaction solution. The aqueous phase was extracted with ethyl acetate (50 mL×3), and the organic phase was dried over anhydrous sodium sulfate. The organic phase was concentrated under reduced pressure to give a crude product. The crude product was purified by preparative column chromatography (ISCO®; Silica Flash Column, Eluent of 0-20% EA/Petroleum ether gradient) to give a solid (0.3 g, 73.6% yield).

ESI-MS m/z: 379 [M+H]$^+$.

Step 10: Synthesis of Compound Int_15-12

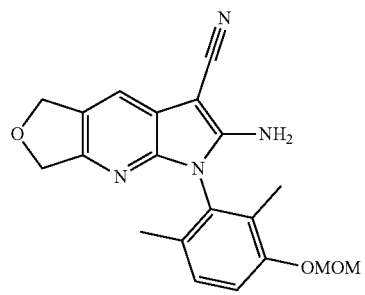

int_15-12

Int_1-8 (83.6 mg, 1.27 mmol, 79.6 μL) was dissolved in DME (5 mL). The reaction solution was cooled to −30° C., and NaH (236 mg, 5.91 mmol, 60% purity) was slowly added to the reaction solution under nitrogen atmosphere. The reaction solution was heated to 0° C. and reacted for 0.5 h. int_15-11 (0.160 g, 422 μmol) and Pd(dppf)CL$_2$·CH$_2$Cl$_2$ (34.45 mg, 42.19 μmol) were then added to the reaction solution at 0° C. The reaction solution was heated to 80° C. and reacted for 1 h under nitrogen atmosphere. LC-MS monitoring showed the reaction was completed. After the reaction solution was cooled to room temperature, water (10 mL) was added to the reaction solution. The aqueous phase was extracted with dichloromethane (10 mL×3), and the organic phase was dried over anhydrous sodium sulfate. The organic phase was concentrated under reduced pressure to give a crude product. The crude product was purified by preparative column chromatography (ISCOR; Silica Flash Column, Eluent of 0-50% EA/Petroleum ether gradient) to give a solid (110 mg, 71.6% yield).

$^1$H NMR (400 MHz, CHLOROFORM-d) δ=7.64 (s, 1H), 7.25-7.18 (m, 2H), 5.31-5.19 (m, 4H), 5.01 (s, 2H), 4.62 (s, 2H), 3.54 (s, 3H), 1.92 (d, J=19.2 Hz, 6H).

ESI-MS m/z: 365 [M+H]$^+$.

Step 11: Synthesis of Compound Int_15-13

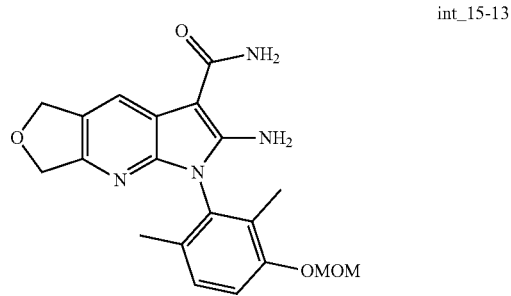

int_15-13

Int_15-12 (80.0 mg, 220 μmol) and LiOH·H$_2$O (64.48 mg, 1.54 mmol) were dissolved in a mixed solution of ethanol (6 mL) and water (2 mL), and H$_2$O$_2$ (360 mg, 2.85 mmol, 305 μL, 27% purity) was added dropwise to the reaction solution at 20° C. The reaction solution was heated to 60° C. and reacted for 0.5 h. LC-MS monitoring showed the reaction was completed. The reaction solution was concentrated under reduced pressure to give a crude product. The crude product was purified by preparative column chromatography (ISCOR; Silica Flash Column, Eluent of 0-100% EA/Petroleum ether gradient) to give a solid (65 mg, 77.4% yield).

MS (ESI): 383 [M+H]$^+$.

Step 12: Synthesis of Compound 15

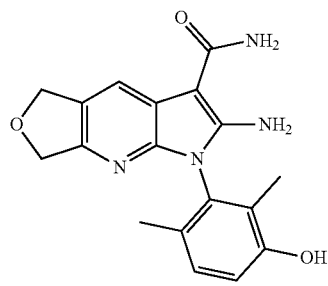

15

Int_15-13 (60.0 mg, 157 μmol) was dissolved in dichloromethane (3 mL) under nitrogen atmosphere, and an HCl/dioxane solution (4 M, 3.00 mL) was added to the reaction solution at 0° C. The reaction solution was reacted at 20° C. for 0.5 h under nitrogen atmosphere. LC-MS monitoring showed the reaction was completed. Ice water (20 mL) was slowly added to the reaction solution. The aqueous phase was adjusted to pH 8 with saturated aqueous sodium bicarbonate solution and extracted with dichloromethane (30 mL×3), and the organic phase was dried over anhydrous sodium sulfate. The organic phase was concentrated under reduced pressure to give a crude product. The crude product was purified by preparative column chromatography (SiO$_2$, DCM/MeOH=10/1) to give compound 15 (35 mg, 65.9% yield).

$^1$H NMR (400 MHZ, DMSO-d6) δ=9.53 (s, 1H), 7.97 (s, 1H), 7.06 (d, J=8.1 Hz, 1H), 6.96-6.87 (m, 3H), 6.74 (s, 2H), 5.10 (s, 2H), 4.81 (s, 2H), 1.76 (s, 3H), 1.67 (s, 3H).

MS (ESI): 339 [M+H]$^+$.

Example 9. Synthesis of Compound 16 and Compound 17

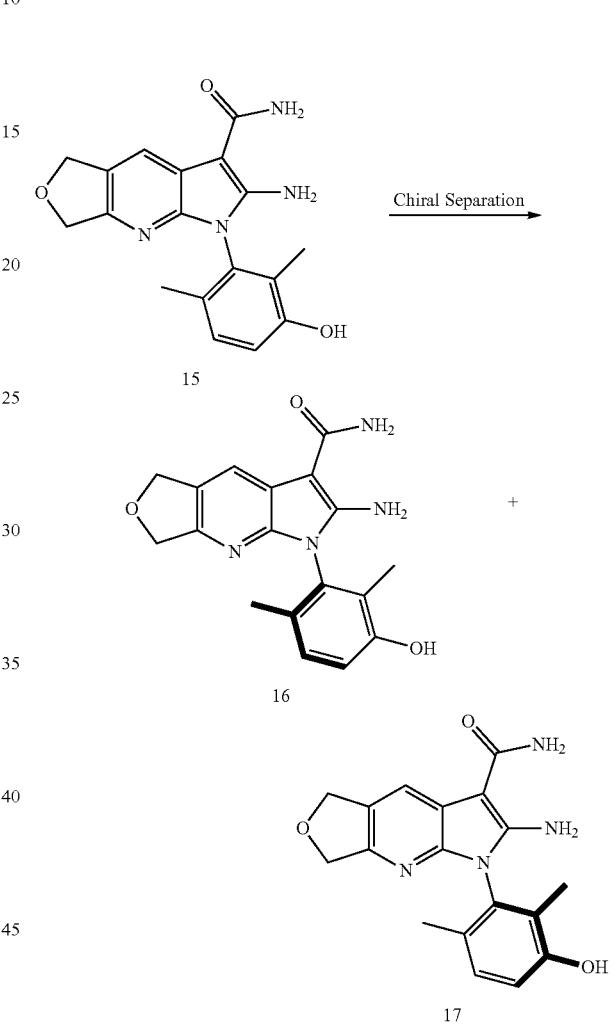

Compound 15 (35 mg, 103 μmol) was subjected to preparative SFC chiral resolution (column: DAICEL CHIRALPAK IG (250 mm×30 mm, 10 μm); mobile phase: A: CO$_2$, B: MeOH (0.1% NH$_3$H$_2$O): B %: 30%-30%, min) to give compound 16 (7 mg, 40% yield) and compound 17 (8 mg, 45.7% yield).

Compound 17: $^1$H NMR (400 MHZ, DMSO-d6) δ=9.50 (s, 1H), 7.94 (s, 1H), 7.03 (d, J=8.1 Hz, 1H), 6.93-6.84 (m, 3H), 6.71 (s, 2H), 5.07 (s, 2H), 4.78 (s, 2H), 1.73 (s, 3H), 1.64 (s, 3H).

MS (ESI): 339 [M+H]$^+$.

Analytical SFC retention time: 3.457 min (Instrument: Waters UPCC with PDA Detector: Column: Chiralpak IG-3, 100×4.6 mm, I.D., 3 μm; Mobile phase: A: CO$_2$, B: Methanol (0.05% DEA): Gradient: from 5% to 40% of B in 4 min and hold 40% for 0.5 min, then hold 5% of B for 1.5 min; Flow rate: 2.8 mL/min; Column temp.: 35° C.; ABPR: 1500 psi).

Compound 16: ¹H NMR (400 MHZ, DMSO-d6) δ=9.52 (s, 1H), 7.96 (s, 1H), 7.05 (d, J=8.1 Hz, 1H), 6.95-6.86 (m, 3H), 6.73 (s, 2H), 5.09 (s, 2H), 4.80 (s, 2H), 1.75 (s, 3H), 1.66 (s, 3H).
MS (ESI): 339 [M+H]⁺.
Analytical SFC retention time: 3.663 min (Instrument: Waters UPCC with PDA Detector; Column: Chiralpak IG-3, 100×4.6 mm, I.D., 3 μm; Mobile phase: A: CO$_2$, B: Methanol (0.05% DEA); Gradient: from 5% to 40% of B in 4 min and hold 40% for 0.5 min, then hold 5% of B for 1.5 min; Flow rate: 2.8 mL/min; Column temp.: 35° C.; ABPR: 1500 psi).
Example 10. Synthesis of Compound 96
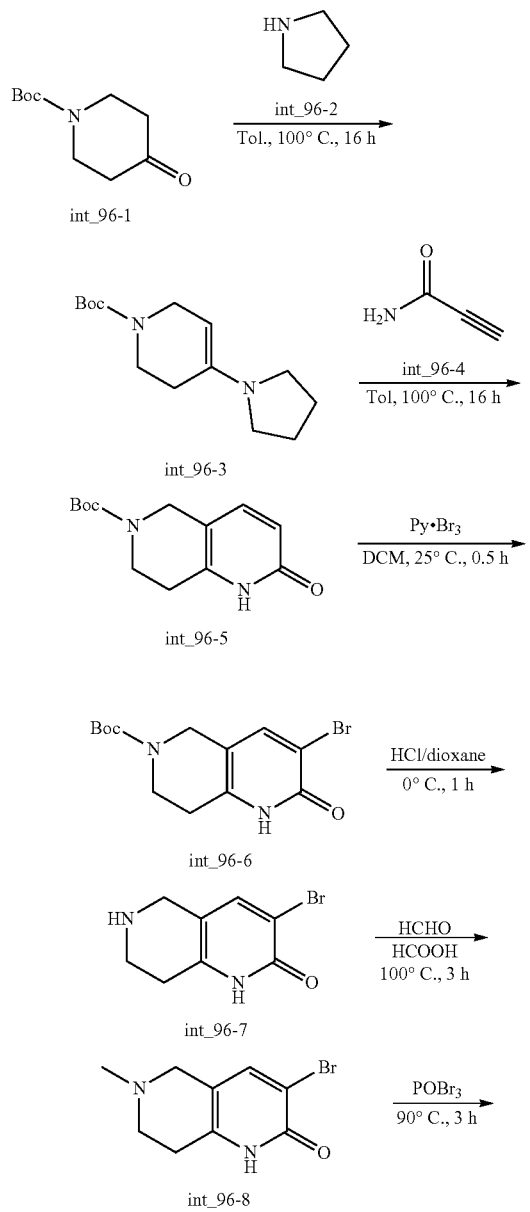
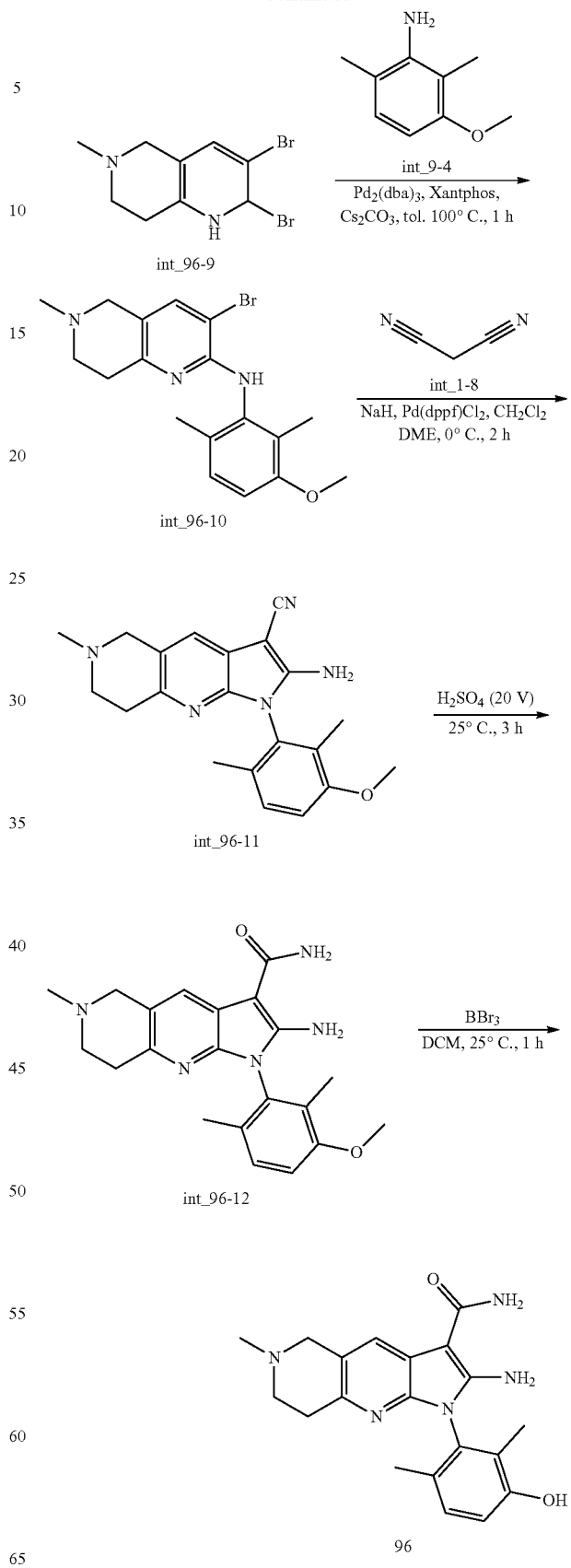

Step 1: Synthesis of Compound Int_96-3

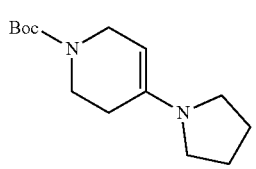
int_96-3

Int_96-1 (40.0 g, 201 mmol), int_96-2 (21.4 g, 301 mmol, 25.1 mL), and TsOH·H₂O (3.82 g, 20.1 mmol) were dissolved in toluene (400 mL). The reaction solution was heated to 100° C. and reacted for 16 h under nitrogen atmosphere. TLC monitoring showed the reaction was completed. The reaction solution was cooled to 0° C. and concentrated under reduced pressure to give a crude product (50 g, 98.7% yield), which was directly used in the next step.

Step 2: Synthesis of Compound Int_96-5

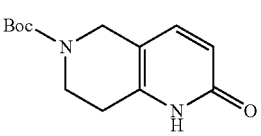
int_96-5

Int_96-3 (50.0 g, 198 mmol) and int_96-4 (20.5 g, 297 mmol) were dissolved in toluene (500 mL). The reaction solution was heated to 100° C. and stirred for 10 h. TLC monitoring showed the reaction was completed. The reaction solution was concentrated under reduced pressure to give a crude product. The crude product was purified by preparative column chromatography (SiO₂, DCM:MeOH=96:4) to give a solid (18.7 g, 37.9% yield).

¹H NMR (400 MHZ, CHLOROFORM-d) δ 1.49 (s, 9H) 2.76 (br t, J=5.56 Hz, 2H) 3.67 (br t, J=5.50 Hz, 2H) 4.32 (br s, 2H) 6.45 (d, J=9.29 Hz, 1H) 7.21 (d, J=9.17 Hz, 1H).

ESI-MS m/z: 251 [M+H]⁺.

Step 3: Synthesis of Compound Int_96-6

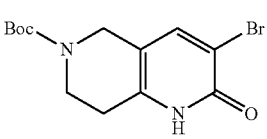
int_96-6

Int_96-5 (10.0 g, 40.0 mmol) was dissolved in dichloromethane (100 mL), and Py·Br₃ (14.1 g, 44.0 mmol) was added to the reaction solution. The reaction solution was stirred at room temperature for 1 h. TLC monitoring showed the reaction was completed. The reaction solution was filtered, and the filtrate was concentrated under reduced pressure to give a crude product. The crude product was purified by preparative column chromatography (SiO₂, DCM:EtOAc=7:3) to give a solid (2.7 g, 20% yield).

¹H NMR (400 MHZ, CHLOROFORM-d) δ 1.49 (s, 9H) 2.78 (br s, 2H) 3.68 (br s, 2H) 4.34 (br s, 2H) 7.61 (s, 1H).

ESI-MS m/z: 329 [M+H]⁺.

Step 4: Synthesis of Compound Int_96-7

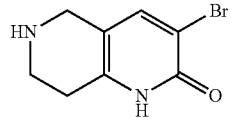
int_96-7

Int_96-6 (2.70 g, 8.20 mmol) was dissolved in an HCl/dioxane solution (30.0 mL). The reaction solution was stirred at 0° C. for 1 h. LC-MS monitoring showed the reaction was completed. The reaction solution was filtered, and the filter cake was collected and dried under vacuum to give a crude product (1.6 g, 85.5% yield), which was directly used in the next step.

ESI-MS m/z: 229 [M+H]⁺.

Step 5: Synthesis of Compound Int_96-8

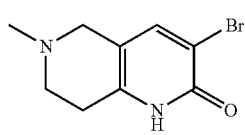
int_96-8

Int_96-7 (2.00 g, 7.53 mmol, hydrochloride) was dissolved in formic acid (20 mL), and HCHO (905 mg, 9.04 mmol, 830 μL, 30.0% purity) was added to the reaction solution. The reaction solution was heated to 100° C. and stirred for 3 h. LC-MS monitoring showed the reaction was completed. The reaction solution was concentrated under reduced pressure to give a crude product (1.3 g, 73.5% yield), which was directly used in the next step.

ESI-MS m/z: 243 [M+H]⁺.

Step 6: Synthesis of Compound Int_96-9

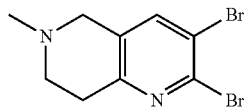
int_96-9

Int_96-8 (1.00 g, 4.11 mmol) was slowly added to POBr₃ (11.8 g, 41.1 mmol, 4.18 mL). The reaction solution was heated to 90° C. and reacted for 3 h. LC-MS monitoring showed the reaction was completed. The reaction solution was cooled to room temperature and adjusted to pH 8 with saturated aqueous sodium bicarbonate solution. The aqueous phase was extracted with ethyl acetate (80 mL×3), and the organic phase was dried over anhydrous sodium sulfate. The organic phase was concentrated under reduced pressure to give a crude product. The crude product was purified by preparative plate chromatography (SiO₂, DCM/MeOH=10/1) to give a solid (230 mg, 18.4% yield).

ESI-MS m/z: 305 [M+H]⁺.

Step 7: Synthesis of Compound Int_96-10

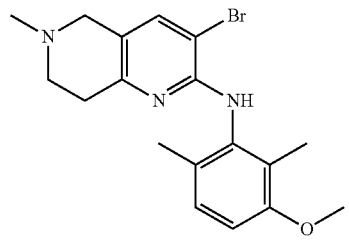

int_96-10

Int_96-9 (220 mg, 719 μmol) and int_9-4 (109 mg, 719 μmol) were dissolved in toluene (3.0 mL), and Cs$_2$CO$_3$ (469 mg, 1.44 mmol), Xantphos (41.6 mg, 71.9 μmol), and Pd$_2$(dba)$_3$ (65.8 mg, 71.9 μmol) were added. The reaction solution was purged with nitrogen three times, heated to 100° C., and reacted for 3 h. LC-MS monitoring showed the reaction was completed. After the reaction solution was cooled to room temperature, water (50 mL) was added to the reaction solution. The aqueous phase was extracted with ethyl acetate (50 mL×3), and the organic phase was dried over anhydrous sodium sulfate. The organic phase was concentrated under reduced pressure to give a crude product. The crude product was purified by preparative column chromatography (SiO$_2$, DCM:MeOH=95:5) to give a solid (227 mg, 84% yield).

ESI-MS m/z: 376 [M+H]$^+$.

Step 8: Synthesis of Compound Int_96-11

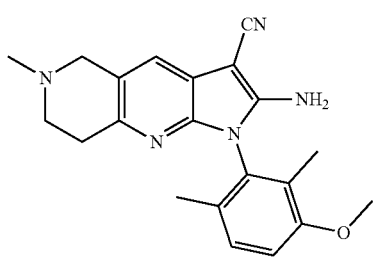

int_96-11

Int_1-8 (87.8 mg, 1.33 mmol, 83.6 μL) was dissolved in DME (3 mL). The reaction solution was cooled to −30° C., and NaH (266 mg, 6.64 mmol, 60.0% purity) was slowly added to the reaction solution under nitrogen atmosphere. The reaction solution was heated to 0° C. and reacted for 0.5 h. Int_96-10 (250 mg, 664 μmol) and Pd(dppf)Cl$_2$·CH$_2$Cl$_2$ (54.3 mg, 66.4 μmol) were then added to the reaction solution at 0° C. The reaction solution was reacted at 0° C. for 2 h under nitrogen atmosphere. LC-MS monitoring showed the reaction was completed. Water (20 mL) was added to the reaction solution. The aqueous phase was extracted with ethyl acetate (20 mL×3), and the organic phase was dried over anhydrous sodium sulfate. The organic phase was concentrated under reduced pressure to give a crude product. The crude product was purified by preparative column chromatography (SiO$_2$, DCM:MeOH=1:0 to 20:1) to give a solid (201 mg, 84.1% yield).

$^1$H NMR (400 MHZ, CHLOROFORM-d) δ 1.84 (s, 3H) 1.90 (s, 3H) 2.54 (s, 3H) 2.83 (br s, 2H) 2.95-3.03 (m, 2H) 3.75 (br s, 2H) 3.88 (s, 3H) 6.95 (d, J=8.36 Hz, 1H) 7.20 (d, J=8.58 Hz, 1H) 7.40 (s, 1 H).

ESI-MS m/z: 362 [M+H]$^+$.

Step 9: Synthesis of Compound Int_96-12

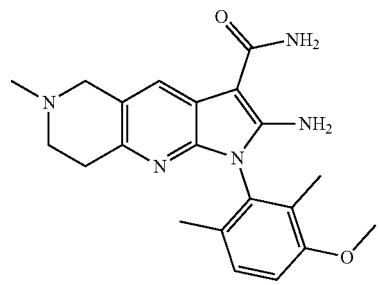

int_96-12

At 0° C., sulfuric acid (3 mL) was slowly added to int_96-11 (220 mg, 609 μmol). The reaction solution was reacted at 25° C. for 2 h. LC-MS monitoring showed the reaction was completed. Ice water (10 mL) was slowly added to the reaction solution. The aqueous phase was adjusted to pH 8 with saturated aqueous sodium bicarbonate solution and extracted with ethyl acetate (50 mL×3), and the organic phase was dried over anhydrous sodium sulfate. The organic phase was concentrated under reduced pressure to give a crude product. The crude product was purified by preparative column chromatography (SiO$_2$, DCM:MeOH=10:1) to give a solid (179 mg, 77.8% yield).

MS (ESI): 380 [M+H]$^+$.

Step 10: Synthesis of Compound 96

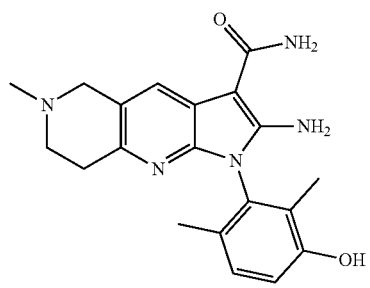

96

Int_96-12 (200 mg, 527 μmol) was dissolved in dichloromethane (3 mL) under nitrogen atmosphere, and BBr$_3$ (660 mg, 2.64 mmol, 254 μL) was added to the reaction solution at 0° C. The reaction solution was reacted at 0° C. for 1 h under nitrogen atmosphere. LC-MS monitoring showed the reaction was completed. Ice water (30 mL) was slowly added to the reaction solution. The aqueous phase was adjusted to pH 8 with saturated aqueous sodium bicarbonate solution and extracted with dichloromethane (50 mL×3), and the organic phase was dried over anhydrous sodium sulfate. The organic phase was concentrated under reduced pressure to give a crude product. The crude product was purified by preparative column chromatography to give compound 96 (103 mg, 53.5% yield).

$^1$H NMR (400 MHZ, DMSO-d6) δ 1.66 (s, 3H) 1.75 (s, 3H) 2.39 (s, 3H) 2.64-2.70 (m, 2H) 2.72 (br d, J=3.96 Hz, 2H) 3.60 (br s, 2H) 6.66 (br s, 2H) 6.82 (br s, 2H) 6.90 (d, J=8.36 Hz, 1H) 7.05 (d, J=8.36 Hz, 1H) 7.72 (s, 1H) 9.51 (s, 1H).

MS (ESI): 366 [M+H]$^+$.

Example 11. Synthesis of Compound 97 and Compound 98

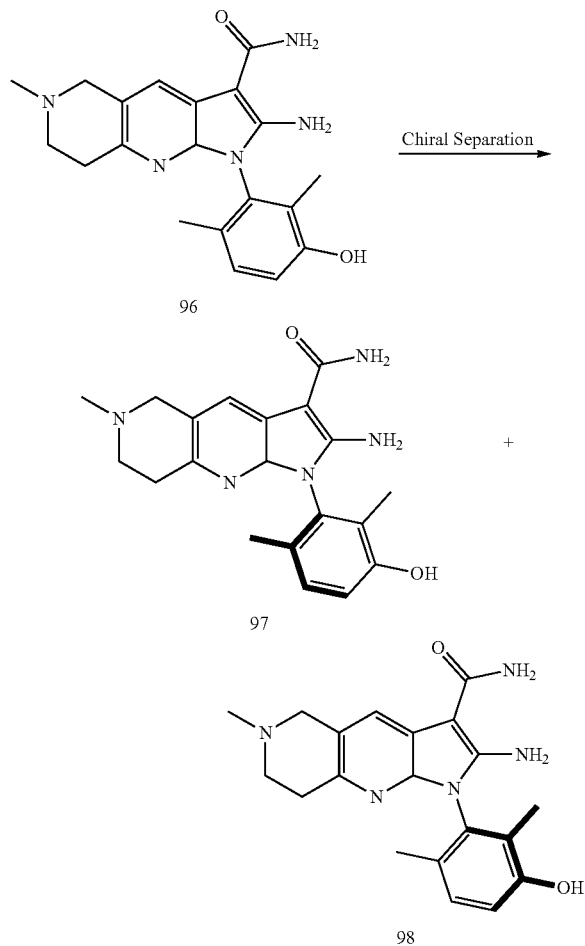

Compound 96 (103 mg, 281 µmol) was subjected to preparative SFC chiral resolution (column: Phenomenex-Cellulose-2 (250 mm×30 mm, 10 µm); mobile phase: A: $CO_2$, B: MeOH (0.1% $NH_3H_2O$); B %: 50%-50%, min) to give compound 97 (23 mg, 44.6% yield) and compound 98 (29 mg, 56.3% yield). Compound 97: $^1$H NMR (400 MHZ, DMSO-d6) δ 1.66 (s, 3H) 1.75 (s, 3H) 2.39 (s, 3H) 2.64-2.70 (m, 2H) 2.72 (br d, J=3.96 Hz, 2H) 3.60 (br s, 2H) 6.66 (br s, 2H) 6.82 (br s, 2H) 6.90 (d, J=8.36 Hz, 1H) 7.05 (d, J=8.36 Hz, 1H) 7.72 (s, 1H) 9.51 (s, 1H).

MS (ESI): 366 [M+H]$^+$.

Analytical SFC retention time: 3.501 min (Instrument: (Agilent 1260 with DAD detector; Column: Cellulose-4, 100×4.6 mm, I.D., 3 µm; Mobile phase: A: $CO_2$, B: Methanol (0.05% DEA); Gradient: 40% of B; Flow rate: 2.8 mL/min; Column temp: 40° C.; ABPR: 100 bar).

Compound 98: $^1$H NMR (400 MHZ, DMSO-d6) δ 1.66 (s, 3H) 1.75 (s, 3H) 2.35 (s, 3H) 2.62 (br d, J=5.28 Hz, 2H) 2.70 (br d, J=5.50 Hz, 2H) 3.54 (s, 2H) 6.65 (br s, 2H) 6.80 (br s, 2H) 6.91 (d, J=8.14 Hz, 1H) 7.04 (d, J=8.36 Hz, 1H) 7.70 (s, 1H) 9.42-9.82 (m, 1H).

MS (ESI): 366 [M+H]$^+$.

Analytical SFC retention time: 4.702 min (Instrument: (Agilent 1260 with DAD detector; Column: Cellulose-4, 100×4.6 mm, I.D., 3 µm; Mobile phase: A: $CO_2$, B: Methanol (0.05% DEA); Gradient: 40% of B; Flow rate: 2.8 mL/min; Column temp: 40° C.; ABPR: 100 bar).

Example 12. Synthesis of Compound 115

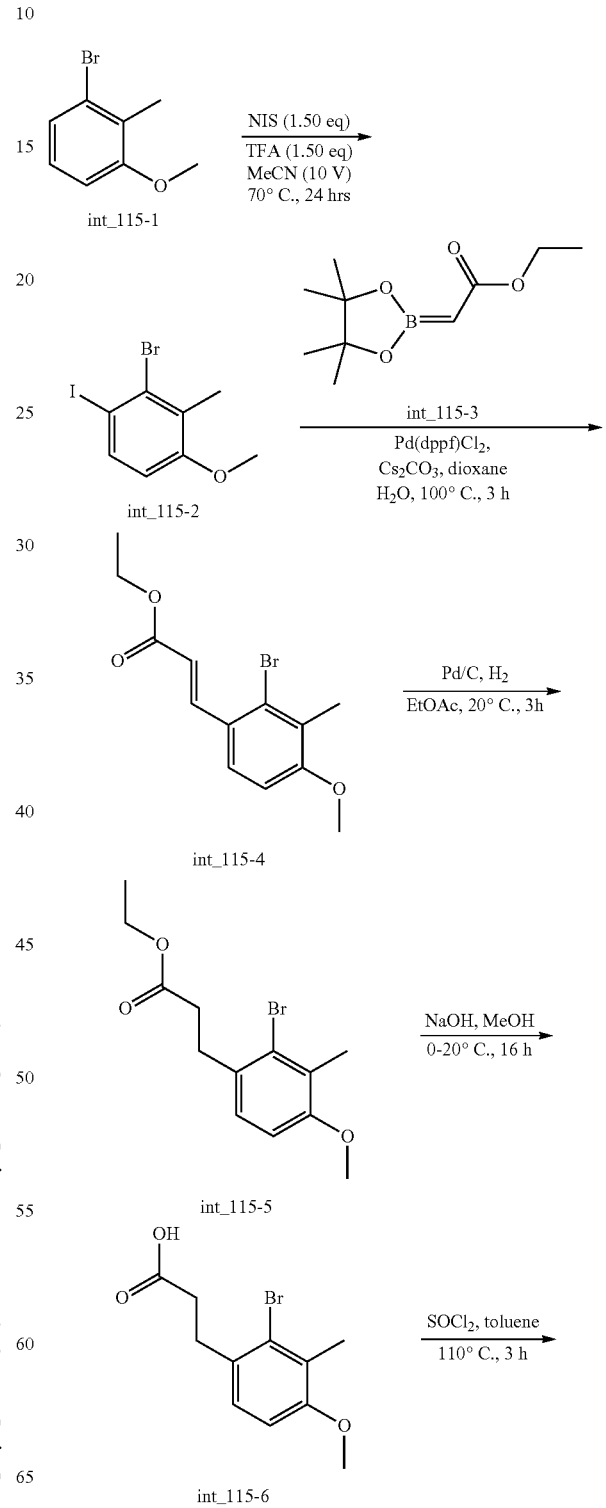

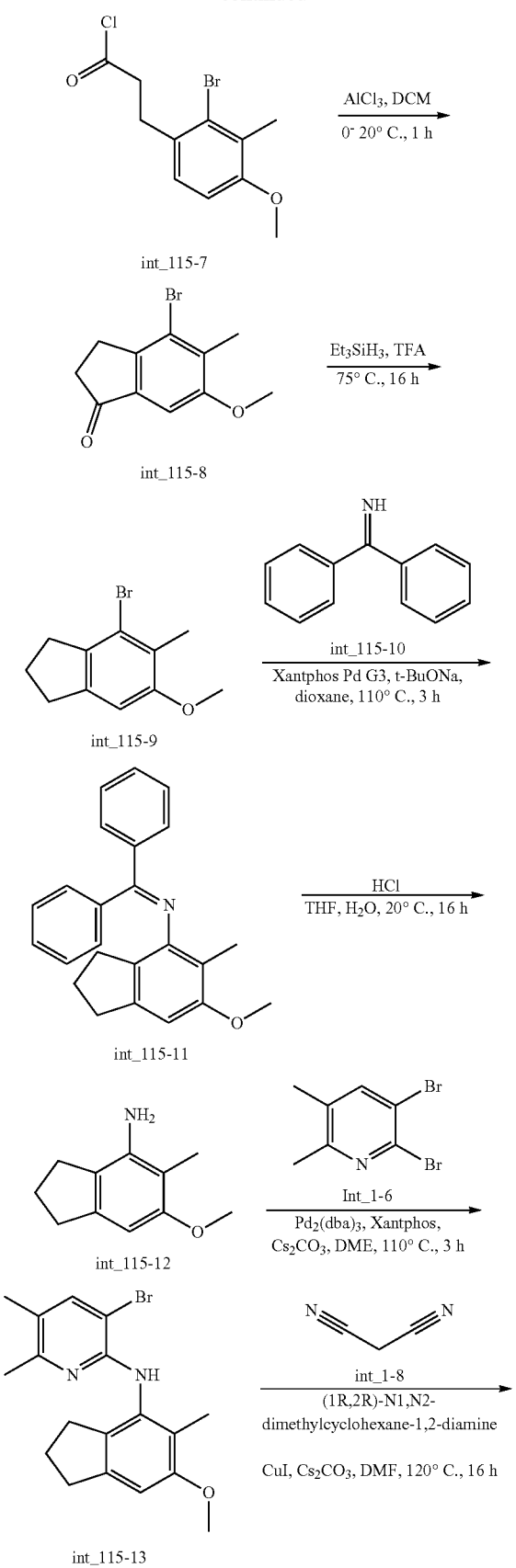
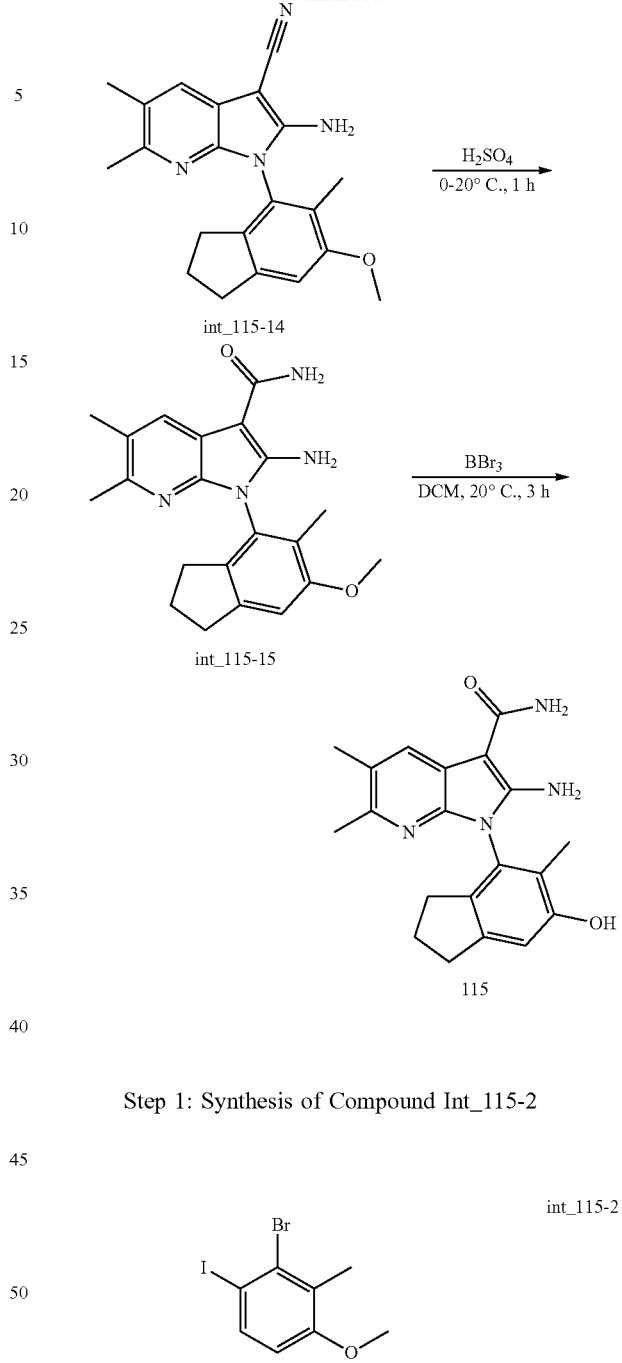

Step 1: Synthesis of Compound Int_115-2

Int_115-1 (20.0 g, 99.5 mmol) was dissolved in acetonitrile (200 mL), and NIS (33.6 g, 149 mmol) and TFA (17.0 g, 149 mmol, 11.1 mL) were added to the reaction solution at room temperature. The reaction solution was heated to 70° C. and reacted for 16 h under nitrogen atmosphere. TLC monitoring showed the reaction was completed. The reaction solution was cooled to 0° C. and concentrated under reduced pressure to give a solid. The solid was dissolved in dichloromethane (100 mL) and washed with water (50 mL×2), and the organic phase was dried over anhydrous sodium sulfate. The organic phase was concentrated under reduced pressure to give a crude product (26.3 g, 80.9% yield), which was directly used in the next step.

¹HNMR (400 MHZ, DMSO-d6) δ 7.75 (d, J=8.8 Hz, 1H), 6.83 (d, J=8.8 Hz, 1H), 3.79 (s, 3H), 2.34 (s, 3H).

Step 2: Synthesis of Compound Int_115-4

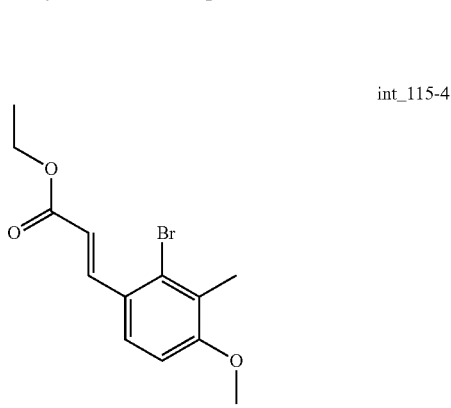 [SMILES: CCOC(=O)/C=C/c1ccc(OC)c(C)c1Br]

Int_115-2 (25.0 g, 76.5 mmol), int_115-3 (17.3 g, 76.5 mmol), Pd(dppf)Cl$_2$ (5.59 g, 7.65 mmol), and Cs$_2$CO$_3$ (2 M, 76.46 mL) were dissolved in 1,4-dioxane (250 mL). The reaction solution was purged with nitrogen three times, heated to 100° C., and stirred for 3 h. TLC monitoring showed the reaction was completed. The reaction solution was concentrated under reduced pressure to give a crude product. The crude product was purified by preparative column chromatography (ISCO®; 330 g SepaFlash® Silica Flash Column, Eluent of 0-10% Ethyl acetate/Petroleum ether gradient) to give a solid (12 g, 52.5% yield).

Step 3: Synthesis of Compound Int_115-5

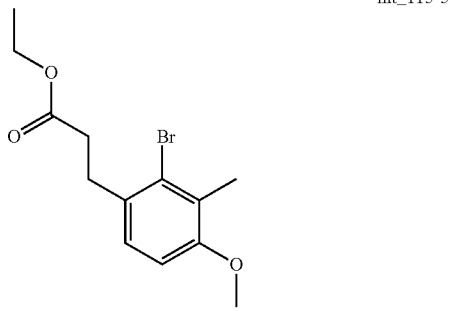

Int_115-4 (12.0 g, 40.1 mmol) and acetic acid (241 mg, 4.01 mmol, 229 μL) were dissolved in ethyl acetate (100 mL), and Pd/C (10.0 g, 401 mmol, 10% purity) was added to the reaction solution. The reaction solution was stirred at room temperature for 1 h, purged with hydrogen three times, and reacted at room temperature for 3 h under hydrogen atmosphere (50 PSI). TLC monitoring showed the reaction was completed. The reaction solution was filtered, and the filtrate was concentrated under reduced pressure to give a crude product (12 g, 99.3% yield), which was directly used in the next step.

¹H NMR (400 MHZ, CHLOROFORM-d) δ 7.09 (d, J=8.3 Hz, 1H), 6.76 (d, J=8.3 Hz, 1H), 4.23-4.09 (m, 3H), 3.88-3.79 (m, 4H), 3.06 (t, J=7.8 Hz, 2H), 2.68-2.55 (m, 3H), 2.35 (s, 3H), 1.36-1.21 (m, 5H).

Step 4: Synthesis of Compound Int_115-6

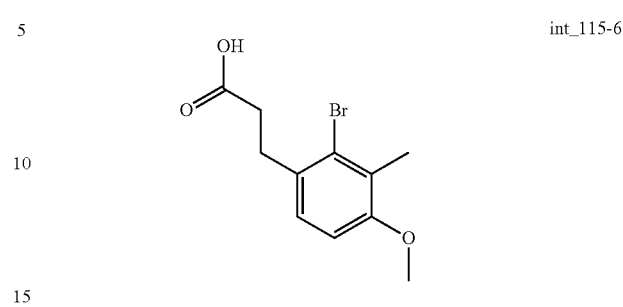

Int_115-5 (12.0 g, 39.8 mmol) was dissolved in methanol (80.0 mL), and NaOH (1 M, 79.7 mL) was added to the reaction solution at 0° C. The reaction solution was heated to room temperature and reacted for 16 h. LC-MS monitoring showed the reaction was completed. 1 N aqueous HCl solution was added dropwise to the reaction solution at 0° C. to adjust the pH to 3-4. The aqueous phase was extracted with ethyl acetate (300 mL×3), and the organic phase was dried over anhydrous sodium sulfate. The organic phase was concentrated under reduced pressure to give a crude product (10 g, 91.9% yield), which was directly used in the next step.

Step 5: Synthesis of Compound Int_115-7

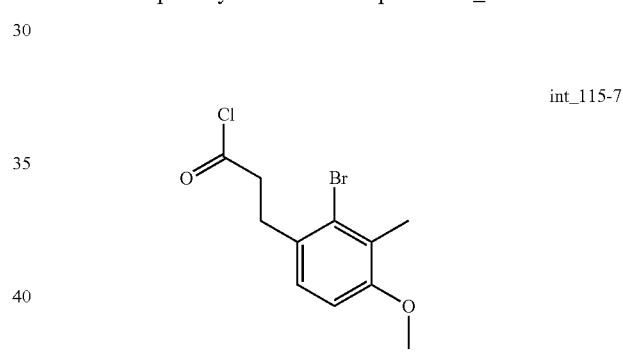

Int_115-6 (10.0 g, 36.6 mmol) was dissolved in toluene (150 mL), and SOCl$_2$ (8.71 g, 73.23 mmol, 5.31 mL) was added to the reaction solution. The reaction solution was heated to 110° C. and stirred for 3 h. TLC monitoring showed the reaction was completed. The reaction solution was concentrated under reduced pressure to give a crude product (10.7 g, 100% yield), which was directly used in the next step.

Step 6: Synthesis of Compound Int_115-8

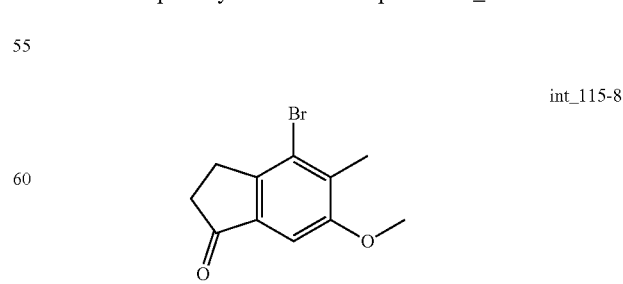

Int_115-7 (10.7 g, 36.6 mmol) was dissolved in dichloromethane (150 mL), and AlCl$_3$ (4.88 g, 36.6 mmol) was added to the reaction solution at 0° C. The reaction solution was heated to room temperature and reacted for 1 h. LC-MS monitoring showed the reaction was completed. The reaction solution was cooled to room temperature and poured into ice water (100 mL). The aqueous phase was extracted with dichloromethane (200 mL×3), and the organic phase was dried over anhydrous sodium sulfate. The organic phase was concentrated under reduced pressure to give a crude product (8 g, 85.6% yield), which was directly used in the next step.

Step 7: Synthesis of Compound Int_115-9

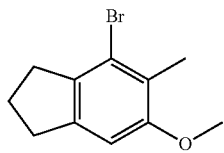
int_115-9

Int_115-8 (8.00 g, 31.4 mmol) was dissolved in TFA (100 mL), and triethylsilane (36.46 g, 313.59 mmol, 50.09 mL) was added to the reaction solution at 0° C. The reaction solution was heated to 75° C. and reacted for 16 h. LC-MS monitoring showed the reaction was completed. The reaction solution was cooled to room temperature and concentrated under reduced pressure to give a solid. The solid was diluted with water (100 mL) and adjusted to pH 8-9 with ammonia water. The aqueous phase was extracted with ethyl acetate (300 mL×3), and the organic phase was dried over anhydrous sodium sulfate. The organic phase was concentrated under reduced pressure to give a crude product. The crude product was purified by preparative column chromatography (SiO$_2$, PE/EtOAc=1/0 to 3/1) to give a product (6 g, 79.4% yield).
$^1$H NMR (400 MHZ, CHLOROFORM-d) δ 6.72 (s, 1H), 3.89-3.79 (m, 4H), 3.05-3.00 (m, 2H), 2.93 (t, J=7.5 Hz, 2H), 2.31 (s, 3H), 2.15-2.05 (m, 2H).

Step 8: Synthesis of Compound Int_115-11

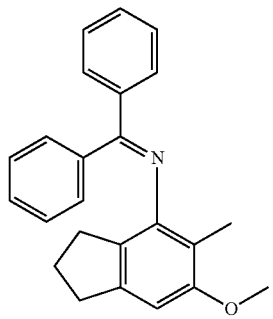
int_115-11

Under nitrogen atmosphere, int_115-9 (1.00 g, 4.15 mmol) and int_115-10 (1.13 g, 6.22 mmol, 1.04 mL) were dissolved in 1,4-dioxane (20 mL), and sodium tert-butoxide (797 mg, 8.29 mmol) and XantPhos Pd G3 (393 mg, 415 μmol) were added to the reaction solution at room temperature. The reaction solution was purged with nitrogen three times, heated to 110° C., and reacted for 3 h. LC-MS monitoring showed the reaction was completed. The reaction solution was cooled to room temperature and concentrated under reduced pressure to give a crude product (2.5 g), which was directly used in the next step.

Step 9: Synthesis of Compound Int_115-12

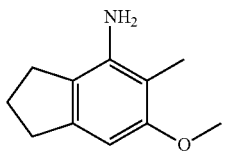
int_115-12

Under nitrogen atmosphere, int_115-11 (2.5 g, 7.32 mmol) was dissolved in a mixed solvent of tetrahydrofuran (20 mL) and water (10 mL), and an aqueous HCl solution (13 M, 21.52 mL) was added to the reaction solution at room temperature. The reaction solution was reacted at room temperature for 16 h. LC-MS monitoring showed the reaction was completed. The reaction solution was concentrated under reduced pressure to give a solid. The solid was diluted with water (20 mL) and adjusted to pH 8-9 with ammonia water. The aqueous phase was extracted with ethyl acetate (100 mL×3), and the organic phase was dried over anhydrous sodium sulfate. The organic phase was concentrated under reduced pressure to give a crude product. The crude product was purified by preparative column chromatography (SiO$_2$, PE/EtOAc=1/0 to 3/1) to give a product (1 g, 77.5% yield).

Step 10: Synthesis of Compound Int_115-13

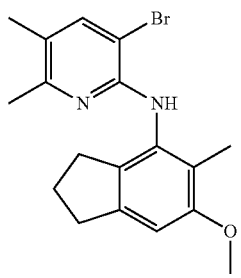
int_115-13

Int_115-12 (800 mg, 4.51 mmol) and int_1-6 (358.76 mg, 1.35 mmol) were dissolved in DME (4.0 mL), and Cs$_2$CO$_3$ (2.94 g, 9.03 mmol), Xantphos (261.16 mg, 451.36 μmol), and Pd$_2$(dba)$_3$ (413 mg, 451 μmol) were added. The reaction solution was purged with nitrogen three times, heated to 110° C., and reacted for 3 h. LC-MS monitoring showed the reaction was completed. After the reaction solution was cooled to room temperature, water (50 mL) was added to the reaction solution. The aqueous phase was extracted with ethyl acetate (50 mL×3), and the organic phase was dried over anhydrous sodium sulfate. The organic phase was concentrated under reduced pressure to give a crude product. The crude product was purified by preparative column chromatography (SiO$_2$, PE/EtOAc=1/0 to 3/1) to give a product (600 mg, 36.8% yield).
ESI-MS m/z: 361 [M+H]$^+$.

Step 11: Synthesis of Compound Int_115-14

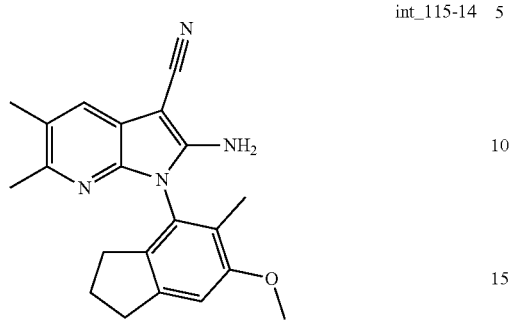

int_115-14

Int_1-8 (252 mg, 3.82 mmol, 240 μL) and int_115-13 (0.6 g, 1.66 mmol) were dissolved in DMF (20 mL), and CuI (158 mg, 830 μmol), Cs$_2$CO$_3$ (1.62 g, 4.98 mmol), and (1R,2R)—N1,N2-dimethylcyclohexane-1,2-diamine (47.3 mg, 332 μmol) were added to the reaction solution under nitrogen atmosphere. The reaction solution was heated to 120° C. and reacted for 16 h under nitrogen atmosphere. LC-MS monitoring showed the reaction was completed. The reaction solution was cooled to room temperature and concentrated under reduced pressure to give a crude product. The crude product was purified by preparative column chromatography (ISCO®; 20 g SepaFlash® Silica Flash Column, Eluent of 0-50% Ethyl acetate/Petroleum ether gradient) to give a product (150 mg, 26.1% yield).

$^1$H NMR (400 MHZ, CHLOROFORM-d) δ 7.50 (s, 1H), 6.94 (s, 1H), 4.67 (s, 2H), 3.88 (s, 3H), 3.04-2.98 (m, 2H), 2.58-2.50 (m, 2H), 2.40 (s, 3H), 2.33 (s, 3H), 2.10-2.02 (m, 2H), 1.86 (s, 3H).

ESI-MS m/z: 347 [M+H]$^+$.

Step 12: Synthesis of Compound Int_115-15

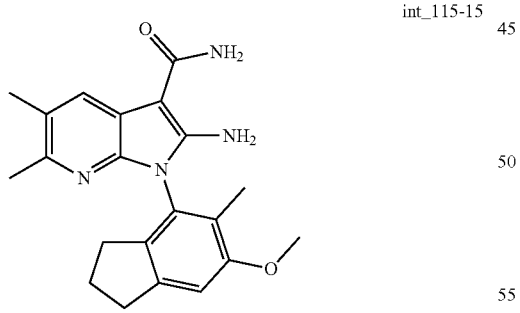

int_115-15

At 0° C., sulfuric acid (8.28 g, 84.4 mmol, 4.50 mL) was slowly added to int_115-14 (0.15 g, 433 μmol). The reaction solution was reacted at 25° C. for 1 h. LC-MS monitoring showed the reaction was completed. Ice water (20 mL) was slowly added to the reaction solution. The aqueous phase was adjusted to pH 8-9 with ammonia water and extracted with ethyl acetate (50 mL×3), and the organic phase was dried over anhydrous sodium sulfate. The organic phase was concentrated under reduced pressure to give a crude product. The crude product was purified by preparative column chromatography (SiO$_2$, Petroleum ether/Ethyl acetate=1/0 to 1/1) to give a solid (80 mg, 50.7% yield).

MS (ESI): 365 [M+H]$^+$.

Step 13: Synthesis of Compound 115

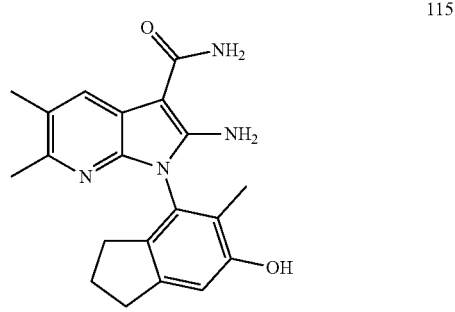 [SMILES: Cc1cc2c(C(N)=O)c(N)n(-c3c(C)c(O)cc4c3CCC4)c2nc1C]

115

Int_115-15 (0.06 g, 164 μmol) was dissolved in dichloromethane (3 mL) under nitrogen atmosphere, and BBr$_3$ (412.45 mg, 1.65 mmol, 158.64 μL) was added to the reaction solution at 0° C. The reaction solution was heated to room temperature and reacted for 3 h under nitrogen atmosphere. LC-MS monitoring showed the reaction was completed. Ice water (30 mL) was slowly added to the reaction solution. The aqueous phase was adjusted to pH 8 with saturated aqueous sodium bicarbonate solution and extracted with dichloromethane (50 mL×3), and the organic phase was dried over anhydrous sodium sulfate. The organic phase was concentrated under reduced pressure to give a crude product. The crude product was purified by preparative column chromatography (ISCO®; 4 g SepaFlash® Silica Flash Column, Eluent of 0-100% Ethyl acetate/Petroleum ether gradient) to give compound 115 (37 mg, 64.4% yield).

$^1$H NMR (400 MHZ, DMSO-d6) δ 9.40 (s, 1H), 7.81 (s, 1H), 6.87 (s, 1H), 6.73 (br s, 2H), 6.62 (br s, 2H), 2.88 (br t, J=8.1 Hz, 3H), 2.26 (d, J=5.3 Hz, 8H), 1.93 (br d, J=6.6 Hz, 2H), 1.67 (s, 3H).

MS (ESI): 351 [M+H]$^+$.

Example 13. Synthesis of Compound 116 and Compound 117

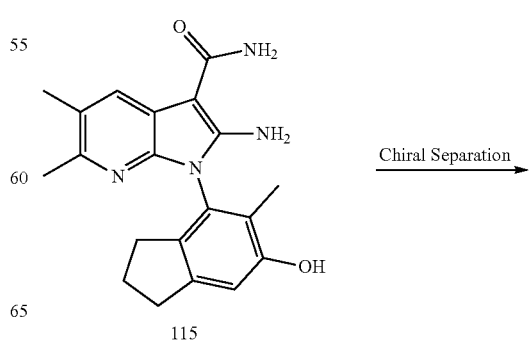

115

Chiral Separation →

-continued

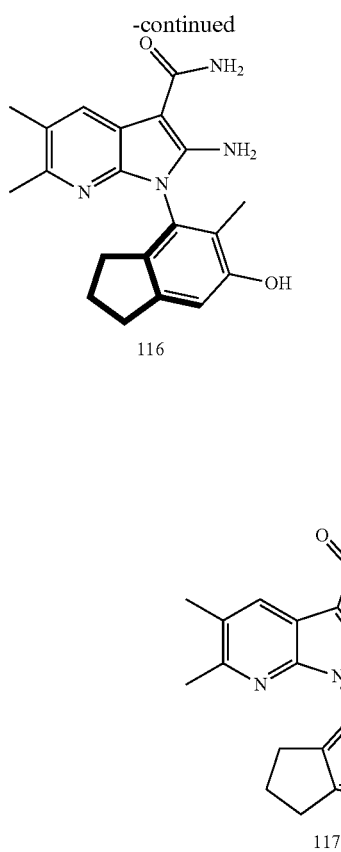

Compound 115 (37 mg, 100 μmol) was subjected to preparative SFC chiral resolution (column: DAICEL CHIRALPAK AS (250 mm×30 mm, 10 μm); mobile phase: A: $CO_2$, B: EtOH (0.1% $NH_3H_2O$); B %: 30%-30%, min) to give compound 116 (9 mg, 48.6% yield) and compound 117 (8 mg, 43.2% yield).

Compound 116: $^1$H NMR (400 MHZ, DMSO-d6) δ 9.40 (s, 1H), 7.81 (s, 1H), 6.87 (s, 1H), 6.73 (br s, 2H), 6.62 (br s, 2H), 2.88 (br t, J=8.1 Hz, 2H), 2.26 (d, J=5.3 Hz, 6H), 1.93 (br d, J=6.6 Hz, 2H), 1.67 (s, 3H).

MS (ESI): 351 [M+H]$^+$.

Analytical SFC retention time: 3.738 min (Instrument: (Waters UPCC with PDA Detector; Column: Chiralpak AS-3, 150×4.6 mm, I.D., 3 μm; Mobile phase: A: $CO_2$, B: Ethanol (0.05% DEA); Gradient: from 5% to 40% of B in 4 min and from 40% to 5% of B in 0.2 min, then hold 5% for 1.8 min; Flow rate: 2.5 mL/min; Column temp: 35° C.; ABPR: 1500 psi).

Compound 117: $^1$H NMR (400 MHZ, DMSO-d6) δ 9.40 (s, 1H), 7.81 (s, 1H), 6.87 (s, 1H), 6.73 (br s, 2H), 6.62 (br s, 2H), 2.88 (br t, J=8.1 Hz, 2H), 2.26 (d, J=5.3 Hz, 6H), 1.93 (br d, J=6.6 Hz, 2H), 1.67 (s, 3H).

MS (ESI): 351 [M+H]$^+$.

Analytical SFC retention time: 4.344 min (Instrument: (Waters UPCC with PDA Detector; Column: Chiralpak AS-3, 150×4.6 mm, I.D., 3 μm; Mobile phase: A: $CO_2$, B: Ethanol (0.05% DEA); Gradient: from 5% to 40% of B in 4 min and from 40% to 5% of B in 0.2 min, then hold 5% for 1.8 min; Flow rate: 2.5 mL/min; Column temp: 35° C.; ABPR: 1500 psi).

Example 14. Synthesis of Compound 137

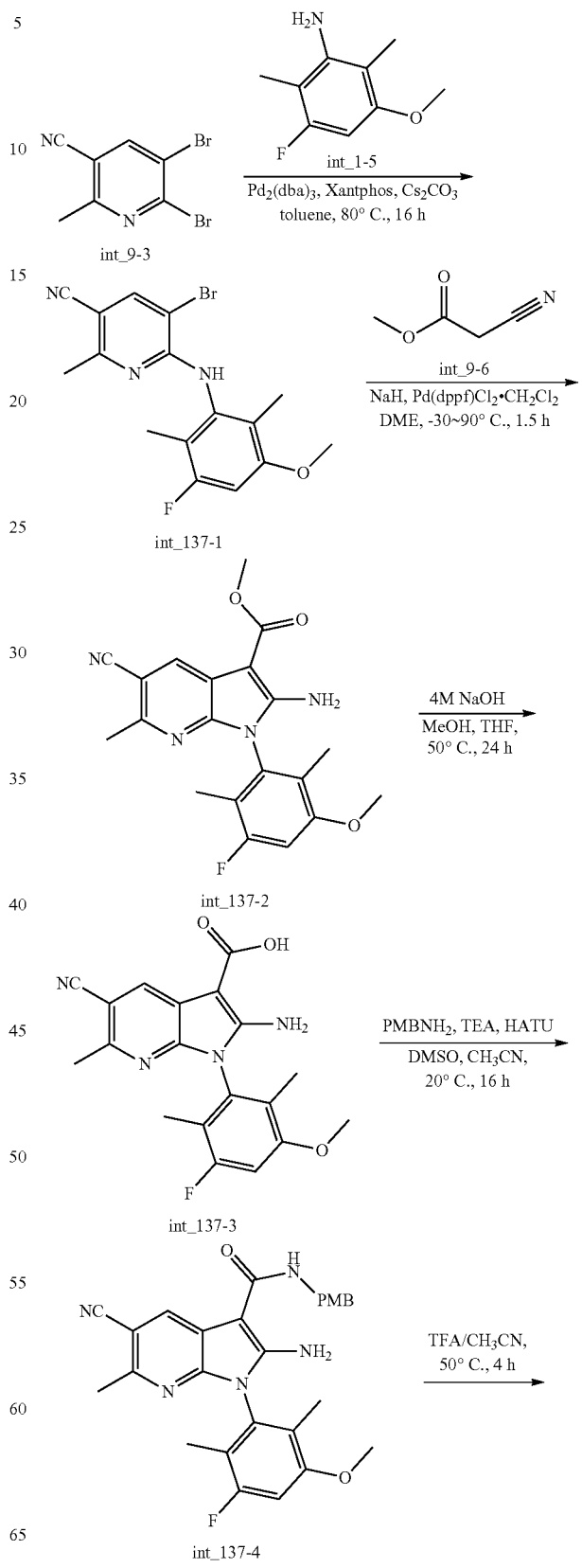

-continued

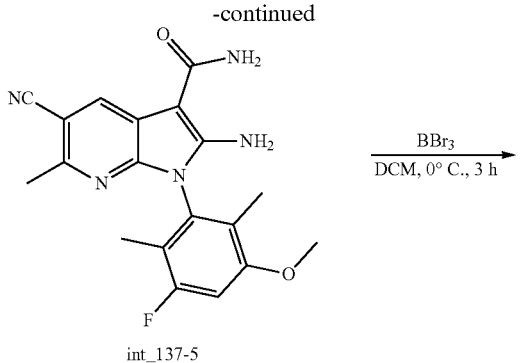

int_137-5

Step 1: Synthesis of Compound Int_137-1

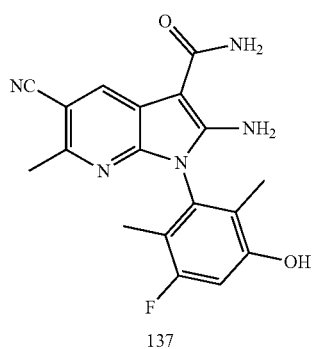

int_137-1

Int_9-3 (3.3 g, 12 mmol) and int_1-5 (2.45 g, 14.5 mmol) were dissolved in toluene (40 mL), and Cs$_2$CO$_3$ (4.71 g, 14.5 mmol), Xantphos (694 mg, 1.2 mmol), and Pd$_2$(dba)$_3$ (1.09 g, 1.2 mmol) were added. The reaction solution was purged with nitrogen three times, heated to 80° C., and reacted for 16 h. LC-MS monitoring showed the reaction was completed. After the reaction solution was cooled to room temperature, water (100 mL) was added to the reaction solution. The aqueous phase was extracted with ethyl acetate (200 mL×3), and the organic phase was dried over anhydrous sodium sulfate. The organic phase was concentrated under reduced pressure to give a crude product. The crude product was purified by preparative column chromatography (SiO$_2$, PE/EtOAc=30/1) to give a solid (1.1 g, 25.1% yield).

ESI-MS m/z: 364 [M+H]$^+$.

Step 2: Synthesis of Compound Int_137-2

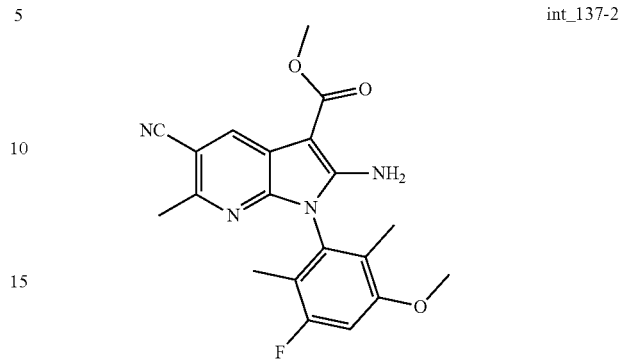

int_137-2

Int_9-6 (859 mg, 8.66 mmol, 767 μL) was dissolved in DME (12 mL). The reaction solution was cooled to −30° C., and NaH (693 mg, 17.3 mmol, 60% purity) was slowly added to the reaction solution under nitrogen atmosphere. The reaction solution was heated to 0° C. and reacted for 0.5 h. Int_137-1 (524 mg, 1.44 mmol) and Pd(dppf)Cl$_2$·CH$_2$Cl$_2$ (118 mg, 144 μmol) were then added to the reaction solution at 0° C. The reaction solution was heated to 90° C. and reacted for 1 h under nitrogen atmosphere. LC-MS monitoring showed the reaction was completed. After the reaction solution was cooled to room temperature, water (50 mL) was added to the reaction solution. The aqueous phase was extracted with ethyl acetate (50 mL×3), and the organic phase was dried over anhydrous sodium sulfate. The organic phase was concentrated under reduced pressure to give a crude product. The crude product was purified by preparative column chromatography (SiO$_2$, PE/EtOAc=3/1) to give a solid (410 mg, 74.4% yield).

ESI-MS m/z: 383 [M+H]$^+$.

Step 3: Synthesis of Compound Int_137-3

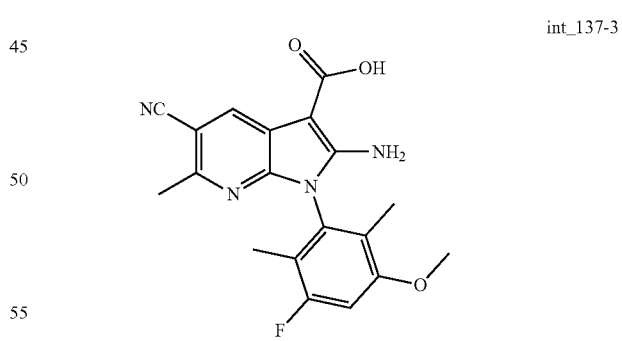

int_137-3

Int_137-2 (350 mg, 915 μmol) and NaOH (4 M, 7 mL) were dissolved in a mixed solvent of methanol (6 mL) and tetrahydrofuran (6 mL). The reaction solution was heated to 50° C. and reacted for 24 h. TLC monitoring showed the reaction was completed. The reaction solution was cooled to room temperature, and tetrahydrofuran (10 mL) was added to the reaction solution. The resulting mixture was concentrated under reduced pressure to give a solid, which was dissolved in DMSO (10 mL) and filtered. The filter cake was washed with water (10 mL), collected, and dried under

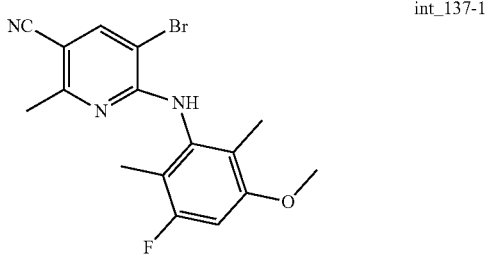

137 vacuum to give a crude product (115 mg, 34.1% yield), which was directly used in the next step.

ESI-MS m/z: 369 [M+H]⁺.

Step 4: Synthesis of Compound Int_137-4

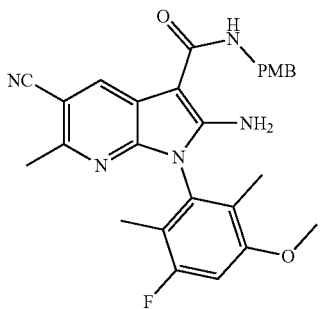

int_137-4

Int_137-3 (368 mg, 1 mmol), PMBNH₂ (756 mg, 5.51 mmol, 716 μL), and TEA (893 mg, 8.82 mmol, 1.23 mL) were dissolved in a mixed solvent of acetonitrile (15 mL) and DMSO (15 mL), and HATU (1.47 g, 3.86 mmol) was slowly added to the reaction solution at 0° C. The reaction solution was then heated to 20° C. and reacted for 16 h. LC-MS monitoring showed the reaction was completed. Water (100 mL) was added to the reaction solution. The aqueous phase was extracted with ethyl acetate (100 mL×3), and the organic phase was dried over anhydrous sodium sulfate. The organic phase was concentrated under reduced pressure to give a crude product. The crude product was purified by preparative column chromatography (SiO₂, PE/EtOAc=2/1) to give a solid (178 mg, 36.5% yield).

ESI-MS m/z: 488 [M+H]⁺.

Step 5: Synthesis of Compound Int_137-5

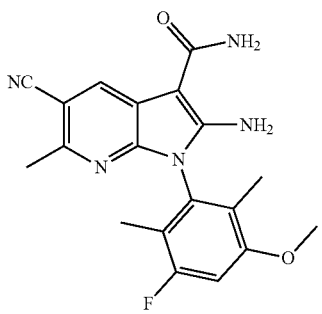

int_137-5

Int_137-4 (170 mg, 348 μmol) and TFA (3 mL) were dissolved in acetonitrile (1 mL). The reaction solution was then heated to 50° C. and reacted for 4 h. LC-MS monitoring showed the reaction was completed. Saturated aqueous sodium bicarbonate solution (20 mL) was added to the reaction solution. The aqueous phase was extracted with ethyl acetate (30 mL×3), and the organic phase was dried over anhydrous sodium sulfate. The organic phase was concentrated under reduced pressure to give a crude product. The crude product was purified by preparative plate chromatography (SiO₂, PE/EtOAc=2/3) to give a solid (60 mg, 46.8% yield).

ESI-MS m/z: 368 [M+H]⁺.

Step 5: Synthesis of Compound 137

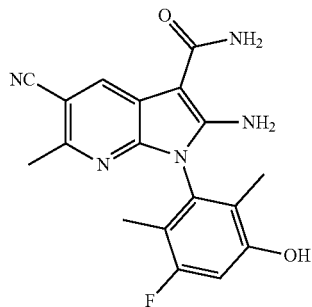

137

Int_137-5 (60 mg, 163 μmol) was dissolved in dichloromethane (3 mL) under nitrogen atmosphere, and BBr₃ (653 mg, 2.60 mmol, 251 μL) was added to the reaction solution at 0° C. The reaction solution was reacted at 0° C. for 3 h under nitrogen atmosphere. LC-MS monitoring showed the reaction was completed. Ice water (20 mL) was slowly added to the reaction solution. The aqueous phase was adjusted to pH 8 with saturated aqueous sodium bicarbonate solution and extracted with ethyl acetate (30 mL×3), and the organic phase was dried over anhydrous sodium sulfate. The organic phase was concentrated under reduced pressure to give a crude product. The crude product was purified by preparative column chromatography (SiO₂, PE/EtOAc=1/2) to give compound 137 (39 mg, 67.5% yield).

MS (ESI): 354 [M+H]⁺.

Example 15. Synthesis of Compound 143

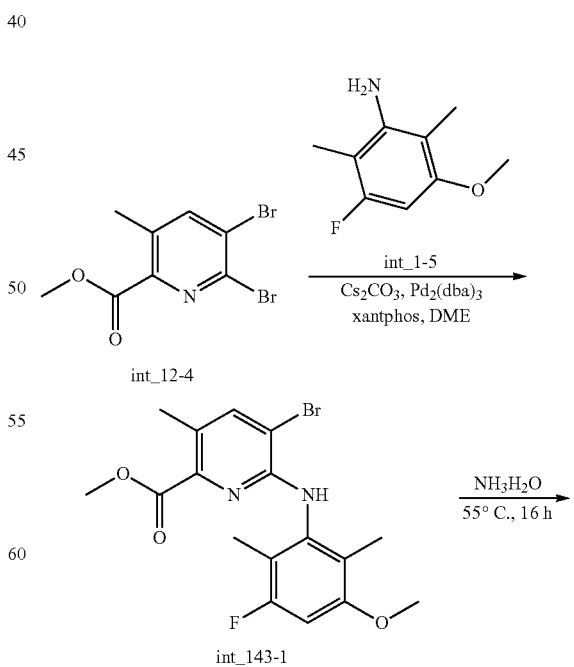

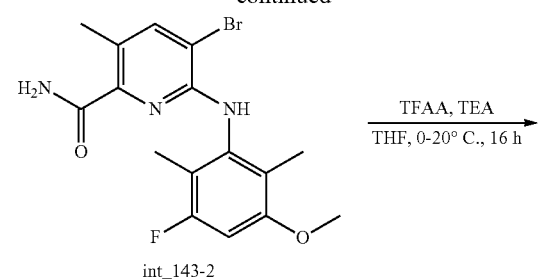
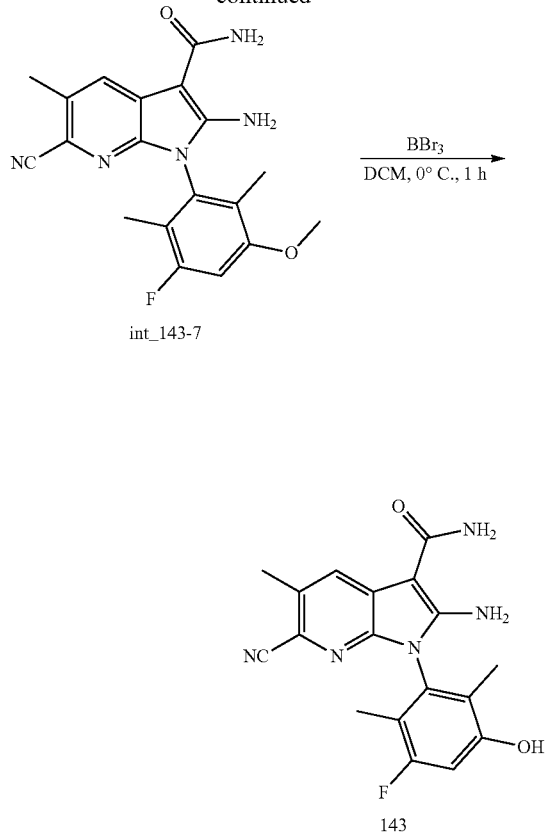
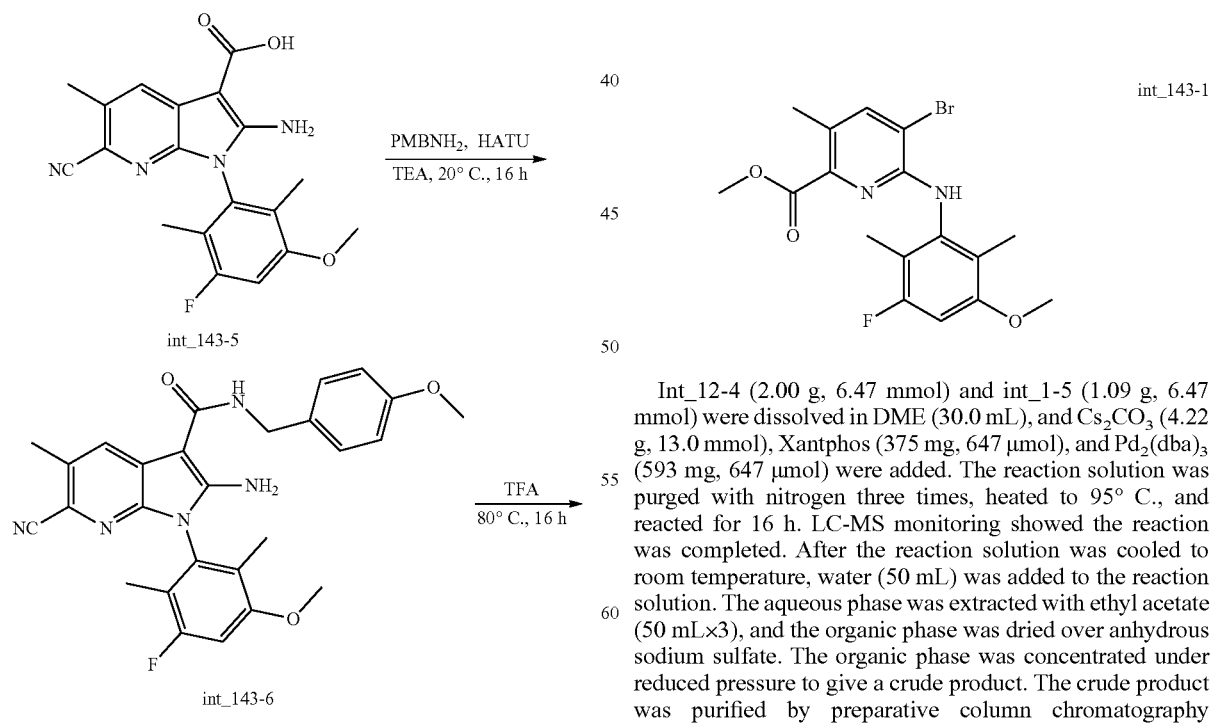

Step 1: Synthesis of Compound Int_143-1

Int_12-4 (2.00 g, 6.47 mmol) and int_1-5 (1.09 g, 6.47 mmol) were dissolved in DME (30.0 mL), and $Cs_2CO_3$ (4.22 g, 13.0 mmol), Xantphos (375 mg, 647 μmol), and $Pd_2(dba)_3$ (593 mg, 647 μmol) were added. The reaction solution was purged with nitrogen three times, heated to 95° C., and reacted for 16 h. LC-MS monitoring showed the reaction was completed. After the reaction solution was cooled to room temperature, water (50 mL) was added to the reaction solution. The aqueous phase was extracted with ethyl acetate (50 mL×3), and the organic phase was dried over anhydrous sodium sulfate. The organic phase was concentrated under reduced pressure to give a crude product. The crude product was purified by preparative column chromatography (ISCO®; Silica Flash Column, Eluent of 0-10% EA/Petroleum ether gradient) to give a solid (1.5 g, 58.3% yield).

ESI-MS m/z: 397 [M+H]$^+$.

Step 2: Synthesis of Compound Int_143-2

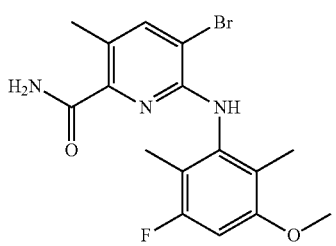

int_143-2

Int_143-1 (993 mg, 2.5 mmol) was dissolved in ammonia water (20.0 mL). The reaction solution was heated to 55° C. and reacted for 16 h. LC-MS monitoring showed the reaction was completed. After the reaction solution was cooled to room temperature, the aqueous phase was extracted with ethyl acetate (30 mL×3), and the organic phase was dried over anhydrous sodium sulfate. The organic phase was concentrated under reduced pressure to give a crude product. The crude product was purified by preparative column chromatography (ISCOR; Silica Flash Column, Eluent of 0-20% EA/Petroleum ether gradient) to give a solid (0.7 g, 73.2% yield).

ESI-MS m/z: 382 [M+H]$^+$.

Step 3: Synthesis of Compound Int_143-3

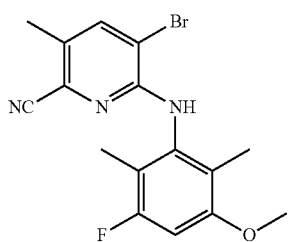

int_143-3

Int_143-2 (0.700 g, 1.83 mmol) was dissolved in tetrahydrofuran (10 mL), and TEA (1.08 g, 10.7 mmol, 1.49 mL) and TFAA (900 mg, 4.28 mmol, 595 µL) were slowly added to the reaction solution at 0° C. The reaction solution was heated to room temperature and stirred for 16 h. TLC monitoring showed the reaction was completed. The reaction solution was poured into ice water. The aqueous phase was extracted with ethyl acetate (50 mL×3), and the organic phase was dried over anhydrous sodium sulfate. The organic phase was concentrated under reduced pressure to give a crude product. The crude product was purified by preparative column chromatography (ISCOR; Silica Flash Column, Eluent of 0-20% EA/Petroleum ether gradient) to give a solid (500 mg, 75% yield).

ESI-MS m/z: 364 [M+H]$^+$.

Step 4: Synthesis of Compound Int_143-4

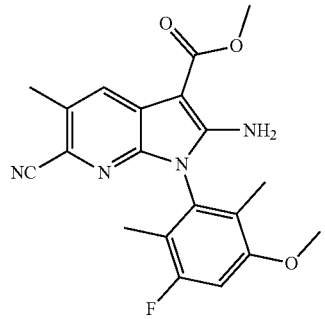

int_143-4

Int_9-6 (1.22 g, 8.66 mmol, 1.24 mL) was dissolved in DME (15 mL). The reaction solution was cooled to −30° C., and NaH (693 mg, 17.3 mmol, 60.0% purity) was slowly added to the reaction solution under nitrogen atmosphere. The reaction solution was heated to 0° C. and reacted for 0.5 h. Int_143-3 (546 mg, 1.5 mmol) and Pd(dppf)Cl$_2$·CH$_2$Cl$_2$ (122 mg, 150 µmol) were then added to the reaction solution at 0° C. The reaction solution was heated to 90° C. and reacted for 1 h under nitrogen atmosphere. LC-MS monitoring showed the reaction was completed. After the reaction solution was cooled to room temperature, water (50 mL) was added to the reaction solution. The aqueous phase was extracted with ethyl acetate (50 mL×3), and the organic phase was dried over anhydrous sodium sulfate. The organic phase was concentrated under reduced pressure to give a crude product. The crude product was purified by preparative column chromatography (ISCOR; Silica Flash Column, Eluent of 0-100% EA/Petroleum ether gradient) to give a solid (510 mg, 88.9% yield).

ESI-MS m/z: 383 [M+H]$^+$.

Step 5: Synthesis of Compound Int_143-5

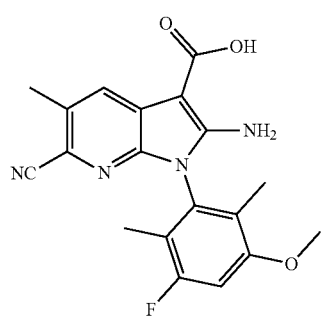

int_143-5

Int_143-4 (382 mg, 1 mmol) and NaOH (4.00 M, 8.23 mL) were dissolved in a mixed solvent of methanol (10 mL) and tetrahydrofuran (5 mL). The reaction solution was heated to 50° C. and reacted for 72 h. TLC monitoring showed the reaction was completed. The reaction solution was cooled to room temperature and concentrated under reduced pressure to give a solid, which was dissolved in water (30 mL). The aqueous phase was extracted with ethyl acetate (30 mL×3) and neutralized with 1 M aqueous hydrochloric acid solution to pH 5-6. The aqueous phase was then extracted with ethyl acetate (30 mL×3), and the organic phases at this time were combined and dried over anhydrous sodium sulfate. The organic phase was concentrated under reduced pressure to give a crude product (205 mg, 55.6% yield). The crude product was directly used in the next step.

ESI-MS m/z: 369 [M+H]⁺.

Step 6: Synthesis of Compound Int_143-6

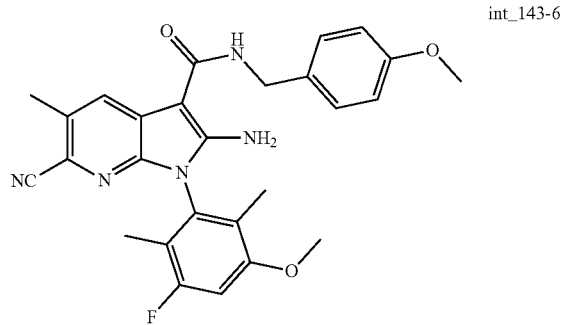

int_143-6

Int_143-5 (235 mg, 640 μmol), PMBNH₂ (263 mg, 1.92 mmol, 249 μL), and TEA (323 mg, 3.20 mmol, 445 μL) were dissolved in a mixed solvent of acetonitrile (5 mL) and DMSO (5 mL), and HATU (851 mg, 2.24 mmol) was slowly added to the reaction solution at 0° C. The reaction solution was then heated to 20° C. and reacted for 16 h. LC-MS monitoring showed the reaction was completed. Water (30 mL) was added to the reaction solution. The aqueous phase was extracted with ethyl acetate (30 mL×3), and the organic phase was dried over anhydrous sodium sulfate. The organic phase was concentrated under reduced pressure to give a crude product. The crude product was purified by preparative column chromatography (ISCOR; Silica Flash Column, Eluent of 0-10% EA/Petroleum ether gradient) to give a solid (175 mg, 56% yield).

ESI-MS m/z: 488 [M+H]⁺.

Step 7: Synthesis of Compound Int_143-7

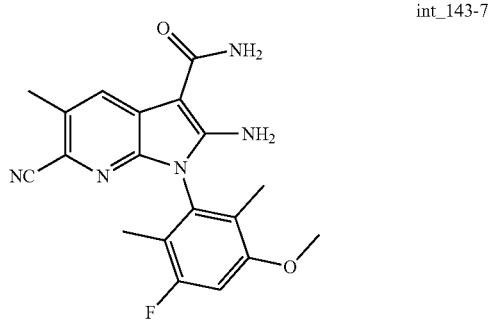

int_143-7

Int_143-6 (100 mg, 205 μmol) was dissolved in TFA (11.5 g, 101 mmol, 7.50 mL). The reaction solution was heated to 80° C. and reacted for 16 h under nitrogen atmosphere. LC-MS monitoring showed the reaction was completed. Saturated aqueous sodium bicarbonate solution (20 mL) was added to the reaction solution. The aqueous phase was extracted with ethyl acetate (30 mL×3), and the organic phase was dried over anhydrous sodium sulfate. The organic phase was concentrated under reduced pressure to give a crude product. The crude product was purified by preparative plate chromatography (SiO₂, PE/EtOAc=1/2) to give a solid (53 mg, 70.3% yield).

ESI-MS m/z: 368 [M+H]⁺.

Step 8: Synthesis of Compound 143

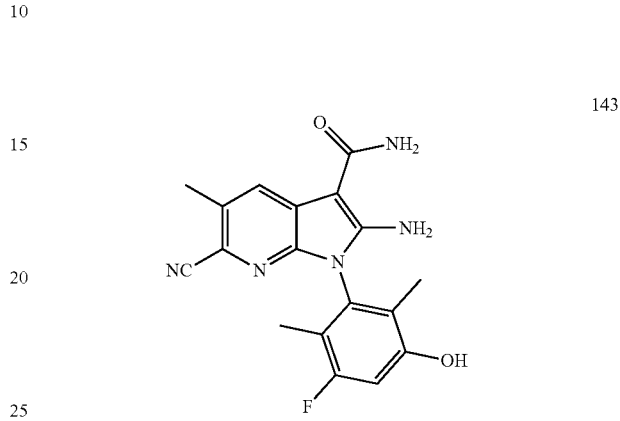

143

Int_143-7 (53 mg, 144 μmol) was dissolved in dichloromethane (3 mL) under nitrogen atmosphere, and BBr₃ (653 mg, 2.60 mmol, 251 μL) was added to the reaction solution at 0° C. The reaction solution was reacted at 0° C. for 3 h under nitrogen atmosphere. LC-MS monitoring showed the reaction was completed. Ice water (20 mL) was slowly added to the reaction solution. The aqueous phase was adjusted to pH 8 with saturated aqueous sodium bicarbonate solution and extracted with ethyl acetate (30 mL×3), and the organic phase was dried over anhydrous sodium sulfate. The organic phase was concentrated under reduced pressure to give a crude product. The crude product was purified by preparative column chromatography (SiO₂, PE/EtOAc=1/2) to give compound 143 (35 mg, 68.7% yield).

MS (ESI): 354 [M+H]⁺.

Example 16. Synthesis of Compound 149

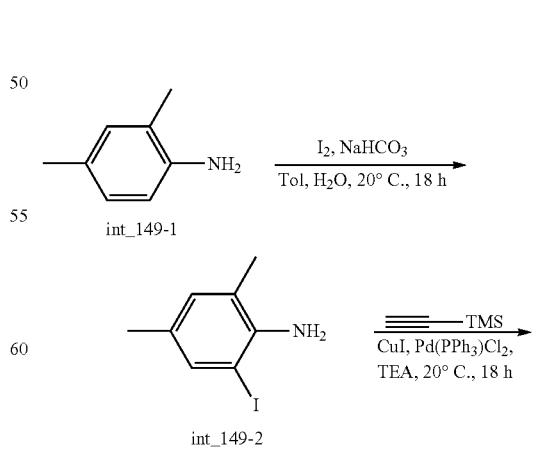

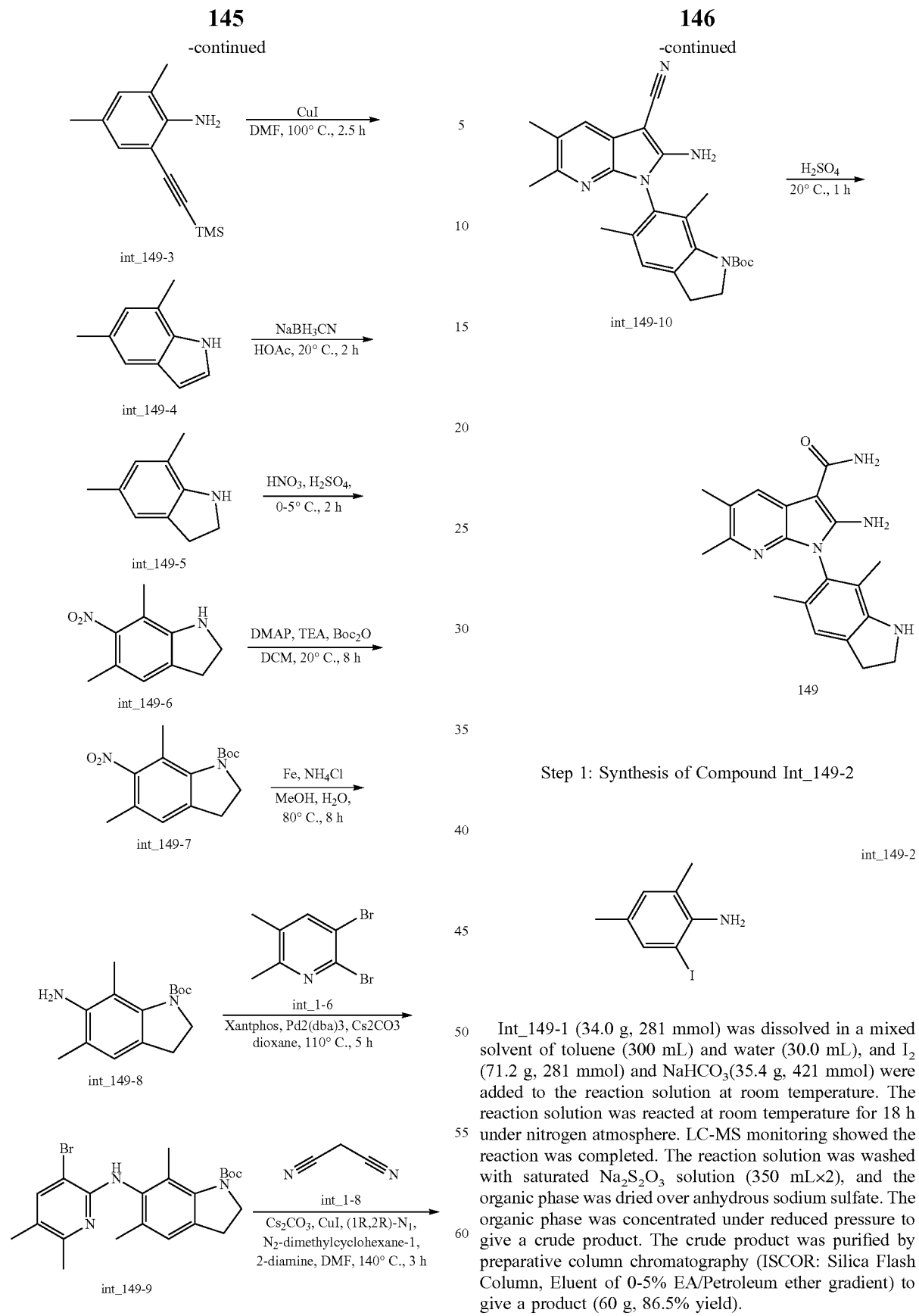

Step 1: Synthesis of Compound Int_149-2

Int_149-1 (34.0 g, 281 mmol) was dissolved in a mixed solvent of toluene (300 mL) and water (30.0 mL), and $I_2$ (71.2 g, 281 mmol) and $NaHCO_3$ (35.4 g, 421 mmol) were added to the reaction solution at room temperature. The reaction solution was reacted at room temperature for 18 h under nitrogen atmosphere. LC-MS monitoring showed the reaction was completed. The reaction solution was washed with saturated $Na_2S_2O_3$ solution (350 mL×2), and the organic phase was dried over anhydrous sodium sulfate. The organic phase was concentrated under reduced pressure to give a crude product. The crude product was purified by preparative column chromatography (ISCOR: Silica Flash Column, Eluent of 0-5% EA/Petroleum ether gradient) to give a product (60 g, 86.5% yield).

$^1$H NMR (400 MHZ, CHLOROFORM-d) δ 7.39-7.37 (m, 1H), 7.29-7.28 (m, 1H), 6.88-6.85 (m, 1H), 2.24-2.22 (m, 3H), 2.21-2.20 (m, 3H).

Step 2: Synthesis of Compound Int_149-3

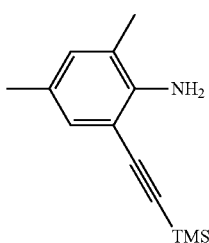

int_149-3

Int_149-2 (60.0 g, 243 mmol), CuI (4.62 g, 24.3 mmol), Pd(PPh₃)₂Cl₂ (3.41 g, 4.86 mmol), and ethynyl(trimethyl)silane (28.6 g, 291 mmol, 40.4 mL) were dissolved in triethylamine (500 mL). The reaction solution was purged with nitrogen three times and stirred at room temperature for 18 h. TLC monitoring showed the reaction was completed. The reaction solution was diluted with water (500 mL). The aqueous phase was extracted with ethyl acetate (500 mL×3), and the organic phase was dried over anhydrous sodium sulfate. The organic phase was concentrated under reduced pressure to give a crude product. The crude product was purified by preparative column chromatography (ISCOR; Silica Flash Column, Eluent of 0-20% Ethyl acetate/Petroleum ether gradient) to give a solid (35 g, 66.3% yield).

MS (ESI): 218 [M+H]⁺.

Step 3: Synthesis of Compound Int_149-4

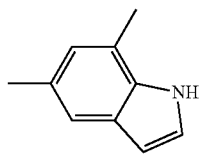

int_149-4

Int_149-3 (1.65 g, 7.59 mmol) and CuI (2.89 g, 15.2 mmol) were dissolved in DMF (40 mL). The reaction solution was purged with nitrogen three times, heated to 100° C., and reacted for 2.5 h. LC-MS monitoring showed the reaction was completed. The reaction solution was filtered, and the filtrate was concentrated under reduced pressure to give a crude product. The crude product was purified by preparative column chromatography (ISCOR; Silica Flash Column, Eluent of 0-30% Ethyl acetate/Petroleum ether gradient) to give a product (0.4 g, 36.3% yield).

¹H NMR (400 MHZ, CHLOROFORM-d) δ 8.06-7.93 (m, 1H), 7.35-7.31 (m, 1H), 7.23-7.18 (m, 1H), 6.88 (s, 1H), 6.56-6.48 (m, 1H), 2.54-2.43 (m, 6H).

MS (ESI): 146 [M+H]⁺.

Step 4: Synthesis of Compound Int_149-5

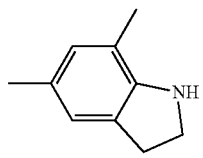

int_149-5

Int_149-4 (11.0 g, 75.8 mmol) was dissolved in acetic acid (100 mL), and NaBH₃CN (9.52 g, 152 mmol) was added to the reaction solution at 0° C. The reaction solution was heated to room temperature and reacted for 2 h. LC-MS monitoring showed the reaction was completed. The reaction solution was diluted with water (300 mL). The aqueous phase was extracted with ethyl acetate (300 mL×3), and the organic phase was dried over anhydrous sodium sulfate. The organic phase was concentrated under reduced pressure to give a crude product. The crude product was purified by preparative column chromatography (ISCO®; Silica Flash Column, Eluent of 0-30% Ethyl acetate/Petroleum ether gradient) to give a product (7.3 g, 65.5% yield). ¹H NMR (400 MHZ, CHLOROFORM-d) δ 6.76-6.69 (m, 1H), 6.65-6.55 (m, 1H), 3.51-3.39 (m, 2H), 3.39-3.28 (m, 1H), 2.96-2.88 (m, 2H), 2.18-1.98 (m, 6H).

MS (ESI): 148 [M+H]⁺.

Step 5: Synthesis of Compound Int_149-6

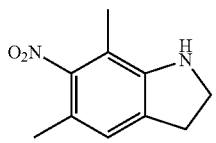

int_149-6

Int_149-5 (1.00 g, 6.79 mmol) was dissolved in H₂SO₄ (20.0 mL) at 0° C., and HNO₃ (611 mg, 6.79 mmol, 437 μL, 70.0% purity) was added dropwise to the reaction solution at 0° C. The reaction solution was heated to 20° C. and stirred for 1 h. LC-MS monitoring showed the reaction was completed. The reaction solution was poured into ice water (150 mL), and the pH of the aqueous phase was adjusted to 8-9 with 6 N NaOH. The aqueous phase was extracted with dichloromethane (200 mL×3), and the organic phase was dried over anhydrous sodium sulfate. The organic phase was concentrated under reduced pressure to give a crude product. The crude product was purified by preparative column chromatography (ISCOR; Silica Flash Column, Eluent of 0-20% Ethyl acetate/Petroleum ether gradient) to give a product (1.1 g, 84.3% yield).

MS (ESI): 193 [M+H]⁺.

Step 6: Synthesis of Compound Int_149-7

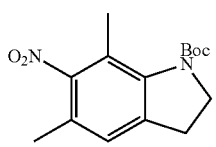

int_149-7

Int_149-6 (1.10 g, 5.72 mmol) was dissolved in dichloromethane (20 mL), and DMAP (140 mg, 1.14 mmol), TEA (1.74 g, 17.2 mmol, 2.39 mL), and Boc$_2$O (2.50 g, 11.5 mmol, 2.63 mL) were added to the reaction solution at 0° C. The reaction solution was heated to room temperature and reacted for 8 h. LC-MS monitoring showed the reaction was completed. The reaction solution was diluted with water (100 mL). The aqueous phase was extracted with ethyl acetate (100 mL×3), and the organic phase was dried over anhydrous sodium sulfate. The organic phase was concentrated under reduced pressure to give a crude product. The crude product was purified by preparative column chromatography (ISCOR; Silica Flash Column, Eluent of 0-20% Ethyl acetate/Petroleum ether gradient) to give a product (1 g, 59.8% yield).

MS (ESI): 293 [M+H]$^+$.

Step 7: Synthesis of Compound Int_149-8

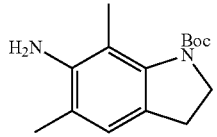

int_149-8

Int_149-7 (0.90 g, 3.08 mmol) was dissolved in a mixed solvent of methanol (20 mL) and water (20 mL), and Fe (2.58 g, 46.2 mmol) and NH$_4$Cl (1.65 g, 30.8 mmol) were added to the reaction solution. The reaction solution was heated to 80° C. and reacted for 8 h. LC-MS monitoring showed the reaction was completed. The reaction solution was cooled to room temperature and concentrated under reduced pressure to give a solid. The solid was diluted with water (100 mL). The aqueous phase was extracted with ethyl acetate (100 mL×3), and the organic phase was dried over anhydrous sodium sulfate. The organic phase was concentrated under reduced pressure to give a crude product. The crude product was purified by preparative column chromatography (ISCOR; Silica Flash Column, Eluent of 0-20% Ethyl acetate/Petroleum ether gradient) to give a product (0.7 g, 86.8% yield).

$^1$H NMR (400 MHZ, DMSO-d6) δ 6.69 (s, 1H), 3.34-3.33 (m, 6H), 2.06-2.02 (m, 3H), 1.93 (s, 3H), 1.45 (s, 9H).

MS (ESI): 263 [M+H]$^+$.

Step 8: Synthesis of Compound Int_149-9

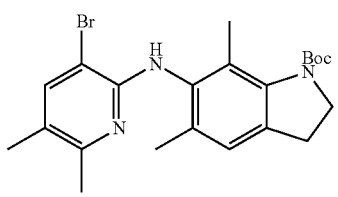

int_149-9

Int_149-8 (0.65 g, 2.48 mmol) and int_1-6 (722 mg, 2.73 mmol) were dissolved in 1,4-dioxane (20 mL), and Cs$_2$CO$_3$ (1.61 g, 4.96 mmol), Xantphos (215 mg, 372 μmol), and Pd:(dba)$_3$ (340 mg, 372 μmol) were added. The reaction solution was purged with nitrogen three times, heated to 110° C., and reacted for 5 h. LC-MS monitoring showed the reaction was completed. After the reaction solution was cooled to room temperature, water (50 mL) was added to the reaction solution. The aqueous phase was extracted with ethyl acetate (50 mL×3), and the organic phase was dried over anhydrous sodium sulfate. The organic phase was concentrated under reduced pressure to give a crude product. The crude product was purified by preparative column chromatography (SiO$_2$, PE/THF=1/0 to 9/1) to give a product (730 mg, 66% yield).

$^1$H NMR (400 MHZ, CHLOROFORM-d) δ 7.48-7.43 (m, 1H), 7.00-6.95 (m, 1H), 6.24-6.06 (m, 1H), 4.16-4.08 (m, 2H), 3.01-2.94 (m, 2H), 2.24-2.16 (m, 6H), 2.16-2.10 (m, 6H), 1.57-1.52 (m, 9H).

ESI-MS m/z: 446 [M+H]$^+$.

Step 9: Synthesis of Compound Int_149-10

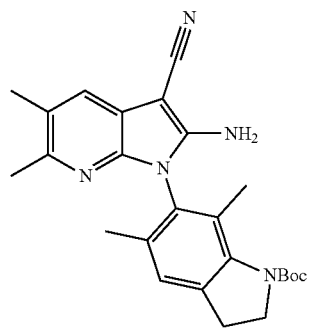

int_149-10

Int_1-8 (370 mg, 5.60 mmol, 353 μL) and int_149-9 (0.50 g, 1.12 mmol) were dissolved in DMF (7 mL), and CuI (427 mg, 2.24 mmol), Cs$_2$CO$_3$ (1.09 g, 3.36 mmol), and (1R, 2R)—N1,N2-dimethylcyclohexane-1,2-diamine (31.9 mg, 224 μmol) were added to the reaction solution under nitrogen atmosphere. The reaction solution was heated to 140° C. and reacted for 3 h under nitrogen atmosphere. LC-MS monitoring showed the reaction was completed. The reaction solution was cooled to room temperature and concentrated under reduced pressure to give a crude product. The crude product was purified by preparative column chromatography (ISCOR; 20 g SepaFlash® Silica Flash Column, Eluent of 0-30% Ethyl acetate/Petroleum ether gradient) to give a product (50 mg, 10.4% yield).

ESI-MS m/z: 432 [M+H]$^+$.

Step 10: Synthesis of Compound 149

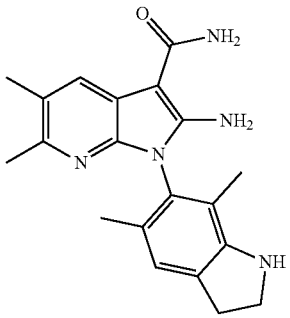

149

At 0° C., sulfuric acid (1 mL) was slowly added to int_149-10 (45.0 mg, 104 μmol). The reaction solution was reacted at 20° C. for 1 h. LC-MS monitoring showed the reaction was completed. Ice water (20 mL) was slowly added to the reaction solution. The aqueous phase was adjusted to pH 8-9 with triethylamine and extracted with ethyl acetate (20 mL×3), and the organic phase was dried over anhydrous sodium sulfate. The organic phase was concentrated under reduced pressure to give a crude product. The crude product was purified by preparative column chromatography to give a solid (30 mg, 82.6% yield).

$^{1}$H NMR (400 MHZ, DMSO-d6) δ 7.83-7.75 (m, 1H), 6.96-6.92 (m, 1H), 6.70-6.57 (m, 4H), 5.33 (br s, 1H), 3.55-3.47 (m, 2H), 3.07-2.92 (m, 2H), 2.29-2.22 (m, 6H), 1.75-1.67 (m, 3H), 1.62-1.55 (m, 3H).

MS (ESI): 350 [M+H]$^{+}$.

Example 17. Synthesis of Compound 150 and Compound 151

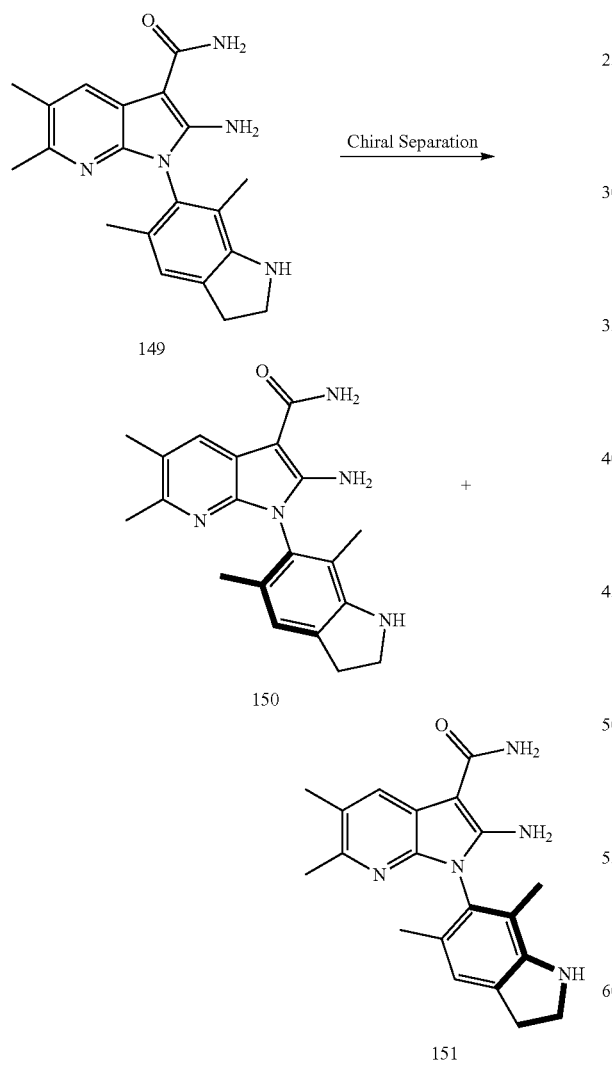

Compound 149 (50 mg, 143 μmol) was subjected to preparative SFC chiral resolution (column: Phenomenex-Cellulose-2 (250 mm×30 mm, 10 μm); mobile phase: A: CO$_2$, B: EtOH (0.1% NH$_3$H$_2$O); B %: 60%-60%, min) to give compound 150 (8 mg, 32% yield) and compound 151 (8 mg, 32% yield).

Compound 150: $^{1}$H NMR (400 MHZ, DMSO-d6) δ 7.83-7.75 (m, 1H), 6.96-6.92 (m, 1H), 6.70-6.57 (m, 4H), 5.33 (br s, 1H), 3.55-3.47 (m, 2H), 3.07-2.92 (m, 2H), 2.29-2.22 (m, 6H), 1.75-1.67 (m, 3H), 1.62-1.55 (m, 3H).

MS (ESI): 350 [M+H]$^{+}$.

Analytical SFC retention time: 3.482 min (Instrument: (Waters UPCC with PDA Detector; Column: Cellulose-2, 100×4.6 mm, I.D., 3 μm; Mobile phase: A: CO$_2$, B: Ethanol (0.05% DEA); Gradient: 40% of B; Flow rate: 2.8 mL/min; Column temp: 35° C.; ABPR: 1500 psi).

Compound 151: $^{1}$H NMR (400 MHZ, DMSO-d6) δ 7.81 (s, 1H), 7.01-6.91 (m, 1H), 6.69-6.55 (m, 4H), 5.37-5.28 (m, 1H), 3.55-3.49 (m, 2H), 3.08-2.92 (m, 2H), 2.30-2.23 (m, 6H), 1.71 (s, 3H), 1.61-1.56 (m, 3H).

MS (ESI): 350 [M+H]$^{+}$.

Analytical SFC retention time: 4.748 min (Instrument: (Waters UPCC with PDA Detector; Column: Cellulose-2, 100×4.6 mm, I.D., 3 μm; Mobile phase: A: CO$_2$, B: Ethanol (0.05% DEA); Gradient: 40% of B; Flow rate: 2.8 mL/min; Column temp: 35° C.; ABPR: 1500 psi).

Example 18. Synthesis of Compound 153

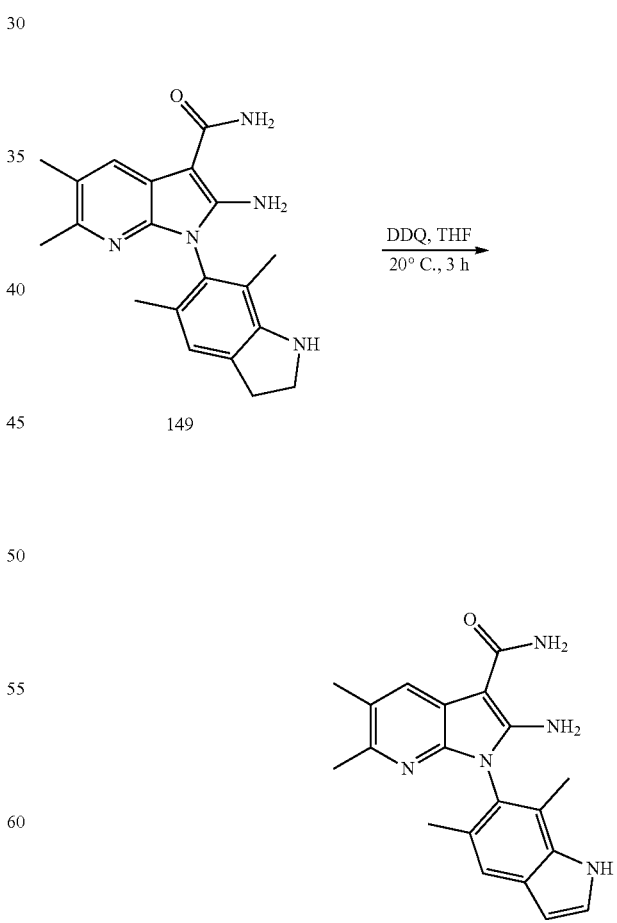

Step 1: Synthesis of Compound 153

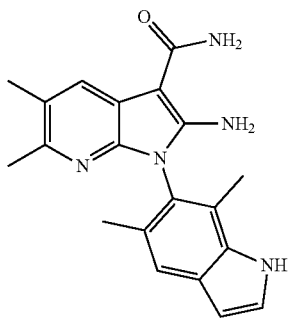

Int_149 (0.16 g, 461 μmol) was dissolved in tetrahydrofuran (5 mL), and DDQ (105 mg, 461 μmol) was added to the reaction solution at room temperature. The reaction solution was reacted at room temperature for 3 h under nitrogen atmosphere. LC-MS monitoring showed the reaction was completed. The reaction solution was filtered, and the filtrate was concentrated under reduced pressure to give a crude product. The crude product was purified by preparative column chromatography (ISCO®; Silica Flash Column, Eluent of 0-65% EA/Petroleum ether gradient) to give a product (120 mg, 74.9% yield).

$^1$H NMR (400 MHZ, DMSO-d6) δ 11.21 (br s, 1H), 7.85-7.81 (m, 1H), 7.44 (t, J=2.8 Hz, 1H), 7.41-7.39 (m, 1H), 6.77-6.68 (m, 2H), 6.63 (br s, 2H), 6.48-6.46 (m, 1H), 2.27 (s, 3H), 2.23-2.20 (m, 3H), 2.05-2.03 (m, 3H), 1.89-1.86 (m, 3H).

MS (ESI): 348 [M+H]$^+$.

Example 19. Synthesis of Compound 176

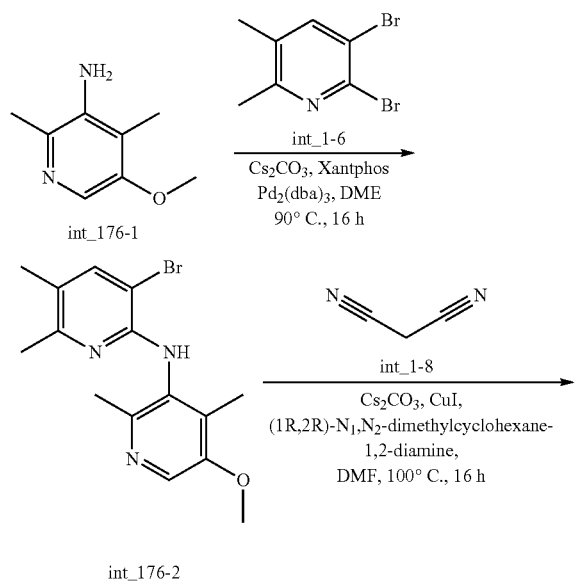

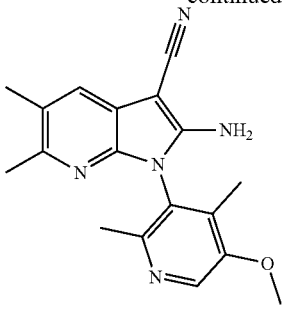

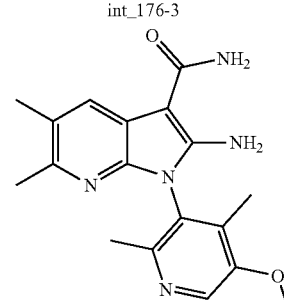

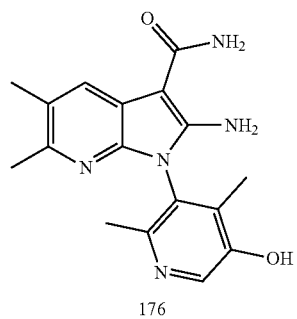

Step 1: Synthesis of Compound Int_176-2

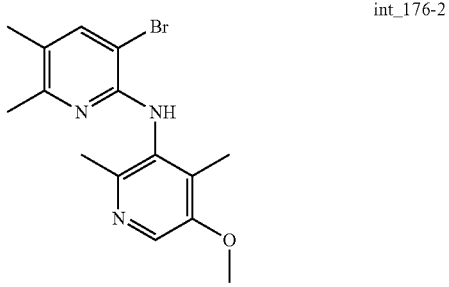

Int_176-1 (1.2 g, 7.89 mmol) and int_1-6 (2.51 g, 9.47 mmol) were dissolved in DME (50 mL), and Cs$_2$CO$_3$ (3.7 g, 11.364 mmol), Xantphos (456 mg, 0.789 mmol), and Pd_(dba)$_3$ (722 mg, 0.789 mmol) were added. The reaction solution was purged with nitrogen three times, heated to 90° C., and reacted for 16 h. LC-MS monitoring showed the reaction was completed. After the reaction solution was cooled to room temperature, water (50 mL) was added to the reaction solution. The aqueous phase was extracted with ethyl acetate (50 mL×3), and the organic phase was dried over anhydrous sodium sulfate. The organic phase was concentrated under reduced pressure to give a crude product. The crude product was purified by preparative column chromatography to give a solid (1.4 g, 52.8% yield).

ESI-MS m/z: 336 [M+H]$^+$.

Step 2: Synthesis of Compound Int_176-3

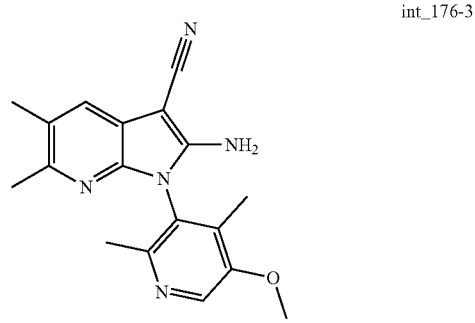

int_176-3

Int_1-8 (283 mg, 4.28 mmol) was dissolved in DME (30 mL). The reaction solution was cooled to −30° C., and NaH (214 mg, 5.355 mmol, 60.0% purity) was slowly added to the reaction solution under nitrogen atmosphere. The reaction solution was heated to 0° C. and reacted for 0.5 h. Int_176-2 (1.2 g, 3.57 mmol) and Pd(dppf)Cl$_2$ (261 mg, 0.357 mmol) were then added to the reaction solution at 0° C. The reaction solution was heated to 90° C. and reacted for 12 h under nitrogen atmosphere. LC-MS monitoring showed the reaction was completed. After the reaction solution was cooled to room temperature, water (50 mL) was added to the reaction solution. The aqueous phase was extracted with ethyl acetate (50 mL×3), and the organic phase was dried over anhydrous sodium sulfate. The organic phase was concentrated under reduced pressure to give a crude product. The crude product was purified by preparative column chromatography to give a solid (670 mg, 58.7% yield).

ESI-MS m/z: 322 [M+H]$^+$.

Step 3: Synthesis of Compound Int_176-4

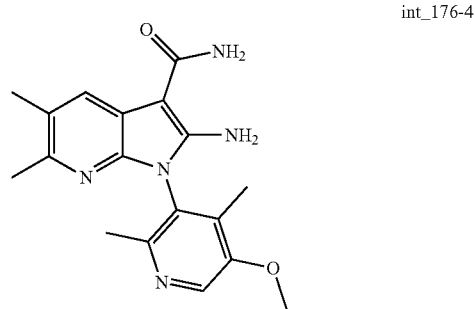

int_176-4

Int_176-3 (670 mg, 2.09 mmol), potassium carbonate (577 mg, 4.17 mmol), and 30% aqueous hydrogen peroxide solution (711 mg, 6.27 mmol) were dissolved in a mixed solvent of DMSO (10 mL) and water (2 mL). The reaction solution was reacted at 25° C. for 2 h. LC-MS monitoring showed the reaction was completed. Water (100 mL) was added to the reaction solution. The aqueous phase was extracted with dichloromethane (100 mL×3), and the organic phase was dried over anhydrous sodium sulfate. The organic phase was concentrated under reduced pressure to give a crude product. The crude product was purified by preparative column chromatography to give a solid (120 mg, 16.9% yield).

MS (ESI): 340 [M+H]$^+$.

Step 4: Synthesis of Compound 176

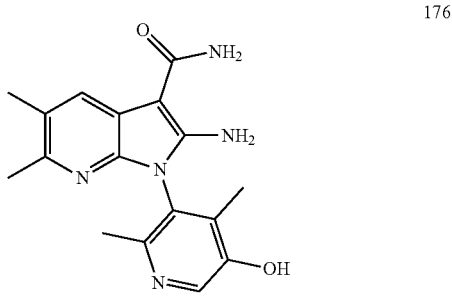 [SMILES: Cc1cc2c(C(N)=O)c(N)n(-c3c(C)ncc(O)c3C)c2nc1C]

176

Int_176-4 (50 mg, 0.147 mmol) was dissolved in dichloromethane (15 mL) under nitrogen atmosphere, and BBr$_3$ (626 mg, 2.5 mmol) was added to the reaction solution at 0° C. The reaction solution was reacted at 0° C. for 2 h under nitrogen atmosphere. LC-MS monitoring showed the reaction was completed. The reaction solution was adjusted to pH 7 with saturated aqueous sodium carbonate solution and extracted with ethyl acetate (40 mL×3), and the organic phase was dried over anhydrous sodium sulfate. The organic phase was concentrated under reduced pressure to give a crude product. The crude product was purified by preparative column chromatography to give compound 176 (12 mg, 25.5% yield).

$^1$H NMR (400 MHZ, DMSO-d6) δ 9.92 (s, 1H), 8.13 (s, 1H), 7.83 (s, 1H), 6.95 (s, 2H), 6.67 (s, 2H), 2.24 (s, 3H), 2.22 (s, 3H), 1.92 (s, 3H), 1.69 (s, 3H).

MS (ESI): 326 [M+H]$^+$.

The target compounds 4, 8, 18-95, 99-114, 118-136, 140-142, 144-148, 152, 154-175, and 177-225 in Table 1 were obtained using the synthesis methods described above with different starting materials.

TABLE 1

| Compound | Compound structure | MS (M + H)$^+$ |
|---|---|---|
| 4 | 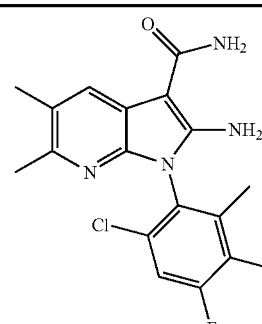 | 363 |

TABLE 1-continued

| Compound | Compound structure | MS (M + H)+ |
|---|---|---|
| 5 | | 343 |
| 6 | | 343 |
| 7 | | 343 |
| 8 | | 363 |
| 9 | 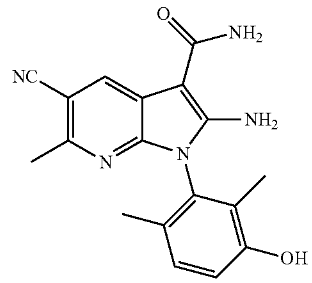 [SMILES: Cc1ccc(O)c(C)c1-n1c(N)c(C(N)=O)c2cc(C#N)c(C)nc21] | 336 |
| 10 | 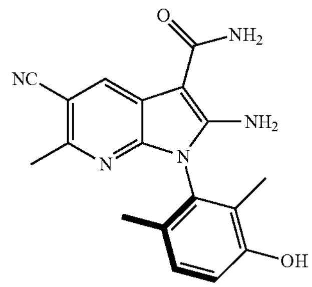 | 336 |
| 11 | 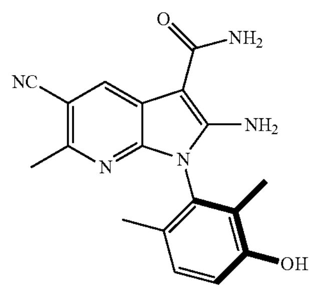 | 336 |
| 12 | 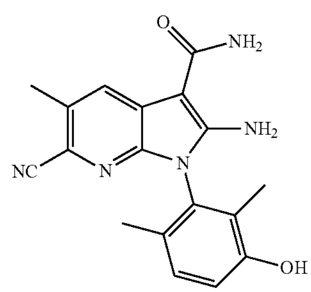 [SMILES: Cc1cc2c(C(N)=O)c(N)n(-c3c(C)ccc(O)c3C)c2nc1C#N] | 336 |
| 13 | 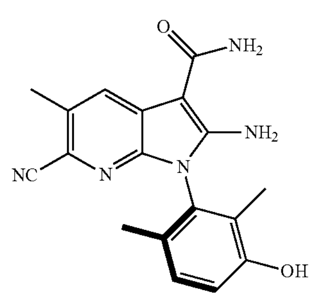 | 336 |

TABLE 1-continued

| Compound | Compound structure | MS (M + H)+ |
|---|---|---|
| 14 | 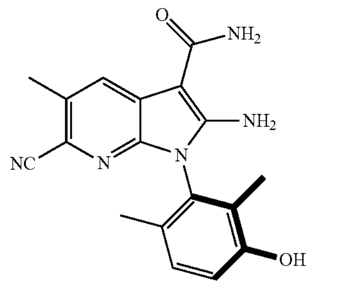 | 336 |
| 15 | 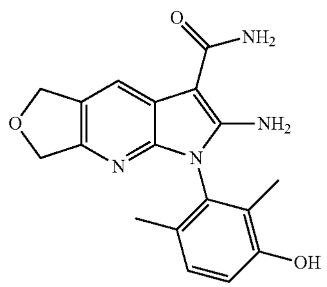 [SMILES: Cc1ccc(O)c(C)c1-n1c(N)c(C(N)=O)c2cc3c(nc21)COC3] | 339 |
| 16 | 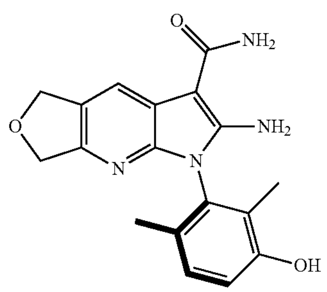 | 339 |
| 17 | 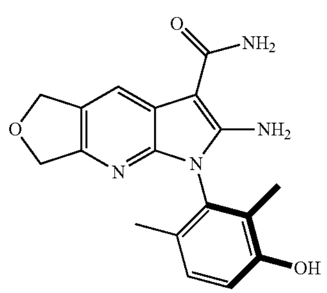 | 339 |
| 18 | 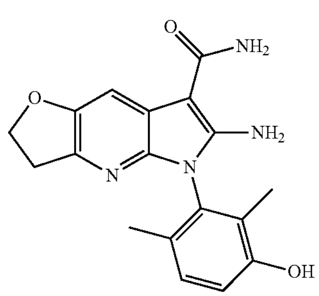 | 339 |
| 19 | | 339 |
| 20 | | 339 |
| 21 | | 339 |
| 22 | | 339 |
| 23 | | 339 |

TABLE 1-continued

| Compound | Compound structure | MS (M + H)+ |
|---|---|---|
| 24 | 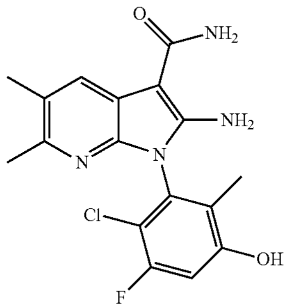 [SMILES: Cc1cc2c(C(N)=O)c(N)n(-c3c(C)c(O)cc(F)c3Cl)c2nc1C] | 363 |
| 25 | 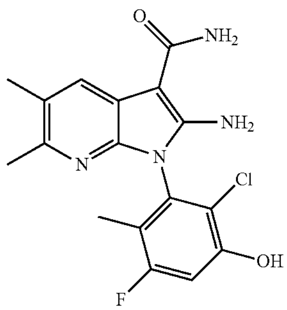 [SMILES: Cc1cc2c(C(N)=O)c(N)n(-c3c(C)c(F)cc(O)c3Cl)c2nc1C] | 363 |
| 26 | 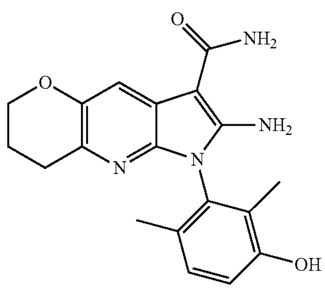 [SMILES: Cc1ccc(O)c(C)c1-n1c(N)c(C(N)=O)c2cc3c(nc21)CCCO3] | 353 |
| 27 | 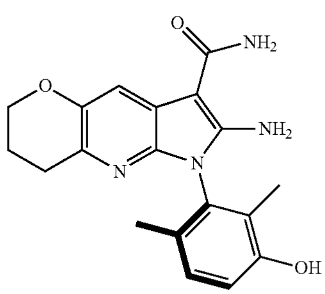 | 353 |
| 28 | 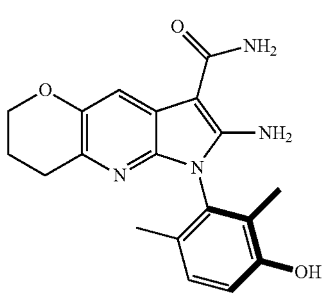 | 353 |
| 29 | 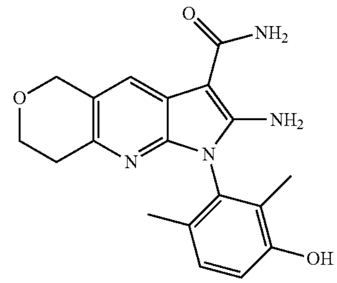 [SMILES: Cc1ccc(O)c(C)c1-n1c(N)c(C(N)=O)c2cc3c(nc21)CCOC3] | 353 |
| 30 | 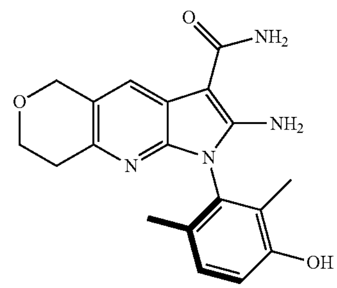 | 353 |
| 31 | 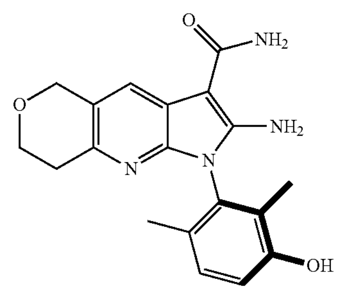 | 353 |
| 32 | 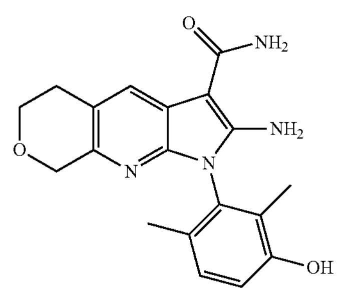 [SMILES: Cc1ccc(O)c(C)c1-n1c(N)c(C(N)=O)c2cc3c(nc21)COCC3] | 353 |
| 33 | 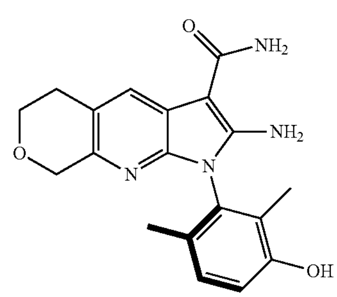 | 353 |

TABLE 1-continued

| Compound | Compound structure | MS (M + H)+ |
|---|---|---|
| 34 | 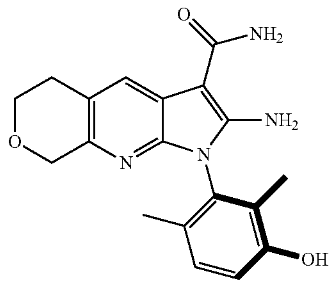 | 353 |
| 35 | 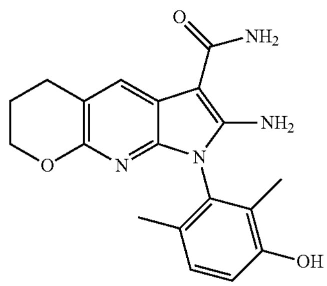 [SMILES: Cc1ccc(O)c(C)c1-n1c(N)c(C(N)=O)c2cc3c(nc21)OCCC3] | 353 |
| 36 | 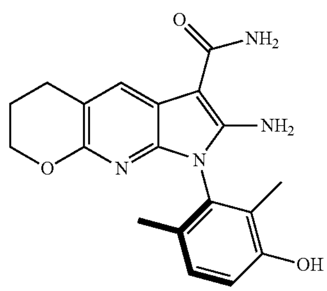 | 353 |
| 37 | 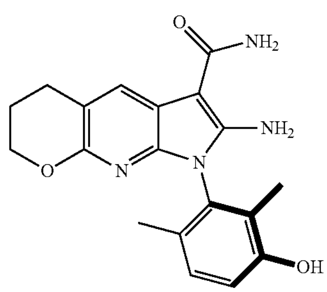 | 353 |
| 38 | 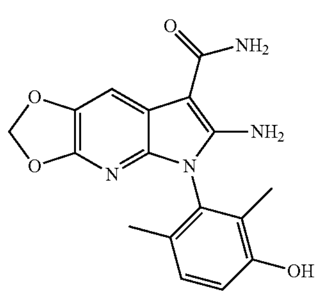 [SMILES: Cc1ccc(O)c(C)c1-n1c(N)c(C(N)=O)c2cc3c(nc21)OCO3] | 341 |

TABLE 1-continued

| Compound | Compound structure | MS (M + H)+ |
|---|---|---|
| 39 | 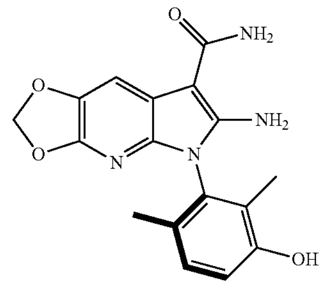 | 341 |
| 40 | 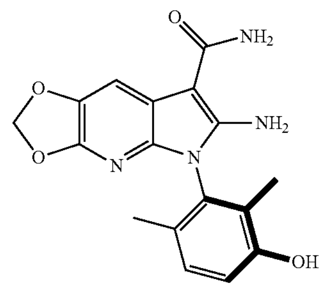 | 341 |
| 41 | 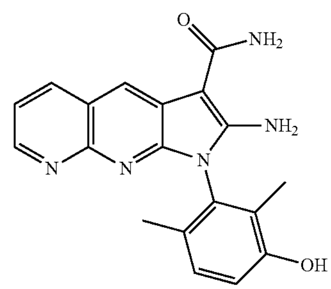 [SMILES: Cc1ccc(O)c(C)c1-n1c(N)c(C(N)=O)c2cc3cccnc3nc21] | 348 |
| 42 | 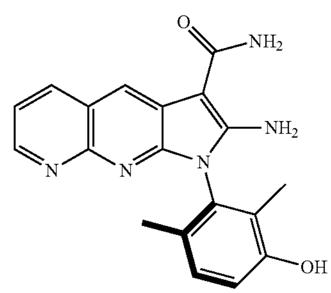 | 348 |
| 43 | 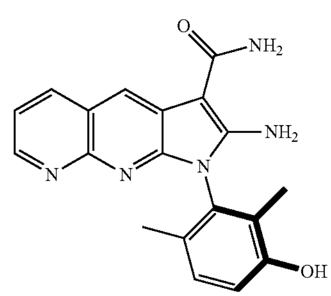 | 348 |

TABLE 1-continued

| Compound | Compound structure | MS (M + H)+ |
|---|---|---|
| 44 | 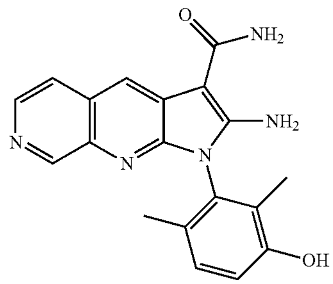 [SMILES: Cc1ccc(O)c(C)c1-n1c(N)c(C(N)=O)c2cc3ccncc3nc21] | 348 |
| 45 | 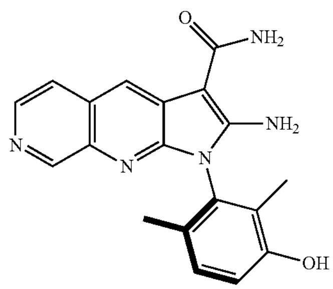 | 348 |
| 46 | 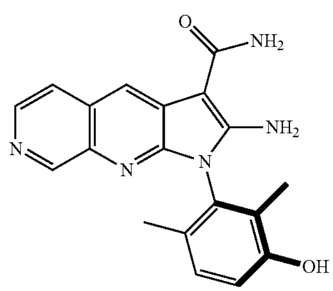 | 348 |
| 47 | 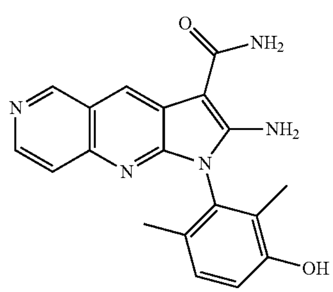 [SMILES: Cc1ccc(O)c(C)c1-n1c(N)c(C(N)=O)c2cc3cnccc3nc21] | 348 |
| 48 | 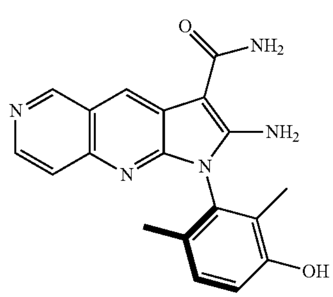 | 348 |
| 49 | 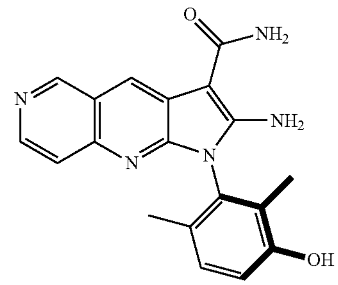 | 348 |
| 50 | 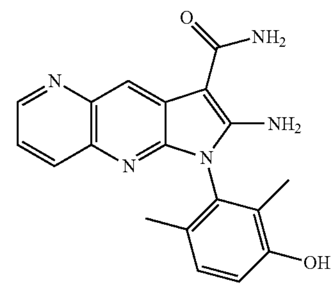 [SMILES: Cc1ccc(O)c(C)c1-n1c(N)c(C(N)=O)c2cc3ncccc3nc21] | 348 |
| 51 | 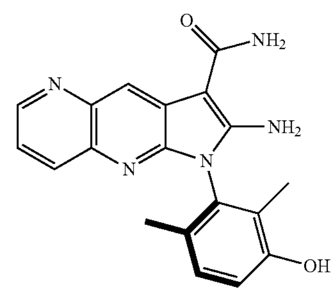 | 348 |
| 52 | 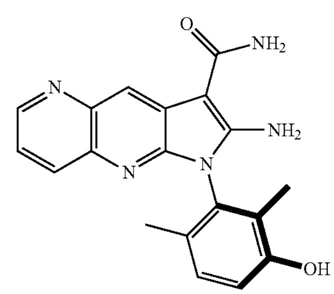 | 348 |
| 53 | 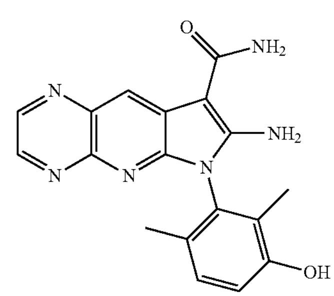 [SMILES: Cc1ccc(O)c(C)c1-n1c(N)c(C(N)=O)c2cc3nccnc3nc21] | 349 |

TABLE 1-continued

| Compound | Compound structure | MS (M + H)+ |
|---|---|---|
| 54 | 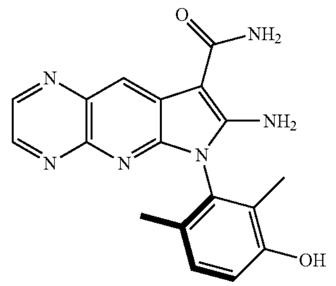 | 349 |
| 55 | 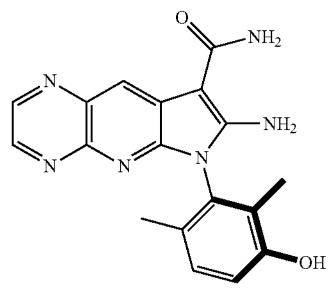 | 349 |
| 56 | 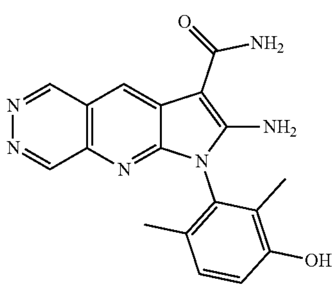 [SMILES: Cc1ccc(O)c(C)c1-n1c(N)c(C(N)=O)c2cc3cnncc3nc21] | 349 |
| 57 | 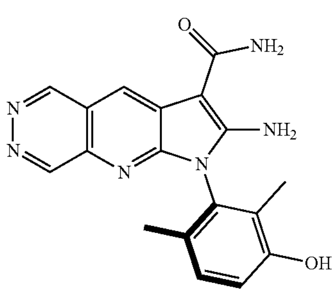 | 349 |
| 58 | 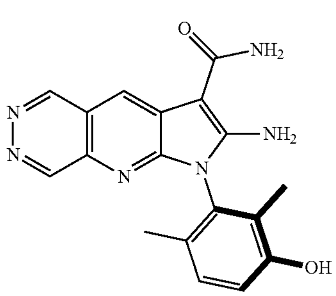 | 349 |

TABLE 1-continued

| Compound | Compound structure | MS (M + H)+ |
|---|---|---|
| 59 | | 348 |
| 60 | | 348 |
| 61 | | 337 |
| 62 | | 337 |
| 63 | | 337 |

TABLE 1-continued

| Compound | Compound structure | MS (M + H)+ |
|---|---|---|
| 64 | 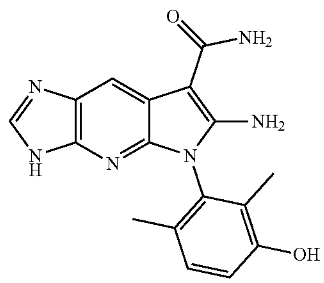 [SMILES: Cc1ccc(O)c(C)c1-n1c(N)c(C(N)=O)c2cc3nc[nH]c3nc21] | 337 |
| 65 | 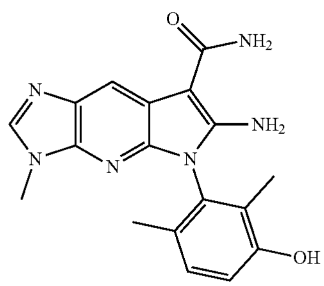 [SMILES: Cc1ccc(O)c(C)c1-n1c(N)c(C(N)=O)c2cc3ncn(C)c3nc21] | 351 |
| 66 | 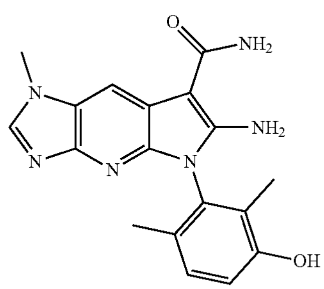 [SMILES: Cc1ccc(O)c(C)c1-n1c(N)c(C(N)=O)c2cc3c(ncn3C)nc21] | 351 |
| 67 | 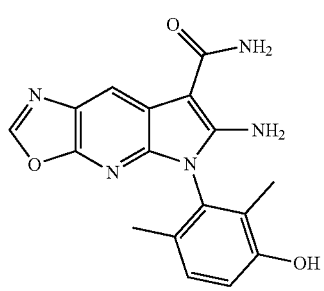 [SMILES: Cc1ccc(O)c(C)c1-n1c(N)c(C(N)=O)c2cc3ncoc3nc21] | 338 |
| 68 | 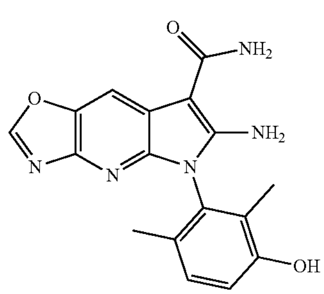 [SMILES: Cc1ccc(O)c(C)c1-n1c(N)c(C(N)=O)c2cc3ocnc3nc21] | 338 |

TABLE 1-continued

| Compound | Compound structure | MS (M + H)+ |
|---|---|---|
| 69 | 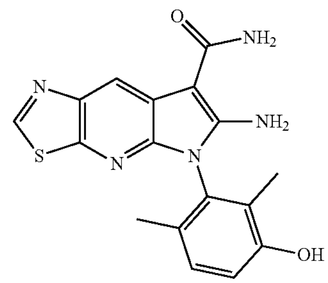 [SMILES: Cc1ccc(O)c(C)c1-n1c(N)c(C(N)=O)c2cc3ncsc3nc21] | 354 |
| 70 | 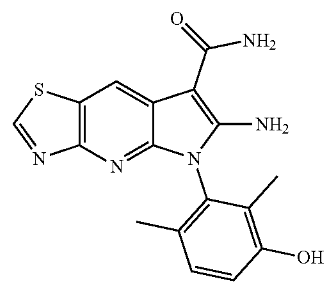 [SMILES: Cc1ccc(O)c(C)c1-n1c(N)c(C(N)=O)c2cc3scnc3nc21] | 354 |
| 71 | 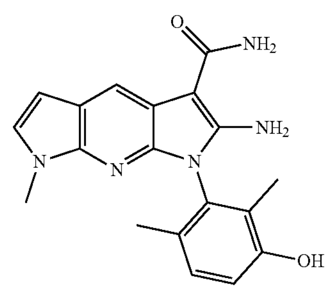 [SMILES: Cc1ccc(O)c(C)c1-n1c(N)c(C(N)=O)c2cc3ccn(C)c3nc21] | 350 |
| 72 | 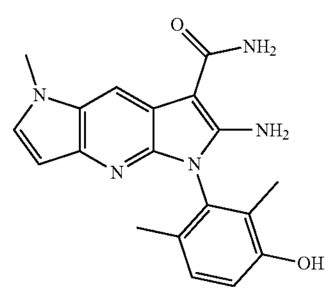 [SMILES: Cc1ccc(O)c(C)c1-n1c(N)c(C(N)=O)c2cc3c(ccn3C)nc21] | 350 |
| 73 | 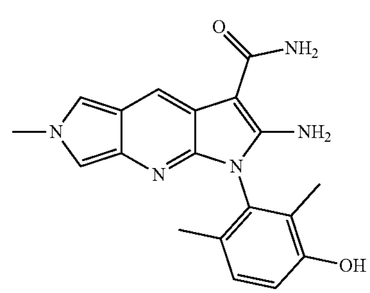 [SMILES: Cc1ccc(O)c(C)c1-n1c(N)c(C(N)=O)c2cc3cn(C)cc3nc21] | 350 |

TABLE 1-continued

| Compound | Compound structure | MS (M + H)+ |
|---|---|---|
| 74 | 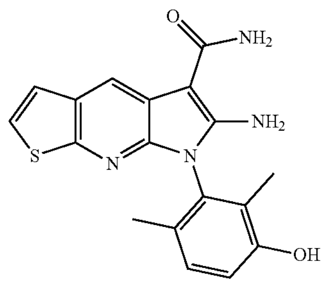 [SMILES: Cc1ccc(O)c(C)c1-n1c(N)c(C(N)=O)c2cc3ccsc3nc21] | 353 |
| 75 | 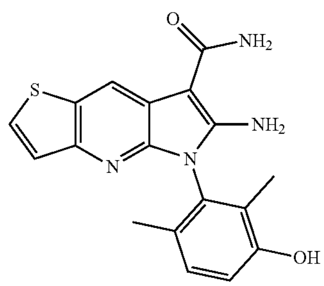 [SMILES: Cc1ccc(O)c(C)c1-n1c(N)c(C(N)=O)c2cc3sccc3nc21] | 353 |
| 76 | 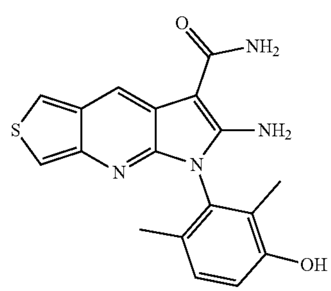 [SMILES: Cc1ccc(O)c(C)c1-n1c(N)c(C(N)=O)c2cc3cscc3nc21] | 353 |
| 77 | 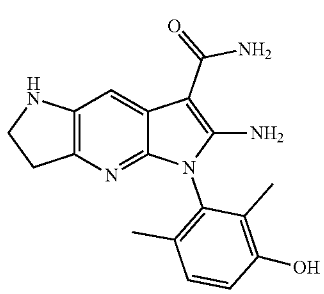 [SMILES: Cc1ccc(O)c(C)c1-n1c(N)c(C(N)=O)c2cc3c(nc21)CCN3] | 338 |
| 78 | 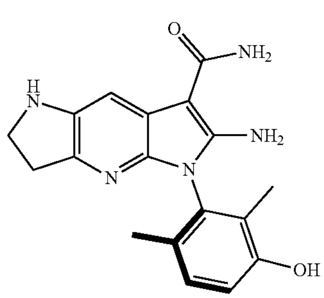 | 338 |
| 79 | | 338 |
| 80 | | 338 |
| 81 | | 338 |
| 82 | | 338 |
| 83 | | 338 |

TABLE 1-continued

| Compound | Compound structure | MS (M + H)+ |
|---|---|---|
| 84 | 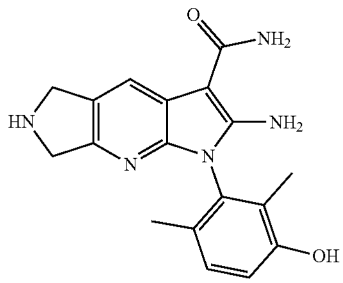 [SMILES: Cc1ccc(O)c(C)c1-n1c(N)c(C(N)=O)c2cc3c(nc21)CNC3] | 338 |
| 85 | 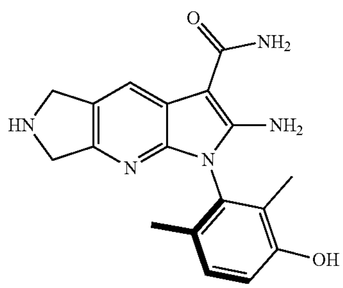 | 338 |
| 86 | 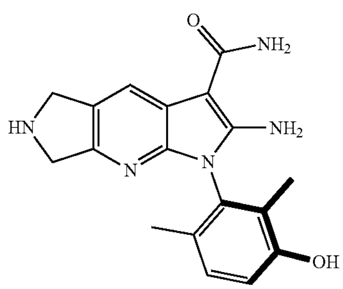 | 338 |
| 87 | 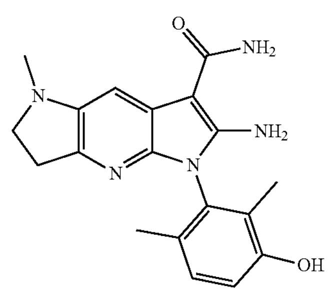 [SMILES: Cc1ccc(O)c(C)c1-n1c(N)c(C(N)=O)c2cc3c(nc21)CCN3C] | 352 |
| 88 | 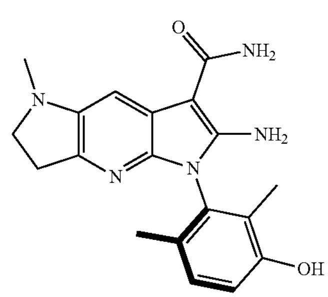 | 352 |
| 89 | 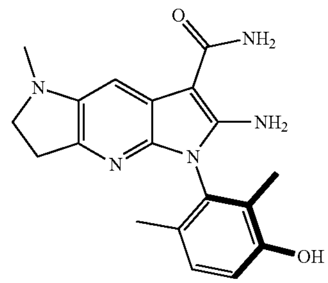 | 352 |
| 90 | 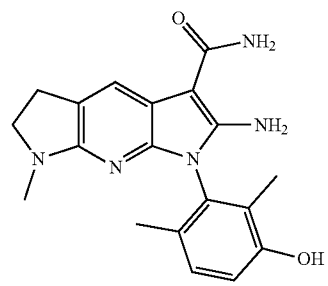 [SMILES: Cc1ccc(O)c(C)c1-n1c(N)c(C(N)=O)c2cc3c(nc21)N(C)CC3] | 352 |
| 91 | 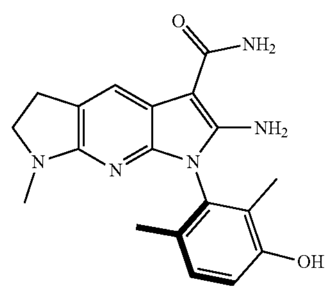 | 352 |
| 92 | 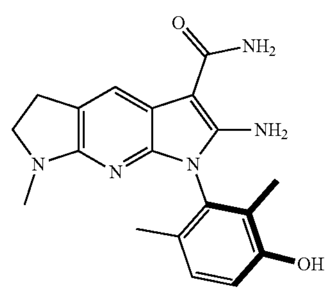 | 352 |
| 93 | 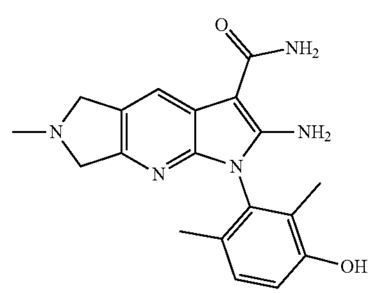 [SMILES: Cc1ccc(O)c(C)c1-n1c(N)c(C(N)=O)c2cc3c(nc21)CN(C)C3] | 352 |

TABLE 1-continued

| Compound | Compound structure | MS (M + H)+ |
|---|---|---|
| 94 | 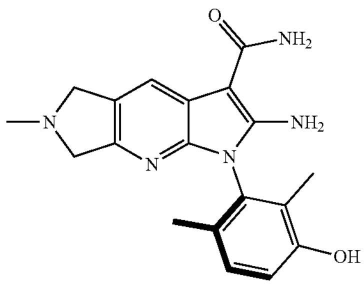 | 352 |
| 95 | 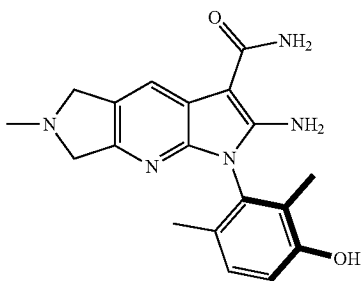 | 352 |
| 96 | 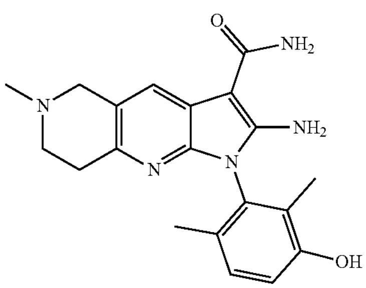 [SMILES: Cc1ccc(O)c(C)c1-n1c(N)c(C(N)=O)c2cc3c(nc21)CCN(C)C3] | 366 |
| 97 | 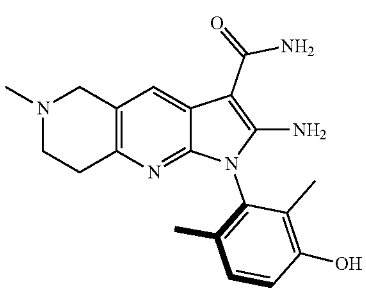 | 366 |
| 98 | 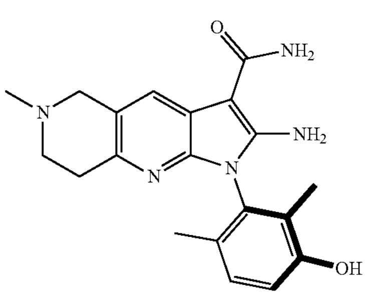 | 366 |
| 99 | | 366 |
| 100 | | 366 |
| 101 | | 366 |
| 102 | | 352 |
| 103 | | 352 |

TABLE 1-continued

| Compound | Compound structure | MS (M + H)+ |
|---|---|---|
| 104 | 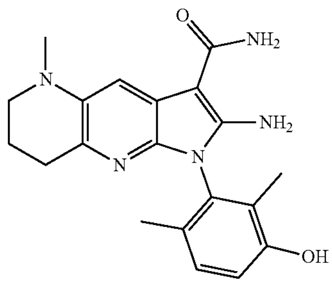 [SMILES: Cc1ccc(O)c(C)c1-n1c(N)c(C(N)=O)c2cc3c(nc21)CCCN3C] | 366 |
| 105 | 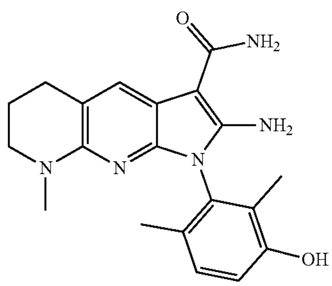 [SMILES: Cc1ccc(O)c(C)c1-n1c(N)c(C(N)=O)c2cc3c(nc21)N(C)CCC3] | 366 |
| 106 | 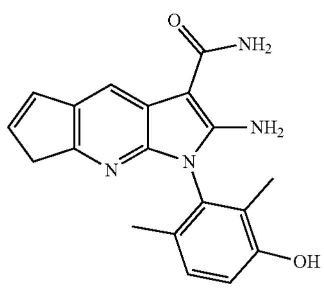 [SMILES: Cc1ccc(O)c(C)c1-n1c(N)c(C(N)=O)c2cc3c(nc21)CC=C3] | 335 |
| 107 | 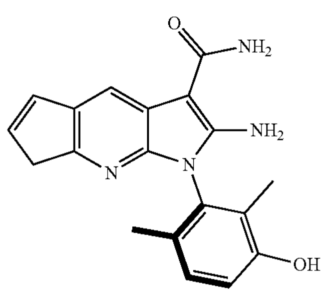 | 335 |
| 108 | 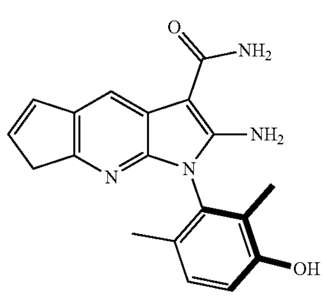 | 335 |
| 109 | | 335 |
| 110 | | 335 |
| 111 | | 335 |
| 112 | | 349 |
| 113 | | 349 |

TABLE 1-continued

| Compound | Compound structure | MS (M + H)+ |
|---|---|---|
| 114 | 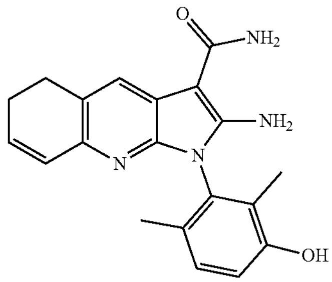 [SMILES: Cc1ccc(O)c(C)c1-n1c(N)c(C(N)=O)c2cc3c(nc21)C=CCC3] | 349 |
| 115 | 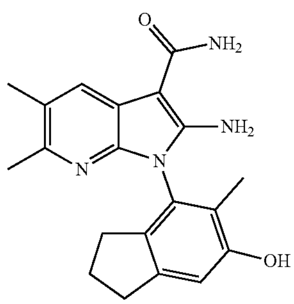 [SMILES: Cc1cc2c(C(N)=O)c(N)n(-c3c(C)c(O)cc4c3CCC4)c2nc1C] | 351 |
| 116 | 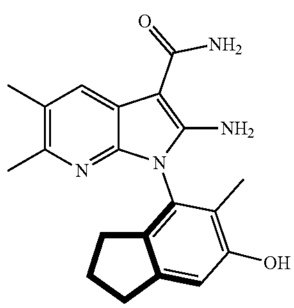 | 351 |
| 117 | 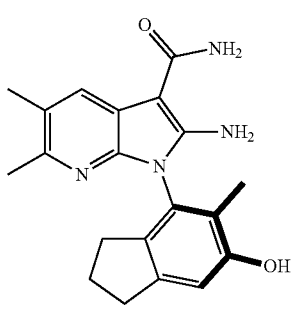 | 351 |
| 118 | 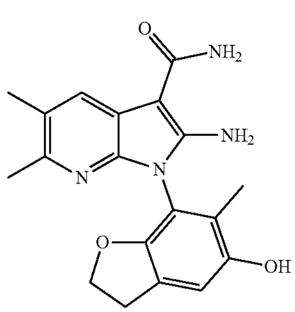 [SMILES: Cc1cc2c(C(N)=O)c(N)n(-c3c(C)c(O)cc4c3OCC4)c2nc1C] | 353 |
| 119 | | 353 |
| 120 | | 353 |
| 121 | | 353 |
| 122 | | 353 |
| 123 | | 353 |

TABLE 1-continued

| Compound | Compound structure | MS (M + H)+ |
|---|---|---|
| 124 | 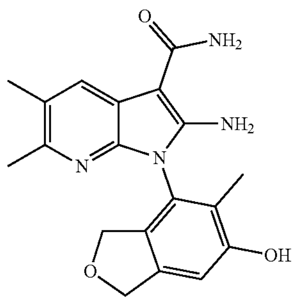 [SMILES: Cc1cc2c(C(N)=O)c(N)n(-c3c(C)c(O)cc4c3COC4)c2nc1C] | 353 |
| 125 | 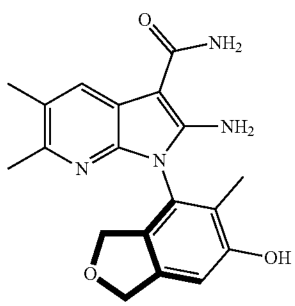 | 353 |
| 126 | 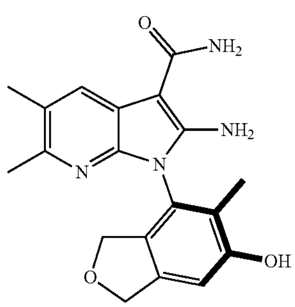 | 353 |
| 127 | 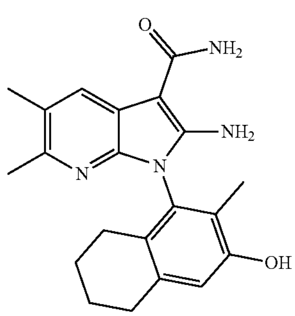 [SMILES: Cc1cc2c(C(N)=O)c(N)n(-c3c(C)c(O)cc4c3CCCC4)c2nc1C] | 365 |
| 128 | 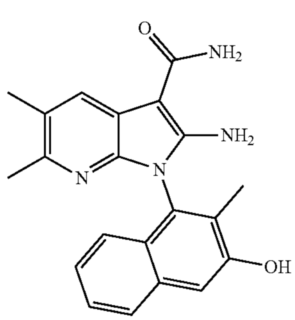 [SMILES: Cc1cc2c(C(N)=O)c(N)n(-c3c(C)c(O)cc4ccccc34)c2nc1C] | 361 |
| 129 | | 351 |
| 130 | | 351 |
| 131 | | 357 |
| 132 | | 357 |
| 133 | | 357 |

TABLE 1-continued

| Compound | Compound structure | MS (M + H)+ |
|---|---|---|
| 134 | 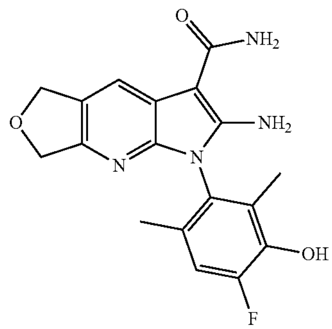 [SMILES: Cc1cc(F)c(O)c(C)c1-n1c(N)c(C(N)=O)c2cc3c(nc21)COC3] | 357 |
| 135 | 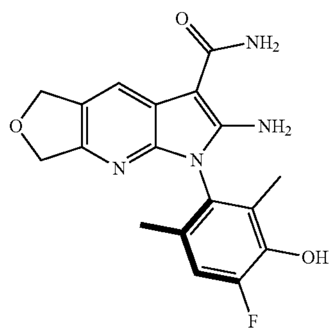 | 357 |
| 136 | 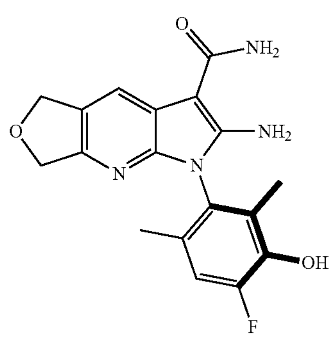 | 357 |
| 137 | 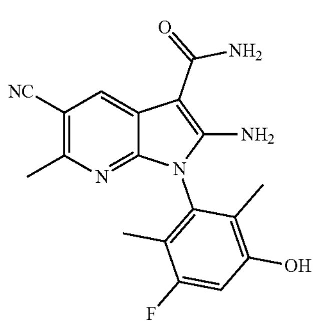 [SMILES: Cc1nc2c(cc1C#N)c(C(N)=O)c(N)n2-c1c(C)c(O)cc(F)c1C] | 354 |
| 138 | 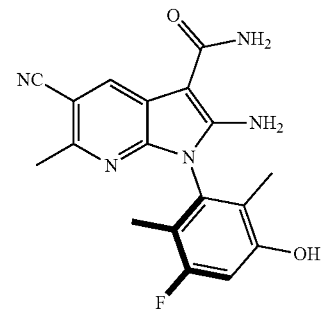 | 354 |
| 139 | 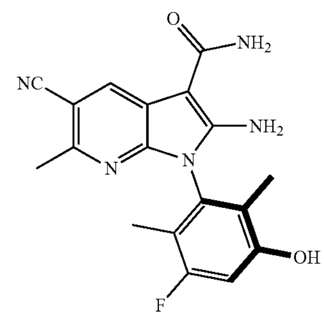 | 354 |
| 140 | 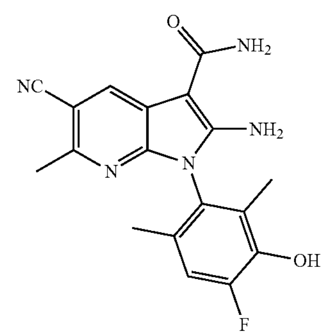 [SMILES: Cc1cc(F)c(O)c(C)c1-n1c(N)c(C(N)=O)c2cc(C#N)c(C)nc21] | 354 |
| 141 | 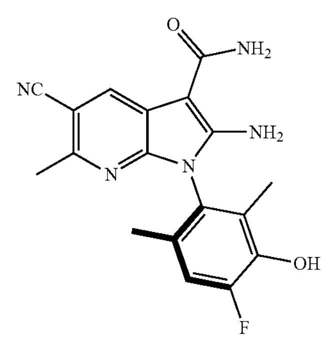 | 354 |

TABLE 1-continued

| Compound | Compound structure | MS (M + H)+ |
|---|---|---|
| 142 | 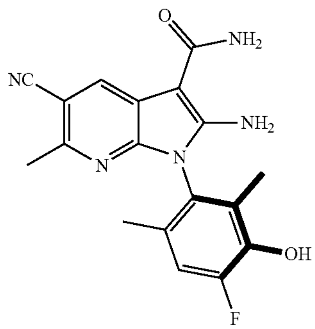 | 354 |
| 143 | 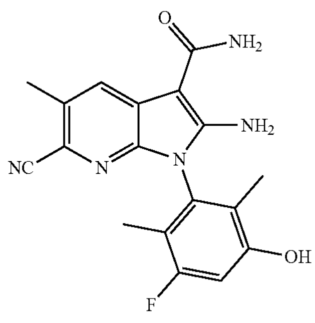 [SMILES: Cc1cc2c(C(N)=O)c(N)n(-c3c(C)c(O)cc(F)c3C)c2nc1C#N] | 354 |
| 144 | 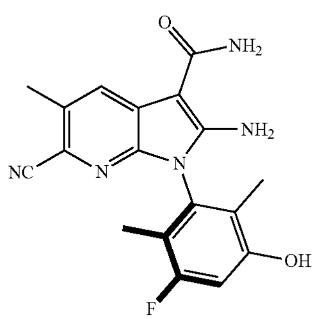 | 354 |
| 145 | 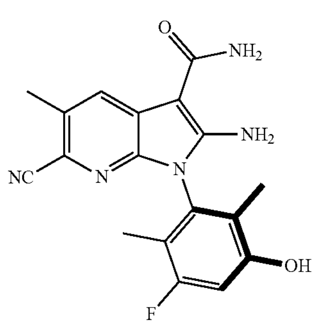 | 354 |
| 146 | | 354 |
| 147 | | 354 |
| 148 | | 354 |
| 149 | | 350 |

TABLE 1-continued

| Compound | Compound structure | MS (M + H)+ |
|---|---|---|
| 150 | 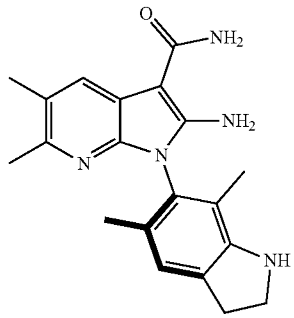 | 350 |
| 151 | 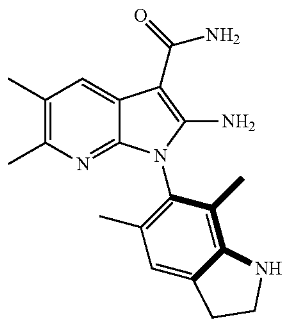 | 350 |
| 152 | 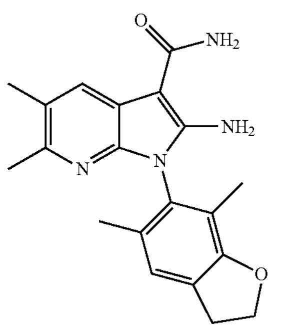 [SMILES: Cc1cc2c(C(N)=O)c(N)n(-c3c(C)cc4c(c3C)OCC4)c2nc1C] | 351 |
| 153 | 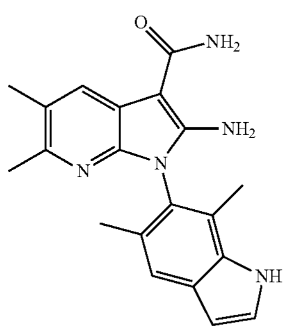 [SMILES: Cc1cc2c(C(N)=O)c(N)n(-c3c(C)cc4cc[nH]c4c3C)c2nc1C] | 348 |
| 154 | 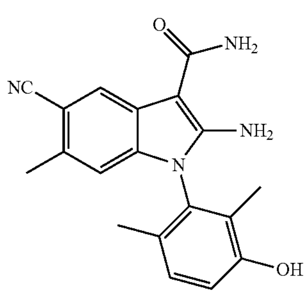 [SMILES: Cc1cc2c(cc1C#N)c(C(N)=O)c(N)n2-c1c(C)ccc(O)c1C] | 335 |
| 155 | | 335 |
| 156 | | 335 |
| 157 | | 335 |
| 158 | | 335 |
| 159 | | 335 |

TABLE 1-continued

| Compound | Compound structure | MS (M + H)+ |
|---|---|---|
| 160 | 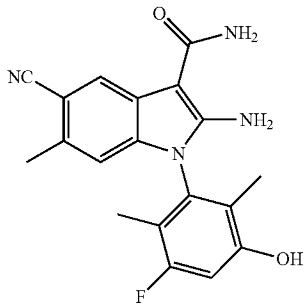 [SMILES: Cc1cc2c(cc1C#N)c(C(N)=O)c(N)n2-c1c(C)c(O)cc(F)c1C] | 353 |
| 161 | 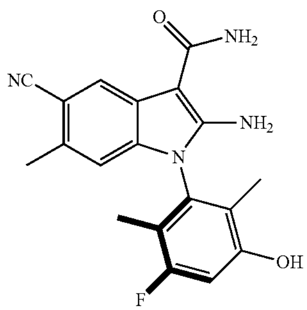 | 353 |
| 162 | 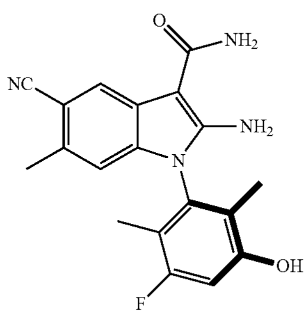 | 353 |
| 163 | 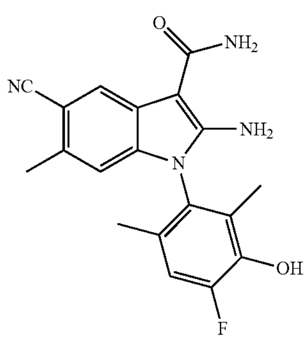 [SMILES: Cc1cc2c(cc1C#N)c(C(N)=O)c(N)n2-c1c(C)cc(F)c(O)c1C] | 353 |
| 164 | 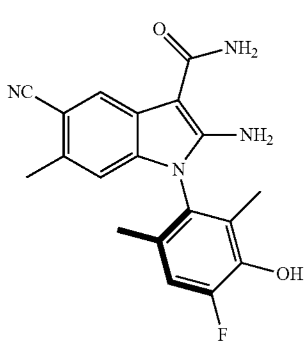 | 353 |
| 165 | | 353 |
| 166 | | 353 |
| 167 | | 353 |
| 168 | | 353 |

TABLE 1-continued

| Compound | Compound structure | MS (M + H)+ |
|---|---|---|
| 169 | 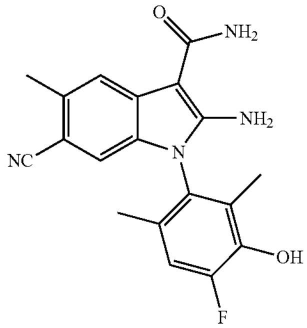 [SMILES: Cc1cc2c(C(N)=O)c(N)n(-c3c(C)cc(F)c(O)c3C)c2cc1C#N] | 353 |
| 170 | 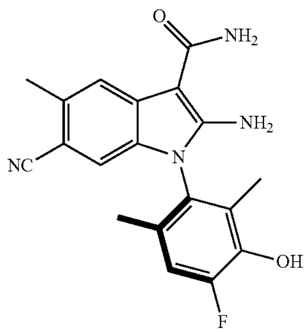 | 353 |
| 171 | 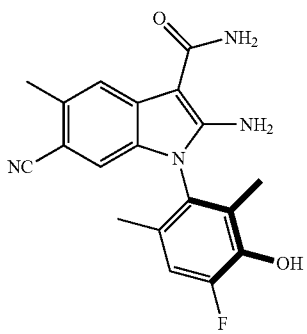 | 353 |
| 172 | 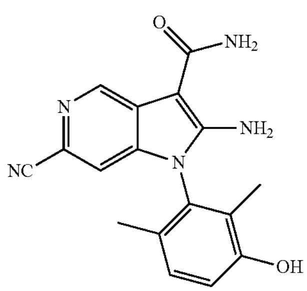 [SMILES: Cc1ccc(O)c(C)c1-n1c(N)c(C(N)=O)c2cnc(C#N)cc21] | 322 |
| 173 | 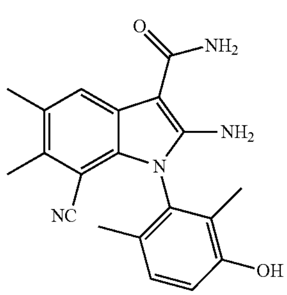 [SMILES: Cc1cc2c(C(N)=O)c(N)n(-c3c(C)ccc(O)c3C)c2c(C#N)c1C] | 349 |
| 174 | | 349 |
| 175 | | 349 |
| 176 | | 326 |
| 177 | | 326 |
| 178 | | 326 |

TABLE 1-continued

| Compound | Compound structure | MS (M + H)+ |
|---|---|---|
| 179 | 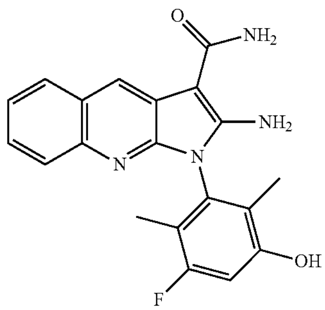 [SMILES: Cc1c(O)cc(F)c(C)c1-n1c(N)c(C(N)=O)c2cc3ccccc3nc21] | 365 |
| 180 | 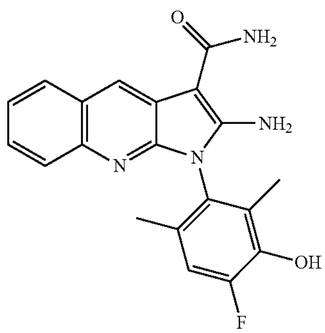 [SMILES: Cc1cc(F)c(O)c(C)c1-n1c(N)c(C(N)=O)c2cc3ccccc3nc21] | 365 |
| 181 | 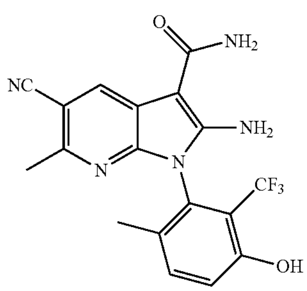 | 390 |
| 182 | 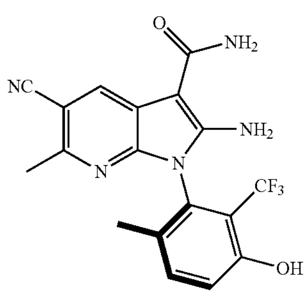 | 390 |
| 183 | 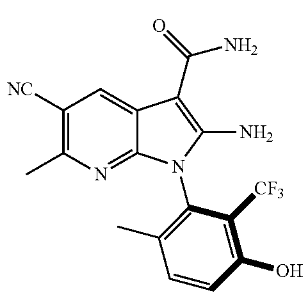 | 390 |
| 184 | 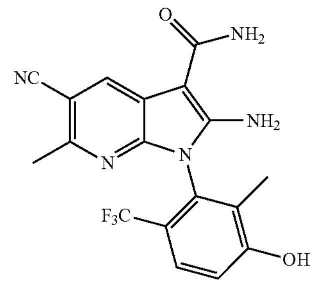 [SMILES: Cc1nc2c(cc1C#N)c(C(N)=O)c(N)n2-c1c(C(F)(F)F)ccc(O)c1C] | 390 |
| 185 | 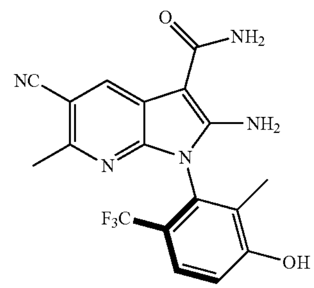 | 390 |
| 186 | 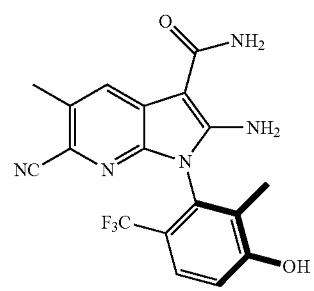 | 390 |
| 187 | 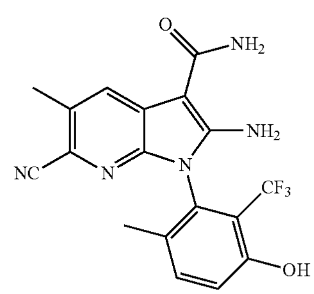 | 390 |
| 188 | 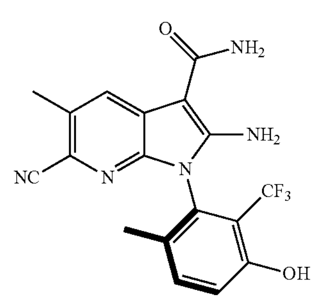 | 390 |

TABLE 1-continued

| Compound | Compound structure | MS (M + H)+ |
|---|---|---|
| 189 | 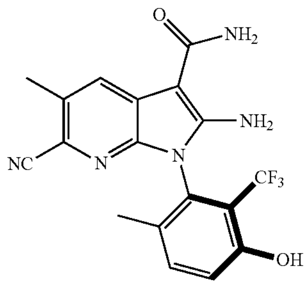 | 390 |
| 190 | 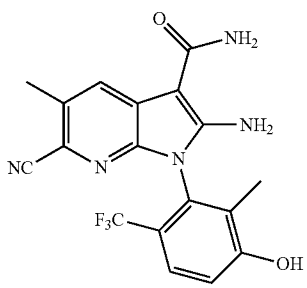 [SMILES: Cc1cc2c(C(N)=O)c(N)n(-c3c(C(F)(F)F)ccc(O)c3C)c2nc1C#N] | 390 |
| 191 | 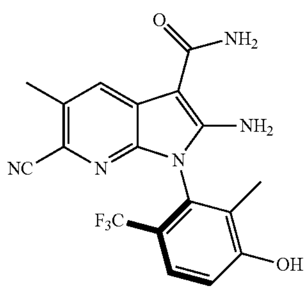 | 390 |
| 192 | 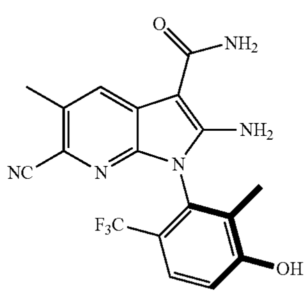 | 390 |
| 193 | 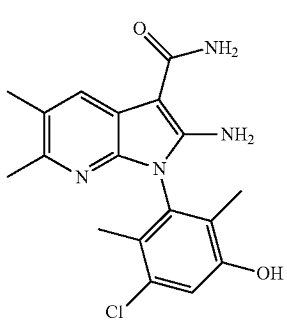 [SMILES: Cc1cc2c(C(N)=O)c(N)n(-c3c(C)c(O)cc(Cl)c3C)c2nc1C] | 359 |
| 194 | | 359 |
| 195 | | 359 |
| 196 | | 403 |
| 197 | | 403 |
| 198 | | 403 |

TABLE 1-continued
| Compound | Compound structure | MS (M + H)+ |
|---|---|---|
| 199 | 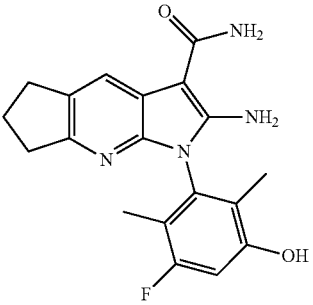 [SMILES: Cc1c(O)cc(F)c(C)c1-n1c(N)c(C(N)=O)c2cc3c(nc21)CCC3] | 355 |
| 200 | 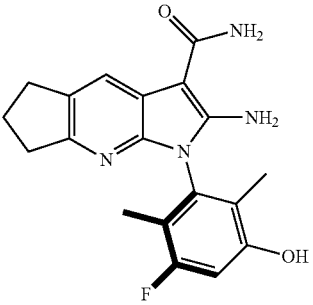 | 355 |
| 201 | 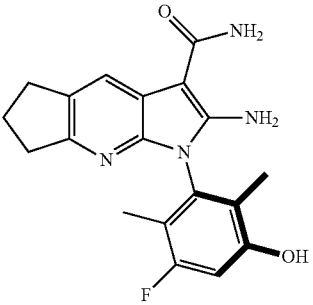 | 355 |
| 202 | 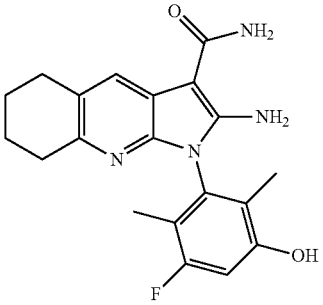 [SMILES: Cc1c(O)cc(F)c(C)c1-n1c(N)c(C(N)=O)c2cc3c(nc21)CCCC3] | 369 |
| 203 | 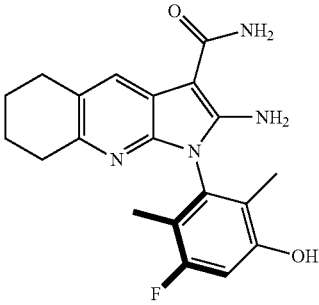 | 369 |
| 204 | 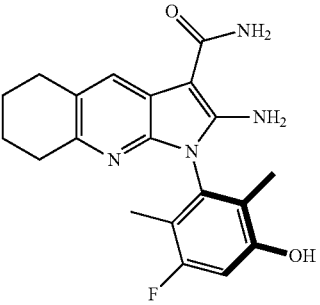 | 369 |
| 205 | 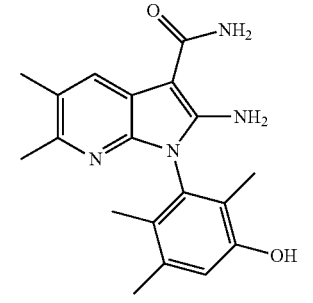 [SMILES: Cc1cc2c(C(N)=O)c(N)n(-c3c(C)c(C)cc(O)c3C)c2nc1C] | 339 |
| 206 | 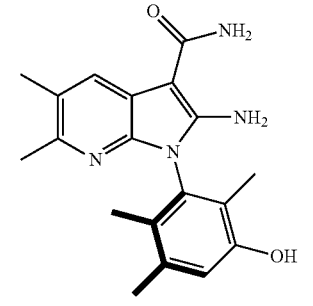 | 339 |
| 207 | 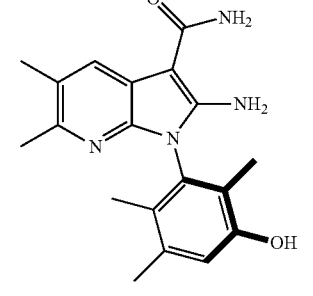 | 339 |
| 208 | 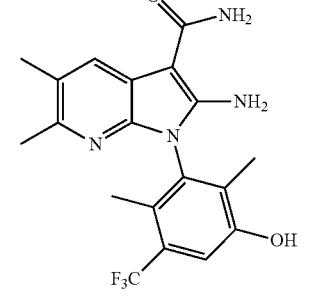 | 393 |

TABLE 1-continued

| Compound | Compound structure | MS (M + H)+ |
|---|---|---|
| 209 | 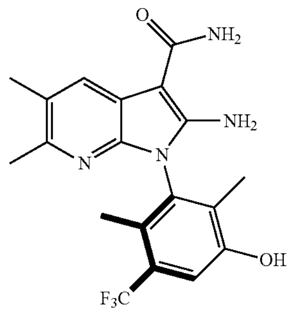 | 393 |
| 210 | 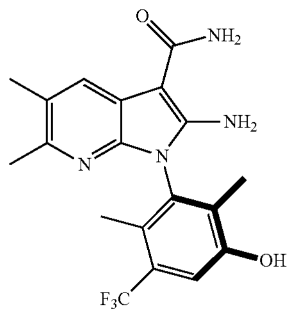 | 393 |
| 211 | 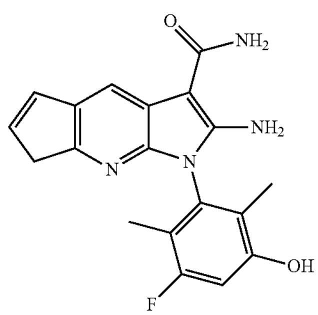 [SMILES: Cc1c(O)cc(F)c(C)c1-n1c(N)c(C(N)=O)c2cc3c(nc21)CC=C3] | 353 |
| 212 | 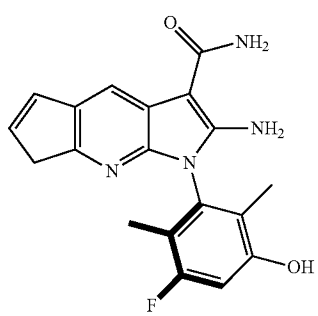 | 353 |
| 213 | 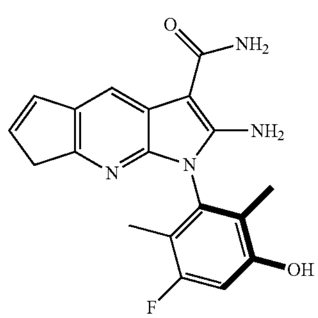 | 353 |
| 214 | 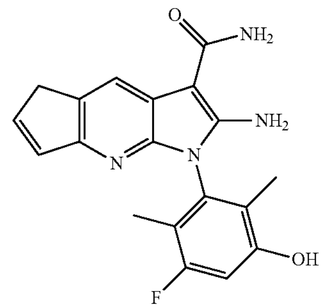 [SMILES: Cc1c(O)cc(F)c(C)c1-n1c(N)c(C(N)=O)c2cc3c(nc21)C=CC3] | 353 |
| 215 | 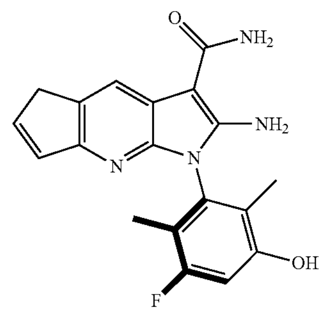 | 353 |
| 216 | 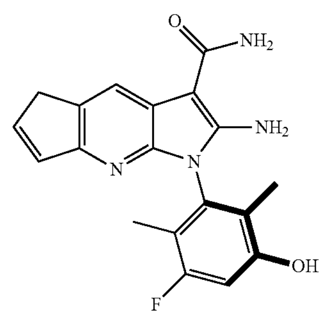 | 353 |
| 217 | 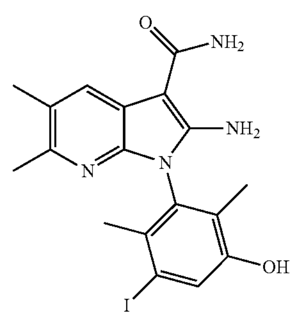 [SMILES: Cc1cc2c(C(N)=O)c(N)n(-c3c(C)c(O)cc(I)c3C)c2nc1C] | 451 |
| 218 | 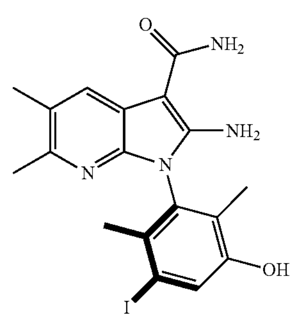 | 451 |

TABLE 1-continued

| Compound | Compound structure | MS (M + H)+ |
|---|---|---|
| 219 | 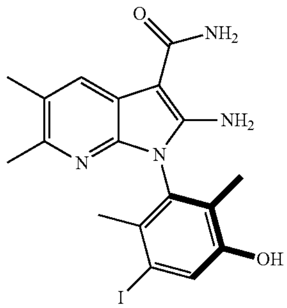 | 451 |
| 220 | 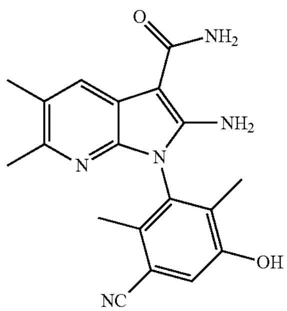 [SMILES: Cc1cc2c(C(N)=O)c(N)n(-c3c(C)c(O)cc(C#N)c3C)c2nc1C] | 350 |
| 221 | 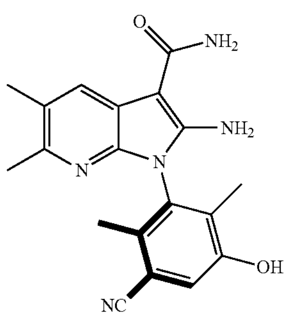 | 350 |
| 222 | 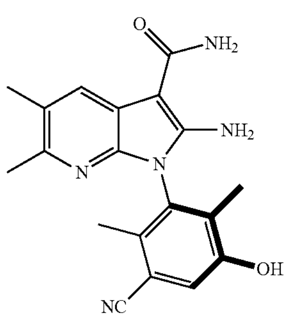 | 350 |
| 223 | 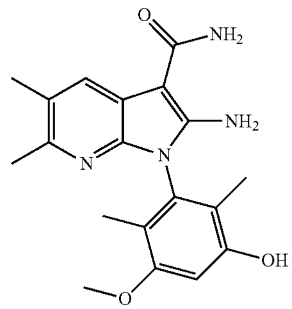 [SMILES: COc1cc(O)c(C)c(-n2c(N)c(C(N)=O)c3cc(C)c(C)nc32)c1C] | 355 |
| 224 | 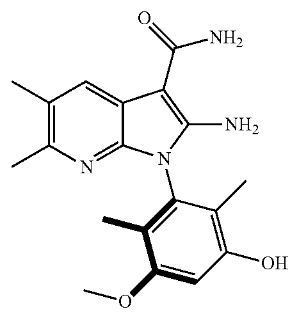 | 355 |
| 225 | 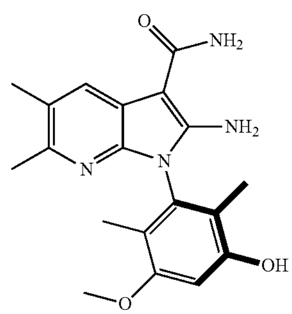 | 355 |

Biological Example 1. In Vitro Assay of Compounds of the Present Invention for Inhibiting MYT1 Kinase Activity Recombinant MYT1 protein and the compounds were pre-incubated at room temperature for 15 min, and 10 μM ATP was then added to start the reaction. The mixture was incubated at room temperature for another 60 min, and the ADP-GLO reagent from Promega was then added. The resulting mixture was incubated in the dark for 40 min, a detection solution was then added, and the mixture was incubated for another 45-60 min. The chemiluminescence was determined using ENVISION. The inhibition rate and $IC_{50}$ were calculated compared to the DMSO group. The results are shown in Table 2 below.

TABLE 2

Inhibitory activity of compounds of the present invention against recombinant protein MYT1 ($IC_{50}$, nM)

| Compound | $IC_{50}$ | Compound | $IC_{50}$ | Compound | $IC_{50}$ | Compound | $IC_{50}$ |
|---|---|---|---|---|---|---|---|
| 1 | +++ | 2 | +++ | 3 | +++ | 4 | +++ |
| 5 | +++ | 6 | +++ | 7 | +++ | 8 | +++ |
| 9 | +++ | 10 | +++ | 11 | +++ | 12 | +++ |
| 13 | +++ | 14 | +++ | 15 | +++ | 16 | +++ |

TABLE 2-continued

Inhibitory activity of compounds of the present invention against recombinant protein MYT1 (IC$_{50}$, nM)

| Compound | IC$_{50}$ | Compound | IC$_{50}$ | Compound | IC$_{50}$ | Compound | IC$_{50}$ |
|---|---|---|---|---|---|---|---|
| 17 | +++ | 18 | +++ | 19 | +++ | 20 | +++ |
| 21 | +++ | 22 | +++ | 23 | +++ | 24 | +++ |
| 25 | +++ | 26 | +++ | 27 | +++ | 28 | +++ |
| 29 | +++ | 30 | +++ | 31 | +++ | 32 | +++ |
| 33 | +++ | 34 | +++ | 35 | +++ | 36 | +++ |
| 37 | +++ | 38 | +++ | 39 | +++ | 40 | +++ |
| 41 | +++ | 42 | +++ | 43 | +++ | 44 | +++ |
| 45 | +++ | 46 | +++ | 47 | +++ | 48 | +++ |
| 49 | +++ | 50 | +++ | 51 | +++ | 52 | +++ |
| 53 | +++ | 54 | +++ | 55 | +++ | 56 | +++ |
| 57 | +++ | 58 | +++ | 59 | +++ | 60 | +++ |
| 61 | +++ | 62 | +++ | 63 | +++ | 64 | +++ |
| 65 | +++ | 66 | +++ | 67 | +++ | 68 | +++ |
| 69 | +++ | 70 | +++ | 71 | +++ | 72 | +++ |
| 73 | +++ | 74 | +++ | 75 | +++ | 76 | +++ |
| 77 | +++ | 78 | +++ | 79 | +++ | 80 | +++ |
| 81 | +++ | 82 | +++ | 83 | +++ | 84 | +++ |
| 85 | +++ | 86 | +++ | 87 | +++ | 88 | +++ |
| 89 | +++ | 90 | +++ | 91 | +++ | 92 | +++ |
| 93 | +++ | 94 | +++ | 95 | +++ | 96 | +++ |
| 97 | +++ | 98 | +++ | 99 | +++ | 100 | +++ |
| 101 | +++ | 102 | +++ | 103 | +++ | 104 | +++ |
| 105 | +++ | 106 | +++ | 107 | +++ | 108 | +++ |
| 109 | +++ | 110 | +++ | 111 | +++ | 112 | +++ |
| 113 | +++ | 114 | +++ | 115 | +++ | 116 | +++ |
| 117 | +++ | 118 | +++ | 119 | +++ | 120 | +++ |
| 121 | +++ | 122 | +++ | 123 | +++ | 124 | +++ |
| 125 | +++ | 126 | +++ | 127 | ++ | 128 | ++ |
| 129 | +++ | 130 | +++ | 131 | +++ | 132 | +++ |
| 133 | +++ | 134 | +++ | 135 | +++ | 136 | +++ |
| 137 | +++ | 138 | +++ | 139 | +++ | 140 | +++ |
| 141 | +++ | 142 | +++ | 143 | +++ | 144 | +++ |
| 145 | +++ | 146 | +++ | 147 | +++ | 148 | +++ |
| 149 | +++ | 150 | +++ | 151 | +++ | 152 | +++ |
| 153 | +++ | 154 | +++ | 155 | +++ | 156 | +++ |
| 157 | +++ | 158 | +++ | 159 | +++ | 160 | +++ |
| 161 | +++ | 162 | +++ | 163 | +++ | 164 | +++ |
| 165 | +++ | 166 | +++ | 167 | +++ | 168 | +++ |
| 169 | +++ | 170 | +++ | 171 | +++ | 172 | +++ |
| 173 | +++ | 174 | +++ | 175 | +++ | 176 | +++ |
| 177 | +++ | 178 | +++ | 179 | +++ | 180 | +++ |
| 181 | +++ | 182 | +++ | 183 | +++ | 184 | +++ |
| 185 | +++ | 186 | +++ | 187 | +++ | 188 | +++ |
| 189 | +++ | 190 | +++ | 191 | +++ | 192 | +++ |
| 193 | +++ | 194 | +++ | 195 | +++ | 196 | +++ |
| 197 | +++ | 198 | +++ | 199 | +++ | 200 | +++ |
| 201 | +++ | 202 | +++ | 203 | +++ | 204 | +++ |
| 205 | +++ | 206 | +++ | 207 | +++ | 208 | +++ |
| 209 | +++ | 210 | +++ | 211 | +++ | 212 | +++ |
| 213 | +++ | 214 | +++ | 215 | +++ | 216 | +++ |
| 217 | +++ | 218 | +++ | 219 | +++ | 220 | +++ |
| 221 | +++ | 222 | +++ | 223 | +++ | 224 | +++ |
| 225 | +++ | | | | | | |

+++ means that IC$_{50}$ is less than or equal to 200 nM
++ means that IC$_{50}$ is 200 nM to 500 nM
+ means that IC$_{50}$ is greater than 500 nM Biological Example 2. In Vitro Anti-Proliferative Activity of Compounds of the Present Invention Against MIA PaCa-2 Cells MIA PaCa-2 cells were seeded on a 384-well plate at 3000 cells/well. After overnight adherence culture, DMSO or the compounds serially diluted 1:5 from 10 UM were added. The viability was assessed 72 h after dosing by measuring the intracellular ATP content. The inhibition percentage of viable cells by the compounds was calculated by comparing with the DMSO group, and the IC$_{50}$ value was calculated. The results are shown in Table 3 below.

TABLE 3

Anti-proliferative activity of compounds of the present invention against MIA PaCa-2 cells

| Compound | Anti-proliferative activity against MIA PaCa-2 cells IC$_{50}$ (nM) | Compound | Anti-proliferative activity against MIA PaCa-2 cells IC$_{50}$ (nM) |
|---|---|---|---|
| 2 | 4322 | 3 | >10000 |
| 6 | >10000 | 7 | >10000 |
| 10 | 4241 | 11 | >10000 |
| 12 | >10000 | 16 | >10000 |
| 17 | >10000 | 97 | >10000 |

TABLE 3-continued

Anti-proliferative activity of compounds of the present invention against MIA PaCa-2 cells

| Compound | Anti-proliferative activity against MIA PaCa-2 cells IC$_{50}$ (nM) | Compound | Anti-proliferative activity against MIA PaCa-2 cells IC$_{50}$ (nM) |
|---|---|---|---|
| 98 | >10000 | 116 | >10000 |
| 117 | >10000 | 150 | >10000 |
| 151 | >10000 | 153 | >10000 |
| RP-6306 | 9223 | | |

The reference compound RP-6306 is compound 182 in WO2021195781A1.

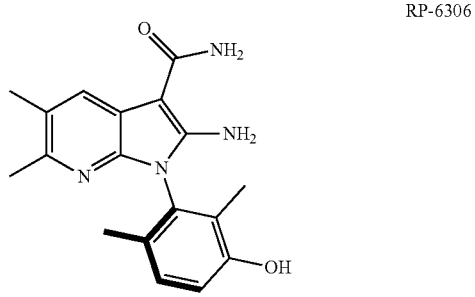

RP-6306

As can be seen from the data in Table 3, the compounds of the present invention used alone have no strong anti-proliferative activity against MIA PaCa-2 cells.

Biological Example 3. In Vitro Anti-Proliferative Activity of Compounds of the Present Invention in Combination with Gemcitabine Against MIA PaCa-2 Cells MIA PaCa-2 cells were seeded on a 384-well plate at 3000 cells/well, and 20 nM gemcitabine was added. After overnight adherence culture, DMSO or the compounds serially diluted 1:5 from 1000 nM were added. The viability was assessed 72 h after dosing by measuring the intracellular ATP content. The inhibition percentage of viable cells by the compounds was calculated by comparing with the DMSO group, and the IC$_{50}$ value was calculated. The results are shown in Table 4 below.

TABLE 4

In vitro anti-proliferative activity of compounds of the present invention in combination with gemcitabine against MIA PaCa-2 cells

| Compound | Anti-proliferative activity against MIA PaCa-2 cells (20 nM gemcitabine) IC$_{50}$ (nM) | Compound | Anti-proliferative activity against MIA PaCa-2 cells (20 nM gemcitabine) IC$_{50}$ (nM) |
|---|---|---|---|
| 2 | 18 | 3 | 1228 |
| 6 | 165 | 7 | >1000 |
| 10 | 45 | 11 | >1000 |
| 12 | 228 | 16 | 101 |
| 17 | >1000 | 97 | 101 |
| 98 | >1000 | 116 | >1000 |
| 117 | >1000 | 150 | >1000 |
| 151 | >1000 | 153 | >1000 |
| RP-6306 | 29 | | |

As can be seen from the data in Table 4, the compounds of the present invention, in combination with gemcitabine, have strong anti-proliferative activity against MIA PaCa-2 cells in vitro, and compound 2 of the present invention, in combination with gemcitabine, has stronger anti-proliferative activity than that of RP-6306.

Biological Example 4. In Vivo Pharmacokinetic Experiment of Compound of the Present Invention CD-1 female mice aged 7 to 10 weeks were intravenously administered and orally administered at a dose of 2 mg/kg and 10 mg/kg, respectively. The mice were fasted for at least 12 h before the administration and given food 4 h after the administration, and they were given ad libitum access to water during the experiment. On the day of the experiment, animals in the intravenous group were administered the corresponding compound by single injection via the tail vein at an administration volume of 10 mL/kg. Animals in the oral group were administered the corresponding compound by single intragastric injection at an administration volume of 10 mL/kg. The animals were weighed before administration, and the administration volume was calculated according to the body weight. The sample collection time was 0.083 h (injection group), 0.167 h, 0.5 h, 1 h, 2 h, 4 h, 8 h, and 24 h. About 200 µL of whole blood was collected through the submaxillary venous plexus at each time point and used to prepare plasma for concentration determination by high-performance liquid chromatography-tandem mass spectrometry (LC-MS/MS). All animals were euthanized with CO$_2$ anesthesia after the PK samples were collected at the last time point. The plasma concentrations were processed using a non-compartmental model of Phoenix WinNonlin™ version 8.3 (Certara) pharmacokinetic software, and the pharmacokinetic parameters were calculated using a linear-log trapezoidal method. The in vivo pharmacokinetic results are shown in Table 5 below.

TABLE 5

Results of in vivo pharmacokinetic evaluation of compound of the present invention

| Route of Administration | Pharmacokinetic parameter | Compound 2 | RP-6306 |
|---|---|---|---|
| Injection (2 mg/kg) | Vdss (L/Kg) | 6.76 | 2.46 |
| | T$_{1/2}$ (h) | 3.32 | 0.56 |
| | Cl (mL/min/Kg) | 94.4 | 46.5 |
| | AUC$_{0-last}$ (h*ng/ml) | 337.7 | 375.5 |

TABLE 5-continued

Results of in vivo pharmacokinetic evaluation
of compound of the present invention

| Route of Administration | Pharmacokinetic parameter | Compound 2 | RP-6306 |
|---|---|---|---|
| Oral administration (10 mg/kg) | $C_{max}$ (ng/ml) | 603.3 | 881 |
| | $T_{1/2}$ (h) | 3.84 | 1.58 |
| | $AUC_{0\text{-}last}$ (h*ng/ml) | 638.2 | 1027.5 |
| | F % | 44.5 | 54.7 |

As can be seen from the data in Table 5, in the pharmacokinetic experiment of the mice, compound 2 of the present invention had a longer half-life $T_{1/2}$ compared to RP-6306, indicating that compound 2 has better metabolic stability in vivo. Moreover, compound 2 showed a greater increase in Vdss compared to RP-6306, indicating that compound 2 is less distributed in plasma and more distributed in other tissues, with greater advantages for treating solid tumors. Thus, compound 2 has unexpectedly improved pharmacokinetic properties compared to RP-6306.

Biological Example 5. In Vitro Permeability Experiment of Compound of the Present Invention In vitro passive permeability or the ability to serve as a P-glycoprotein (P-gp) transport substrate was tested using MDCK cells (MDCK wild type) or MDCK cells stably transduced with MDR1 (MDCK-MDR1), respectively. The permeability experiment was performed in duplicate in a transwell system at a single concentration (5 μM). The cells were incubated for 90 min. Apical-to-basolateral (A to B, A-B) transport and basolateral-to-apical (B to A, B-A) transport of the corresponding compound were determined, and the permeation rate (apparent permeability) ($P_{app} \times 10^{-6}$ cm/sec) and efflux ratio ($P_{app}$ (B-A)/$P_{app}$ (A-B)) of the test compound were calculated. Digoxin, metoprolol, and atenolol were used as controls. The results of the in vitro permeability experiment are shown in Table 6 below.

As can be seen from the data in Table 6, compound 2 of the present invention had faster apical-to-basolateral (A to B, A-B) transport rates on MDCK cells and MDCK-MDR1 cells and lower efflux ratios ($P_{app}$ (B-A)/$P_{app}$ (A-B)) on MDCK cells and MDCK-MDR1 cells compared to RP-6306, indicating that compound 2 has superior permeability to that of RP-6306.

Biological Example 6. In Vitro Solubility and Stability Experiments of Compound of the Present Invention Preparation of a standard curve: 10.01 mg of sample was weighed out and placed in a volumetric flask, and the volume was brought to 10 mL with acetonitrile/water (v/v, 9/1) to prepare 1.001 mg/mL of standard solution; the standard solution was then serially diluted to 0.5005 mg/mL, 0.1001 mg/mL, 0.05005 mg/mL, 0.01001 mg/mL, and 0.001001 mg/mL to generate the standard curve, and a linear equation was fitted by taking the peak area of the sample as a vertical axis and the concentration as a horizontal axis.

Solubility and stability test: 15 mg of sample was added to 3 mL of vehicle (FaSSIF, FeSSIF, SGF, or water) to prepare a corresponding suspension at a target concentration of 5 mg/mL. The prepared suspension was stirred on a shaker (800 rpm) at 37° C. for 0.5 h, and the suspension was then filtered. The filtrate was diluted with a diluent to a corresponding multiple so that the peak height could not exceed the standard curve, and the solubility and purity were detected using HPLC.

The results of the in vitro solubility and stability experiments of the compound of the present invention are shown in Table 7 below.

TABLE 6

Results of in vitro permeability experiment of compound of the present invention

| | | | $P_{app}$ ($10^{-6}$ cm · s$^{-1}$) | | | | |
|---|---|---|---|---|---|---|---|
| Compound | Cell type | Direction | Sample - 01 | Sample - 02 | Mean | RSD | $P_{app}$(B-A)/ $P_{app}$(A-B) |
| Digoxin | MDCK-MDR1 | A-B | 0.96 | 0.96 | 0.96 | 0.00 | 21.42 |
| | | B-A | 17.69 | 23.46 | 20.58 | 0.20 | |
| | MDCK-Wild type | A-B | 1.90 | 1.68 | 1.79 | 0.09 | 2.69 |
| | | B-A | 4.64 | 4.96 | 4.80 | 0.05 | |
| Metoprolol | MDCK-MDR1 | A-B | 37.59 | 36.32 | 36.96 | 0.02 | 0.55 |
| | | B-A | 20.11 | 20.17 | 20.14 | 0.00 | |
| | MDCK-Wild type | A-B | 26.48 | 22.20 | 24.34 | 0.12 | 0.87 |
| | | B-A | 18.61 | 23.97 | 21.29 | 0.18 | |
| Atenolol | MDCK-MDR1 | A-B | 0.93 | 0.91 | 0.92 | 0.02 | 0.99 |
| | | B-A | 0.91 | 0.92 | 0.91 | 0.01 | |
| | MDCK-Wild type | A-B | 0.52 | 0.49 | 0.51 | 0.05 | 1.99 |
| | | B-A | 1.02 | 1.01 | 1.01 | 0.01 | |
| Compound 2 | MDCK-MDR1 | A-B | 21.08 | 19.91 | 20.50 | 0.04 | 1.71 |
| | | B-A | 35.27 | 34.76 | 35.01 | 0.01 | |
| | MDCK-Wild type | A-B | 27.93 | 26.28 | 27.10 | 0.04 | 1.56 |
| | | B-A | 39.97 | 44.50 | 42.24 | 0.08 | |
| RP-6306 | MDCK-MDR1 | A-B | 13.93 | 13.97 | 13.95 | 0.00 | 2.64 |
| | | B-A | 37.61 | 36.17 | 36.89 | 0.03 | |
| | MDCK-Wild type | A-B | 15.13 | 19.10 | 17.12 | 0.16 | 2.17 |
| | | B-A | 38.54 | 35.91 | 37.22 | 0.05 | |

TABLE 7

Results of in vitro solubility experiment of compound of the present invention

| Compound | Vehicle | Initial pH value | Solubility (mg/mL) 0.5 h | HPLC purity (%, 220 nm) 0.5 h |
|---|---|---|---|---|
| RP-6306 | FaSSIF | 6.52 | 0.049 | 58.88 |
|  | FeSSIF | 4.98 | 0.182 | 74.51 |
|  | SGF | 1.2 | 3.863 | 98.18 |
|  | Water | 7.7 | 0.013 | 40.92 |
|  | Methanol | N.D. | 20.187 | N.D. |
|  | Tetrahydrofuran | N.D. | 4.522 | N.D. |
| Compound 2 | FaSSIF | 6.52 | 0.061 | 88.76 |
|  | FeSSIF | 4.98 | 0.327 | 95.98 |
|  | SGF | 1.2 | 4.865 | 98.69 |
|  | Water | 7.7 | 0.27 | 96.4 |
|  | Methanol | N.D. | 40.568 | N.D. |
|  | Tetrahydrofuran | N.D. | 6.114 | N.D. |

N.D. denotes not detected

As can be seen from the data in Table 7, compound 2 of the present invention has higher solubility in various vehicles (FaSSIF, FeSSIF, SGF, water, methanol, and tetrahydrofuran) compared to RP-6306, and compound 2 is more stable than RP-6306 in FaSSIF, FeSSIF, and water.

Biological Example 7. In Vivo Pharmacodynamic Study—Mouse HT29 Subcutaneous Xenograft Tumor Model HT29 is a colon cancer cell. Each nude mouse was grafted subcutaneously with $5 \times 10^6$ HT29 cells. When the tumor grew to 100-200 mm$^3$, the compound was administered orally once a day alone or in combination with gemcitabine injected intraperitoneally once a week, and the tumor volume was measured twice a week and at the end of administration. Tumor growth inhibition rate of the compound was calculated according to the following equation: tumor growth inhibition (TGI)=1−(tumor volume on day 28 in treatment group−tumor volume on day 1 in treatment group)/(tumor volume on day 28 in vehicle control group−tumor volume on day 1 in treatment group).

The test results show that the compound of the present invention has better activity in the mouse HT29 subcutaneous xenograft tumor model.

Biological Example 8. In Vivo Pharmacodynamic Study—Mouse HCC1569 Subcutaneous Xenograft Tumor Model HCC1569 is a breast cancer cell. Each nude mouse was grafted subcutaneously with $10 \times 10^6$ HCC1569 cells. When the tumor grew to 100-200 mm$^3$, the compound was administered orally once a day alone or in combination with gemcitabine injected intraperitoneally once a week, and the tumor volume was measured twice a week and at the end of administration. Tumor growth inhibition rate of the compound was calculated according to the following equation: tumor growth inhibition (TGI)=1−(tumor volume on day 28 in treatment group−tumor volume on day 1 in treatment group)/(tumor volume on day 28 in vehicle control group−tumor volume on day 1 in treatment group).

The test results show that the compound of the present invention has better activity in the mouse HCC1569 subcutaneous xenograft tumor model.

Biological Example 9. In Vivo Pharmacodynamic Study–Mouse OVCAR-3 Subcutaneous Xenograft Tumor Model OVCAR-3 is an ovarian cancer cell. Each nude mouse was grafted subcutaneously with $10 \times 10^6$ OVCAR-3 cells. When the tumor grew to 100-200 mm$^3$, the compound was administered orally once a day alone or in combination with gemcitabine injected intraperitoneally once a week, and the tumor volume was measured twice a week and at the end of administration. Tumor growth inhibition rate of the compound was calculated according to the following equation: tumor growth inhibition (TGI)=1−(tumor volume on day 28 in treatment group−tumor volume on day 1 in treatment group)/(tumor volume on day 28 in vehicle control group−tumor volume on day 1 in treatment group).

The test results show that the compound of the present invention has better activity in the mouse OVCAR-3 subcutaneous xenograft tumor model.

Biological Example 10. In Vitro Manual Patch-Clamp Experiment for Detecting Inhibitory Activity of Compound Against hERG Ion Channels An HEK-293 cell line stably expressing the hERG potassium channel was used. The HEK293 cell line stably expressing the hERG potassium channel was cultured in a DMEM medium containing 10% fetal bovine serum and 0.8 mg/mL G418 at 37° C. with 5% carbon dioxide.

Cell passage: the old medium was removed, and the cells were washed once with PBS: 1 mL of TrypLE™ Express solution was then added, and the cells were incubated at 37° C. for about 0.5 min. When the cells were detached from the bottom of the dish, about 5 mL of complete medium pre-heated at 37° C. was added. The cell suspension was gently pipetted to separate the aggregated cells. The cell suspension was transferred to a sterile centrifuge tube and centrifuged at 1000 rpm for 5 min to collect the cells. The cells were seeded in 6-cm cell culture dishes at a seeded cell amount of $2.5 \times 10^5$ cells/dish (final volume: 5 mL) for expansion or maintenance culture. In order to maintain the electrophysiological activity of the cells, the cell density must not exceed 80%.

The fluids used during electrophysiology were recorded:
extracellular fluid: 140 mM NaCl. 3.5 mM KCl, 1 mM MgCl$_2$·6H2O, 2 mM CaCl$_2$·2H2O, 10 mM D-Glucose, 10 mM HEPES, and 1.25 mM NaH$_2$PO$_4$·2H2O, adjusted to pH=7.4 with NaOH;
intracellular fluid: 20 mM KCl, 115 mM K-Aspartic, 1 mM MgCl$_2$·6H2O, 5 mM EGTA, 10 mM HEPES, and 2 mM Na2-ATP, adjusted to pH=7.2 with KOH.

Patch-clamp detection: the cells were isolated with TrypLE™ Express before the test, and $4 \times 10^3$ of cells were seeded on a cover glass: the test detection was performed 18 h after the culture in a 24-well plate (final volume: 500 μL). The voltage stimulation scheme of the whole-cell patch clamp for recording the whole-cell hERG potassium current was as follows: when a whole-cell seal was formed, the cell membrane voltage was clamped at −80 mV. The clamping voltage was depolarized from −80 mV to −50 mV and maintained for 0.5 s (used for leakage current detection), then stepped to 30 mV and maintained for 2.5 s, and rapidly returned to −50 mV and maintained for 4 s to excite the tail current of the hERG channel. The data were collected repeatedly every 10 s to observe the effect of the drug on the hERG tail current. The leakage current was detected with the stimulus of −50 mV for 0.5 s. The test data were collected by EPC-10 amplifier (HEKA) and stored in PatchMaster (HEKA) software.

A capillary glass tube was drawn into a recording electrode using a micropipette puller. Under an inverted microscope, a microelectrode manipulator was manipulated to contact the recording electrode with the cell. Suction was applied under negative pressure to form a GΩ seal. After forming the GΩ seal, a rapid capacitance compensation was given. Under the continuous negative voltage, the cell membrane was ruptured to form a whole-cell recording mode. Then, a slow capacitance compensation was given, and the membrane capacitance and series resistance were recorded without leakage compensation.

Administration was started when the hERG current of the whole-cell record was stable. Each drug concentration was maintained for 5 min (or until the current was stable) before the next concentration was measured. Multiple concentrations were measured for each test compound. The cover glass seeded with the cells was placed in a recording bath of the inverted microscope. The test compound and the compound-free extracellular fluid sequentially flowed through the recording bath from low concentrations to high concentrations using a gravity perfusion method to act on the cells, and liquid exchange was performed using a vacuum pump during recording. The current detected in the compound-free extracellular fluid for each cell was used as its own control group. Multiple cells were tested repeatedly and independently: All electrophysiological experiments were performed at room temperature.

Data analysis: the current acted for each drug concentration and the current of the blank control were standardized $$\left(\frac{\text{Peak tail current compound}}{\text{Peak tail current vehicle}}\right),$$

and then the inhibition rate corresponding to each drug concentration was calculated $$\left(1 - \frac{\text{Peak tail current compound}}{\text{Peak tail current vehicle}}\right).$$

The mean and standard error were calculated for each concentration, and the half maximal inhibitory concentration of each compound was calculated using the following equation:

$$\text{inhibition} = \frac{1}{1 + \left(\frac{IC_{50}}{C}\right)^h}$$

The dose-dependent effect was fitted non-linearly using the above equation, wherein C represents the concentration of the test article, $IC_{50}$ is the half maximal inhibitory concentration, and h represents the Hill coefficient. Curve fitting and calculation of $IC_{50}$ were performed using IGOR software.

Conclusion: the compound of the present invention has no significant inhibitory activity against hERG.

Biological Example 11. Study on Inhibition Against Cytochrome P450 Isoenzyme

Experimental procedures: firstly; the test compound (10.0 mM) was diluted to prepare a working solution (100× final concentration) at a concentration of 1.00 mM, and working solutions of positive inhibitors for P450 isoenzymes (CYP2C9 (diclofenac was used as a probe substrate), CYP2D6 (dextromethorphan was used as a probe substrate), and CYP3A (midazolam or testosterone was used as a probe substrate)) and the specific probe substrates thereof were prepared simultaneously: human liver microsomes stored in a refrigerator below −80° C. were thawed on ice, and after all thawed, the human liver microsomes were diluted with a potassium phosphate buffer (PB) to prepare a working solution at a specific concentration (0.127 mg/mL). 20.0 μL of the probe substrate (20.0 μL of PB was added into the blank well) and 158 μL of the working solution of human liver microsomes were added into a reaction plate which was then placed on ice for use: then 2.00 μL of the test compound (N=1) and a specific inhibitor (N=2) were added into the corresponding well, a corresponding organic solvent was added in the group without the inhibitor (test compound or positive inhibitor), and the organic phases of the test compound control sample and the positive control sample were 1:1 DMSO:MeOH and 1:9 DMSO:MeOH, respectively: after pre-incubation in a water bath at 37° C. for 10 min, 20.0 μL of a coenzyme factor (NADPH) solution was added into the reaction plate: for the CYP3A metabolic reaction using midazolam as the probe substrate, the reaction time was 3 min, for the CYP2D6 reaction using dextromethorphan as the probe substrate, the reaction time was 20 min, and other reactions were all performed for 10 min: 400 μL of pre-cooled acetonitrile solution (containing 200 ng/mL tolbutamide and labetalol as the internal standard) was added to terminate the reaction: the reaction plate was placed on a shaker and shaken for 10 min: the reaction plate was centrifuged at 4° C. at 4000 rpm for 20 min: 200 μL of the supernatant was collected and added to 100 μL of water to dilute the sample; and finally, the plate was sealed, oscillated, shaken evenly, and subjected to LC/MS/MS detection.

Data analysis: XL fit was used to plot the relationship between the control group percentage and the concentration of the test compound, and for non-linear regression analysis of the data. The $IC_{50}$ values were determined using a 3- or 4-parameter logic equation:

3-parameter logic equation:

$$y = \frac{\max}{1 + \left(\frac{x}{IC_{50}}\right)^{-hillslope}},$$

and 4-parameter logic equation:

$$y = \min + \frac{\max - \min}{1 + \left(\frac{x}{IC_{50}}\right)^{-hillslope}}.$$

Conclusion: the compound of the present invention has no significant inhibitory effect on all subtypes of CYP enzyme.

Biological Example 12. Metabolic Stability of Hepatocytes

Several 96-well sample precipitation plates were prepared, designated T0, T15, T30, T60, T90, T0-MC, T90-MC, and blank substrate, respectively. The recovery medium and incubation medium were taken out in advance and placed in a 37° C. water bath for pre-heating. Cryopreserved hepatocytes were taken out from the liquid nitrogen tank and immediately immersed in the 37° C. water bath (for about 90 s). After the cryopreserved hepatocytes were thawed and loosened, they were poured into a centrifuge tube containing 40 mL of recovery medium, and the tube was gently inverted to allow the cells to be resuspended in the recovery medium. The cells were centrifuged at room temperature at 100× g for 5 min, and the supernatant was removed. The hepatocytes were resuspended in an appropriate volume of incubation medium, and the cell viability was calculated using a trypan blue staining method. 198 μL of hepatocyte suspension (0.51×10⁶ cells/mL) was added to the pre-heated incubation plate. For the medium control group, 198 μL of hepatocyte-free incubation medium was added to the TO-MC and T90-MC incubation plates. All incubation plates were pre-incubated in a 37° C. incubator for 10 min.

Then 2 μL of working solutions of the test article and the control compound were added, and the mixture was mixed well. The incubation plate was immediately placed into a shaker in the incubator, and the reaction was started while starting a timer. 2 duplicate samples were prepared for each time point of each compound. The incubation conditions were 37° C., saturated humidity; and 5% $CO_2$.

In the test system, the final concentration of the test article was 1 μM, the final concentration of the control sample was 3 μM, the final concentration of hepatocytes was $0.5 \times 10^6$ cells/mL, and the final concentration of the total organic solvent was 0.96%, of which the final concentration of DMSO was 0.1%. At the end of the incubation for the corresponding time point, the incubation plate was taken out, and 25 μL of mixtures of the compound and the control compound with cells were added to the sample plates containing 125 μL of acetonitrile stop solution (containing 200 ng/ml of tolbutamide and labetalol as the internal standard). For the blank sample plate, 25 μL of hepatocyte-free incubation medium was added directly. After being sealed, all sample plates were shaken on a shaker at 600 rpm for 10 min and then centrifuged at 3220×g for 20 min. The supernatants of the test article and the control sample were diluted with ultrapure water in a ratio of 1:3. All samples were mixed well and analyzed by LC/MS/MS.

Data analysis: the percentage of compound remaining after incubation was calculated using the following equation:

$$\% \text{ Remaining (at Appointed Time)} = \frac{\text{Peak Area Ratios of Test Article versus Internal Standard at Appointed Time}}{\text{Peak Area Ratios of Test Article versus Internal Standard at 0 min}} \times 100\%$$

$t_{1/2}$ and Clint were calculated using the following first-order kinetic equation:

$$C_t = C_0 \cdot e^{-k \cdot t}, \text{ when } C_t = \frac{1}{2}C_0, t_{1/2} = \frac{\ln 2}{k} = \frac{0.693}{k}.$$

$$CLint(hep) = k/\text{million cells per mL}.$$

Conclusion: the compound of the present invention has good metabolic stability of hepatocytes.

Although specific embodiments of the present invention have been described above, it will be appreciated by those skilled in the art that these embodiments are merely illustrative and that many changes or modifications can be made to these embodiments without departing from the principles and spirit of the present invention. The protection scope of the present invention is therefore defined by the appended claims.

The invention claimed is:

1. A compound of general formula (1) or an optical isomer, a pharmaceutically acceptable salt, a hydrate or a solvate thereof:

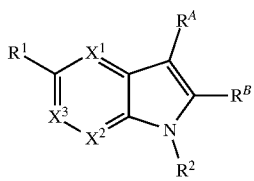

(1)

wherein in general formula (1):

$R^A$ is —C(O)NH($R^4$);

$R^4$ is —H;

$R^B$ is —N($R^3$)$_2$;

$R^3$ is —H;

$X^1$ is $CR^{a1}$;

$R^{a1}$ is —H;

$X^2$ is N;

$X^3$ is $CR^{a3}$;

$R^{a3}$ is

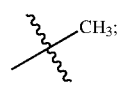

$R^1$ is —CN or

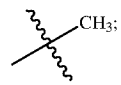

$R^2$ is

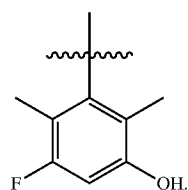 [SMILES: *c1c(C)c(O)cc(F)c1C]

2. The compound or the optical isomer, the pharmaceutically acceptable salt, the hydrate or the solvate thereof according to claim 1, wherein in general formula (1), the compound is selected from the group consisting of:

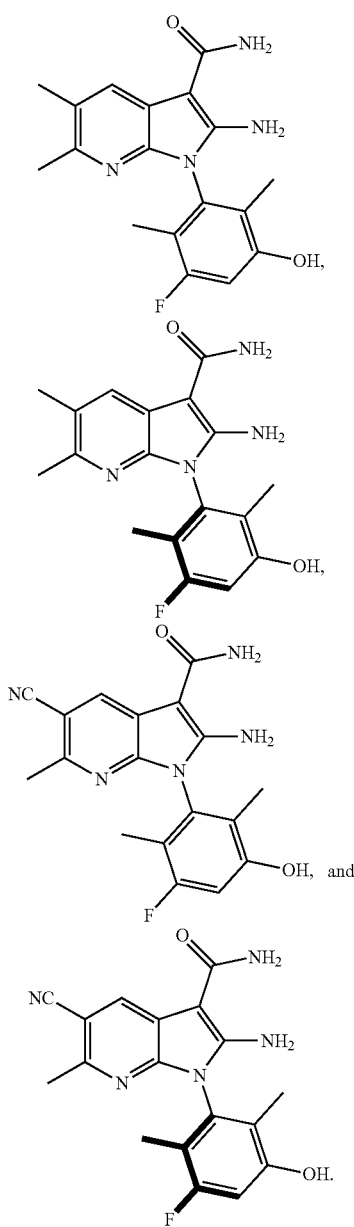

3. The compound or the optical isomer, the pharmaceutically acceptable salt, the hydrate or the solvate thereof according to claim 2, wherein the compound is:

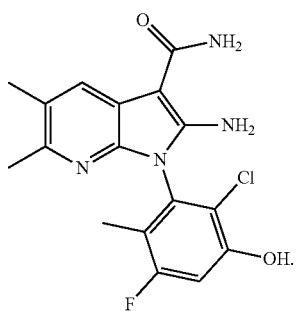 [SMILES: Cc1cc2c(C(N)=O)c(N)n(-c3c(C)c(F)cc(O)c3Cl)c2nc1C]

4. The compound or the optical isomer, the pharmaceutically acceptable salt, the hydrate or the solvate thereof according to claim 2, wherein the compound is:

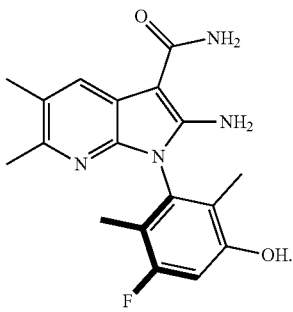

5. The compound or the optical isomer, the pharmaceutically acceptable salt, the hydrate or the solvate thereof according to claim 2, wherein the compound is:

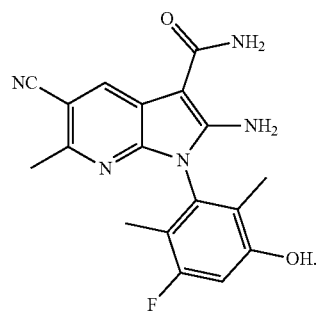 [SMILES: Cc1nc2c(cc1C#N)c(C(N)=O)c(N)n2-c1c(C)c(O)cc(F)c1C]

6. The compound or the optical isomer, the pharmaceutically acceptable salt, the hydrate or the solvate thereof according to claim 2, wherein the compound is:

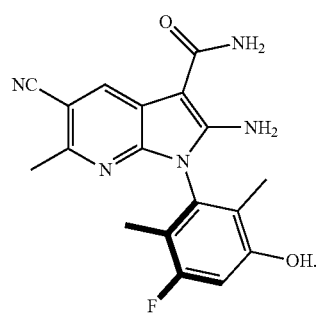

7. A pharmaceutical composition, comprising a pharmaceutically acceptable excipient or carrier, and the compound or the optical isomer, the pharmaceutically acceptable salt, the hydrate or the solvate thereof according to claim 1 as an active ingredient.

8. A compound of general formula (1) or an optical isomer, a pharmaceutically acceptable salt, a hydrate or a solvate thereof:

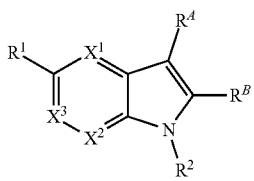

wherein in general formula (1):

$R^A$ is —C(O)NH($R^4$);

$R^4$ is —H;

$R^B$ is —N($R^3$)$_2$;

$R^3$ is —H;

$X^1$ is CR$^{a1}$;

$R^{a1}$ is —H;

$X^2$ is N;

$X^3$ is CR$^{a3}$;

$R^{a3}$ and $R^1$, together with the carbon atom to which they are each attached, form the following structural unit:

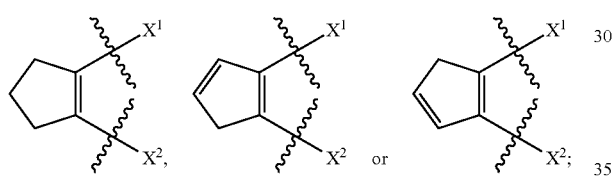

$R^2$ is

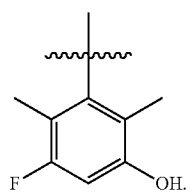 [SMILES: *c1c(C)c(O)cc(F)c1C]

9. The compound or the optical isomer, the pharmaceutically acceptable salt, the hydrate or the solvate thereof according to claim 8, wherein in general formula (1), the compound is selected from the group consisting of:

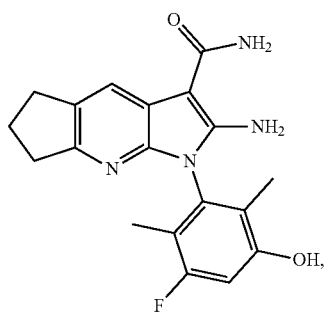

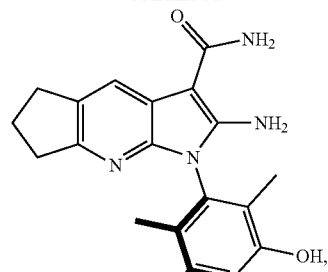

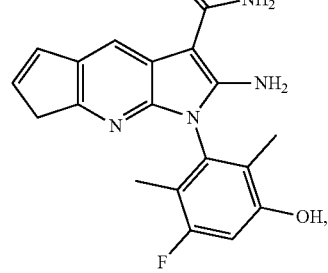

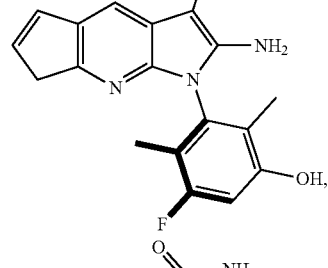

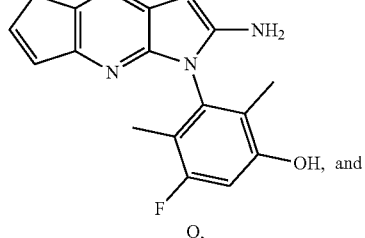

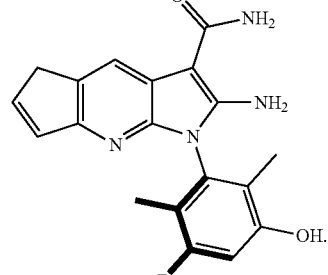

10. The compound or the optical isomer, the pharmaceutically acceptable salt, the hydrate or the solvate thereof according to claim 9, wherein the compound is:

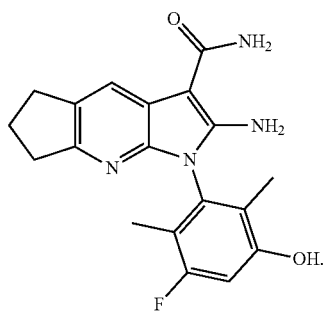 [SMILES: Cc1c(O)cc(F)c(C)c1-n1c(N)c(C(N)=O)c2cc3c(nc21)CCC3]

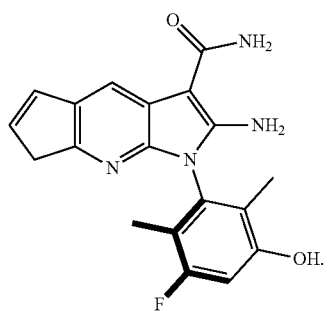

11. The compound or the optical isomer, the pharmaceutically acceptable salt, the hydrate or the solvate thereof according to claim 9, wherein the compound is:

14. The compound or the optical isomer, the pharmaceutically acceptable salt, the hydrate or the solvate thereof according to claim 9, wherein the compound is:

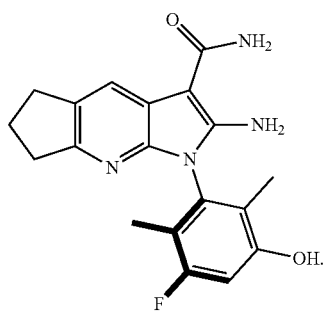

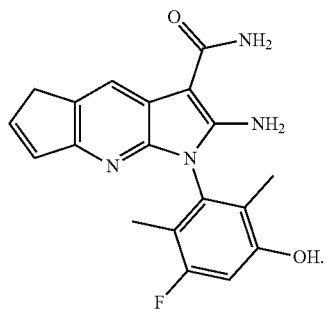

12. The compound or the optical isomer, the pharmaceutically acceptable salt, the hydrate or the solvate thereof according to claim 9, wherein the compound is:

15. The compound or the optical isomer, the pharmaceutically acceptable salt, the hydrate or the solvate thereof according to claim 9, wherein the compound is:

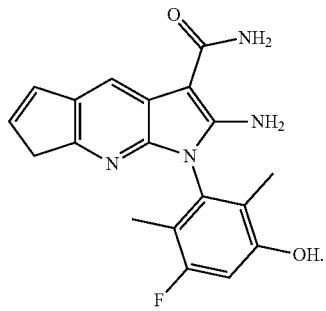 [SMILES: Cc1c(O)cc(F)c(C)c1-n1c(N)c(C(N)=O)c2cc3c(nc21)CC=C3]

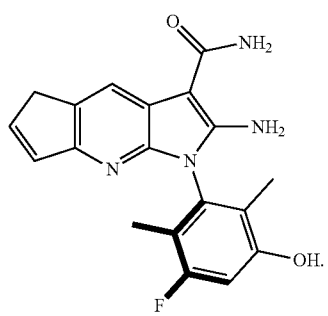

13. The compound or the optical isomer, the pharmaceutically acceptable salt, the hydrate or the solvate thereof according to claim 9, wherein the compound is:

16. A pharmaceutical composition, comprising a pharmaceutically acceptable excipient or carrier, and the compound or the optical isomer, the pharmaceutically acceptable salt, the hydrate or the solvate thereof according to claim 8 as an active ingredient.

* * * * *